(12) United States Patent
Pyeon et al.

(10) Patent No.: US 8,012,678 B2
(45) Date of Patent: Sep. 6, 2011

(54) BIOMARKERS FOR HUMAN PAPILLOMA VIRUS-ASSOCIATED CANCER

(75) Inventors: Dohun Pyeon, Centennial, CO (US); Paul F. Lambert, Madison, WI (US); Michael A. Newton, Madison, WI (US); Paul G. Ahlquist, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 264 days.

(21) Appl. No.: 12/220,465

(22) Filed: Jul. 24, 2008

(65) Prior Publication Data

US 2009/0136486 A1 May 28, 2009

Related U.S. Application Data

(60) Provisional application No. 60/961,774, filed on Jul. 24, 2007.

(51) Int. Cl.
*G01N 33/574* (2006.01)
*C12Q 1/00* (2006.01)

(52) U.S. Cl. .................. 435/4; 435/235.1; 435/7.23

(58) Field of Classification Search .................. None
See application file for complete search history.

(56) References Cited

U.S. PATENT DOCUMENTS

| | | | |
|---|---|---|---|
| 6,235,470 B1 | 5/2001 | Sidransky et al. | |
| 6,803,189 B2 | 10/2004 | Keesee et al. | |
| 7,125,663 B2 | 10/2006 | Schlegel et al. | |
| 2003/0087270 A1* | 5/2003 | Schlegel et al. | 435/6 |

OTHER PUBLICATIONS

Pyeon et al (Cancer Res. 67:4605-4619, May 2007, IDS item #1, filed Nov. 12, 2008.*
Nalam et al, Bio Repr 77:167c-168, 2007, abstract only.*
Affymetrix Catalog; Produkt: Human Genome U133A Array; Array Finder; Affymetrix Product Catalog; Jul. 2002.
Hunter et al.; Opinion-Profiling Early Head and Neck Cancer; Nature Reviews Cancer; vol. 5, No. 2; Feb. 2005; p. 127-135.
Ginos M.A. et al.; Identification of a gene expression sgnature associated with recurrent disease in squamous cell carcinoma of the head an neck; Cancer Research, American Association for Cancer Research, Baltimore, MD, US; vol. 64, No. 1; Jan. 2004; p. 55-63.
Simpson A.J.G. et al.; Cancer/Testis Antigens, Gametogenesis and Cancer; Nature Reviews. Cancer, Nature Publishing Group; London, GB; vol. 5, No. 8; Aug. 2005; p. 615-625.
Chung C.H. et al; Molecular classification of head and neck squamous cell carcinomas using patterns of gene expression; Cancer Cell; Cell Press, US; vol. 5, No. 5; May 2004; p. 489-500.
Cromer A. et al.; Identification of genes associated with tumorgenesis and matastatic potential of hypopharyngeal cancer by microarray analysis; Oncogene; Nature Publishing Group; GB, Basingtoke, Hants; vol. 23, No. 14; Apr. 2004; p. 2484-2498.
PCT Search Report PCT/US2008/071081.
Pyeon D, et al., "Fundamental differences in cell cycle deregulation in human papillomavirus-positive and human papillomavirus-negative head/neck and cervical cancers," Cancer Res. 67:4605-4619 (2007).
Pyeon D, et al., "Fundamental differences in cell-cycle deregulation in human papillomavirus-positive and -negative head/neck and cervical cancers," 23rd International Papillomavirus Conference (Prague, Czech Republic; Sep. 1-7, 2006).
Slebos R, et al., "Gene expression differences associated with human papillomavirus status in head and neck squamous cell carcinoma," Clin. Cancer Res. 12:701-709 (2006).
Baak JPA, et al., "Predictive testing of early CIN behaviour by molecular biomarkers," Cell Oncol. 27(5-6):277-80 (2005).
Martin Cara, et al., "Molecular profiling of cervical neoplasia," Expert. Rev. Mol. Dian. 6(2): 217-229 (2006).
Baak JPA, et al., "Dynamic behavioural interpretation of cervical intraepithelial neoplasia with molecular biomarkers," J. Clin. Pathol. 59(10): 1017-1028 (2007).
Mukherjee G, et al., "MCM immunocytochemistry as a first line cervical screening test in developing countries: a prospective cohort study in a regional cancer centre in India," Br J Cancer. 1107-1111 (2007).

* cited by examiner

*Primary Examiner* — Misook Yu
*Assistant Examiner* — Lei Yao
(74) *Attorney, Agent, or Firm* — Quarles & Brady, LLP

(57) ABSTRACT

Cervical cancer cells and HPV$^+$ head and neck cancer cells express three testis-specific genes not normally expressed in somatic cells: testicular cell adhesion molecule 1 (TCAM1), synaptonemal complex protein 2 (SYCP2) and stromal antigen 3 (STAG3). Among the three markers, TCAM1 and SYCP2 are early detection markers. Various methods for identifying a human or non-human animal as a candidate for further examination for cervical cancer, preneoplastic lesion for cervical cancer, head and neck cancer, or preneoplastic lesion for head and neck cancer are disclosed. Methods of detecting said cancers and preneoplastic lesions, methods of screening for drugs for treating said cancers and preneoplastic lesions, methods for monitoring the effectiveness of a treatment for said cancers, and methods of treating said cancers are also disclosed. Further disclosed are kits that can be used to practice the above methods.

11 Claims, 15 Drawing Sheets
(10 of 15 Drawing Sheet(s) Filed in Color)

BIOMARKERS FOR HUMAN PAPILLOMA VIRUS-ASSOCIATED CANCER

CROSS-REFERENCE TO RELATED APPLICATION

This application claims the benefit of U.S. Provisional Patent Application No. 60/961,774 filed Jul. 24, 2007, incorporated herein by reference as if set forth in its entirety.

STATEMENT REGARDING FEDERALLY SPONSORED RESEARCH OR DEVELOPMENT

This invention was made with United States government support awarded by the following agency: NIH CA097944 and CA022443 and CA064364. The United States has certain rights in this invention.

BACKGROUND OF THE INVENTION

Cervical cancer is the second most common malignancy in women worldwide and is a major cause of morbidity and mortality. Human papillomaviruses (HPV) are DNA viruses that infect and replicate in cutaneous and mucosal epithelia. High-risk mucosotropic HPV genotypes, including HPV16, HPV18 and HPV31, are associated with nearly all cervical cancers.

Head and neck cancer, which arises in mucosal epithelia lining various cavities in the head and neck region, such as the oral cavity and throat, is the sixth most common cancer in the United States with a survival rate of about 50%. 20-30% of head and neck cancers are associated with HPV; whereas the rest are linked to other risk factors, such as tobacco and alcohol.

The art, however, needs methods for predicting and diagnosing HPV, as well as diseases associated with HPV.

BRIEF SUMMARY

Cervical cancer (CC) cells and HPV$^+$ head and neck cancer (HNC) cells express three testis-specific genes not normally expressed in somatic cells: testicular cell adhesion molecule 1 (TCAM1), synaptonemal complex protein 2 (SYCP2) and stromal antigen 3 (STAG3). Among the three markers, TCAM1 and SYCP2 are early detection markers. Various methods for identifying a human or non-human animal as a candidate for further examination for CC, preneoplastic lesion for CC, HNC and preneoplastic lesion for HNC are disclosed. Methods of detecting CC and preneoplastic lesions thereof, methods of detecting HNC and preneoplastic lesions thereof, methods of screening for drugs for treating said cancers and preneoplastic lesions, methods for monitoring the effectiveness of a treatment for said cancers, and methods of treating said cancers are also disclosed. Further disclosed are kits that can be used to practice the above methods.

These and other features, objects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The patent or application file contains at least one drawing executed in color. Copies of this patent or patent application publication with color drawings will be provided by the Office upon request and payment of the necessary fee.

Figure 1:
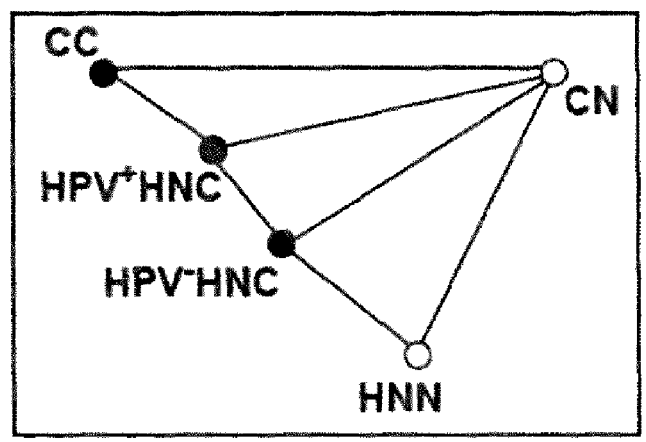
FIG. 1: Global gene expression analysis showed similarities and differences among HPV$^+$ HNC, HPV$^-$ HNC and CC. (A) Multidimensional scaling measurements between all indicated pairs of tumor and normal classes of the distances between class-averaged log 2 expression levels over all 54,675 Affymetrix probe sets. The relative distances between each class are approximated in the two-dimensional projection at the left and tabulated at below. (B) Pairwise comparisons of expression alterations from normal for three cancers are shown as scatter plots of average log 2 fold change from normal. Pearson correlations (R) measure global concordance in expression alterations between cancer pairs. Genes are highlighted that show differential expression between HPV$^+$ HNC and HPV$^-$ HNC; tracking into the HPV$^+$ HNC vs. HPV$^+$ CC comparison, these genes are predominantly equivalently expressed between these HPV$^+$ cancers. Dotted lines show median expression changes of red and blue genes, and red and blue arrows indicate the median shifted from HPV$^+$ HNC/HPV$^-$ HNC comparison to HPV$^+$ HNC/CC comparison. (C) Differential expression analysis revealed genes significantly altered between the respective tissue classes. The results of three pairwise comparisons are summarized in the Venn diagram and tabulated fully in Table 3 (HPV$^+$ vs. HPV$-$), Supplementary Table S5 (Tumor vs. Normal) and Supplementary Table S6 (HNC vs. CC).
Figure 1:
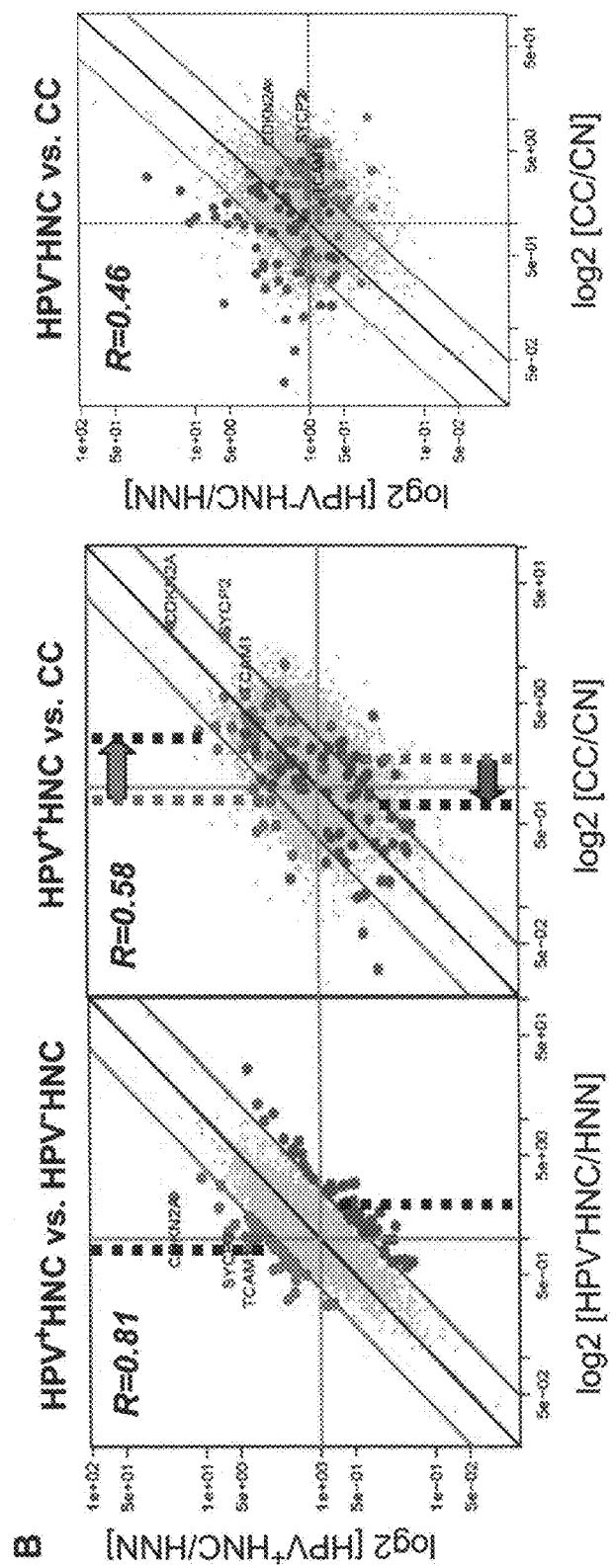
Figure 1:
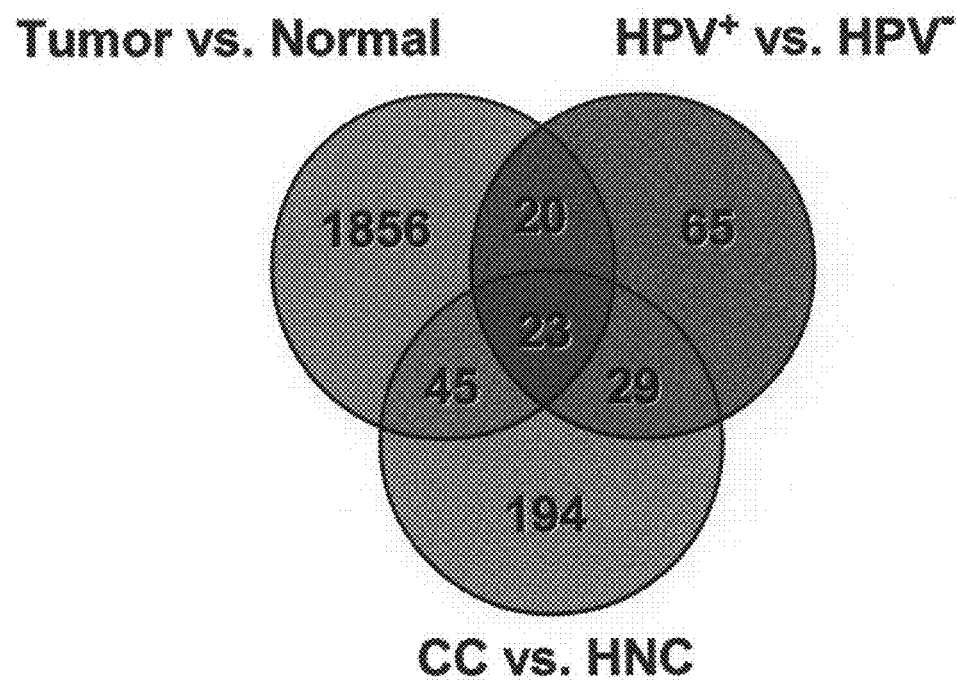

While the present invention is susceptible to various modifications and alternative forms, exemplary embodiments thereof are shown by way of example in the drawings and are described herein in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DESCRIPTION OF EXEMPLARY EMBODIMENTS

The present invention is based, in part, on the inventors' observation that human primary tumors of CC cells and HPV⁺ HNC cells expressed three testis-specific genes not normally expressed in somatic cells. These three testis-specific genes were TCAM1, SYCP2 STAG3. TCAM1 was also upregulated in preneoplastic lesions of cervical cells. Consistent with this finding, which suggests that TCAM1 upregulation is an early event in cancer development, TCAM1 expression was upregulated in early passages of NIKS (a spontaneously immortalized human keratinocyte cell line; see, 54) following HPV infection. A similar observation was made for SYCP2. Therefore, TCAM1 and SYCP2 can be detection markers not only for CC and HNC, but also for the corresponding preneoplastic lesions.

While not intending to be bound to any particular theory, the inventors believe that patients may develop an immune response to these three testis-specific antigens when they are overexpressed in preneoplastic and cancerous tissues; therefore, detecting or measuring the level of an antibody to one of these antigens in a body fluid, such as blood, provides a useful detection tool for CCs and HNCs as well as the corresponding preneoplastic lesions. In addition, TCAM1 resembles intracellular adhesion molecules in amino acid sequence and is expected to be located on cell surface. Accordingly, TCAM1 can be digested at a cell surface, and the extracellular domain part can be released into circulation. Cells containing TCAM1 also can be exfoliated and released into circulation. Either way, a body fluid can be used for detecting the upregulation of TCAM1 in cancer or preneoplastic cells.

The three testis-specific antigens are well known in the art. For example, the amino acid sequences for TCAM1 from mouse and rat can be found at NCBI GenBank Accession numbers CAM23792 (SEQ ID NO:1) and BAA75217 (SEQ ID NO:2), respectively; whereas the cDNA sequence for TCAM1 from human, mouse and rat can be found at NCBI GenBank Accession numbers NR_002947 (SEQ ID NO:3), NM_029467 (SEQ ID NO:4) and NM_021673 (SEQ ID NO:5), respectively.

Likewise, the amino acid sequences for SYCP2 from human, mouse, rat, pig, frog and chimpanzee can be found at NCBI GenBank Accession numbers CAM28338 (SEQ ID NO:6), NP_796165 (SEQ ID NO:7), NP_570091 (SEQ ID NO:8), CAN13245 (SEQ ID NO:9), NP_001072339 (SEQ ID NO:10) and XP_001141311 (SEQ ID NO:11), respectively; whereas the cDNA sequence for SYCP2 from human, mouse, rat, pig, frog and chimpanzee can be found at NCBI GenBank Accession numbers NM_014258 (SEQ ID NO:12), NM_177191 (SEQ ID NO:13), NM_130735 (SEQ ID NO:14), CR956363 (SEQ ID NO:15), NM_001078871 (SEQ ID NO:16) and XM_514753 (SEQ ID NO:17), respectively.

Furthermore, the amino acid sequences for STAG3 from human, mouse, rat, chimpanzee and duck-billed platypus can be found at NCBI GenBank Accession numbers CAB59367 (SEQ ID NO:18), NP_058660 (SEQ ID NO:19), NP_446182 (SEQ ID NO:20), XP_519253 (SEQ ID NO:21) and XP_001516109 (SEQ ID NO:22), respectively; whereas the cDNA sequence for STAG3 from human, mouse, rat, chimpanzee and duck-billed platypus can be found at NCBI GenBank Accession numbers NM_001025202 (SEQ ID NO:23), NM_016964 (SEQ ID NO:24), NM_053730 (SEQ ID NO:25), XM_519253 (SEQ ID NO:26) and XM_001516059 (SEQ ID NO:27), respectively.

As used herein, "cervical cancer" (CC) refers to carcinoma of the uterine cervix (e.g., carcinoma in situ, invasive carcinoma and metastatic carcinoma). CC is preceded with a well-recognized preneoplastic lesion, cervical intraepithelial neoplasia (CIN) or squamous intraepithelial lesions (SIL) in the case of squamous cell carcinoma, and cervical glandular epithelial neoplasia in the case of adenocarcinoma.

As used herein, "head and neck cancer" (HNC) refers to cancer that arises in mucosal epithelia in the head or neck region, such as cancers in the nasal cavity, sinuses (e.g., paranasal sinuses), lip, mouth (e.g., oral cavity), salivary gland, throat (e.g., nasopharynx, oropharynx and hypopharynx), larynx, thyroid and parathyroid. One example of HNC is squamous cell carcinoma.

Although the examples below used samples from subjects with CC and HNC, the inventors contemplate that the methods can be used with any HPV-associated cancer including, but not limited to, anal cancer, CC, HNC, penile cancer, vaginal cancer and vulvar cancer.

In a first aspect, the present invention is summarized as a method for identifying a human or non-human animal as a candidate for further examination for CC. The method includes the steps of obtaining a tissue sample from a region of the cervix of the human or non-human animal, measuring the expression of TCAM1, SYCP2 or STAG3 at the mRNA or protein level in the cells of the tissue sample, and comparing the expression level to a normal standard, wherein a higher than normal expression indicates that the human or non-human animal is a candidate for further examination for CC.

In one embodiment of the first aspect, the tissue sample can be a cervical smear such as a Papanicolaou (Pap) smear. In another embodiment of the first aspect, the tissue sample can be a fluid collected by vaginal rinsing.

In a second aspect, the present invention is summarized as a method for detecting CC in a human or non-human animal. The method includes the steps of obtaining a tissue sample from a region of the cervix of the human or non-human animal, measuring the expression of TCAM1, SYCP2 and/or STAG3 at the protein or mRNA level in the cells of the tissue sample, and comparing the expression level to a normal standard wherein a higher than normal expression indicates CC.

In one embodiment of the second aspect, the tissue sample can be a cervical smear such as a Pap smear or biopsy sample from the cervix. In another embodiment of the second aspect, the tissue sample can be a fluid collected by vaginal rinsing. Optionally, the method also includes the step of observing CC in the human or non-human animal, e.g., by standard pathological evaluation of a biopsy tissue specimen from the cervix (e.g., histopathological analysis). Known techniques such as radiographic imaging studies may be employed to evaluate for the presence of metastatic lesions.

In a third aspect, the present invention is summarized as a method for detecting preneoplastic lesion of the cervix in a human or non-human animal. The method includes the steps of obtaining a tissue sample from a region of the cervix of the human or non-human animal, measuring the expression of TCAM1 or SYCP2 at the protein and/or mRNA level in the cells of the tissue sample, and comparing the expression level to a normal standard wherein a higher than normal expression indicates a preneoplastic lesion in the cervix.

In one embodiment of the third aspect, the tissue sample can be a cervical smear, such as a Pap smear or a biopsy sample from the cervix. In another embodiment of the third aspect, the tissue sample can be a fluid collected by vaginal rinsing. Optionally, the method also includes the step of observing a preneoplastic lesion of the cervix in the human or non-human animal, e.g., by standard pathological evaluation of a biopsy tissue specimen from the cervix (e.g., histopathological analysis).

In a fourth aspect, the present invention is summarized as a method for identifying a human or non-human animal as a candidate for further examination for HNC. The method includes the steps of obtaining a tissue sample from a head or neck region of the human or non-human animal, measuring the expression of TCAM1 at the protein level, SYCP2 at the protein level, or STAG3 at the protein or mRNA level in the cells of the tissue sample, and comparing the expression level to a normal standard wherein a higher than normal expression indicates that the human or non-human animal is a candidate for further examination for HNC.

In one embodiment of the fourth aspect, the tissue sample can be a saliva specimen, preferably containing exfoliated epithelial cells, or mouth rinse, preferably containing exfoliated epithelial cells. In obtaining a mouth rinse sample, it is preferred that both the mouth and throat are rinsed. In another embodiment of the fourth aspect, the tissue sample can be a mouth swab sample.

In a fifth aspect, the present is summarized as a method for detecting HNC in a human or non-human animal. The method includes the steps of obtaining a tissue sample from a head or neck region of the human or non-human animal, measuring the expression of TCAM1 at the protein level, SYCP2 at the protein level, or STAG3 at the protein or mRNA level in the cells of the tissue sample, and comparing the expression level to a normal standard wherein a higher than normal expression indicates head and neck cancer.

In one embodiment of the fifth aspect, the tissue sample can be obtained from a head or neck region at least part of which is suspected of being cancerous or having preneoplastic development. In another embodiment of the fifth aspect, the tissue sample can be a saliva specimen, preferably containing exfoliated epithelial cells, or mouth rinse, preferably containing exfoliated epithelial cells. In obtaining a mouth rinse sample, it is preferred that both the mouth and throat are rinsed. In yet another embodiment of the fifth aspect, the tissue sample can be a mouth swab sample. Optionally, the method includes the step of observing HNC in the human or non-human animal, e.g., by standard pathological evaluation of a biopsy tissue specimen from the head and neck region (e.g., histopathological analysis). Known techniques such as radiographic imaging studies may be employed to evaluate for the presence of metastatic lesions.

In a sixth aspect, the present invention is summarized as a method for detecting preneoplastic lesion for HNC in a human or non-human animal. The method includes the steps of obtaining a tissue sample from a head or neck region of the human or non-human animal, measuring the expression of TCAM1 or SYCP2 at the protein or mRNA level in the cells of the tissue sample, and comparing the expression level to a normal standard wherein a higher than normal expression indicates a preneoplastic lesion in the head and neck region.

In one embodiment of the sixth aspect, the tissue sample can be obtained from a head or neck region at least part of which is suspected of being cancerous or having preneoplastic development. In another embodiment of the sixth aspect, the tissue sample can be a saliva specimen, preferably containing exfoliated epithelial cells, or mouth rinse, preferably containing exfoliated epithelial cells. In obtaining a mouth rinse sample, it is preferred that both the mouth and throat are rinsed. In yet another embodiment of the sixth aspect, the tissue sample can be a mouth swab sample. Optionally, the method includes the step of observing a preneoplastic lesion in the head and neck region of the human or non-human animal, e.g., by standard pathological evaluation of a biopsy tissue specimen from the head and neck region (e.g., histopathological analysis).

In a seventh aspect, the present invention is summarized as a method for identifying a human or non-human animal as a candidate for further examination for CC, preneoplastic lesion for CC, HNC, preneoplastic lesion for HNC or HPV infection. The method includes the steps of determining the level of TCAM1 in a body fluid from the human or non-human animal, comparing the level to a normal standard, and identifying the human or non-human animal as a candidate for further examination for CC, preneoplastic lesion for CC, HNC, preneoplastic lesion for HNC or HPV infection when the level exceeds the normal standard.

In one embodiment of the seventh aspect, the body fluid can be blood, plasma, serum, lymph, ascitic fluid, a gynecological fluid, urine, a fluid collected by vaginal rinsing, a saliva specimen or a fluid collected by mouth rinsing.

In an eighth aspect, the present invention is summarized as a method for identifying a human or non-human animal as a candidate for further examination for CC, preneoplastic lesion for CC, HNC, preneoplastic lesion for HNC or HPV infection. The method includes the steps of determining the level of TCAM1 antibodies in a body fluid from the human or non-human animal, comparing the level to a normal standard, and identifying the human or non-human animal as a candidate for further examination for CC, preneoplastic lesion for CC, HNC, preneoplastic lesion for HNC or HPV infection when the level exceeds the normal standard.

In one embodiment of the eighth aspect, the body fluid can be blood, plasma, serum, lymph, ascitic fluid, a gynecological fluid, urine, a fluid collected by vaginal rinsing, a saliva specimen or a fluid collected by mouth rinsing.

In a ninth aspect, the present invention is summarized as a method for detecting HPV infection in a human or non-human animal. The method includes the steps of obtaining a tissue sample from the human or non-human animal, measuring the expression of TCAM1 and SYCP2 at the protein or mRNA level in the cells of the tissue sample, and comparing the expression level to a normal standard wherein a higher than normal expression indicates HPV infection.

A normal standard employed in any of the above methods can be readily established by one of ordinary skill in the art. For example, the expression level in HPV$^-$ cells of the same human or non-human animal, preferably in the same type of cells from the same tissue during an HPV$^-$ or cancer/preneoplastic lesion-free period, can be used as a normal standard. As another example, the expression level in HPV$^-$ cells of a different human or non-human animal, preferably in the same type of cells from the same tissue during a HPV$^-$ or cancer/preneoplastic lesion-free period, can be used as a normal standard. Given that testis-specific antigens are typically not expressed in somatic cells, any significant expression detected would represent a higher than normal expression. Similarly, TCAM1 protein level or TCAM1 antibody level in a body fluid from HPV$^-$ or cancer/preneoplastic lesion-free individuals can likewise be used as a normal standard.

Any tissue sample used in the methods of the present invention can be subjected to a variety of well-known, post-collection preparative and storage techniques (e.g., nucleic acid and/or protein extraction, fixation, storage, freezing, ultrafiltration, concentration, centrifugation, etc.) prior to being used for detecting or measuring the expression of a marker provided herein.

When the mouth, throat or cervix area is rinsed to collect a tissue sample for detecting TCAM1, a suitable protease, such as trypsin, chymotrypsin or arginine carboxylase, that can cleave and release the entire or a substantial part of the extracellular domain of TCAM1 can be included in the rinsing fluid.

In a tenth aspect, the present invention is summarized as a method for identifying an agent as a candidate for treating CC or HNC. The method includes the steps of exposing CC cells or HNC cells expressing TCAM1, SYCP2 or STAG3 to a test agent, measuring the expression level of the marker, and comparing the expression level to that of control cells not exposed to the test agent, wherein a lower than control expression indicates that the agent is a candidate for treating CC or HNC. The cancer cells used can be either established cancer cell lines or cancer cells from one or more patients.

In an eleventh aspect, the present invention is summarized as a method for determining the effectiveness of a treatment for CC or HNC. The method includes the steps of measuring the expression of TCAM1, SYCP2 or STAG3 in a first sample from a CC or HNC patient prior to providing at least a portion of the treatment to the patient, measuring the expression of the marker in a second sample from the patient after said portion of the treatment is provided to the patient, and comparing the expression levels of the first sample and second sample, wherein a lower expression level in the second sample indicates that the treatment is effective.

In a twelfth aspect, the present invention is summarized as a method for treating or preventing CC, a preneoplastic lesion of CC, HNC, or a preneoplastic lesion of HNC in a human or non-human animal. The method includes the step of administering to the human or non-human animal having CC or HNC an active agent in an amount effective to treat CC or HNC, wherein the active agent contains a therapeutic agent (e.g., a chemotherapeutic agent) for CC, HNC or preneoplastic lesions thereof and a binding agent that can bind to TCAM1 (e.g., a ligand or antibody of TCAM1). The therapeutic agent and the binding agent are linked together. The therapeutic agent can be linked to the binding agent either covalently, through a linker or a chemical bond, or noncovalently, through ionic, van der Waals, electrostatic or hydrogen bonds. The therapeutic agent is typically a cytotoxic agent that can cause the death of a target cell. Similarly, an active agent can also contain a therapeutic agent and a targeting nucleic acid that can hybridize to a portion of the mRNA of TCAM1, SYCP2 or STAG3, wherein the therapeutic agent and the targeting nucleic acid are linked together.

As used herein, "antibody" includes an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). For example, the term includes bivalent or bispecific molecules, diabodies, triabodies and tetrabodies. Bivalent and bispecific molecules are described in, e.g., Kostelny et al., J Immunol 148:1547 (1992); Pack & Pluckthun, Biochemistry 31:1579 (1992); Zhu et al., Protein Sci. 6:781 (1997); Hu et al., Cancer Res. 56:3055 (1996); Adams et al., Cancer Res. 53:4026 (1993); and McCartney et al., Protein Eng. 8:301 (1995). The term "antibody" also includes antigen binding forms of antibodies, including fragments with antigen-binding capability (e.g., Fab', F(ab')$_2$, Fab, Fv and rIgG). The term also refers to recombinant single chain Fv fragments (scFv). Preferably, antibodies employed to practice the present invention bind to its target protein with an affinity (association constant) of equal to or greater than $10^7$ M$^{-1}$.

In a thirteenth aspect, the present invention is summarized as a kit for detecting the expression of TCAM1, SYCP2 or STAG3. The kit includes at least one of (i) an agent such as an antibody or a ligand that specifically binds to TCAM1, SYCP2 or STAG3 and (ii) a nucleic acid (e.g., a primer for PCR amplification or a probe for detection) that hybridizes to a polynucleotide containing a nucleotide sequence of TCAM1, SYCP2 or STAG3 cDNA or complements thereof. The kit also includes at least one control sample having a known amount of (i) a polypeptide containing an amino acid sequence of TCAM1, SYCP2 or STAG3 or (ii) a polynucleotide containing a nucleotide sequence of TCAM1, SYCP2 or STAG3 cDNA or complements thereof.

Examples of control samples include CC cells, preneoplastic cervical cells, normal cervical cells, HNC cells, preneoplastic head and neck cells, normal head and neck cells, an extract of any of the foregoing cells, a body fluid sample of a human or non-human animal having CC or HNC cancer, and a body fluid sample of a normal human or non-human animal.

In one embodiment of the thirteenth aspect, the control sample can be an isolated polypeptide containing an amino acid sequence of TCAM1, SYCP2 or STAG3. In another embodiment of the thirteenth aspect, the control sample can be an isolated nucleic acid containing a nucleotide sequence of TCAM1, SYCP2 or STAG3 cDNA or complements thereof.

Expression of a marker provided herein may be assessed by any of a wide variety of well-known methods for detecting the expression of a gene at the protein or mRNA level. Non-limiting examples of such methods include immunological methods for detection of a target protein, protein purification methods, protein function or activity assays, nucleic acid hybridization methods, nucleic acid reverse transcription methods and nucleic acid amplification methods.

Preferably, expression of a marker can be assessed at the protein level using an antibody (e.g., a radio-labeled, chromophore-labeled, fluorophore-labeled or enzyme-labeled antibody) or an antibody derivative (e.g., an antibody conjugated with a substrate or with the protein or ligand of a protein-ligand pair (e.g., biotin-streptavidin)) that binds specifically to the marker protein or fragment thereof. For example, enzyme linked immunosorbent assays (ELISAs), Western blot analysis and in situ hybridizations can be employed for this purpose.

Alternatively, expression of a marker can be assessed at the mRNA level by preparing and detecting/measuring mRNA/cDNA from cells. For example, RT-PCR (e.g., quantitative RT-PCR), Southern blot analysis, Northern blot analysis, and in situ hybridizations can be used for this purpose. It is well within the capability of one of ordinary skill in the art to design primers and probes for assessing the expression of a marker at the mRNA level.

As for any cell surface protein, the expression of TCAM1 can be analyzed either qualitatively or quantitatively by flow cytometry. In addition, in vivo medical imaging can be used to detect or quantify the expression of TCAM1. For example, a suitable contrast agent can be linked to a TCAM1 binding agent (e.g., a TCAM1 ligand or antibody) and administered to an individual. Cells that express TCAM1 can be imaged as the contrast agent is retained by these cells due to the binding of the antibody to TCAM1 on the surface of the cells. Similarly, a suitable contrast agent can be linked to a targeting nucleic acid that can hybridize to TCAM1 mRNA and administered to an individual. Cells that express TCAM1 will retain the contrast agent as the targeting nucleic acid hybridizes to TCAM1 mRNA in these cells. As a result, cells that express TCAM1 can be imaged. Any suitable medical imaging techniques can be used. Examples of such techniques include ultrasound, computerized tomography (CT), magnetic resonance imaging (MRI) and nuclear medicine techniques such as gamma ray detection by a gamma ray detector (e.g., a gamma scintillation camera or a 3-dimensional imaging camera), positron emission tomography (PET) and single photon emission computed tomography (SPECT). One of ordinary skill in the art can readily link a contrast agent to a TCAM1 binding agent or TCAM1 mRNA targeting nucleic acid (e.g., covalently through a linker or a chemical bond). For example, for MRI detection, a superparamagnetic iron oxide nanoparticle (SPION) can be conjugated to a TCAM1 antibody or TCAM1 mRNA targeting nucleic acid for administration and MRI detection. For nuclear medicine detection, radionuclide-labeled TCAM1 antibody or radionuclide-labeled TCAM1 mRNA targeting nucleic acid can be administered and radiation emission from the nucleotide can be measured and an image thereof can be obtained. WO 2006/023888 describes linking a medical imaging contrast agent to a nucleic acid probe for imaging gene expression in various tissues by, e.g., MRI. WO 2006/023888 is herein incorporated by reference as if set forth in its entirety.

By way of example, but not limitation, examples of the present invention are described below.

EXAMPLES

Example 1

Differences in Gene Expression in Human Papillomavirus-Positive and -Negative Head/Neck and Cervical Cancers and Gene Expression in Preneoplastic Lesion of Cervical Cancer Appendix I Appendix I provides supplementary methods figures, and tables and is herein incorporated by reference in its entirety.

Materials and Methods

Tissue samples: 15 and 27 HNC samples were from the University of Iowa and Harvard School of Public Health, respectively. 5 and 9 HNN samples were from the University of Iowa and the National Disease Research Interchange (NDRI), respectively (Supplementary Table S1). CC and normal cervical samples were from the Gynecologic Oncology Group. Patient information is presented in Table 1A and Supplementary Table S1. All tissue samples were fresh frozen in liquid nitrogen and collected with patients' consent under approval of the Institutional Review Boards from all participating institutions. Also, all the tumor samples were primary resections collected before the initiation of chemotherapy radiotherapy. Each sample was processed, and RNA was prepared and labeled as described in Supplementary Methods.

Human and HPV microarrays: Human gene expression was profiled using Affymetrix U133 Plus 2.0 Arrays (Affymetrix; Santa Clara, Calif.). For HPV detection and genotyping, 70-mer oligonucleotide probes with a $T_M$ of 80° C. (Supplementary Methods) were designed using Oligowiz 1.0 (16), were purchased from MWG-Biotech (High Point, N.C.) and were spotted in quadruplicate on epoxy glass slides (TeleChem International, Inc.; Sunnyvale, Calif.) with a BioRobotics MicroGrid II (Genomic Solutions; Ann Arbor, Mich.). HPV array hybridization was carefully optimized using RNA from known $HPV^+$ and $HPV^-$ keratinocyte cell lines (Supplementary Methods). HPV arrays were hybridized with biotin-labeled cRNA, processed as in Supplementary Methods, and scanned using an Agilent DNA Microarray Scanner (Agilent; Palo Alto, Calif.). Images were analyzed using Axon GenePix Pro 5.1 Software (Molecular Devices; Sunnyvale, Calif.). 10 µg of cRNA was used for Affymetrix microarray hybridization and scanning at the University of Wisconsin Biotechnology Gene Expression Center (Madison, Wis.). To obtain statistically significant sample number in each group while minimizing unnecessary sample processing and microarray use, inventors selected HNC samples based in part on HPV status.

Statistical analysis: Tools in R (17) and Bioconductor (18) were adapted for statistical analysis. Probe set summary measures were computed by robust multiarray averaging (19) applied to the combined set of 84 microarrays. Average base-2 log expression was used to summarize each probe-set's expression within a tissue class. Multidimensional scaling allowed global (i.e., averaged over the genome) comparisons between classes, and class-restricted nonparametric bootstrap sampling (20) was used to measure the significance of observed differences between global correlations computed on pairs of tumor classes. Permutation testing was used to confirm that each measured correlation was significantly non-zero. The primary analysis of differential gene expression at the probe-set level was done in three pairwise comparisons: Tumor versus Normal, HPV$^+$ vs. HPV$^-$, and HNC vs. CC. Fold changes and t-statistics were used to identify differentially expressed probe sets; the latter were converted to q-values to control false discovery rate (21).

Enrichment of gene ontology (GO) categories for differentially expressed genes was measured using random-set testing methods (22, 23). Briefly, the proportion of significantly altered genes and the average log fold change for all genes in each of 2760 GO categories were compared, respectively, to their distributions on a random set of genes in order to obtain standardized enrichment Z scores. A category was considered significantly enriched for altered genes if both of these Z scores exceeded 4 (nominal p-value $3\times10^{-5}$). Calculations used version 1.0 of the R package allez, and the October 2005 build of Bioconductor package hgu133plus2. The same Z score standardization applied to class-averaged expression profiles (above) was used to compute GO profiles for each tissue class. These were correlated between classes to assess the similarity of tissue classes.

Figure 2:
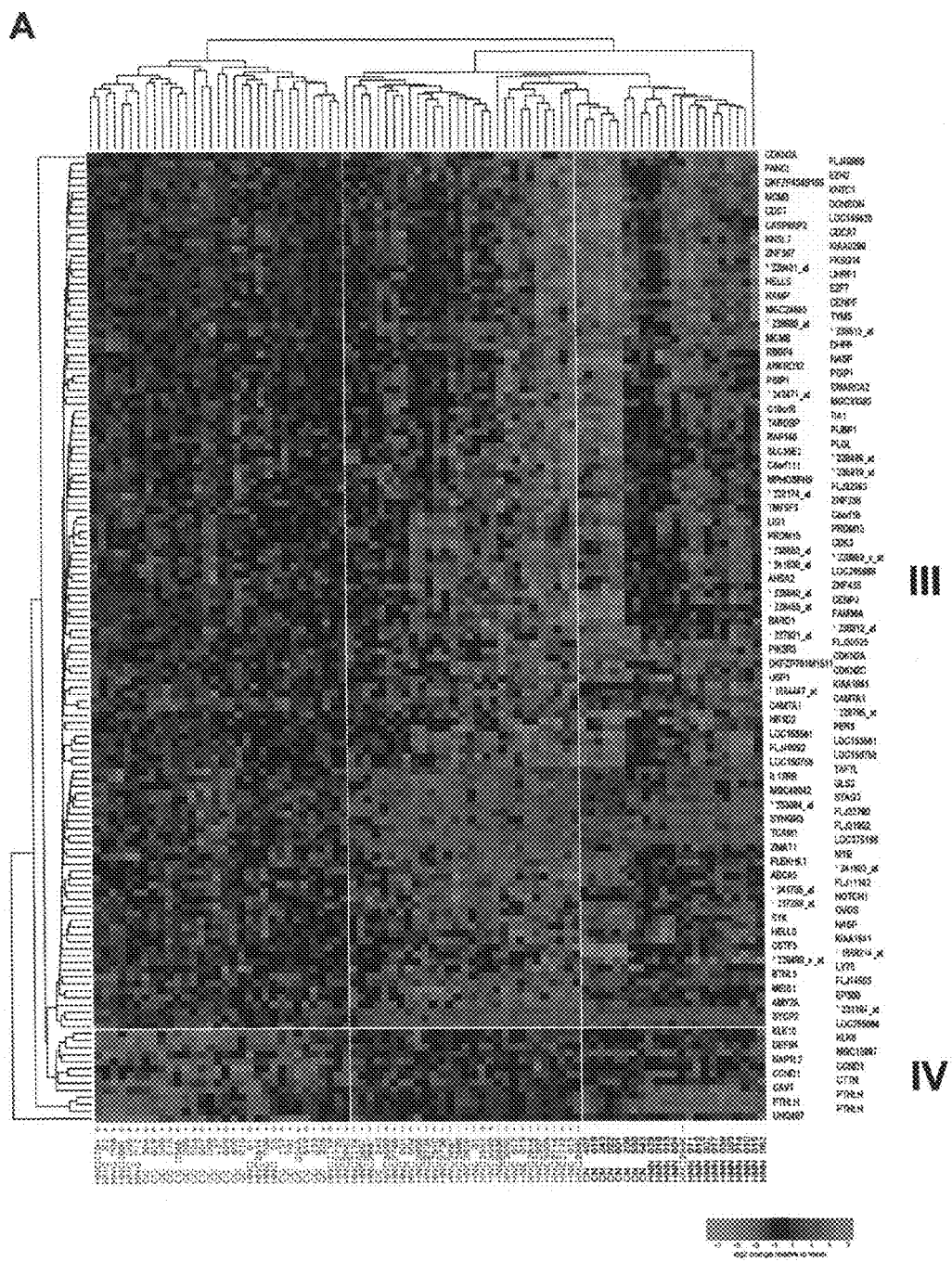
FIG. 2: Gene expression signatures for HPV$^+$ vs. HPV$^-$ cancers and HNC vs. CC cancers. (A) Normalized expression values are shown for all 84 samples and 137 probe sets that were significantly differentially expressed between the HPV$^+$ cancers and the HPV$^-$ cancers. As shown in the key at the bottom right, colors indicate high (red) and low (green) expression, corresponding to a +7.5 to −8.2 log 2 scale of fold change relative to each gene's average across all 84 microarrays. These genes were ordered by hierarchical clustering based on similarities in their expression changes across the samples (see, dendogram at left). Gene sets III and IV showed significantly up- or downregulated probe sets, respectively. HPV$^+$ cancer samples are indicated as red text and HPV$^-$ cancer samples are indicated as blue text on the bottom of a heat map. X axis is patient sample; Y axis is the probe sets, which are listed in order below in Table 2A. (B) Like (A), but using 291 probe sets that were significantly differentially expressed between CC and HNC. Again, X axis is patient sample; Y axis is the probe sets, which are listed in order below in Table 2B. Gene sets V and VII showed significantly upregulated probe sets in CC vs. HNC, while gene set VI showed significantly downregulated probe sets. CC samples are indicated as red text, and HNC samples are indicated as blue text on the bottom of the heat map. * indicates probe set ID that does not have annotated gene name. HPV status is shown as + and − on each sample ID.
Figure 2:
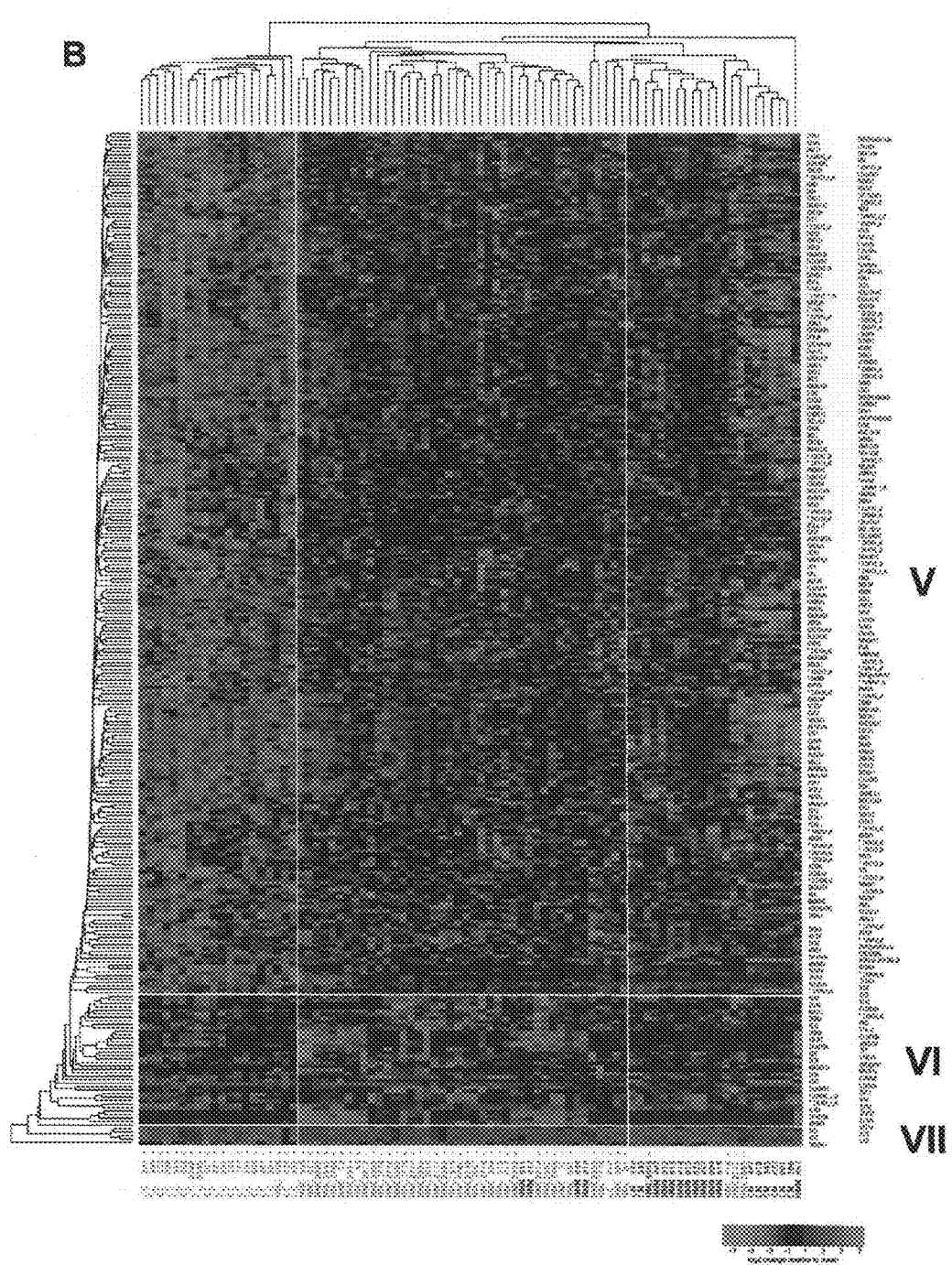

The inventors developed a parametric testing strategy (20) to evaluate the significance of apparent profile-defined tumor subgroups of the HPV$^+$HNC tumors (Supplementary FIG. S4A-C). Specifically, a multivariate normal distribution was fit to data from the 16 HPV$^+$ HNC arrays using n=100 genes most differentially expressed between HPV$^+$ cancers and HPV$^-$ cancers (FIG. 2A). The rationale was that such a unimodal Gaussian distribution represents a baseline null hypothesis of no actual subgrouping from which the significance of apparent subgroups could be gauged. Because the sample covariance matrix was rank deficient, inventors an empirical Bayes estimate of covariance (24) and repeatedly ($10^4$ times) sampled multivariate random n-vectors from a centered normal population with this covariance matrix. Using each bootstrap sample we divided the 16 tumors according to the subgrouping derived at the penultimate merge of a hierarchical cluster analysis. Each split was scored by the average of the squared t-statistics between the two subgroups, which is large if the subgroups are relatively well separated. The average squared t statistic on the subgroups identified by hierarchical clustering of the actual data was compared to the distribution of such scores derived, as above, on the null hypothesis that the profiles emerge from a single, multivariate normal, population, and a p-value was computed. To assess sensitivity, the inventors repeated the calculations at a range of gene set sizes n.

Tissue culture, quantitative reverse transcriptase-PCR, Western blot analysis and immunohistochemistry were performed as described in Supplementary Methods.

Results

Tissue samples, microarray profiling, and HPV status: Eighty four samples including 42 HNC, 14 head and neck normals (HNN), 20 CC and 8 cervical normals (CN) were cryosectioned, and selected sections were stained with hematoxylin and eosin, verified free of autolysis and freezing artifacts, and analyzed histopathologically. Relevant patient information is summarized in Table 1A and Supplementary Table S1. All tumor samples were collected prior to chemo- or radiotherapy. For all normal tissues and tumors with less than 90% cancer cells (61/84), laser microdissection was performed to capture normal epithelial or tumor cells, respectively (Supplementary FIG. S1). Complementary RNA (cRNA) was prepared and hybridized to Affymetrix U133 Plus 2.0 microarrays containing oligonucleotide probes for all known expressed human mRNAs. Normalization was performed as described in Experimental Procedures. Resulting microarray data were deposited to the NCBI Gene Expression Omnibus database under general accession number GSE6791 and sample accession numbers in Supplementary Table S1.

HPV status and genotype were determined by hybridization to custom-made 70-mer oligonucleotide microarrays containing probes for all 37 known mucosotropic HPV genotypes plus positive and negative control probes. These microarrays were sufficiently sensitive to detect HPV in cell lines harboring a few extrachromosomal copies or a single integrated copy of HPV DNA. No normal tissue showed any significant HPV signal but, consistent with prior findings (3), 16 of 42 HNCs harbored HPV (13 HPV16, two HPV33, and one HPV18; Table 1B). About half of CC were HPV16-positive, with lesser numbers carrying HPV genotypes 18, 31, 33, 35, 58 or 66 (Table 1B). Three of 20 CCs hybridized well to control cell mRNA probes but showed no detectable HPV signal. PCR with consensus HPV L1 primers MY09-MY11 (25) confirmed absence of detectable HPV DNA in these samples (Supplementary FIG. S2).

Since these samples shared some expression patterns with HPV$^+$ CC and HNCs (see, below), they may contain HPV, possibly with sequence variations inhibiting detection by these sequence-specific methods (26). However, varying the HPV status assigned to these three CCs had only minimal effects on the gene expression signature differentiating HPV$^+$ and HPV$^-$ cancers. Comparisons of HPV$^+$ and HPV$^-$ cancers with these samples included as HPV$^-$ CC, as HPV$^+$ CC, or excluded all revealed HPV-specific expression signatures dominated by a robust common core of nearly 140 genes. The analysis below reports HPV$^+$ and HPV$^-$ cancer comparisons based on the original HPV$^-$ assignment of these CCs, since this yielded the best-conserved core expression signature (137 genes), while the alternate assumptions each added some additional genes whose differential expression levels were not as well conserved across the analyses.

Gene expression relationships among HPV$^+$ and HPV$^-$ HNCs and CCs: Global pairwise comparisons of complete mRNA expression profiles between all tumor and normal sample classes were performed by multidimensional scaling (27). This analysis (FIG. 1A) measures for each pair of tumor and normal classes the distances between class-averaged log 2 expression levels over all 54,675 Affymetrix probe sets. Not surprisingly, the most closely related classes were HPV$^+$ HNC and HPV$^-$ HNC (average distance=0.17). Notably, next closest were the two HPV$^+$ cancers, HPV$^+$ HNC and HPV$^+$ CC, whose distance of 0.21 was closer than either to its corresponding normal (0.29, 0.53).

The global effect of virus-specific and tissue-specific factors is further illustrated in FIG. 1B, which compares for paired tumor classes the log 2 average expression levels, relative to corresponding normals, of all probe sets. The indicated Pearson correlation coefficients confirm that the highest correlation is between HPV$^+$ HNC and HPV$^-$ HNC (R=0.81). The substantial correlation between HPV$^+$ HNCs and HPV$^+$ CCs (R=0.58), well above HPV$^+$ CCs and HPV$^-$ HNCs (R=0.46), again implies a substantial role for virus-dependent, tissue-independent factors in gene expression changes. HPV$^+$ HNC vs. HPV$^+$ CC correlation exceeds the HPV$^-$ HNC vs. HPV$^+$ CC correlation in over 90% of bootstrap sampled data sets, and all correlations were significant by permutation analysis. Thus, both HPV status and tissue type contribute to the relatedness and distinction of HPV$^+$ HNCs, HPV$^-$ HNCs and HPV$^+$ CCs.

To offset variation in probe set-level measurements, the inventors performed similar correlation analyses on fold changes averaged over Gene Ontology (GO) gene classes rather than individual probe-sets, reinforcing the findings above (Supplementary FIG. S3A).

While HPV+ HNC and HPV− HNC exhibited generally high positive correlation in gene expression changes from normal, many genes had altered expression between these two classes. FIG. 1B highlights 47 genes selectively upregulated (red points) and 45 genes selectively downregulated (blue points) by >2.6 fold in HPV+ HNC relative to HPV− HNC (see also, Supplementary Table S3A and S3B). Notably, for genes that were highly upregulated in HPV+ HNC relative to HPV− HNC, parallel comparison of expression levels between HPV+ HNC and CC shifted their distribution in the plot dramatically rightward, revealing substantial correlated expression in these two HPV+ cancers (red arrow and points in FIG. 1B, middle panel).

Conversely, genes that were significantly downregulated in HPV+ HNC relative to HPV− HNC showed a substantial but opposite leftward shift into greater correlation in a comparison plot of expression levels between HPV+ HNC and CC (blue arrow and points in FIG. 1B, middle panel). Thus, the tumor-specific expression changes in these genes correlated much more strongly with the presence of HPV than the tissue site.

To further analyze gene expression changes based on tumor/normal, HPV+/HPV−, and HNC/CC differences, the inventors identified for each comparison differentially expressed genes with fold change >2 and t-test q-value <0.001. By these criteria, as shown in FIG. 1C, 1701 and 243 genes were up- and downregulated, respectively, in tumors relative to normals, while 124 and 13 genes were up- and downregulated in HPV+ relative to HPV− cancers, and 256 and 35 genes were up- and downregulated in CC relative to HNC.

More specifically, in tumor/normal comparisons (Supplementary FIG. S3B and Table S5), HPV+ HNC, HPV− HNC and CC all were upregulated relative to normals for a gene set I including keratins (KRT8, 17, 18), caveolin (CAV2), interferon α-inducible protein 6-16 (G1P3), matrix metallopeptidase 12 (MMP12), collagens (COL4A1, COL4A2) and phospholipid scramblase 1 (PLSCR1), and downregulated for another set II including other keratins (KRT4, 13, 15), programmed cell death 4 (PDCD4), protein tyrosine kinase 6 (PTK6), epithelial membrane protein 1 (EMP1), extracellular matrix protein 1 (ECM1), interleukin 1 receptor (IL1R2) and transglutaminase 3 (TGM3).

Relative to HPV− HNC (FIG. 2A, Table 2A), HPV+ HNC and CC showed significantly increased expression of gene set III, including PC4/SFRS1-interacting protein 1 (PSIP1), V-myb (MYB), synaptogyrin 3 (SYNGR3), SWI/SNF-related, matrix-associated, actin-dependent regulator of chromatin (SMARCA2), SYCP2, p16 (CDKN2A), lymphoid-specific helicase (HELLS) and TCAM1, while expression was decreased for gene set IV, including parathyroid hormone-like hormone (PTHLH), cortactin (CTTN), kallikreins (KLK8, 10), cyclin D1 (CCND1), caveolin 1 (CAV1) and defensin β4 (DEFB4). At the GO category level (Supplementary Table S4A), HPV+ cancers were upregulated relative to HPV− cancers for annotations related to DNA replication and cell cycle, and downregulated in genes involved in epidermal development and hormone activity.

In comparison between CC and HNC (FIG. 2B, Supplementary Table S6), CCs showed significantly upregulated expression of gene sets V and VII, including estrogen receptor 1 (ESR1), keratin 19 (KRT19), X (inactive)-specific transcript (XIST) and zinc finger protein 367 (ZNF367), while HNC showed increased expression of gene set VI (FIG. 2B, Supplementary Table S6), including dermatopontin (DPT), desmocollin 1 (DSC1), melanoma antigen A12 (MAGEA12) and chromosome Y open reading frame 15B (CY or f15B).

A distinct subgroup in HPV+ cancers: Hierarchical clustering of differentially expressed genes between HPV+ and HPV− cancers revealed two subgroups of HPV+ cancers (Supplementary FIGS. S4A and S4B). These subgroups (α and β) were not correlated with any identified sample characteristics including anatomical site, age, or clinical stage (Supplementary Table S1A) and were robustly preserved when the grouping was repeated using different agglomeration methods for clustering and varying numbers of differentially expressed genes.

The smaller subgroup, α showed high up-regulation of a set of B lymphocyte/lymphoma-related genes including baculoviral IAP repeat 3 (BIRC3), butyrophilin-like 9 (BTNL9), DKFZ P564O0823, homeobox C6 (HOXC6), and B-cell CLL/lymphoma 11A (BCL11A) (Supplementary FIG. S4C, Supplementary Table S7). B cell-related gene expression by this tumor subgroup was not due to tumor-infiltrating B cells, since there was no correlation between this subgroup and expression of CD19, CD20, and immunoglobulins, which are expressed in B cells throughout most or all circulating stages (28).

Subgroup α also was upregulated relative to other HPV+ cancers for genes expressed by endothelial cells, including vascular cell adhesion molecule 1 (VCAM1) and zinc finger protein 62 (ZNF62) and downregulated for genes, including several small proline-rich proteins (SPRR1A and SPRR2A), keratins (KRT6B and KRT16), and gap junction proteins (GJB2 and GJB6) (Supplementary FIG. S4C; Supplementary Table S7). Expression of synaptopodin (SYNPO2), an important regulator of cell migration (29), was increased >20-fold in this subgroup relative to other HPV+ cancers, suggesting potentially increased invasiveness.

Due to variations among microarray platforms and methods, reproducibility of expression profiling has been one of the biggest challenges in microarray studies of cancer (30). Chung et al. (5) recently reported dividing 60 HNCs into four subgroups by gene expression patterns. However, clustering of the inventors' samples based on the genes reported as differentially-expressed signatures of these four subgroups revealed little significant correlation. Possible causes for this lack of correlation include use of whole samples in the prior study vs. selectively microdissected samples here, differences in the microarray platforms used, or limitations in sample group sizes in these studies. Supplementary FIG. S5A shows the best association of our HNC samples into four groups based on the prior signature gene sets. Though weak, the B lymphocyte/lymphoma-related subset α identified in Supplementary FIG. S4 showed the most similarity for Chung et al.'s subgroup 2, in that most genes in Chung et al.'s set E were downregulated and, for two of the 6 relevant tumors (HNC005, HNC012), some genes in set F were upregulated, primarily including mesenchymal markers associated with poorer clinical outcomes (5, 31): syndecan, vimentin, and some collagens (Supplementary Table S8).

Figure 3:
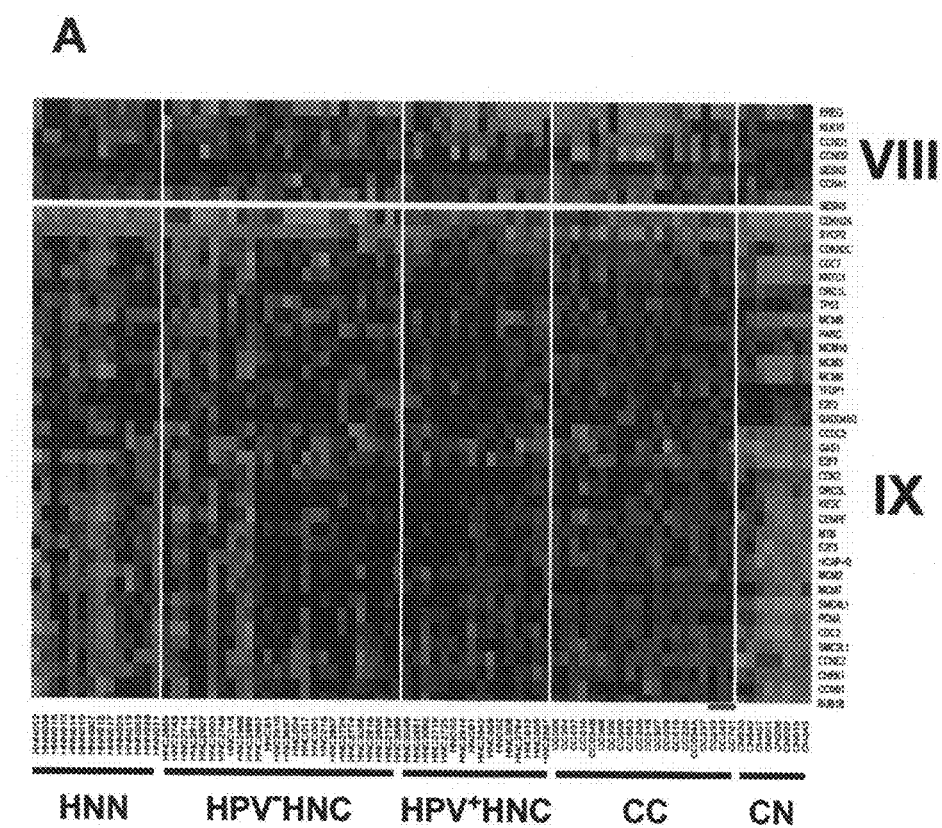
FIG. 3: Cell cycle-related genes were upregulated in HPV$^+$ cancers. X axis is patient sample; y axis is probe sets, which are listed in order below in Table 3A. Highly upregulated genes in HPV$^+$ cancers were analyzed by gene ontology grouping (A). Cell cycle-related genes were selected and plotted on a heat map. HPV$^-$ CCs are indicated with blue bars. Up- and downregulated genes were indicated in cell cycle pathway provided by the KEGG database (B). The red and blue boxes indicate upregulated genes in HPV$^+$ and HPV$^-$ cancers compared to corresponding normal tissue, respectively. A part of the cell cycle-related genes was analyzed using qRT-PCR (C). Fold changes of the gene expression in near-diploid immortalized keratinocytes (NIKS) relative to gene expression in NIKS-16 are shown. Data are represented as mean+/−standard deviation.
Figure 3:
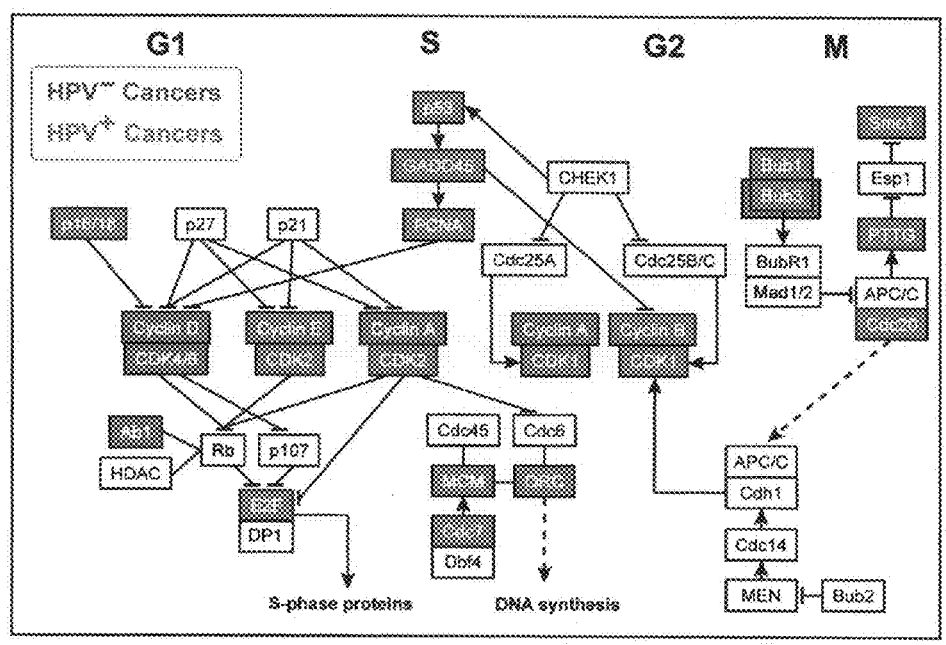
Figure 3:
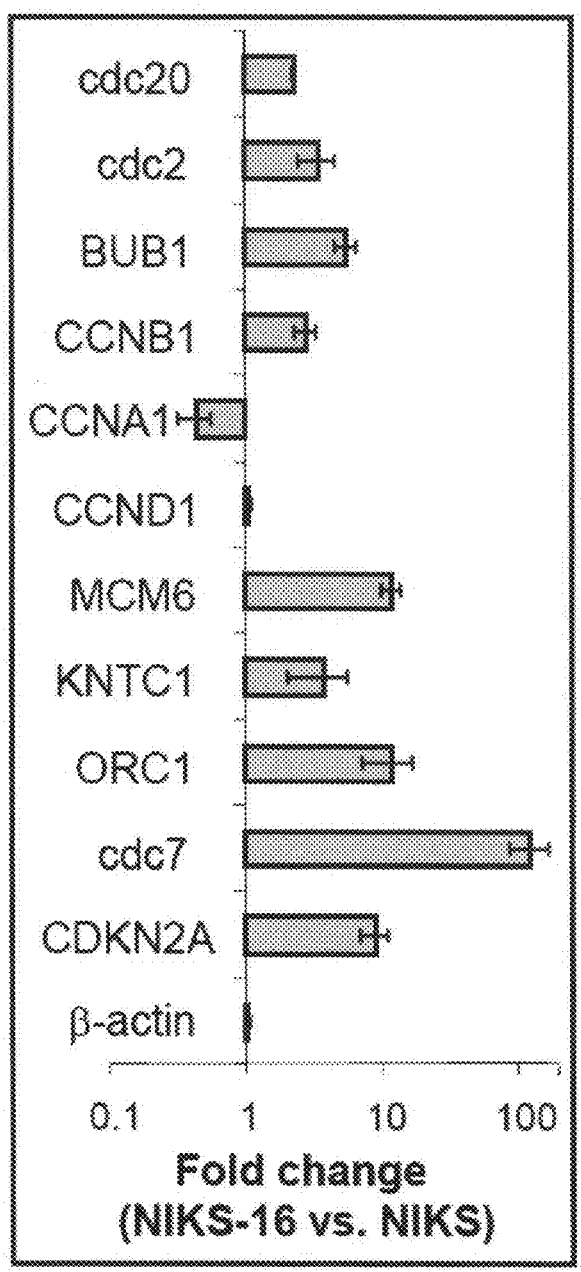

HPV+ and HPV− cancers are activated in different components of the cell cycle pathway: E7 oncoproteins of high risk HPVs induce DNA replication and mitosis by multiple mechanisms including interacting with pRb, HDACs and other factors to activate cell cycle-regulated transcription factors such as E2F (32-34). However, the extent of resulting gene expression changes, the full contributions of other HPV genes and additional genetic changes to oncogenesis, and the relation of these effects to those in HPV− HNC have not been determined. To test for differential expression in HPV+ versus HPV− cancers, we examined cell cycle-related genes based on GO classification. A significant subset of cell cycle-regulated genes was differentially expressed in HPV+ HNC and CC relative to HPV− HNC (FIG. 3A, Table 2B). As shown in FIG. 3B, HPV− HNCs upregulated, relative to HPV+ cancers, a small set of cell cycle-specific genes including cyclin D1/D2 (CCND1 and CCND2) (G1-associated) and cyclin A1 (CCNA1) (FIGS. 3A, set VIII, and 3B).

By contrast, HPV+ cancers upregulated, relative to HPV− HNC, a much larger set of cell cycle-specific genes such as cyclin E2 (CCNE2; G1-associated), cyclin B1 (CCNB1; G2-associated), and multiple MCMs (FIGS. 3A, set IX, and 3B). Among these, many genes that enhance DNA replication and cell mitosis including proliferating cell nuclear antigen (PCNA), E2Fs, cdc2, cdc7 and MCMs were significantly upregulated in HPV+ HNC and CC relative to HPV− HNC, implying that the HPV+ cancers were more active in cell division.

Figure 4:
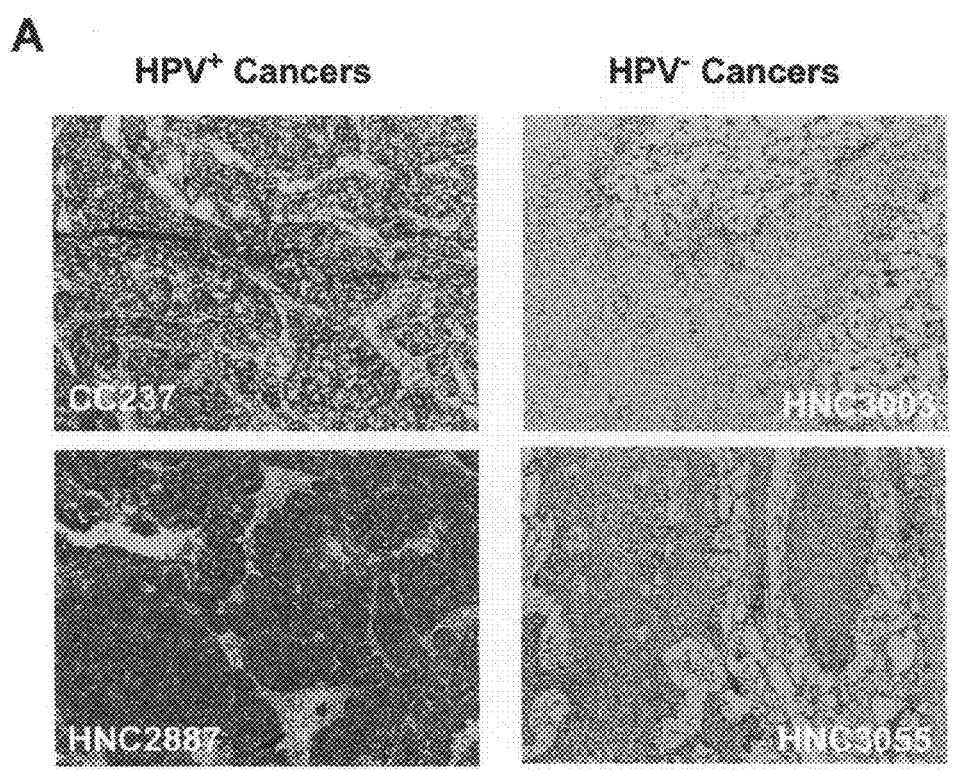
FIG. 4: Proliferating cell nuclear antigen (PCNA) protein expression was upregulated in HPV⁺ cancers. Using anti-human PCNA antibody, immunohistochemistry (IHC) was performed with sections of 11 HPV⁺ and 10 HPV⁻ cancers. IHC images were analyzed and quantified as described previously (53; see, Supplementary Methods). Representative IHC images (A) and calculated density of all samples (B) are shown. Red bars indicate the mean values of each class. Tissue was also briefly counter-stained with hematoxylin.
Figure 4:
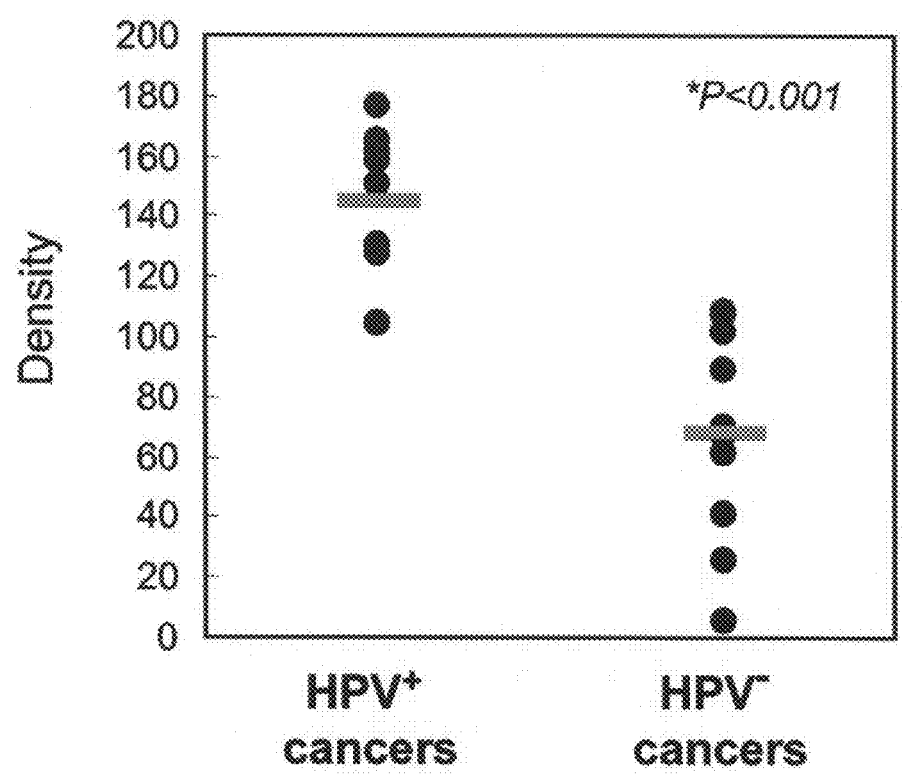

A subset of these genes were analyzed by quantitative reverse transcriptase-polymerase chain reaction (qRT-PCR) with total RNA extracted from naturally immortalized human keratinocyte lines NIKS-16 and NIKS, which have and lack an extrachromosomal HPV16 genome, respectively (35). In keeping with the microarray results, p16, cdc7, origin recognition complex 1 (ORC1), kinetochore-associated protein (KNTC1), MCM6, cyclin B1 (CCNB1), BUB1, cdc2 and cdc20 were highly upregulated by HPV16, while cyclin A1 (CCNA1) was downregulated (FIG. 3C). Since the NIKS-16 cells were only 5 to 6 passages after stable HPV16 transfection, these results indicate that HPV deregulates a subset of cell cycle-related genes soon after being acquired by cells. To eliminate possible effects of the prior spontaneous immortalization of NIKS cells, the inventors measured gene expression levels in normal (i.e., early passage) cervical epithelial cells transduced with HPV16 E6 and/or E7 oncogenes. The results confirmed NIKS data, showing an upregulation of CCNB1, cdc2, ORC1 and p16 by HPV16 E6 and E7 expression (Supplementary FIG. S6). Moreover, immunohistochemistry showed that tumor cells in HPV+ cancers expressed significantly ($p<0.001$) higher levels of PCNA protein than HPV− tumor cells (FIG. 4). In addition, PCNA protein levels were highly correlated with cell cycle-related gene expression levels (Supplementary Table S9). Together, these results indicate that HPV acts in HPV+HNCs and CCs to deregulate the cell cycle pathway in shared ways that are markedly distinct from HPV−HNCs.

Figure 5:
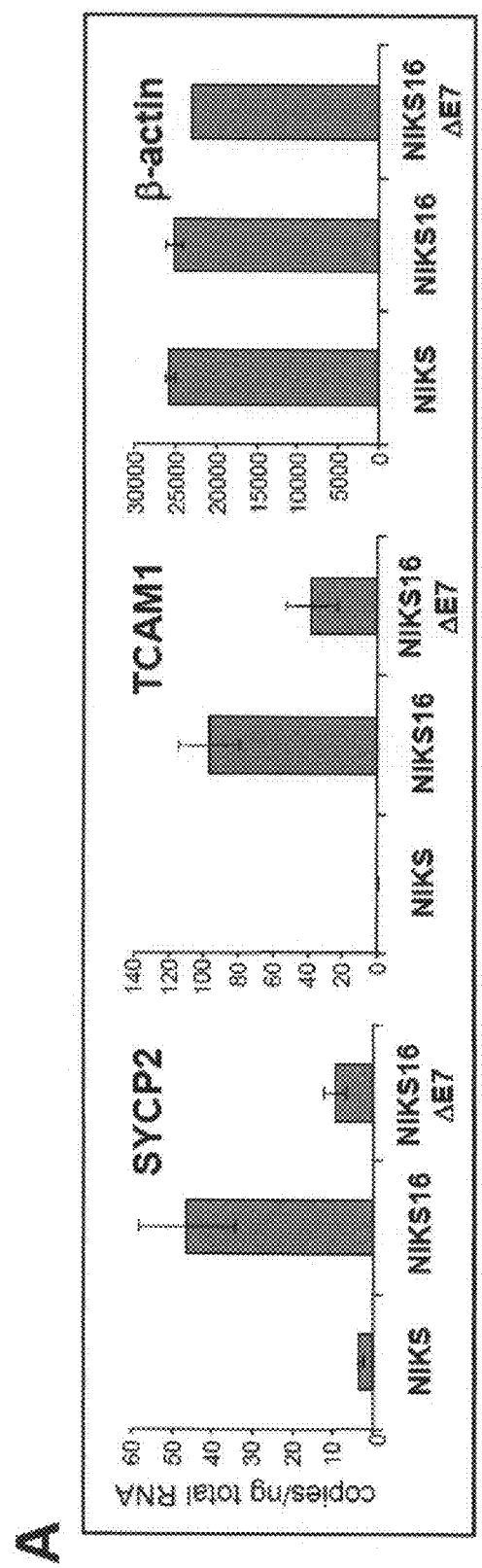
FIG. 5: Testis-specific genes SYCP2 and TCAM1 were induced by HPV16. Real time qRT-PCR was performed with total RNA extracted from NIKS cells with and without HPV16 (A). Also, total RNA from NIKS-16 cells without HPV16 E7 protein expression was used to show that testis-specific gene induction was partially by E7 protein. SYCP2 induction in HPV⁺ cell lines was confirmed with Western blot analysis using anti-human SYCP2 antibody (B). Real time qRT-PCR was performed with total RNA extracted from primary cervical keratinocytes with either or both HPV16 E6 and E7 delivered by recombinant retrovirus. Retrovirus without HPV16 gene was used as mock control (C). STAG3 mRNA expression in various cell lines was quantified using qRT-PCR, and relative fold change to NIKS cells were plotted (D). Data are represented as mean+/−standard deviation.
Figure 5:
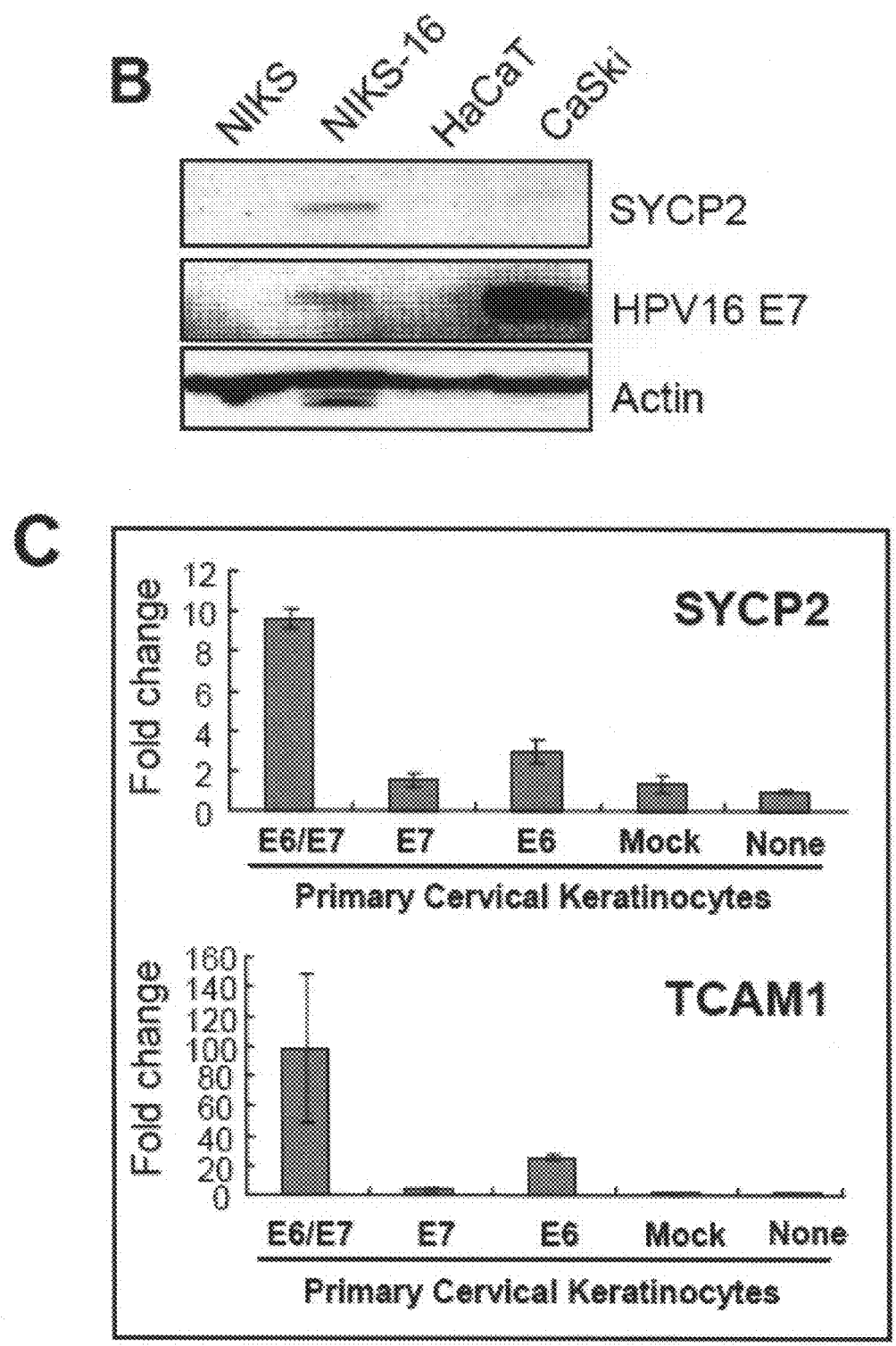
Figure 5:
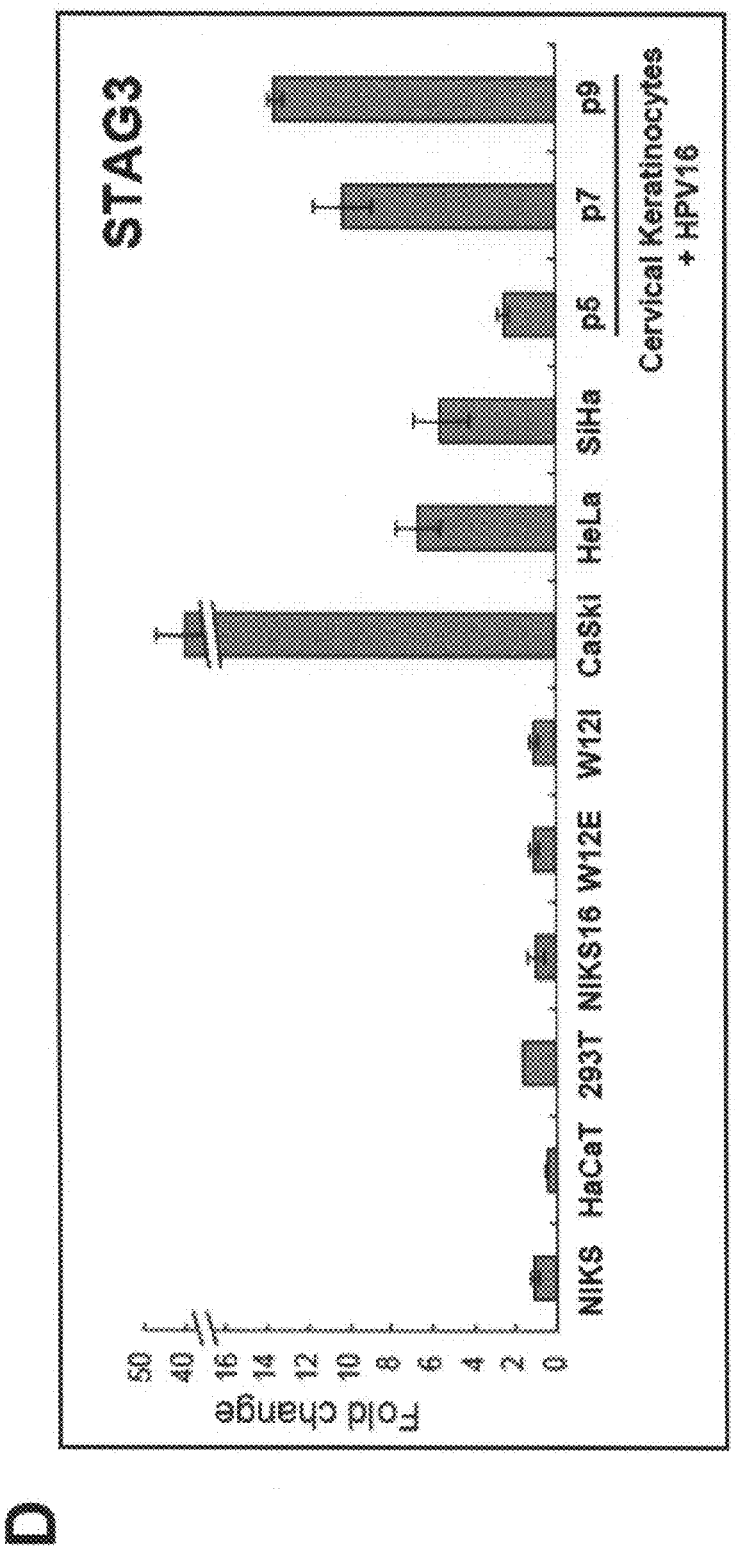

Upregulation of Novel Testis antigens in HPV+ cancers: Genes highly upregulated in HPV+ cancers relative to HPV− HNC included two testis-specific genes not normally expressed in somatic cells—SYCP2 and TCAM1 (FIG. 2A and Table 2A). qRT-PCR showed that SYCP2 and TCAM1 expression increased >15 and >100,000 fold, respectively, in HPV16+ NIKS-16 relative to HPV16− NIKS cells (FIG. 5A). SYCP2 also was detected at the protein level in NIKS-16 but not NIKS cells (FIG. 5B). Comparative studies with NIKS16ΔE7 cells (FIG. 5A) and in primary cervical keratinocytes with or without HPV16 E6 and/or E7 expression (FIG. 5C), showed that SYCP2 and TCAM1 expression are synergistically upregulated by E6 and E7.

A third testis-specific gene upregulated in HPV+ HNC and CC relative to HPV− HNC was STAG3 (Table 2A). Unlike SYCP2 and TCAM1, STAG3 mRNA was not upregulated in early passage NIKS-16 relative to NIKS cells nor in early passage HPV+ W12 cells (FIG. 5D). However, in three HPV+ cervical carcinoma cell lines (i.e., CaSki, HeLa and SiHa), STAG3 expression was increased ~6-40-fold over NIKS. Additionally, the inventors observed a passage-dependent, increased expression of STAG3 in cervical epithelial cells harboring HPV16 (cervical keratinocytes +HPV16; FIG. 5D). These data suggest that STAG3 induction was not an immediate effect of the virus, but rather a delayed response.

SYCP2 and TCAM1 were induced by HPV16 in human neonatal keratinocytes and cervical keratinocytes within a few cell passages, and this induction was dependent on E6 and E7 (FIGS. 5A and 5C). TCAM1 (52) in particular could be a useful biomarker and therapeutic target as it is expressed on the cell surface and thus is directly accessible.

Figure 6:
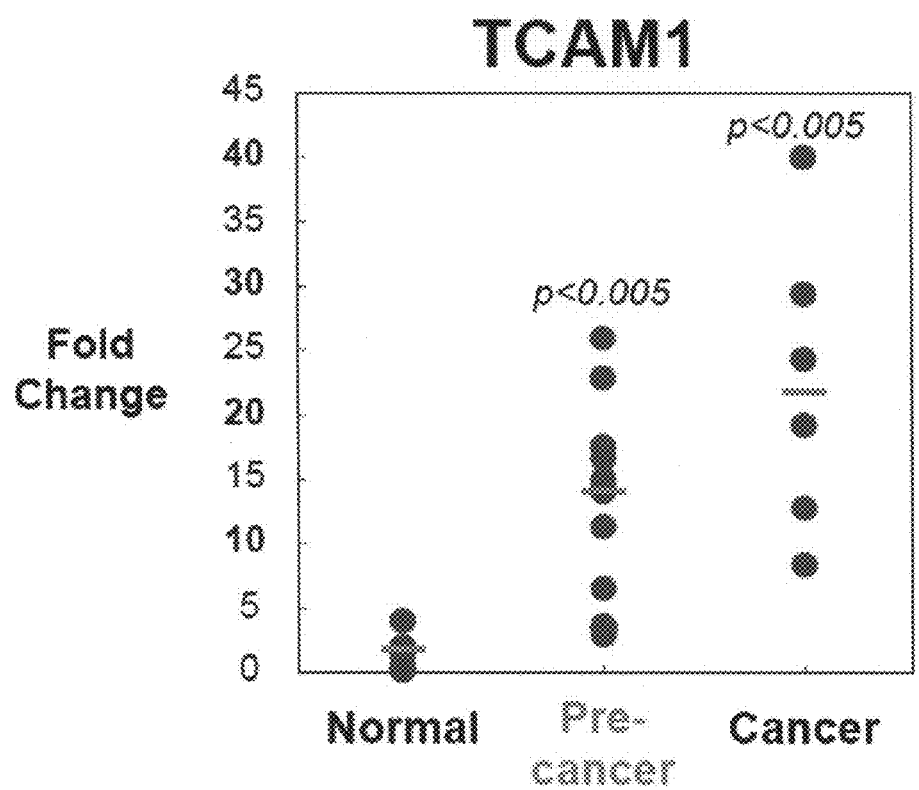
FIG. 6: TCAM1 expression was significantly induced in preneoplastic lesions of cervix (CIN).

TCAM1 expression in preneoplastic lesion of cervical cancer: TCAM1 expression in HPV+ preneoplastic lesions of cervix (CIN stages 1-3) was studied, and the inventors found that TCAM1 expression was induced significantly in preneoplastic lesions of cervix (see, pre-cancer in FIG. 6).

TABLE 1A

Patient information.

| Head and Neck Cancers | | |
|---|---|---|
| Cases and Controls | N = 54/56[A] | % |
| Case | 40 | 74.1 |
| Control | 14 | 25.9 |
| Age (mean = 59.9, ±15.2) | | |
| ≤55 years | 19 | 35.2 |
| >55 years | 35 | 64.8 |
| Gender | | |
| Female | 20 | 37.0 |
| Male | 34 | 63.0 |
| Tumor Site | | |
| Oral Cavity | 32 | 59.3 |
| Oropharynx | 22 | 40.7 |
| Normal Controls Only | N = 14 | % |
| Age (mean = 58.0, ±23.6) | | |
| ≤55 years | 6 | 42.9 |
| >55 years | 8 | 57.1 |
| Gender | | |
| Female | 9 | 64.3 |
| Male | 5 | 35.7 |
| Tumor Site | | |
| Oral Cavity | 9 | 64.3 |
| Oropharynx | 5 | 35.7 |
| Cases Only | N = 40/42[A] | % |
| Age (mean = 60.0, ±11.3) | | |
| ≤55 years | 13 | 32.5 |
| >55 years | 27 | 67.5 |
| Gender | | |
| Female | 11 | 27.5 |
| Male | 29 | 72.5 |
| Tumor Site | | |
| Oral Cavity | 23 | 57.5 |
| Oropharynx | 17 | 42.5 |
| Stage | | |
| I/II | 6 | 15.0 |
| III | 8 | 20.0 |
| IV | 10 | 25.0 |
| Unknown | 16 | 40.0 |
| Grade | | |
| Poorly/undifferentiated | 12 | 30.0 |
| Well/moderately diff'd | 28 | 70.0 |

TABLE 1A-continued

Patient information.

Cervical Cancers

| Cases and Controls | N = 28 | % |
|---|---|---|
| Case | 20 | 71.4 |
| Control | 8 | 28.5 |
| Age (mean = 43.9, ±10.4) | | |
| ≤45 years | 18 | 64.3 |
| >45 years | 10 | 35.7 |
| Normal Controls Only | N = 8 | % |
| Age (mean = 58.0, ±23.6) | | |
| ≤45 years | 3 | 37.5 |
| >45 years | 5 | 62.5 |
| Cases Only | N = 20 | % |
| Age (mean = 42.5, ±10.6) | | |
| ≤45 years | 7 | 35.0 |
| >45 years | 13 | 67.0 |
| Stage | | |
| IB | 16 | 80.0 |
| II/III | 3 | 15.0 |
| IV | 1 | 5.0 |
| Grade | | |
| Poorly/undifferentiated | 12 | 60.0 |
| Well/moderately diff'd | 8 | 40.0 |

[A]Two patients have missing data.

TABLE 1B

HPV status in tumor samples.

| | Head and Neck | | Cervix | |
|---|---|---|---|---|
| Diagnosis | Cancer | Normal | Cancer | Normal |
| Total | 42 | 14 | 20 | 8 |
| HPV negative | 26 | 14 | 3 | 8 |
| HPV positive | 16 | — | 17 | — |
| HPV16 | 13 | — | 8 | — |
| HPV18 | 1 | — | 3 | — |
| HPV31 | — | — | 1 | — |
| HPV33 | 2 | — | 1 | — |
| HPV35 | — | — | 2 | — |
| HPV58 | — | — | 1 | — |
| HPV66 | — | — | 1 | — |

TABLE 2A

Differentially expressed genes in HPV+ cancers vs. HPV− cancers.

| Probeset ID* | Gene title | Gene symbol | t-statistic | Overlaps† |
|---|---|---|---|---|
| 207039_at | cyclin-dependent kinase inhibitor 2A (melanoma, p16, inhibits CDK4) | CDKN2A | 6.73 | T/N, CC/HNC |
| 228286_at | hypothetical protein FLJ40869 | FLJ40869 | 5.45 | CC/HNC |
| 218397_at | Fanconi anemia, complementation group L | FANCL | 5.63 | CC/HNC |
| 203358_s_at | enhancer of zeste homolog 2 (*Drosophila*) | EZH2 | 6.41 | CC/HNC |
| 218783_at | DKFZP434B168 protein | DKFZP434B168 | 6.00 | CC/HNC |
| 206316_s_at | kinetochore associated 1 | KNTC1 | 6.26 | T/N, CC/HNC |
| 201555_at | MCM3 minichromosome maintenance deficient 3 (*S. cerevisiae*) | MCM3 | 5.88 | T/N, CC/HNC |
| 221677_s_at | downstream neighbor of SON | DONSON | 6.08 | T/N, CC/HNC |
| 204510_at | CDC7 cell division cycle 7 (*S. cerevisiae*) | CDC7 | 6.42 | T/N, CC/HNC |
| 227255_at | casein kinase | LOC149420 | 5.59 | CC/HNC |
| 222201_s_at | CASP8 associated protein 2 | CASP8AP2 | 5.09 | T/N, CC/HNC |
| 224428_s_at | cell division cycle associated 7 | CDCA7 | 4.36 | CC/HNC |
| 219306_at | kinesin-like 7 | KNSL7 | 5.45 | CC/HNC |
| 212621_at | KIAA0286 protein | KIAA0286 | 4.60 | T/N |
| 229551_x_at | zinc finger protein 367 | ZNF367 | 6.29 | T/N, CC/HNC |
| 222848_at | leucine zipper protein FKSG14 | FKSG14 | 4.37 | T/N, CC/HNC |
| 228401_at | — | — | 4.49 | T/N, CC/HNC |
| 225655_at | ubiquitin-like, containing PHD and RING finger domains, 1 | UHRF1 | 4.69 | T/N, CC/HNC |
| 227350_at | Helicase, lymphoid-specific | HELLS | 5.13 | T/N, CC/HNC |
| 228033_at | E2F transcription factor 7 | E2F7 | 4.36 | T/N, CC/HNC |
| 218585_s_at | RA-regulated nuclear matrix-associated protein | RAMP | 4.99 | T/N, CC/HNC |
| 209172_s_at | centromere protein F, 350/400 ka (mitosin) | CENPF | 4.51 | T/N, CC/HNC |
| 226456_at | hypothetical protein MGC24665 | MGC24665 | 6.23 | T/N |
| 202589_at | thymidylate synthetase | TYMS | 5.51 | T/N |
| 239680_at | — | — | 5.19 | CC/HNC |
| 236513_at | — | — | 4.85 | CC/HNC |
| 224320_s_at | MCM8 minichromosome maintenance deficient 8 | MCM8 | 5.73 | T/N |
| 202532_s_at | dihydrofolate reductase | DHFR | 5.24 | None |
| 210371_s_at | retinoblastoma binding protein 4 | RBBP4 | 4.73 | T/N, CC/HNC |
| 201970_s_at | nuclear autoantigenic sperm protein (histone-binding) | NASP | 6.42 | T/N, CC/HNC |
| 223542_at | ankyrin repeat domain 32 | ANKRD32 | 4.40 | T/N, CC/HNC |
| 209337_at | PC4 and SFRS1 interacting protein 1 | PSIP1 | 6.01 | CC/HNC |
| 205961_s_at | PC4 and SFRS1 interacting protein 1 | PSIP1 | 5.59 | CC/HNC |
| 206542_s_at | SWI/SNF related, matrix associated, actin-dep chromatin regulator | SMARCA2 | 4.88 | None |
| 242471_at | — | — | 4.97 | None |
| 229442_at | hypothetical protein MGC33382 | MGC33382 | 4.45 | T/N, CC/HNC |
| 203482_at | chromosome 10 open reading frame 6 | C10orf6 | 6.24 | CC/HNC |
| 201448_at | TIA1 cytotoxic granule-associated RNA binding protein | TIA1 | 5.60 | None |
| 221264_s_at | TAR DNA binding protein | TARDBP | 5.57 | None |
| 214093_s_at | Far upstream element (FUSE) binding protein 1 | FUBP1 | 4.78 | None |

TABLE 2A-continued

Differentially expressed genes in HPV+ cancers vs. HPV− cancers.

| Probeset ID* | Gene title | Gene symbol | t-statistic | Overlaps† |
|---|---|---|---|---|
| 209285_s_at | retinoblastoma-associated protein 140 | RAP140 | 5.56 | None |
| 230120_s_at | plasminogen-like | PLGL | 5.39 | None |
| 217122_s_at | solute carrier family 35, member E2 | SLC35E2 | 7.47 | None |
| 228466_at | Clone IMAGE: 111714 mRNA sequence | — | 5.59 | None |
| 212179_at | chromosome 6 open reading frame 111 | C6orf111 | 5.31 | None |
| 235919_at | — | — | 5.10 | None |
| 215731_s_at | M-phase phosphoprotein 9 | MPHOSPH9 | 4.64 | None |
| 229886_at | FLJ32363 protein | FLJ32363 | 5.87 | None |
| 228174_at | — | — | 6.44 | None |
| 212774_at | zinc finger protein 238 | ZNF238 | 4.65 | None |
| 226478_at | Transmembrane 7 superfamily member 3 | TM7SF3 | 4.64 | None |
| 42361_g_at | chromosome 6 open reading frame 18 | C6orf18 | 5.76 | CC/HNC |
| 202726_at | ligase 1, DNA, ATP-dependent | LIG1 | 6.26 | None |
| 231931_at | PR domain containing 15 | PRDM15 | 7.15 | CC/HNC |
| 230777_s_at | PR domain containing 15 | PRDM15 | 6.54 | CC/HNC |
| 229468_at | cyclin-dependent kinase 3 | CDK3 | 5.45 | None |
| 230653_at | — | — | 5.15 | None |
| 220969_s_at | — | — | 4.93 | CC/HNC |
| 241838_at | — | — | 4.90 | None |
| 235231_at | hypothetical protein LOC285989 | LOC285989 | 4.47 | None |
| 212980_at | AHA1, activator of heat shock 90 kDa protein ATPase homolog 2 | AHSA2 | 4.47 | None |
| 219676_at | zinc finger protein 435 | ZNF435 | 5.16 | None |
| 226040_at | Hypothetical protein LOC283585 | — | 4.43 | None |
| 223513_at | centromere protein J | CENPJ | 5.41 | T/N, CC/HNC |
| 228455_at | CDNA FLJ43677 fis, clone SYNOV4009295 | — | 5.28 | CC/HNC |
| 225786_at | Family with sequence similarity 36, member A | FAM36A | 4.56 | CC/HNC |
| 205345_at | BRCA1 associated RING domain 1 | BARD1 | 5.04 | CC/HNC |
| 227921_at | — | — | 4.97 | None |
| 230312_at | — | — | 4.35 | None |
| 225841_at | hypothetical protein FLJ30525 | FLJ30525 | 6.64 | T/N |
| 202743_at | phosphoinositide-3-kinase, regulatory subunit 3 (p55, gamma) | PIK3R3 | 5.96 | None |
| 209644_x_at | cyclin-dependent kinase inhibitor 2A (melanoma, p16, inhibits CDK4) | CDKN2A | 6.39 | T/N |
| 225355_at | hypothetical protein DKFZP761M1511 | DKFZP761M1511 | 5.05 | None |
| 204159_at | cyclin-dependent kinase inhibitor 2C (p18, inhibits CDK4) | CDKN2C | 5.83 | None |
| 202412_s_at | ubiquitin specific protease 1 | USP1 | 5.55 | T/N |
| 243539_at | KIAA1841 protein | KIAA1841 | 4.86 | None |
| 1554447_at | CDNA clone MGC: 32876 IMAGE: 4734912, complete cds | — | 4.53 | CC/HNC |
| 213268_at | calmodulin binding transcription activator 1 | CAMTA1 | 5.53 | None |
| 1555370_a_at | calmodulin binding transcription activator 1 | CAMTA1 | 4.80 | None |
| 229795_at | — | — | 4.27 | T/N |
| 225768_at | nuclear receptor subfamily 1, group D, member 2 | NR1D2 | 4.51 | CC/HNC |
| 221045_s_at | period homolog 3 (*Drosophila*) | PER3 | 6.43 | CC/HNC |
| 232889_at | hypothetical protein LOC153561 | LOC153561 | 4.97 | None |
| 213089_at | hypothetical protein LOC153561 | LOC153561 | 4.58 | None |
| 213605_s_at | FLJ40092 protein | FLJ40092 | 5.95 | None |
| 221973_at | Hypothetical protein LOC150759 | LOC150759 | 5.14 | T/N, CC/HNC |
| 213703_at | hypothetical protein LOC150759 | LOC150759 | 5.46 | None |
| 220325_at | TAF7-like RNA polymerase II, TATA box binding protein-assoc factor | TAF7L | 5.11 | None |
| 219255_x_at | interleukin 17 receptor B | IL17RB | 5.67 | None |
| 205531_s_at | glutaminase 2 (liver, mitochondrial) | GLS2 | 4.44 | None |
| 230011_at | similar to mouse meiosis defective 1 gene | MGC40042 | 5.34 | None |
| 219753_at | stromal antigen 3 | STAG3 | 6.09 | None |
| 233064_at | Hypothetical gene supported by AL365406; BC034005 | — | 7.85 | None |
| 1553611_s_at | hypothetical protein FLJ33790 | FLJ33790 | 5.15 | None |
| 205691_at | synaptogyrin 3 | SYNGR3 | 4.84 | T/N |
| 1558217_at | hypothetical protein FLJ31952 | FLJ31952 | 4.64 | None |
| 233320_at | testicular cell adhesion molecule 1 | TCAM1 | 7.07 | T/N, CC/HNC |
| 1556244_s_at | hypothetical protein LOC375196 | LOC375196 | 7.56 | None |
| 226344_at | Zinc finger, matrin type 1 | ZMAT1 | 5.47 | None |
| 204798_at | v-myb myeloblastosis viral oncogene homolog (avian) | MYB | 5.12 | None |
| 230469_at | pleckstrin homology domain containing, family K member 1 | PLEKHK1 | 6.22 | None |
| 241903_at | — | — | 5.20 | CC/HNC |
| 213353_at | ATP-binding cassette, sub-family A (ABC1), member 5 | ABCA5 | 4.35 | CC/HNC |
| 221103_s_at | hypothetical protein FLJ11142 | FLJ11142 | 5.67 | None |
| 241705_at | — | — | 4.63 | None |
| 218902_at | Notch homolog 1, translocation-associated (*Drosophila*) | NOTCH1 | 5.57 | None |
| 237269_at | — | — | 4.92 | CC/HNC |
| 228245_s_at | ovostatin | OVOS | 4.30 | T/N |
| 244023_at | Spleen tyrosine kinase | SYK | 4.98 | None |
| 242918_at | Nuclear autoantigenic sperm protein (histone-binding) | NASP | 4.60 | None |
| 242890_at | Helicase, lymphoid-specific | HELLS | 4.45 | T/N |
| 220940_at | KIAA1641 | KIAA1641 | 4.22 | None |
| 229666_s_at | cleavage stimulation factor, 3′ pre-RNA, subunit 3, 77 kDa | CSTF3 | 4.44 | None |
| 1559214_at | — | — | 4.52 | T/N |
| 229490_s_at | — | — | 4.32 | T/N |
| 205668_at | lymphocyte antigen 75 | LY75 | 4.26 | None |

TABLE 2A-continued

Differentially expressed genes in HPV+ cancers vs. HPV− cancers.

| Probeset ID* | Gene title | Gene symbol | t-statistic | Overlaps† |
|---|---|---|---|---|
| 228434_at | Butyrophilin-like 9 | BTNL9 | 4.87 | None |
| 228262_at | hypothetical protein FLJ14503 | FLJ14503 | 5.40 | None |
| 204069_at | Meis1, myeloid ecotropic viral integration site 1 homolog (mouse) | MEIS1 | 4.97 | T/N, CC/HNC |
| 1562921_at | E1A binding protein p300 | EP300 | 4.28 | CC/HNC |
| 208498_s_at | amylase, alpha 2A; pancreatic | AMY2A | 5.32 | None |
| 231164_at | Hypothetical gene supported by AK095200; BC042853 | — | 6.91 | T/N |
| 206546_at | synaptonemal complex protein 2 | SYCP2 | 7.49 | T/N, CC/HNC |
| 1557570_a_at | hypothetical protein LOC285084 | LOC285084 | 5.88 | T/N |
| 209792_s_at | kallikrein 10 | KLK10 | −4.32 | None |
| 206125_s_at | kallikrein 8 (neuropsin/ovasin) | KLK8 | −5.68 | CC/HNC |
| 207356_at | defensin, beta 4 | DEFB4 | −4.28 | CC/HNC |
| 226448_at | hypothetical gene supported by BC009447 | MGC15887 | −4.40 | T/N |
| 219368_at | nucleosome assembly protein 1-like 2 | NAP1L2 | −5.63 | None |
| 208712_at | cyclin D1 (PRAD1: parathyroid adenomatosis 1) | CCND1 | −4.50 | None |
| 208711_s_at | cyclin D1 (PRAD1: parathyroid adenomatosis 1) | CCND1 | −5.27 | None |
| 214073_at | cortactin | CTTN | −5.10 | None |
| 203065_s_at | caveolin 1, caveolae protein, 22 kDa | CAV1 | −4.58 | T/N |
| 210355_at | parathyroid hormone-like hormone | PTHLH | −4.45 | T/N |
| 1556773_at | Parathyroid hormone-like hormone | PTHLH | −4.43 | T/N |
| 211756_at | parathyroid hormone-like hormone | PTHLH | −4.46 | T/N |
| 230835_at | KIPV467 | UNQ467 | −4.37 | CC/HNC |

*In order as shown in FIG. 2A.
†Probe sets differentially expressed in other comparisons are indicated as T/N (tumor vs. normal) and CC/HNC (CC vs. HNC). Please see FIG. 1C.

TABLE 2B

Differentially expressed genes in cancers vs. normals.

| Probeset ID* | Gene title | Gene symbol | t-statistic |
|---|---|---|---|
| 212990_at | Synaptojanin 1 | SYNJ1 | 5.238 |
| 227375_at | Hypothetical protein DKFZp566D1346 | DKFZP566D1346 | 5.318 |
| 212061_at | U2-associated SR140 protein | SR140 | 5.115 |
| 225216_at | Chromosome X open reading frame 39 | CXorf39 | 4.849 |
| 227471_at | HECT domain and ankyrin repeat containing, E3 ubiquitin protein ligase 1 | HACE1 | 5.366 |
| 213387_at | KIAA1240 protein | KIAA1240 | 6.097 |
| 226894_at | — | — | 6.056 |
| 209187_at | Down-regulator of transcription 1, TBP-binding (negative cofactor 2) | DR1 | 5.601 |
| 233898_s_at | FGFR1 oncogene partner 2 | FGFR1OP2 | 4.697 |
| 229173_at | — | — | 5.926 |
| 225539_at | Zinc finger protein 295 | ZNF295 | 6.652 |
| 214820_at | Chromosome 21 open reading frame 107 | C21orf107 | 5.467 |
| 230427_s_at | — | — | 6.054 |
| 204727_at | WD repeat and HMG-box DNA binding protein 1 | WDHD1 | 6.172 |
| 203689_s_at | Fragile X mental retardation 1 | FMR1 | 5.614 |
| 212836_at | Polymerase (DNA-directed), delta 3, accessory subunit | POLD3 | 5.813 |
| 203347_s_at | Likely ortholog of mouse metal response element binding transcription factor 2 | M96 | 5.724 |
| 234995_at | Hypothetical protein AY099107 | LOC152185 | 6.488 |
| 202293_at | Stromal antigen 1 | STAG1 | 7.607 |
| 229027_at | — | — | 6.052 |
| 228334_x_at | KIAA1712 | KIAA1712 | 5.785 |
| 204634_at | NIMA (never in mitosis gene a)-related kinase 4 | NEK4 | 6.113 |
| 219171_s_at | Zinc finger protein 236 | ZNF236 | 4.82 |
| 234997_x_at | — | — | 4.747 |
| 226115_at | ELYS transcription factor-like protein TMBS62 | ELYS | 5.106 |
| 202294_at | — | — | 8.547 |
| 229022_at | — | — | 6.763 |
| 204835_at | Polymerase (DNA directed), alpha | POLA | 6.672 |
| 203401_at | Phosphoribosyl pyrophosphate synthetase 2 | PRPS2 | 6.139 |
| 225021_at | Zinc finger protein 532 | ZNF532 | 5.759 |
| 220617_s_at | Zinc finger protein 532 | ZNF532 | 6.463 |
| 203482_at | Chromosome 10 open reading frame 6 | C10orf6 | 6.155 |
| 226730_s_at | Ubiquitin specific protease 37 | USP37 | 6.055 |
| 218515_at | Chromosome 21 open reading frame 66 | C21orf66 | 5.504 |
| 212943_at | KIAA0528 gene product | KIAA0528 | 5.973 |
| 218397_at | Fanconi anemia, complementation group L | FANCL | 6.272 |
| 225017_at | Hypothetical protein FLJ12892 | FLJ12892 | 5.375 |
| 228286_at | Hypothetical protein FLJ40869 | FLJ40869 | 5.694 |
| 229303_at | — | — | 5.471 |
| 232362_at | Sarcoma antigen NY-SAR-41 | NY-SAR-41 | 5.009 |
| 225318_at | DDHD domain containing 2 | DDHD2 | 4.732 |
| 214306_at | Optic atrophy 1 (autosomal dominant) | OPA1 | 5.141 |
| 222629_at | REV1-like (yeast) | REV1L | 6.239 |

TABLE 2B-continued

Differentially expressed genes in cancers vs. normals.

| Probeset ID* | Gene title | Gene symbol | t-statistic |
|---|---|---|---|
| 224974_at | Likely ortholog of mouse Sds3 | SDS3 | 6.108 |
| 213140_s_at | Synovial sarcoma translocation gene on chromosome 18-like 1 | SS18L1 | 5.802 |
| 208798_x_at | Golgin-67 | GOLGIN-67 | 5.185 |
| 210425_x_at | — | — | 5.537 |
| 227199_at | Chromosome 21 open reading frame 106 | C21orf106 | 6.379 |
| 236910_at | Mitochondrial ribosomal protein L39 | MRPL39 | 6.352 |
| 228940_at | NADH dehydrogenase (ubiquinone) 1 beta subcomplex, 4, 15 kDa | NDUFB4 | 5.908 |
| 230516_at | Chromosome 7 open reading frame 30 | C7orf30 | 5.057 |
| 243332_at | — | — | 5.676 |
| 225595_at | MRNA; cDNA DKFZp566P1124 (from clone DKFZp566P1124) | — | 4.672 |
| 225594_at | MRNA; cDNA DKFZp566P1124 (from clone DKFZp566P1124) | — | 5.378 |
| 218793_s_at | Sex comb on midleg-like 1 (*Drosophila*) | SCML1 | 5.387 |
| 239577_at | — | — | 4.466 |
| 222201_s_at | CASP8 associated protein 2 | CASP8AP2 | 5.367 |
| 218979_at | Chromosome 9 open reading frame 76 | C9orf76 | 5.468 |
| 218757_s_at | UPF3 regulator of nonsense transcripts homolog B (yeast) | UPF3B | 7.293 |
| 202633_at | Topoisomerase (DNA) II binding protein 1 | TOPBP1 | 7.354 |
| 227255_at | Casein kinase | LOC149420 | 4.722 |
| 201555_at | MCM3 minichromosome maintenance deficient 3 (*S. cerevisiae*) | MCM3 | 7.992 |
| 239413_at | KIAA0912 protein | Cep152 | 7.158 |
| 206316_at | Kinetochore associated 1 | KNTC1 | 7.584 |
| 228859_at | Prematurely terminated mRNA decay factor-like | LOC91431 | 6.037 |
| 221677_s_at | Downstream neighbor of SON | DONSON | 8.188 |
| 225655_at | Ubiquitin-like, containing PHD and RING finger domains, 1 | UHRF1 | 8.055 |
| 228401_at | — | — | 7.279 |
| 219306_at | Kinesin-like 7 | KNSL7 | 6.072 |
| 235609_at | — | — | 6.233 |
| 203209_at | Replication factor C (activator 1) 5, 36.5 kDa | RFC5 | 5.279 |
| 203432_at | Thymopoietin | TMPO | 4.836 |
| 206102_at | KIAA0186 gene product | KIAA0186 | 5.766 |
| 204510_at | CDC7 cell division cycle 7 (*S. cerevisiae*) | CDC7 | 7.611 |
| 203358_s_at | Enhancer of zeste homolog 2 (*Drosophila*) | EZH2 | 6.571 |
| 218783_at | DKFZP434B168 protein | DKFZP434B168 | 5.005 |
| 224428_s_at | Cell division cycle associated 7 | CDCA7 | 4.567 |
| 214804_at | FSH primary response (LRPR1 homolog, rat) 1 | FSHPRH1 | 5.661 |
| 203744_at | High-mobility group box 3 | HMGB3 | 6.469 |
| 212060_at | U2-associated SR140 protein | SR140 | 5.261 |
| 218304_s_at | Oxysterol binding protein-like 11 | OSBPL11 | 5.936 |
| 228386_s_at | Hypothetical protein DKFZp564B1023 | DKFZP564B1023 | 5.527 |
| 215009_s_at | SEC31-like 1 (*S. cerevisiae*) | SEC31L1 | 5.184 |
| 226350_at | Choroideremia-like (Rab escort protein 2) | CHML | 6.435 |
| 1565951_s_at | Choroideremia-like (Rab escort protein 2) | CHML | 5.487 |
| 242923_at | Hypothetical protein MGC15634 | MGC15634 | 4.925 |
| 205296_at | Retinoblastoma-like 1 (p107) | RBL1 | 4.687 |
| 203276_at | Lamin B1 | LMNB1 | 5.178 |
| 238756_at | Growth arrest-specific 2 like 3 | GAS2L3 | 4.914 |
| 228577_x_at | KIAA1229 protein | KIAA1229 | 5.562 |
| 231909_x_at | KIAA1229 protein | KIAA1229 | 5.05 |
| 226164_x_at | KIAA1238 protein | KIAA1238 | 4.309 |
| 228397_at | — | — | 4.259 |
| 239680_at | — | — | 6.372 |
| 236513_at | — | — | 5.773 |
| 231931_at | PR domain containing 15 | PRDM15 | 6.115 |
| 230777_at | PR domain containing 15 | PRDM15 | 5.542 |
| 208174_x_at | U2(RNU2) small nuclear RNA auxiliary factor 1-like 2 | U2AF1L2 | 5.364 |
| 213876_x_at | U2(RNU2) small nuclear RNA auxiliary factor 1-like 2 | U2AF1L2 | 5.517 |
| 42361_g_at | Chromosome 6 open reading frame 18 | C6orf18 | 4.599 |
| 64408_s_at | Calmodulin-like 4 | CALML4 | 4.377 |
| 220969_s_at | — | — | 4.24 |
| 230209_at | Hypothetical protein MGC11349 | MGC11349 | 4.501 |
| 203262_s_at | Family with sequence similarity 50, member A | FAM50A | 6.106 |
| 213947_s_at | Nucleoporin 210 | NUP210 | 5.367 |
| 230395_at | DORA reverse strand protein 1 | DREV1 | 4.248 |
| 1562497_at | MKL/myocardin-like 2 | MKL2 | 5.24 |
| 223797_at | — | — | 4.519 |
| 244625_at | — | — | 4.668 |
| 235646_at | — | — | 5.002 |
| 242737_at | — | — | 6.262 |
| 219280_at | Chromosome 21 open reading frame 107 | C21orf107 | 7.491 |
| 222343_at | BCL2-like 11 (apoptosis facilitator) | BCL2L11 | 6.325 |
| 230534_at | Hypothetical protein MGC15634 | MGC15634 | 5.384 |
| 238699_s_at | Calcium/calmodulin-dependent serine protein kinase (MAGUK family) | CASK | 4.742 |
| 232370_at | Hypothetical protein LOC254057 | LOC254057 | 4.482 |
| 204143_s_at | rTS beta protein | HSRTSBETA | 4.634 |
| 237246_at | — | — | 4.651 |
| 215623_x_at | SMC4 structural maintenance of chromosomes 4-like 1 (yeast) | SMC4L1 | 5.25 |

TABLE 2B-continued

Differentially expressed genes in cancers vs. normals.

| Probeset ID* | Gene title | Gene symbol | t-statistic |
|---|---|---|---|
| 241954_at | — | — | 4.48 |
| 204224_s_at | GTP cyclohydrolase 1 (dopa-responsive dystonia) | GCH1 | 4.677 |
| 222603_at | KIAA1815 | KIAA1815 | 5.974 |
| 223275_at | HMT1 hnRNP methyltransferase-like 6 (S. cerevisiae) | HRMT1L6 | 4.656 |
| 228778_at | — | — | 6.636 |
| 203991_s_at | Ubiquitously transcribed tetratricopeptide repeat, X chromosome | UTX | 6.092 |
| 214678_x_at | — | — | 5.425 |
| 203992_s_at | Ubiquitously transcribed tetratricopeptide repeat, X chromosome | UTX | 6.441 |
| 204061_at | Protein kinase, X-linked | PRKX | 4.969 |
| 229305_at | MLF1 interacting protein | MLF1IP | 4.709 |
| 218883_s_at | MLF1 interacting protein | MLF1IP | 6.342 |
| 219990_at | FLJ23311 protein | FLJ23311 | 4.99 |
| 210371_s_at | Retinoblastoma binding protein 4 | RBBP4 | 6.888 |
| 218733_at | Hypothetical protein FLJ10546 | FLJ10546 | 5.501 |
| 233841_s_at | Likely ortholog of mouse Sds3 | SDS3 | 5.987 |
| 221919_at | Heterogeneous nuclear ribonucleoprotein A1 | HNRPA1 | 5.492 |
| 212515_s_at | DEAD (Asp-Glu-Ala-Asp) box polypeptide 3, X-linked | DDX3X | 4.514 |
| 220553_s_at | PRP39 pre-mRNA processing factor 39 homolog (yeast) | PRPF39 | 4.995 |
| 201970_s_at | Nuclear autoantigenic sperm protein (histone-binding) | NASP | 5.843 |
| 212200_at | KIAA0692 protein | KIAA0692 | 5.66 |
| 215017_s_at | Chromosome 1 open reading frame 39 | C1orf39 | 4.318 |
| 235142_at | Zinc finger and BTB domain containing 8 | ZBTB8 | 4.617 |
| 219157_at | Kelch-like 2, Mayven (Drosophila) | KLHL2 | 6.137 |
| 236769_at | Hypothetical protein LOC158402 | LOC158402 | 5.643 |
| 227133_at | Chromosome X open reading frame 39 | CXorf39 | 4.437 |
| 220520_s_at | Hypothetical protein FLJ20130 | FLJ20130 | 5.257 |
| 217936_at | Rho GTPase activating protein 5 | ARHGAP5 | 5.74 |
| 223167_s_at | Ubiquitin specific protease 25 | USP25 | 5.464 |
| 205281_s_at | Phosphatidylinositol glycan, class A (paroxysmal nocturnal hemoglobinuria) | PIGA | 5.451 |
| 226302_at | — | — | 4.823 |
| 213285_at | Transmembrane protein 30B | TMEM30B | 4.978 |
| 228565_at | Mixed lineage kinase 4 | KIAA1804 | 4.999 |
| 227356_at | CDNA: FLJ22198 fis, clone HRC01218 | — | 4.591 |
| 228201_at | ADP-ribosylation factor-like 2-like 1 | ARL2L1 | 4.742 |
| 228812_at | — | — | 4.625 |
| 225227_at | Homo sapiens, clone IMAGE: 5299642, mRNA | — | 4.459 |
| 232398_at | Hypothetical protein DKFZp434P055 | DKFZp434P055 | 5.822 |
| 233504_at | Chromosome 9 open reading frame 84 | C9orf84 | 5.832 |
| 1554447_at | CDNA clone MGC: 32876 IMAGE: 4734912, complete cds | — | 5.544 |
| 218966_at | Myosin VC | MYO5C | 6.466 |
| 1556105_at | Par-3 partitioning defective 3 homolog (C. elegans) | PARD3 | 7.135 |
| 235635_at | — | — | 4.637 |
| 228455_at | CDNA FLJ43677 fis, clone SYNOV4009295 | — | 5.957 |
| 225786_at | Family with sequence similarity 36. member A | FAM36A | 4.716 |
| 223513_at | Centromere protein J | CENPJ | 4.285 |
| 217894_at | Potassium channel tetramerisation domain containing 3 | KCTD3 | 6.689 |
| 204146_at | RAD51 associated protein 1 | RAD51AP1 | 4.219 |
| 203213_at | Cell division cycle 2, G1 to S and G2 to M | CDC2 | 5.255 |
| 201663_s_at | SMC4 structural maintenance of chromosomes 4-like 1 (yeast) | SMC4L1 | 4.65 |
| 201664_at | SMC4 structural maintenance of chromosomes 4-like 1 (yeast) | SMC4L1 | 6.127 |
| 225834_at | Similar to RIKEN cDNA 2700049P18 gene | MGC57827 | 7.226 |
| 228323_at | AF15q14 protein | AF15Q14 | 5.322 |
| 223381_at | Cell division cycle associated 1 | CDCA1 | 4.969 |
| 228033_at | E2F transcription factor 7 | E2F7 | 6.759 |
| 204641_at | NIMA (never in mitosis gene a)-related kinase 2 | NEK2 | 4.905 |
| 209172_s_at | Centromere protein F, 350/400ka (mitosin) | CENPF | 4.919 |
| 218585_s_at | RA-regulated nuclear matrix-associated protein | RAMP | 5.95 |
| 222680_s_at | RA-regulated nuclear matrix-associated protein | RAMP | 6.996 |
| 222740_at | ATPase family, AAA domain containing 2 | ATAD2 | 5.314 |
| 222848_at | leucine zipper protein FKSG14 | FKSG14 | 5.878 |
| 229551_x_at | Zinc finger protein 367 | ZNF367 | 8.85 |
| 227350_at | Helicase, lymphoid-specific | HELLS | 6.363 |
| 205034_at | Cyclin E2 | CCNE2 | 7.033 |
| 223542_at | Ankyrin repeat domain 32 | ANKRD32 | 7.339 |
| 216228_s_at | WD repeat and HMG-box DNA binding protein 1 | WDHD1 | 4.689 |
| 226747_at | KIAA1344 | KIAA1344 | 5.709 |
| 228597_at | Chromosome 21 open reading frame 45 | C21orf45 | 5.181 |
| 209337_at | PC4 and SFRS1 interacting protein 1 | PSIP1 | 5.364 |
| 205961_s_at | PC4 and SFRS1 interacting protein 1 | PSIP1 | 4.401 |
| 226925_at | acid phosphatase-like 2 | ACPL2 | 4.686 |
| 202983_at | SWI/SNF related, matrix associated, actin dependent regulator of chromatin, subfamily a, member 3 | SMARCA3 | 4.929 |
| 225768_at | Nuclear receptor subfamily 1, group D, member 2 | NR1D2 | 5.387 |
| 229442_at | Hypothetical protein MGC33382 | MGC33382 | 5.117 |
| 212840_at | KIAA0794 protein | KIAA0794 | 4.926 |
| 201329_s_at | v-ets erythroblastosis virus E26 oncogene homolog 2 (avian) | ETS2 | 6.218 |

TABLE 2B-continued

Differentially expressed genes in cancers vs. normals.

| Probeset ID* | Gene title | Gene symbol | t-statistic |
|---|---|---|---|
| 201328_at | v-ets erythroblastosis virus E26 oncogene homolog 2 (avian) | ETS2 | 4.879 |
| 208078_s_at | SNF1-like kinase \ | SNF1LK | 4.865 |
| 1555411_a_at | Cyclin L1 | CCNL1 | 6.615 |
| 1555827_at | Cyclin L1 | CCNL1 | 5.578 |
| 241495_at | Cyclin L1 | CCNL1 | 4.355 |
| 241903_at | — | — | 5.813 |
| 243030_at | — | — | 5.475 |
| 205345_at | BRCA1 associated RING domain 1 | BARD1 | 4.352 |
| 213353_at | ATP-binding cassette, sub-family A (ABC1), member 5 | ABCA5 | 5.381 |
| 240452_at | — | — | 4.398 |
| 230097_at | — | — | 4.269 |
| 236322_at | — | — | 4.201 |
| 242146_at | — | — | 5.106 |
| 1559156_at | Protein inhibitor of activated STAT, 1 | PIAS1 | 4.832 |
| 235926_at | — | — | 4.262 |
| 244753_at | — | — | 4.129 |
| 232058_at | Actinin, alpha 4 | ACTN4 | 4.419 |
| 203767_s_at | Steroid sulfatase (microsomal), arylsulfatase C, isozyme S | STS | 4.633 |
| 213150_at | Homeo box A10 | HOXA10 | 4.669 |
| 235292_at | LOC441069 | — | 4.149 |
| 226374_at | — | — | 4.552 |
| 204286_s_at | Phorbol-12-myristate-13-acetate-induced protein 1 | PMAIP1 | 4.648 |
| 210540_s_at | UDP-Gal:betaGlcNAc beta 1,4-galactosyltransferase, polypeptide 4 | B4GALT4 | 4.992 |
| 237269_at | — | — | 4.908 |
| 226420_at | Ecotropic viral integration site 1 | EVI1 | 5.871 |
| 218901_at | Phospholipid scramblase 4 | PLSCR4 | 6.1 |
| 235165_at | Par-6 partitioning defective 6 homolog beta (C. elegans) | PARD6B | 4.241 |
| 221045_s_at | Period homolog 3 (Drosophila) | PER3 | 4.957 |
| 221973_at | Hypothetical protein LOC150759 | LOC150759 | 4.445 |
| 238593_at | Hypothetical protein FLJ22531 | FLJ22531 | 4.248 |
| 216248_s_at | Nuclear receptor subfamily 4, group A, member 2 | NR4A2 | 4.868 |
| 204622_x_at | Nuclear receptor subfamily 4, group A, member 2 | NR4A2 | 4.882 |
| 206698_at | Kell blood group precursor (McLeod phenotype) | XK | 4.927 |
| 227492_at | — | — | 6.648 |
| 1562921_at | E1A binding protein p300 | EP300 | 4.238 |
| 235144_at | RAS and EF hand domain containing | RASEF | 6.912 |
| 1553986_at | RAS and EF hand domain containing | RASEF | 4.273 |
| 229842_at | — | — | 4.773 |
| 209692_at | Eyes absent homolog 2 (Drosophila) | EYA2 | 6.153 |
| 219313_at | Hypothetical protein DKFZp434C0328 | DKFZp434C0328 | 5.167 |
| 204069_at | Meis1, myeloid ecotropic viral integration site 1 homolog (mouse) | MEIS1 | 4.556 |
| 214464_at | CDC42 binding protein kinase alpha (DMPK-like) | CDC42BPA | 4.303 |
| 214723_x_at | KIAA1641 | KIAA1641 | 5.208 |
| 200800_s_at | Heat shock 70 kDa protein 1A /// heat shock 70 kDa protein 1B | HSPA1A /// HSPA1B | 5.342 |
| 201169_s_at | Basic helix-loop-helix domain containing, class B, 2 | BHLHB2 | 4.172 |
| 214651_s_at | Homeo box A9 | HOXA9 | 7.526 |
| 209905_at | Homeo box A9 | HOXA9 | 7.791 |
| 228904_at | — | — | 5.333 |
| 206546_at | Synaptonemal complex protein 2 | SYCP2 | 5.824 |
| 233320_at | Testicular cell adhesion molecule 1 | TCAM1 | 4.918 |
| 229400_at | Homeo box D10 | HOXD10 | 5.335 |
| 227671_at | X (inactive)-specific transcript | XIST | 5.623 |
| 231592_at | — | — | 4.565 |
| 224589_at | X (inactive)-specific transcript | XIST | 4.966 |
| 205778_at | Kallikrein 7 (chymotryptic, stratum corneum) | KLK7 | −4.171 |
| 206125_s_at | Kallikrein 8 (neuropsin/ovasin) | KLK8 | −4.858 |
| 206192_at | Corneodesmosin | CDSN | −4.747 |
| 235514_at | Hypothetical protein FLJ25084 | FLJ25084 | −4.359 |
| 223582_at | Monogenic, audiogenic seizure susceptibility 1 homolog (mouse) | MASS1 | −4.856 |
| 239352_at | — | — | −4.807 |
| 207356_at | Defensin, beta 4 | DEFB4 | −4.625 |
| 205054_at | Nebulin | NEB | −6.402 |
| 203562_at | Fasciculation and elongation protein zeta 1 (zygin I) | FEZ1 | −4.482 |
| 221898_at | Lung type-I cell membrane-associated glycoprotein | T1A-2 | −4.543 |
| 228492_at | Ubiquitin specific protease 9, Y-linked (fat facets-like, Drosophila) | USP9Y | −6.254 |
| 223646_s_at | Chromosome Y open reading frame 15B | CYorf15B | −7.48 |
| 204410_at | Eukaryotic translation initiation factor 1A, Y-linked | EIF1AY | −5.799 |
| 206700_s_at | Jumonji, AT rich interactive domain 1D (RBP2-like) | JARID1D | −8.832 |
| 223645_s_at | Chromosome Y open reading frame 15B | CYorf15B | −7.22 |
| 230760_at | Zinc finger protein, Y-linked | ZFY | −6.432 |
| 213068_at | Dermatopontin | DPT | −6.491 |
| 213909_at | Leucine rich repeat containing 15 | LRRC15 | −5.414 |
| 201893_x_at | Decorin | DCN | −4.228 |
| 223475_at | CocoaCrisp | LOC83690 | −4.253 |
| 210467_x_at | Melanoma antigen, family A, 12 | MAGEA12 | −4.686 |

TABLE 2B-continued

Differentially expressed genes in cancers vs. normals.

| Probeset ID* | Gene title | Gene symbol | t-statistic |
|---|---|---|---|
| 232523_at | MEGF10 protein | MEGF10 | −5.346 |
| 206584_at | Lymphocyte antigen 96 | LY96 | −4.524 |
| 236313_at | Cyclin-dependent kinase inhibitor 2B (p15, inhibits CDK4) | CDKN2B | 4.437 |
| 205225_at | Estrogen receptor 1 | ESR1 | 4.321 |
| 207039_at | Cyclin-dependent kinase inhibitor 2A (melanoma, p16, inhibits CDK4) | CDKN2A | 4.922 |
| 232170_at | S100 calcium binding protein A7-like 1 | S100A7L1 | −4.32 |
| 207324_s_at | Desmocollin 1 | DSC1 | −3.977 |
| 224646_x_at | — | — | −4.37 |
| 224997_x_at | H19, imprinted maternally expressed untranslated mRNA | H19 | −4.791 |
| 224348_s_at | — | — | −4.566 |
| 205403_at | Interleukin 1 receptor, type II | IL1R2 | −5.361 |
| 211372_s_at | Interleukin 1 receptor, type II | IL1R2 | −4.172 |
| 205000_at | DEAD (Asp-Glu-Ala-Asp) box polypeptide 3, Y-linked | DDX3Y | −8.052 |
| 214131_at | Chromosome Y open reading frame 15B | CYorf15B | −6.626 |
| 204409_s_at | Eukaryotic translation initiation factor 1A, Y-linked | EIF1AY | −5.951 |
| 201909_at | Ribosomal protein S4, Y-linked 1 | RPS4Y1 | −8.251 |
| 201650_at | Keratin 19 | KRT19 | 4.223 |
| 224588_at | X (inactive)-specific transcript | XIST | 9.351 |
| 224590_at | X (inactive)-specific transcript | XIST | 8.602 |
| 214218_s_at | X (inactive)-specific transcript | XIST | 9.127 |
| 221728_x_at | X (inactive)-specific transcript | XIST | 9.808 |
| 230835_at | KIPV467 | UNQ467 | −4.315 |

*In order as shown in FIG. 2B.

TABLE 3A

Cell cycle genes up- or down-regulated in HPV+ cancers vs. HPV− cancers.

| Probeset ID* | Gene title | Gene symbol | t-statistic |
|---|---|---|---|
| 205767_at | Epiregulin | EREG | −3.47 |
| 209792_s_at | Kallikrein 10 | KLK10 | −4.25 |
| 208711_s_at | Cyclin D1 | CCND1 | −5.43 |
| 208712_at | Cyclin D2 | CCND2 | −4.48 |
| 1553869_at | Sestrin 3 | SESN3 | −3.39 |
| 205899_at | Cyclin A1 | CCNA1 | −4.06 |
| 235683_at | Sestrin 3 | SESN3 | −4.05 |
| 207039_at | Cyclin-dependent kinase inhibitor 2A (melanoma, p16, inhibits CDK4) | CDKN2A | 7.09 |
| 206546_at | Synaptonemal complex protein 2 | SYCP2 | 7.36 |
| 204159_at | Cyclin-dependent kinase inhibitor 2C (p18, inhibits CDK4) | CDKN2C | 5.73 |
| 204510_at | CDC7 cell division cycle 7 | CDC7 | 6.51 |
| 206316_s_at | Kinetochore associated 1 | KNTC1 | 6.28 |
| 205085_at | Origin recognition complex, subunit 1-like | ORC1L | 4.96 |
| 201746_at | Tumor protein p53 | TP53 | 3.57 |
| 224320_s_at | MCM8 minichromosome maintenance deficient 8 | MCM8 | 5.61 |
| 213204_at | p53-associated parkin-like cytoplasmic protein | PARC | 5.90 |
| 222962_s_at | MCM10 minichromosome maintenance deficient 10 | MCM10 | 2.74 |
| 201555_at | MCM3 minichromosome maintenance deficient 3 | MCM3 | 5.95 |
| 201930_at | MCM6 minichromosome maintenance deficient 6 | MCM6 | 5.56 |
| 244550_at | Transcription factor Dp-1 | TFDP1 | 3.00 |
| 228361_at | E2F transcription factor 2 | E2F2 | 4.94 |
| 204121_at | Growth arrest and DNA-damage-inducible, gamma | GADD45G | 2.16 |
| 225297_at | Coiled-coil domain containing 5 (spindle associated) | CCDC5 | 3.42 |
| 204457_s_at | Growth arrest-specific 1 | GAS1 | 2.17 |
| 228033_at | E2F transcription factor 7 | E2F7 | 4.39 |
| 204252_at | Cyclin-dependent kinase 2 | CDK2 | 3.77 |
| 210028_s_at | Origin recognition complex, subunit 3-like (yeast) | ORC3L | 4.12 |
| 209408_at | Kinesin family member 2C | KIF2C | 5.52 |
| 209172_s_at | Centromere protein F, 350/400ka (mitosin) | CENPF | 4.55 |
| 219588_s_at | Leucine zipper protein 5 | LUZP5 | 4.86 |
| 203693_s_at | E2F transcription factor 3 | E2F3 | 4.05 |
| 218663_at | Chromosome condensation protein G | HCAP-G | 3.55 |
| 202107_s_at | MCM2 minichromosome maintenance deficient 2, mitotin | MCM2 | 4.37 |
| 208795_s_at | MCM7 minichromosome maintenance deficient 7 | MCM7 | 4.06 |
| 201664_at | SMC4 structural maintenance of chromosomes 4-like 1 | SMC4L1 | 4.44 |
| 201202_at | Proliferating cell nuclear antigen | PCNA | 5.12 |
| 203213_at | Cell division cycle 2, G1 to S and G2 to M | CDC2 | 3.27 |
| 204240_s_at | SMC2 structural maintenance of chromosomes 2-like 1 | SMC2L1 | 1.73 |
| 205034_at | Cyclin E2 | CCNE2 | 3.59 |

TABLE 3A-continued

Cell cycle genes up- or down-regulated in HPV+ cancers vs. HPV− cancers.

| Probeset ID* | Gene title | Gene symbol | t-statistic |
|---|---|---|---|
| 205393_s_at | CHK1 checkpoint homolog | CHEK1 | 1.05 |
| 214710_s_at | Cyclin B1 | CCNB1 | 1.20 |
| 203755_at | BUB1 budding uninhibited by benzimidazoles 1 homolog beta | BUB1B | 2.77 |

*In order as shown in FIG. 3A.

Example 2

Confirmation of TCAM1, SYCP2 and STAG3 Expression in Human Papillomavirus-Positive Cancers Materials and Methods The above methods were repeated in a second, but larger, group of subjects. The group consisted of 128 samples collected. 79 were HPV+ and 47 were HPV−. Additional details on the subjects are shown below in Table 3.

TABLE 4

Patient information.

| Cases and Controls | N = 128 | 100% |
|---|---|---|
| Normal Controls Only | N = 16 | 12.5% |
| Cases Only | N = 112 | 87.5% |
| Pathology | | |
| CIN1 | N = 14 | 10.9% |
| CIN2 | N = 21 | 16.4% |
| CIN3 | N = 41 | 32.0% |
| Cancer | N = 28 | 21.9% |
| Metaplasia | N = 7 | 5.5% |
| Adenocarcinoma in situ | N = 1 | 0.8% |

Results

Figure 7:
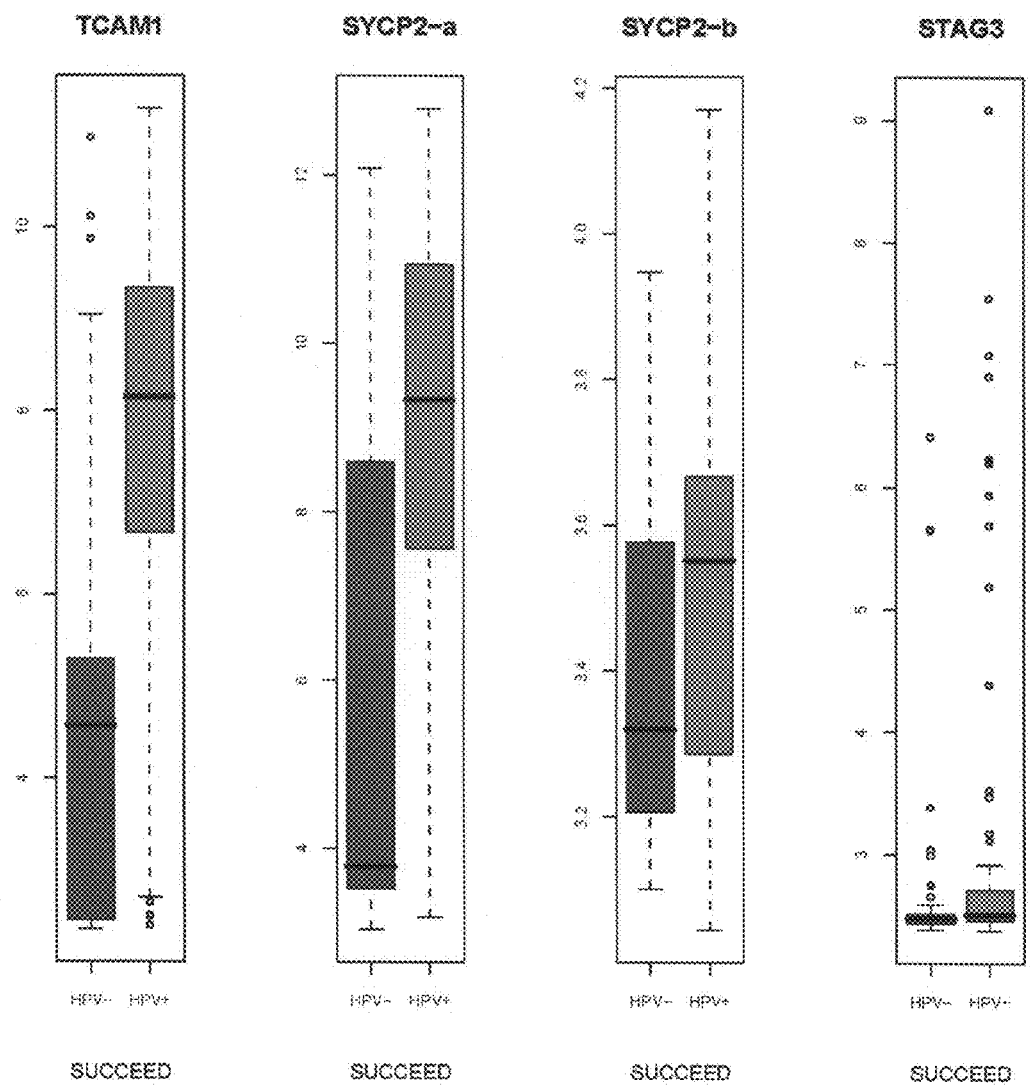
FIG. 7: TCAM1, SYCP2 and STAG2 were all significant induced in HPV+ samples compared to HPV− samples in a second, and larger, study. In the box plots, blue bars indicate HPV+; whereas red bars indicate HPV−; the bars range from 25th to 75th percentiles of each sample. Solid black lines indicate the median. The lines extending from the bars indicate the largest/smallest data point, and circles represent outliers.

As shown in FIG. 7, TCAM1, SYCP2 and STAG3 were significantly upregulated in HPV+ samples, confirming the result shown above in Example 1.

REFERENCES

1. Burd E, "Human papillomavirus and cervical cancer," Clin. Micro. Reviews 16:1-17 (2003).
2. Gillison M & Lowy D, "A causal role for human papillomavirus in head and neck cancer," Lancet 363:1488-1489 (2004).
3. Smith E, et al., "Human papillomavirus in oral exfoliated cells and risk of head and neck cancer," J. Natl. Cancer Inst. 96:449-455 (2004).
4. Hunter K, et al., "Profiling early head and neck cancer," Nat. Rev. Cancer 5:127-135 (2005).
5. Chung C, et al., "Molecular classification of head and neck squamous cell carcinomas using patterns of gene expression," Cancer Cell 5:489-500 (2004).
6. Cromer A, et al., "Identification of genes associated with tumorigenesis and metastatic potential of hypopharyngeal cancer by microarray analysis," Oncogene 23:2484-2498 (2004).
7. Ginos M, et al., "Identification of a gene expression signature associated with recurrent disease in squamous cell carcinoma of the head and neck," Cancer Res. 64:55-63 (2004).
8. Slebos R, et al., "Gene expression differences associated with human papillomavirus status in head and neck squamous cell carcinoma," Clin. Cancer Res. 12:701-709 (2006).
9. Hebner C & Laimins L, "Human papillomaviruses: basic mechanisms of pathogenesis and oncogenicity," Rev. Med. Virol. 16:83-97 (2006).
10. Geng Y, et al., "Regulation of cyclin E transcription by E2Fs and retinoblastoma protein," Oncogene 12:1173-1180 (1996).
11. Ohtani K, et al., "Cell growth-regulated expression of mammalian MCM5 and MCM6 genes mediated by the transcription factor E2F," Oncogene 18:2299-2309 (1999).
12. Thomas M, et al., "The role of the HPV E6 oncoprotein in malignant progression," Papillomavirus Research 115-131 (Campo M, ed.; Norfolk, England; Caister Academic Press; 2006).
13. McCance D, "The biology of the E7 protein of HPV-16," Papillomavirus Research 133-144 (Campo M, ed.; Norfolk, England; Caister Academic Press; 2006).
14. Riley R, et al., "Dissection of human papillomavirus E6 and E7 function in transgenic mouse models of cervical carcinogenesis," Cancer Res. 63:4862-4871 (2003).
15. Hoffmann M, et al., "Human papillomaviruses in head and neck cancer: 8 year-survival-analysis of 73 patients," Cancer Lett. 218:199-206 (2005).
16. Nielsen H, et al., "Design of oligonucleotides for microarrays and perspectives for design of multi-transcriptome arrays," Nucleic Acids Res 31:3491-3496 (2003).
17. Ihaka R & Gentleman R, "A language for data analysis and graphics," J. Comput. Graph. Stat. 5:299-314 (1996).
18. Gentleman R, et al., "Bioconductor: open software development for computational biology and bioinformatics," Genome Biol. 5:R80 (2004).
19. Irizarry R, et al., "Exploration, normalization, and summaries of high density oligonucleotide array probe level data," Biostatistics 4:249-264 (2003).
20. Efron B & Tibshirani R, "An introduction to the bootstrap," (New York; Chapman & Hall; 1993).
21. Storey J & Tibshirani R, "Statistical significance for genomewide studies," Proc. Natl. Acad. Sci. USA 100:9440-9445 (2003).
22. Sengupta S, et al., "Genome-wide expression profiling reveals EBV-associated inhibition of MHC class I expression in nasopharyngeal carcinoma," Cancer Res. 66:7999-8006 (2006).
23. Newton M, et al., "Random-set methods identify distinct aspects of the enrichment signal in gene-set analysis," Ann. Appl. Stat. 1:185-106 (2007).
24. Ledoit O & Wolf M, "A well-conditioned estimator for large-dimensional covariance matrices," J. Multivariate Analysis 88:365-411 (2004).
25. Nelson J, et al., "A novel and rapid PCR-based method for genotyping human papillomaviruses in clinical samples," J. Clin. Microbiol. 38:688-695 (2000).
26. Walboomers J & Meijer C, "Do HPV-negative cervical carcinomas exist?" J. Pathol. 181:253-254 (1997).

27. Khan J, et al., "Gene expression profiling of alveolar rhabdomyosarcoma with cDNA microarrays," Cancer Res. 58:5009-5013 (1998).
28. Clark E & Lane P, "Regulation of human B-cell activation and adhesion," Annu. Rev. Immunol. 9:97-127 (1991).
29. Asanuma K, et al., "Synaptopodin orchestrates actin organization and cell motility via regulation of RhoA signaling," Nat. Cell. Biol. 8:485-491 (2006).
30. Tinker A, et al., "The challenges of gene expression microarrays for the study of human cancer," Cancer Cell 9:333-339 (2006).
31. Chung C, et al., "Gene expression profiles identify epithelial-to-mesenchymal transition and activation of nuclear factor-{kappa} B signaling as characteristics of a high-risk head and neck squamous cell carcinoma," Cancer Res. 66:8210-8218 (2006).
32. Brake T, et al., "Comparative analysis of cervical cancer in women and in a human papillomavirus-transgenic mouse model: identification of minichromosome maintenance protein 7 as an informative biomarker for human cervical cancer," Cancer Res. 63:8173-8180 (2003).
33. Longworth M, et al., "HPV31 E7 facilitates replication by activating E2F2 transcription through its interaction with HDACs," EMBO J. 24:1821-1830 (2005).
34. Arroyo M, et al., "Association of the human papillomavirus type 16 E7 protein with the S-phase-specific E2F-cyclin A complex," Mol. Cell. Biol. 13:6537-6546 (1993).
35. Flores E, et al., "The human papillomavirus type 16 E7 oncogene is required for the productive stage of the viral life cycle," J. Virol. 74:6622-6631 (2000).
36. Asano M & Wharton R, "E2F mediates developmental and cell cycle regulation of ORC1 in *Drosophila*," EMBO J. 18:2435-2448 (1999).
37. Yamada M, et al., "A 63-base pair DNA segment containing an Sp1 site but not a canonical E2F site can confer growth-dependent and E2F-mediated transcriptional stimulation of the human ASK gene encoding the regulatory subunit for human Cdc7-related kinase," J. Biol. Chem. 277:27668-27681 (2002).
38. Thacker S, et al., "The contribution of E2F-regulated transcription to Drosophila PCNA gene function," Curr. Biol. 13:53-58 (2003).
39. Furukawa Y, et al., "The role of cellular transcription factor E2F in the regulation of cdc2 mRNA expression and cell cycle control of human hematopoietic cells," J. Biol. Chem. 269:26249-26258 (1994).
40. Skoczylas C, et al., "PP2A-dependent transactivation of the cyclin A promoter by SV40 ST is mediated by a cell cycle-regulated E2F site," Virology 332:596-601 (2005).
41. Strati K, et al., "Identification of biomarkers that distinguish HPV-positive versus HPV-negative head and neck cancers in a mouse model," Proc. Natl. Acad. Sci. USA 103:14152-14157 (2006).
42. Li W, et al., "The expression of key cell cycle markers and presence of human papillomavirus in squamous cell carcinoma of the tonsil," Head Neck 26:1-9 (2004).
43. Khleif S, et al., "Inhibition of cyclin D-CDK4/CDK6 activity is associated with an E2F-mediated induction of cyclin kinase inhibitor activity," Proc. Natl. Acad. Sci. USA 93:4350-5354 (1996).
44. Kraunz K, et al., "Dietary folate is associated with p16 (INK4A) methylation in head and neck squamous cell carcinoma," Int. J. Cancer 119:1553-1557 (2006).
45. Bartkova J, et al., "Abnormal patterns of D-type cyclin expression and G1 regulation in human head and neck cancer," Cancer Res. 55:949-956 ( ).
46. Opitz O G, Harada H, Suliman Y, et al. A mouse model of human oral-esophageal cancer. J Clin Invest 2002; 110: 761-9.
47. Simpson A J, Caballero O L, Jungbluth A, Chen Y T, Old L J. Cancer/testis antigens, gametogenesis and cancer. Nat Rev Cancer 2005; 5:615-25.
48. Offenberg H H, Schalk J A, Meuwissen R L, et al. SCP2: a major protein component of the axial elements of synaptonemal complexes of the rat. Nucleic Acids Res 1998; 26:2572-9.
49. Prieto I, Suja J A, Pezzi N, et al. Mammalian STAG3 is a cohesin specific to sister chromatid arms in meiosis I. Nat Cell Biol 2001; 3:761-6.
50. Ollinger R, Alsheimer M, Benavente R. Mammalian protein SCP1 forms synaptonemal complex-like structures in the absence of meiotic chromosomes. Mol Biol Cell 2005; 16:212-7.
51. Duensing S, Munger K. Mechanisms of genomic instability in human cancer: insights from studies with human papillomavirus oncoproteins. Int J Cancer 2004; 109:157-62.
52. Ono M, Nomoto K, Nakazato S. Gene structure of rat testicular cell adhesion molecule 1 (TCAM-1), and its physical linkage to genes coding for the growth hormone and BAF60b, a component of SWI/SNF complexes. Gene 1999; 226:95-102.
53. Zhang, D., Pier, T., McNeel, D. G., Wilding, G., and Friedl, A. Effects of a monoclonal anti-alphavbeta3 integrin antibody on blood vessels—a pharmacodynamic study. Invest New Drugs, 2007; 25:49-55.
54. Allen-Hoffmann B L, et al., "Normal growth and differentiation in a spontaneously immortalized near-diploid human keratinocyte cell line, NIKS," J. Invest. Dermatol. 114:444-455 (2000).

Although the invention has been described in connection with specific embodiments, it is understood that the invention is not limited to such specific embodiments but encompasses all such modifications and variations apparent to a skilled artisan that fall within the scope of the appended claims.

We claim:

1. A method for identifying a human as a candidate for further examination for human papillomavirus (HPV) positive cervical cancer, the method comprising the steps of:
   obtaining a tissue sample from a region of the cervix of the human;
   measuring the expression of a member selected from testicular cell adhesion molecule 1 (TCAM1), synaptonemal complex protein 2 (SYCP2), and stromal antigen 3 (STAG3) in the cells of the tissue sample; and
   comparing the expression level to a normal standard wherein a higher than normal expression indicates that the human is a candidate for further examination for cervical cancer.

2. The method of claim 1, wherein the tissue sample is a cervical smear.

3. The method of claim 1, wherein the tissue sample is a fluid collected by vaginal rinsing.

4. A method of screening for human papillomavirus (HPV) positive cervical cancer in a human comprising the steps of:
   obtaining a tissue sample from a region of the cervix of the human;
   measuring the expression of a member selected from TCAM1, SYCP2, and STAG3 in the cells of the tissue sample; and
   comparing the expression level to a normal standard wherein a higher than normal expression indicates cervical cancer.

5. The method of claim 4, wherein the tissue sample is a cervical smear.

6. The method of claim 4, wherein the tissue sample is a fluid collected by vaginal rinsing.

7. The method of claim 4, further comprising the step of observing cervical cancer in the human.

8. A method of screening for preneoplastic lesion for human papillomavirus (HPV) positive cervical cancer in a human, the method comprising the steps of:
   obtaining a tissue sample from a region of the cervix of the human;
   measuring the expression of a member selected from TCAM1 and SYCP2 in the cells of the tissue sample; and
   comparing the expression level to a normal standard wherein a higher than normal expression indicates a preneoplastic lesion in the cervix.

9. The method of claim 8, wherein the tissue sample is a cervical smear.

10. The method of claim 8, wherein the tissue sample is a fluid collected by vaginal rinsing.

11. The method of claim 8, further comprising the step of observing a preneoplastic lesion in a region of the cervix.

* * * * *

UNITED STATES PATENT AND TRADEMARK OFFICE
CERTIFICATE OF CORRECTION

PATENT NO. : 8,012,678 B2
APPLICATION NO. : 12/220465
DATED : September 6, 2011
INVENTOR(S) : Pyeon et al.

It is certified that error appears in the above-identified patent and that said Letters Patent is hereby corrected as shown below:

Column 3, line 54 "SYCP2 STAG3" should be --SYCP2 and STAG3--

Column 9, line 58 "administration" should be --administeration--

Column 10, lines 29-30 "chemotherapy radiotherapy" should be --chemotherapy and radiotherapy--

Signed and Sealed this
Twenty-eighth Day of February, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,012,678 B2 | Page 1 of 1 |
| APPLICATION NO. | : 12/220465 | |
| DATED | : September 6, 2011 | |
| INVENTOR(S) | : Pyeon et al. | |

It is certified that error appears in the above-identified patent and that said Letters Patent is hereby corrected as shown below:

Column 1, line 14 "This invention was made with United States government support awarded by the following agency: NIH CA097944 and CA022443 and CA064364. The United States has certain rights in this invention." should be --This invention was made with government support under CA097944, CA022443 and CA064364 awarded by the National Institutes of Health. The government has certain rights in the invention.--

Column 9, line 58 "administeration" should be --administration--

Signed and Sealed this
Fifteenth Day of May, 2012

David J. Kappos
*Director of the United States Patent and Trademark Office*

SEQUENCE LISTING

<160> NUMBER OF SEQ ID NOS: 27

<210> SEQ ID NO 1
<211> LENGTH: 548
<212> TYPE: PRT
<213> ORGANISM: Mus musculus

<400> SEQUENCE: 1

Met Lys Met Leu Leu Leu Gly Val Trp Thr Leu Leu Ala Leu Ile Pro

-continued

```
1               5               10              15
Cys Pro Gly Ala Ala Glu Glu Leu Phe Gln Val Ser Val His Pro Asn
                20              25              30
Glu Ala Leu Val Glu Phe Gly His Ser Leu Thr Val Asn Cys Ser Thr
                35              40              45
Thr Cys Pro Asp Pro Gly Pro Ser Gly Ile Glu Thr Phe Leu Lys Lys
    50              55              60
Thr Gln Leu Ser Lys Gly Ser Gln Trp Lys Glu Phe Leu Leu Glu Asp
65              70              75              80
Ile Thr Glu Asp Leu Val Leu Gln Cys Phe Phe Ser Cys Ala Gly Glu
                85              90              95
Gln Lys Asp Thr Val Leu Ala Ile Thr Met Tyr Gln Pro Pro Glu Gln
                100             105             110
Val Ile Leu Asp Leu Gln Pro Glu Trp Val Ala Val Asp Glu Ala Phe
                115             120             125
Thr Val Thr Cys His Val Pro Ser Val Ala Pro Leu Gln Ser Leu Thr
                130             135             140
Leu Thr Leu Leu Gln Gly Asp Gln Glu Leu His Arg Lys Asp Phe Leu
145             150             155             160
Ser Leu Ser Leu Val Ser Gln Arg Ala Glu Val Thr Ala Thr Val Arg
                165             170             175
Ala His Arg Asp Asn Asp Arg Arg Asn Phe Ser Cys Arg Ala Glu Leu
                180             185             190
Asp Leu Ser Pro His Gly Gly Gly Leu Phe His Gly Ser Ser Ala Thr
                195             200             205
Lys Gln Leu Arg Ile Phe Glu Phe Ser Gln Asn Pro Gln Ile Trp Val
                210             215             220
Pro Ser Leu Leu Glu Val Gly Lys Ala Glu Ile Val Ser Cys Glu Val
225             230             235             240
Thr Arg Val Phe Pro Ala Gln Glu Ala Val Phe Arg Met Phe Leu Glu
                245             250             255
Asp Gln Glu Leu Ser Pro Phe Ser Ser Trp Arg Glu Asp Ala Ala Trp
                260             265             270
Ala Ser Ala Thr Ile Gln Ala Met Glu Thr Gly Asp Gln Glu Leu Thr
                275             280             285
Cys Leu Val Ser Leu Gly Pro Val Glu Gln Lys Thr Arg Lys Pro Val
                290             295             300
Tyr Val Tyr Ser Phe Pro Pro Ile Leu Glu Ile Glu Asp Ala Tyr
305             310             315             320
Pro Leu Ala Gly Thr Asp Val Asn Val Thr Cys Ser Gly His Val Leu
                325             330             335
Thr Ser Pro Ser Pro Thr Leu Arg Leu Gln Gly Ser Leu Asn His Ser
                340             345             350
Ala Pro Gly Lys Pro Ala Trp Leu Leu Phe Thr Ala Arg Glu Glu Asp
                355             360             365
Asp Gly Arg Thr Leu Ser Cys Glu Ala Ser Leu Glu Val Gln Gly Gln
                370             375             380
Arg Leu Val Arg Thr Thr Glu Ser Gln Leu His Val Leu Tyr Lys Pro
385             390             395             400
Arg Phe Gln Glu Ser Arg Cys Pro Gly Asn Gln Ile Trp Val Glu Gly
                405             410             415
Met His Gln Met Leu Ala Cys Ile Pro Glu Gly Asn Pro Thr Pro Val
                420             425             430
```

```
Leu Val Cys Val Trp Asn Gly Met Ile Phe Asp Leu Asp Val Pro Gln
            435                 440                 445

Lys Ala Thr Gln Asn His Thr Gly Thr Tyr Cys Cys Thr Ala Thr Asn
        450                 455                 460

Pro Leu Gly Ser Val Ser Lys Asp Ile Thr Ile Val Gln Gly Leu
465                 470                 475                 480

Pro Glu Gly Ile Ser Ser Thr Ile Phe Ile Ile Ile Phe Thr
                485                 490                 495

Leu Gly Met Ala Val Ile Thr Val Ala Leu Tyr Leu Asn Tyr Gln Pro
                500                 505                 510

Cys Lys Gly Asn Ser Arg Lys Arg Met His Arg Pro Arg Glu Gln Ser
                515                 520                 525

Lys Gly Glu Glu Ser Gln Phe Ser Asp Ile Arg Ala Glu Gly Cys His
            530                 535                 540

Ala His Leu Cys
545

<210> SEQ ID NO 2
<211> LENGTH: 548
<212> TYPE: PRT
<213> ORGANISM: Rattus norvegicus

<400> SEQUENCE: 2

Met Lys Met Leu Leu Leu Gly Ile Trp Thr Leu Leu Ala Leu Ile Pro
1               5                   10                  15

Cys Pro Gly Thr Thr Glu Val Leu Phe Gln Val Ser Val His Pro Asn
                20                  25                  30

Gln Ala Leu Val Glu Phe Gly His Ser Leu Thr Ile Asn Cys Ser Thr
            35                  40                  45

Thr Cys Pro Asp Pro Gly Pro Ser Gly Ile Glu Thr Phe Leu Lys Lys
        50                  55                  60

Thr Gln Leu Ser Lys Gly Ser Gln Trp Lys Glu Phe Leu Leu Glu Gly
65                  70                  75                  80

Ile Thr Glu Asn Ser Val Leu Gln Cys Phe Phe Ser Cys Ala Gly Val
                85                  90                  95

Gln Lys Asp Thr Ala Leu Asp Ile Thr Met Tyr Gln Pro Pro Glu Gln
                100                 105                 110

Val Ile Leu Asp Leu Gln Pro Glu Trp Val Ala Ile Asp Glu Ala Phe
            115                 120                 125

Thr Val Lys Cys His Val Pro Ser Val Ala Pro Leu Gln Ser Leu Thr
        130                 135                 140

Leu Thr Leu Leu Gln Gly Asp Gln Glu Leu His Arg Lys Asp Phe Leu
145                 150                 155                 160

Ser Leu Ser Leu Val Ser Gln Arg Ala Glu Val Thr Val Asn Val Arg
                165                 170                 175

Ala Gln Arg Glu Asn Asp Arg His Asn Phe Ser Cys Arg Ala Glu Leu
                180                 185                 190

Asp Leu Ser Pro His Gly Gly Gly Leu Phe His Gly Ser Ser Ala Thr
            195                 200                 205

Lys Gln Leu Arg Ile Phe Glu Phe Ser Gln Asn Pro Gln Ile Leu Val
        210                 215                 220

Pro Ser Leu Leu Glu Val Gly Met Ala Glu Thr Met Ser Cys Glu Val
225                 230                 235                 240

Val Arg Val Phe Pro Ala Gln Glu Ala Val Phe Arg Met Phe Leu Glu
                245                 250                 255
```

```
Asp Gln Glu Leu Ser Pro Phe Ser Ser Trp Lys Gly Asp Ala Ala Trp
            260                 265                 270

Ala Ser Ala Thr Ile Gln Ala Met Glu Thr Gly Asp Gln Glu Leu Thr
        275                 280                 285

Cys Leu Val Ser Val Gly Pro Val Gln Lys Ala Arg Lys Pro Val
    290                 295                 300

His Val Tyr Ser Phe Pro Pro Val Leu Glu Ile Glu Asp Ala Tyr
305                 310                 315                 320

Pro Gln Ala Gly Thr Asp Val Asn Val Thr Cys Ser Gly His Val Leu
                325                 330                 335

Thr Ser Pro Ser Pro Thr Leu Arg Leu Gln Ser Gly Ser Leu Asn Leu Ser
            340                 345                 350

Ala Pro Gly Glu Pro Ala Trp Leu Arg Phe Thr Ala Arg Glu Glu Asp
        355                 360                 365

Asp Gly Arg Thr Leu Ser Cys Glu Ala Ser Leu Val Val Gln Gly Gln
    370                 375                 380

Arg Leu Val Lys Thr Thr Lys Ile Gln Leu His Val Leu Tyr Lys Pro
385                 390                 395                 400

Arg Phe Gln Glu Ser Asp Cys Pro Gly Asn Gln Ile Trp Val Glu Gly
                405                 410                 415

Met Asp Gln Met Leu Ala Cys Ile Pro Glu Gly Asn Pro Ile Pro Ala
            420                 425                 430

Leu Val Cys Ile Trp Asn Gly Met Thr Phe Asp Leu Glu Val Pro Gln
        435                 440                 445

Lys Ala Thr Gln Asn His Thr Gly Thr Tyr Ser Cys Thr Ala Thr Asn
    450                 455                 460

Ser Leu Gly Ser Val Ser Lys Asp Ile Ala Val Leu Val Gln Gly Leu
465                 470                 475                 480

His Glu Gly Ile Ser Ser Thr Ile Phe Ile Ile Ile Phe Thr
                485                 490                 495

Leu Gly Met Ala Val Ile Thr Ile Ala Leu Tyr Leu Asn Tyr Gln Pro
            500                 505                 510

Cys Lys Arg Asn Gly Arg Lys Arg Thr His Arg Gln Lys Glu Gln Asn
        515                 520                 525

Lys Gly Gly Glu Arg Gln Phe Ser Asp Ile Gln Ala Glu Glu Cys His
    530                 535                 540

Ala His Leu Cys
545

<210> SEQ ID NO 3
<211> LENGTH: 3291
<212> TYPE: DNA
<213> ORGANISM: Homo sapiens

<400> SEQUENCE: 3
ttttaataga gacggggttt catcatgttg gccaggatgg tcttgatctc ttgaccttgt     60
gatccgcccg cctcggcctc ccaaagtgct gggattacag gcgtgagcca ccgcgcctgg   120
ccgatgtggt tcatatttca ggggtcccgg aagagttgtt tgaggtttct atttggccaa   180
gtcaggccct ggtggagttt ggacagtccc tagtggtcaa ctgcagcact acttgcccag   240
acccaggacc cagtggaatt gagaccttct taaagaaaac tcaggtgggc aaagggcctc   300
agtggaaaga gtttcttctg gaggatgtca cagagaattc catcctgcag tgcttcttct   360
cttgtgcagg gattcaaaag gacacaagcc ttggcatcac tgtgtatcag ccaccagagc   420
aagtgatcct ggagctgcag cctgcctggg tggccgtgga cgaagccttc acagtgaagt   480
```

```
gtcatgtacc cagtgtagca cccttggaga gtctcaccct tgcccttctc cagggtaacc    540
aagaactgca tagaaagaac tttacgagct tggctgtggc ctcccaaaga gctgaagtca    600
tcatcagtgt cagagcccaa aaggagaatg acagatgcaa ttcttcctgc catgcagaac    660
tggacttgag tttgcaaggt gggaggctct ttcaaggcag ctcacccatc agaatagtcc    720
ggatctttga attctctcag agtccccaca tctgggtctc ttcccttttg gaggctggga    780
tggcggagac tgtgagctgc gaggtggcta gggtgtttcc agccaaagaa gttatgttcc    840
acatgttcct ggaagaccaa gagctgagct ccttcctttc tgggaggggg acacagcat     900 gggccaatgc taccattcgg accatggagg ctggtgatca ggaactgtct tgctttgcat    960
ctctgggtgc aatggaacag aagacaagaa agctagtgca tagctacaat aagtggcctg   1020
gctcttcctt tttcatacgg gttctctgct gctgaaaaca cagagtaacg ggttggtgat   1080
tcggctgtag acatccctgc tgcccttttgc tgggtatgct ctcaagtgaa catgagtctt   1140
catctttctc tggcttccct ccaccaatcc tggagctaaa agaatcatac ccattggcag   1200
ggactgacat taatgtgacc tgctcagggc atgtattaac atcacccagc cctactcttc   1260
ggcttcaggg agccccagac ctccctgctg gggagcctgc ctggcttcta cttactgcca   1320
gggaggaaga tgatggctga aatttctcct gcgaggcctc tttggtggtg cagggtcagc   1380
ggttgatgaa aaccactgtg atccagctcc atatcctatg caagccacag ttagaggaat   1440
ccagttgccc tggcaaacag acctggctgg aagggatgga acacacgctc gcctgcgtcc   1500
caaagggaaa cccagctcca gccttggtgt gtacctggaa tggggtggtc tttgaccttg   1560
aagtgccaca gaaggcaacc tagaaccaca ctggaaccta ccgctacaca gccactaacc   1620
agctgggctc tgtcagcaaa gacattgctg tcattgttca aggactggat gaaggaatca   1680
gctctaccct ctttgtcatt attaccgttg cccttggagt gggtgtcatc accatagcac   1740
tgtatttgag ctatcggccc tgcaaagtgg acaggaggaa attgctctat aggcagaaag   1800
aggaggacaa agaggaggaa agccagtttg ctgttcagga agagaaaagt acaactcata   1860
taattgacag ctatttgatt gaatgagact tctgctactg tggtttccca gggagggaag   1920
aagggataga ggagaaagga agaaacacaa tggcaggctg cattccccytt tgtgtacgtc   1980 tgtcctgtaa aacggtgttt caggccccca tgcccatgt cctgtgtgtc caatatgtcc    2040
acaagctcac ctttctctct ctgtctcttt tttttttttt gagatggagt ctcgctgttg   2100
tcgcctaggc tggagtgcaa tgatgcgatc tcggctcact gcaacttcag cttcccgggt   2160
tcaggtgatt ctcctgcctc agcctccctg gcagctggga ttacaggtgc acaccacaac   2220
tcctgtctaa ttttttgtatt tttcgtagag atggggtttc accatgttga ccaggctggt   2280
ctcaaactcc tgacctcaag tgatccgccc accttggcct cccaaaatgc tgggattaca   2340
ggtgtgagcc actgcaccca gccacctttc tctttagagc tcactctagt cattaagaat   2400
ctcagtctca atgtttgatt tgtaagaagg cctcttgctc cttgccaggt gcttcatcag   2460
tccactctta gatacaaaaa aaagatcctg ctgtttcttt atggtttcca ctgcccttt    2520 ctcttaaaca tcatactaaa gtcaggcaca tcttagaaat gcaactcata tttcatggtt   2580
ttctgattac taactgggaa ctaaatttgt agtccaggga caggactttg aagggagtaa   2640
gtatcaaata tggggctagg aatcagagct ctgttcccat ctccactttc ccttgctccc   2700
ctgacctggg cttctggagt gccagctccc agagctgagc ttgttgacat cattaaggat   2760
cagtggcaag cttcaactca gtaaccatct gttgtgggtc ttgggggagt atacagatgg   2820
taagaaattc cactttgggc cagacaagca tcctatctag cccagtgttc tgtctctgaa   2880
```

```
gtagaaggta gagttcttcc atgaaattgg cctcataggt taagagctcc aaacatctct    2940
gaattccttt tcatagagtg atcaactgtg agttcgcatt tgtcagtttt ttttttttac    3000
ccatgtgggt gtctaggtta gagttgcaat gtttactctc cctttctatc aataaggaca    3060
tattttcttc tgtctgtaag caatttcctt gaagcttcaa gaagaatcct cttgtgaaaa    3120
tgttcatatg attttatgat tctgcttcct tccctgtcct tgggaaagag tatattcacc    3180
ctcagagaag gcgtgaggaa tcaccaaacc agatcttttc tcccaaatca gtcaagaaat    3240
gttcactgga atgttgctat ggtaaaaata aaagtggttt tatgatgtcc a             3291

<210> SEQ ID NO 4
<211> LENGTH: 3291
<212> TYPE: DNA
<213> ORGANISM: Mus musculus

<400> SEQUENCE: 4
ttttaataga gacggggttt catcatgttg gccaggatgg tcttgatctc ttgaccttgt      60
gatccgcccg cctcggcctc ccaaagtgct gggattacag gcgtgagcca ccgcgcctgg     120
ccgatgtggt tcatatttca ggggtcccgg aagagttgtt tgaggtttct atttggccaa     180
gtcaggccct ggtggagttt ggacagtccc tagtggtcaa ctgcagcact acttgcccag     240
acccaggacc cagtggaatt gagaccttct taaagaaaac tcaggtgggc aaagggcctc     300
agtggaaaga gtttcttctg gaggatgtca cagagaattc catcctgcag tgcttcttct     360
cttgtgcagg gattcaaaag gacacaagcc ttggcatcac tgtgtatcag ccaccagagc     420
aagtgatcct ggagctgcag cctgcctggg tggccgtgga cgaagccttc acagtgaagt     480
gtcatgtacc cagtgtagca cccttggaga gtctcaccct tgcccttctc cagggtaacc     540
aagaactgca tagaaagaac tttacgagct tggctgtggc ctcccaaaga gctgaagtca     600
tcatcagtgt cagagcccaa aaggagaatg acagatgcaa ttcttcctgc catgcagaac     660
tggacttgag tttgcaaggt gggaggctct ttcaaggcag ctcacccatc agaatagtcc     720
ggatctttga attctctcag agtccccaca tctgggtctc ttcccttttg gaggctggga     780
tggcggagac tgtgagctgc gaggtggcta gggtgtttcc agccaaagaa gttatgttcc     840
acatgttcct ggaagaccaa gagctgagct ccttcctttc ctgggagggg acacagcat      900 gggccaatgc taccattcgg accatggagg ctggtgatca ggaactgtct tgctttgcat     960
ctctgggtgc aatggaacag aagacaagaa agctagtgca tagctacaat aagtggcctg    1020
gctcttcctt tttcatacgg gttctctgct gctgaaaaca cagagtaacg ggttggtgat    1080
tcggctgtag acatccctgc tgcccttttgc tgggtatgct ctcaagtgaa catgagtctt    1140
catctttctc tggcttccct ccaccaatcc tggagctaaa agaatcatac ccattggcag    1200
ggactgacat taatgtgacc tgctcagggc atgtattaac atcacccagc cctactcttc    1260
ggcttcaggg agccccagac ctccctgctg ggagcctgc ctggcttcta cttactgcca     1320
gggaggaaga tgatggctga aatttctcct gcgaggcctc tttggtggtg cagggtcagc    1380
ggttgatgaa aaccactgtg atccagctcc atatcctatg caagccacag ttagaggaat    1440
ccagttgccc tggcaaacag acctggctgg aagggatgga acacacgctc gcctgcgtcc    1500
caaagggaaa cccagctcca gccttggtgt gtacctggaa tggggtggtc tttgaccttg    1560
aagtgccaca gaaggcaacc tagaaccaca ctggaaccta ccgctacaca gccactaacc    1620
agctgggctc tgtcagcaaa gacattgctg tcattgttca aggactggat gaaggaatca    1680
gctctaccct ctttgtcatt attaccgttg cccttggagt gggtgtcatc accatagcac    1740
```

-continued

```
tgtatttgag ctatcggccc tgcaaagtgg acaggaggaa attgctctat aggcagaaag      1800
aggaggacaa agaggaggaa agccagtttg ctgttcagga agagaaaagt acaactcata      1860
taattgacag ctatttgatt gaatgagact tctgctactg tggtttccca gggagggaag      1920
aagggataga ggagaaagga agaaacacaa tggcaggctg cattcccctt tgtgtacgtc      1980
tgtcctgtaa aacggtgttt caggccccca tgcccatgt cctgtgtgtc caatatgtcc       2040
acaagctcac ctttctctct ctgtctcttt ttttttttt gagatggagt ctcgctgttg       2100
tcgcctaggc tggagtgcaa tgatgcgatc tcggctcact gcaacttcag cttcccgggt     2160
tcaggtgatt ctcctgcctc agcctccctg gcagctggga ttacaggtgc acaccacaac     2220
tcctgtctaa ttttttgtatt tttcgtagag atggggtttc accatgttga ccaggctggt   2280
ctcaaactcc tgacctcaag tgatccgccc accttggcct cccaaaatgc tgggattaca    2340
ggtgtgagcc actgcaccca gccacctttc tctttagagc tcactctagt cattaagaat    2400
ctcagtctca atgtttgatt tgtaagaagg cctcttgctc cttgccaggt gcttcatcag    2460
tccactctta gatacaaaaa aaagatcctg ctgtttcttt atggtttcca ctgccctttt    2520
ctcttaaaca tcatactaaa gtcaggcaca tcttagaaat gcaactcata tttcatggtt    2580
ttctgattac taactgggaa ctaaatttgt agtccaggga caggactttg aagggagtaa    2640
gtatcaaata tggggctagg aatcagagct ctgttcccat ctccactttc ccttgctccc   2700
ctgacctggg cttctggagt gccagctccc agagctgagc ttgttgacat cattaaggat   2760
cagtggcaag cttcaactca gtaaccatct gttgtgggtc ttgggggagt atacagatgg   2820
taagaaattc cactttgggc cagacaagca tcctatctag cccagtgttc tgtctctgaa   2880
gtagaaggta gagttcttcc atgaaattgg cctcataggt taagagctcc aaacatctct   2940
gaattccttt tcatagagtg atcaactgtg agttcgcatt tgtcagtttt tttttttttac 3000 ccatgtgggt gtctaggtta gagttgcaat gtttactctc ccttttcatc aataaggaca  3060
tattttcttc tgtctgtaag caatttcctt gaagcttcaa gaagaatcct cttgtgaaaa   3120
tgttcatatg attttatgat tctgcttcct tccctgtcct tgggaaagag tatattcacc   3180
ctcagagaag gcgtgaggaa tcaccaaacc agatcttttc tcccaaatca gtcaagaaat   3240
gttcactgga atgttgctat ggtaaaaata aaagtggttt tatgatgtcc a             3291
```

<210> SEQ ID NO 5
<211> LENGTH: 1647
<212> TYPE: DNA
<213> ORGANISM: Rattus norvegicus

<400> SEQUENCE: 5

```
atgaaaatgc ttctgttggg tatctggacg ctgctggcct tgatcccttg tccagggacc       60
acagaagtgc tgtttcaggt gtctgttcat ccaaatcagg ccctggtaga gttcggacac     120
tccctaacca tcaactgcag taccacttgc ccagaccccg ggcccagtgg aatcgagacc      180
ttcttaaaga aaacccagct aagcaaaggg tcccagtgga aggagttcct cctggagggc     240
atcacagaga actctgtgct gcaatgcttc ttctcttgtg cggggggtgca gaaagacaca     300 gcacttgaca tcaccatgta ccaaccacca gagcaggtga tcctggacct gcagcctgag    360
tgggtggcca ttgatgaagc cttcacagtg aagtgtcacg tgcctagtgt ggcacccctg     420
cagagcctca cccttaccct cctccagggt gaccaagaac tgcacaggaa agacttcctg    480
agtttatctt tggtgtccca aagagctgag gtcaccgtca atgtcagagc ccagcgggag   540
aacgacaggc acaatttctc ctgccgagca gaactggatc tgagcccaca cggtggggt     600
```

```
ttgtttcatg gcagctcagc caccaagcaa ctccggatct ttgaattctc tcagaatccc      660
cagatcttgg tgccttcact gctggaagtt gggatggccg agactatgag ctgtgaggtg      720
gttagggtgt tcccagccca ggaagctgtc ttccgaatgt ttctggaaga ccaggagctg      780
agcccttctc cctcctggaa aggagatgca gcatgggcca gtgctaccat tcaggccatg      840
gagaccggtg accaggagct gacctgcctt gtgtctgtgg gtcctgtgga gcagaaagca      900
agaaaaccag tgcatgtcta cagtttccct ccaccagtcc tggagataga agatgcttac      960
ccacaggcag ggacagacgt taatgtgacc tgctcaggtc acgtgctaac atcgcccagc     1020
cctactcttc ggctccaggg atccctaaac ctctctgctc ccggggagcc tgcctggctt     1080
cggtttactg ccagggagga agatgatggc cggactctct cctgtgaggc ctctttggtg     1140
gtgcagggcc agcgactggt caaaaccacc aagatccagc ttcatgtgtt atacaagcca     1200
aggtttcagg aatccgactg ccctggcaac agatatgggt agaagggat ggatcagatg     1260 cttgcctgca tcccagaggg aaaccccatc ccggctttgg tgtgtatctg aatgggatg      1320 acctttgacc ttgaggtacc tcagaaggcc acccagaacc acacaggaac ttacagctgc     1380
acagccacca actccctagg ctctgtcagc aaagacatcg ctgtccttgt ccaaggcctg     1440
catgagggaa tcagctcgtc caccatcttc atcatcatca ttttcaccct cggcatggct     1500
gtgatcacca tagcattata tctgaactac cagcccctgca aaagaaacgg taggaaacgg     1560
acgcacaggc agaaagagca gaacaaaggc ggggagagac agttctcgga tatacaagcc     1620
gaggagtgcc acgcgcacct ctgctga                                         1647

<210> SEQ ID NO 6
<211> LENGTH: 1023
<212> TYPE: PRT
<213> ORGANISM: Homo sapiens

<400> SEQUENCE: 6

Met Pro Ile Arg Pro Asp Leu Gln Gln Leu Glu Lys Cys Ile Asp Asp
1               5                   10                  15

Ala Leu Arg Lys Asn Asp Phe Lys Pro Leu Lys Thr Leu Leu Gln Ile
            20                  25                  30

Asp Ile Cys Glu Asp Val Lys Ile Lys Cys Ser Lys Gln Phe Phe His
        35                  40                  45

Lys Val Asp Asn Leu Ile Cys Arg Glu Leu Asn Lys Glu Asp Ile His
    50                  55                  60

Asn Val Ser Ala Ile Leu Val Ser Val Gly Arg Cys Gly Lys Asn Ile
65                  70                  75                  80

Ser Val Leu Gly Gln Ala Gly Leu Leu Thr Met Ile Lys Gln Gly Leu
                85                  90                  95

Ile Gln Lys Met Val Ala Trp Phe Glu Lys Ser Lys Asp Ile Ile Gln
            100                 105                 110

Ser Gln Gly Asn Ser Lys Asp Glu Ala Val Leu Asn Met Ile Glu Asp
        115                 120                 125

Leu Val Asp Leu Leu Val Ile His Asp Val Ser Asp Glu Gly Lys
    130                 135                 140

Lys Gln Val Val Glu Ser Phe Val Pro Arg Ile Cys Ser Leu Val Ile
145                 150                 155                 160

Asp Ser Arg Val Asn Ile Cys Ile Gln Gln Glu Ile Ile Lys Lys Met
                165                 170                 175

Asn Ala Met Leu Asp Lys Met Pro Gln Asp Ala Arg Lys Ile Leu Ser
            180                 185                 190
```

```
Asn Gln Glu Met Leu Ile Leu Met Ser Ser Met Gly Glu Arg Ile Leu
        195                 200                 205
Asp Ala Gly Asp Tyr Asp Leu Gln Val Gly Ile Val Glu Ala Leu Cys
        210                 215                 220
Arg Met Thr Thr Glu Lys Gln Arg Gln Glu Leu Ala His Gln Trp Phe
225                 230                 235                 240
Ser Met Asp Phe Ile Ala Lys Ala Phe Lys Arg Ile Lys Asp Ser Glu
                245                 250                 255
Phe Glu Thr Asp Cys Arg Ile Phe Leu Asn Leu Val Asn Gly Met Leu
            260                 265                 270
Gly Asp Lys Arg Arg Val Phe Thr Phe Pro Cys Leu Ser Ala Phe Leu
        275                 280                 285
Asp Lys Tyr Glu Leu Gln Ile Pro Ser Asp Glu Lys Leu Glu Glu Phe
        290                 295                 300
Trp Ile Asp Phe Asn Leu Gly Ser Gln Thr Leu Ser Phe Tyr Ile Ala
305                 310                 315                 320
Gly Asp Asn Asp Asp His Gln Trp Glu Ala Val Thr Val Pro Glu Glu
                325                 330                 335
Lys Val Gln Ile Tyr Ser Ile Glu Val Arg Glu Ser Lys Lys Leu Leu
            340                 345                 350
Thr Ile Ile Leu Lys Asn Thr Val Lys Ile Ser Lys Arg Glu Gly Lys
        355                 360                 365
Glu Leu Leu Leu Tyr Phe Asp Ala Ser Leu Glu Ile Thr Asn Val Thr
        370                 375                 380
Gln Lys Ile Phe Gly Ala Thr Lys His Arg Glu Ser Ile Arg Lys Gln
385                 390                 395                 400
Gly Ile Ser Val Ala Lys Thr Ser Leu His Ile Leu Phe Asp Ala Ser
                405                 410                 415
Gly Ser Gln Ile Leu Val Pro Glu Ser Gln Ile Ser Pro Val Gly Glu
            420                 425                 430
Glu Leu Val Ser Leu Lys Glu Lys Ser Lys Ser Pro Lys Glu Phe Ala
        435                 440                 445
Lys Pro Ser Lys Tyr Ile Lys Asn Ser Asp Lys Gly Asn Arg Asn Asn
        450                 455                 460
Ser Gln Leu Glu Lys Thr Thr Pro Ser Lys Arg Lys Met Ser Glu Ala
465                 470                 475                 480
Ser Met Ile Val Ser Gly Ala Asp Arg Tyr Thr Met Arg Ser Pro Val
                485                 490                 495
Leu Phe Ser Asn Thr Ser Ile Pro Pro Arg Arg Arg Ile Lys Pro
            500                 505                 510
Pro Leu Gln Met Thr Ser Ser Ala Glu Lys Pro Ser Val Ser Gln Thr
        515                 520                 525
Ser Glu Asn Arg Val Asp Asn Ala Ala Ser Leu Lys Ser Arg Ser Ser
        530                 535                 540
Glu Gly Arg His Arg Arg Asp Asn Ile Asp Lys His Ile Lys Thr Ala
545                 550                 555                 560
Lys Cys Val Glu Asn Thr Glu Asn Lys Asn Val Glu Phe Pro Asn Gln
                565                 570                 575
Asn Phe Ser Glu Leu Gln Asp Val Ile Pro Asp Ser Gln Ala Ala Glu
            580                 585                 590
Lys Arg Asp His Thr Ile Leu Pro Gly Val Leu Asp Asn Ile Cys Gly
        595                 600                 605
Asn Lys Ile His Ser Lys Trp Ala Cys Trp Thr Pro Val Thr Asn Ile
```

```
                610                 615                 620
Glu Leu Cys Asn Asn Gln Arg Ala Ser Thr Ser Ser Gly Asp Thr Leu
625                 630                 635                 640

Asn Gln Asp Ile Val Ile Asn Lys Lys Leu Thr Lys Gln Lys Ser Ser
                645                 650                 655

Ser Ser Ile Ser Asp His Asn Ser Glu Gly Thr Gly Lys Val Lys Tyr
            660                 665                 670

Lys Lys Glu Gln Thr Asp His Ile Lys Ile Asp Lys Ala Glu Val Glu
                675                 680                 685

Val Cys Lys Lys His Asn Gln Gln Asn His Pro Lys Tyr Ser Gly
690                 695                 700

Gln Lys Asn Thr Glu Asn Ala Lys Gln Ser Asp Trp Pro Val Glu Ser
705                 710                 715                 720

Glu Thr Thr Phe Lys Ser Val Leu Leu Asn Lys Thr Ile Glu Ser
                725                 730                 735

Leu Ile Tyr Arg Lys Lys Tyr Ile Leu Ser Lys Asp Val Asn Thr Ala
                740                 745                 750

Thr Cys Asp Lys Asn Pro Ser Ala Ser Lys Asn Val Gln Ser His Arg
            755                 760                 765

Lys Ala Glu Lys Glu Leu Thr Ser Glu Leu Asn Ser Trp Asp Ser Lys
770                 775                 780

Gln Lys Lys Met Arg Glu Lys Ser Lys Gly Lys Glu Phe Thr Asn Val
785                 790                 795                 800

Ala Glu Ser Leu Ile Ser Gln Ile Asn Lys Arg Tyr Lys Thr Lys Asp
                805                 810                 815

Asp Ile Lys Ser Thr Arg Lys Leu Lys Glu Ser Leu Ile Asn Ser Gly
                820                 825                 830

Phe Ser Asn Lys Pro Val Val Gln Leu Ser Lys Glu Lys Val Gln Lys
            835                 840                 845

Lys Ser Tyr Arg Lys Leu Lys Thr Thr Phe Val Asn Val Thr Ser Glu
850                 855                 860

Cys Pro Val Asn Asp Val Tyr Asn Phe Asn Leu Asn Gly Ala Asp Asp
865                 870                 875                 880

Pro Ile Ile Lys Leu Gly Ile Gln Glu Phe Gln Ala Thr Ala Lys Glu
                885                 890                 895

Ala Cys Ala Asp Arg Ser Ile Arg Leu Val Gly Pro Arg Asn His Asp
            900                 905                 910

Glu Leu Lys Ser Ser Val Lys Thr Lys Asp Lys Lys Ile Ile Thr Asn
                915                 920                 925

His Gln Lys Lys Asn Leu Phe Ser Asp Thr Glu Thr Glu Tyr Arg Cys
930                 935                 940

Asp Asp Ser Lys Thr Asp Ile Ser Trp Leu Arg Glu Pro Lys Ser Lys
945                 950                 955                 960

Pro Gln Leu Ile Asp Tyr Ser Arg Asn Lys Asn Val Lys Asn His Lys
                965                 970                 975

Ser Gly Lys Ser Arg Ser Ser Leu Glu Lys Gly Gln Pro Ser Ser Lys
            980                 985                 990

Met Thr Pro Ser Lys Asn Ile Thr Lys Lys Met Asp Lys Thr Ile Pro
                995                1000                1005

Glu Gly Arg Ile Arg Leu Pro Arg Lys Ala Thr Lys Thr Lys Lys
            1010                1015                1020

<210> SEQ ID NO 7
<211> LENGTH: 1500
```

```
<212> TYPE: PRT
<213> ORGANISM: Mus musculus

<400> SEQUENCE: 7

Met Pro Val Arg Pro Asp Leu Gln Gln Leu Glu Lys Cys Ile Asp Asp
1               5                   10                  15

Ala Leu Arg Lys Asn Asp Phe Lys Pro Leu Leu Ala Leu Leu Gln Ile
            20                  25                  30

Asp Ile Cys Glu Asp Val Lys Ile Lys Cys Ser Lys Gln Phe Leu Arg
        35                  40                  45

Lys Leu Asp Asp Leu Ile Cys Arg Glu Leu Asn Lys Lys Asp Ile Gln
    50                  55                  60

Thr Val Ser Ser Ile Leu Ile Ser Ile Gly Arg Cys Ser Lys Asn Ile
65                  70                  75                  80

Phe Ile Leu Gly Gln Ala Gly Leu Gln Thr Met Ile Lys Gln Gly Leu
                85                  90                  95

Val Gln Lys Met Val Ser Trp Phe Glu Asn Ser Lys Glu Ile Ile Leu
            100                 105                 110

Asn Gln Gln Gln Ser Lys Asp Glu Ala Val Met Asn Met Ile Glu Asp
        115                 120                 125

Leu Phe Asp Leu Leu Met Val Ile Tyr Asp Ile Ser Asp Glu Gly Lys
130                 135                 140

Asn Gln Val Leu Glu Ser Phe Ile Pro Gln Ile Cys Ala Leu Val Ile
145                 150                 155                 160

Asp Ser Arg Val Asn Phe Cys Ile Gln Gln Glu Ala Leu Lys Lys Met
                165                 170                 175

Asn Leu Met Leu Asp Arg Ile Pro Gln Asp Ala Asn Lys Ile Leu Ser
            180                 185                 190

Asn Gln Glu Met Leu Thr Leu Met Ser Asn Met Gly Glu Arg Ile Leu
        195                 200                 205

Asp Val Gly Asp Tyr Glu Leu Gln Val Gly Ile Val Glu Ala Leu Cys
210                 215                 220

Arg Met Thr Thr Glu Lys Arg Arg Gln Glu Leu Ala Tyr Glu Trp Phe
225                 230                 235                 240

Ser Met Asp Phe Ile Ala Asn Ala Phe Lys Glu Ile Lys Asp Cys Glu
                245                 250                 255

Phe Glu Thr Asp Cys Arg Ile Phe Leu Asn Leu Val Asn Gly Ile Leu
            260                 265                 270

Gly Asp Lys Arg Arg Val Tyr Thr Phe Pro Cys Leu Ser Ala Phe Leu
        275                 280                 285

Gly Lys Tyr Glu Leu Gln Ile Pro Ser Asp Glu Lys Leu Glu Glu Phe
290                 295                 300

Trp Ile Asp Phe Asn Leu Gly Ser His Thr Leu Ser Phe Tyr Ile Ala
305                 310                 315                 320

Gly Asp Glu Glu Asp His Gln Trp Glu Ala Val Thr Val Pro Glu Glu
                325                 330                 335

Lys Val Gln Met Tyr Asn Ile Glu Val Arg Glu Ser Lys Lys Leu Leu
            340                 345                 350

Thr Leu Thr Leu Lys Asn Ile Val Lys Ile Ser Lys Lys Glu Gly Lys
        355                 360                 365

Glu Leu Leu Phe Tyr Phe Asp Glu Ser Leu Glu Ile Thr Asn Val Thr
370                 375                 380

Lys Lys Val Phe Gly Gly Asn Lys Tyr Lys Glu Phe Thr Arg Lys Gln
385                 390                 395                 400
```

-continued

```
Gly Ile Ser Val Ala Lys Thr Ser Ile His Val Leu Phe Asp Ala Ser
                405                 410                 415

Gly Ser Gln Ile Leu Val Pro Glu Ser Gln Pro Ser Pro Val Lys Glu
            420                 425                 430

Asn Leu Ile His Leu Lys Glu Lys Ser Asp Ile Gln Lys Lys Leu Val
        435                 440                 445

Asn Pro Leu Glu Leu Gly Asn Ser Ser Ser Gln Asp Glu Ile Thr Thr
    450                 455                 460

Pro Ser Arg Lys Lys Met Ser Glu Ala Ser Met Ile Val Pro Asp Thr
465                 470                 475                 480

Asp Arg Tyr Thr Val Arg Ser Pro Ile Leu Leu Ile Asn Thr Ser Thr
                485                 490                 495

Pro Arg Arg Ser Arg Glu Pro Leu Gln Ala Ile Asn Ser Val Glu Lys
            500                 505                 510

Ala Val Ser Lys Thr Ser Glu Ser Gly Met Asp Tyr Ala Ala Ser Pro
        515                 520                 525

Lys Ser Arg Gln Ser Asp Gly Arg Lys Arg Trp Asn Asn Arg Ala Asn
    530                 535                 540

His Asn Lys Thr Thr Ala Val Ile Gln Asn Lys Gln Tyr Glu Asp Asn
545                 550                 555                 560

Glu Ser Pro Asp Gln Asn Phe Asn Glu Ile Glu Asp Thr Leu Ser Asn
                565                 570                 575

Val Ser Ser Ala Val Gly Lys Val Asp Lys Pro Val Leu Pro Gly Val
            580                 585                 590

Leu Asp Ile Ser Lys Asn Thr Thr His Ser Arg Trp Ala Cys Trp Thr
        595                 600                 605

Pro Val Thr Thr Ile Lys Leu Cys Asn Asn Gln Arg Ser Arg Ala Leu
    610                 615                 620

Pro Gly Asp Thr Cys Thr Gln Asp Thr Gly Val Asn Lys Lys Cys Thr
625                 630                 635                 640

Lys Gln Lys Ser Val Ser Asp Asp Ser Glu Glu Thr Gln Lys Gly
                645                 650                 655

Lys Tyr Ser Lys Asp Val Ile Lys Cys Asn Lys Ser Asp Glu Ala Glu
                660                 665                 670

Phe Cys Glu Arg Asn Ile Gln Glu Gln Asn His Pro Lys Tyr Ser Gln
            675                 680                 685

Lys Lys Asn Thr Ala Asn Ala Lys Lys Ser Asp Trp His Ile Glu Ser
        690                 695                 700

Glu Thr Thr Tyr Lys Ser Val Leu Leu Asn Lys Thr Thr Glu Glu Ser
705                 710                 715                 720

Leu Ile Tyr Lys Lys Thr Cys Val Leu Ser Lys Asp Val Asn Thr Thr
                725                 730                 735

Ile Cys Asp Lys Ser Pro Ser Arg Lys Ser Lys Arg Asn His Thr Lys
            740                 745                 750

Ser Arg Lys Glu Leu Met Ser Glu Leu Thr Ser Cys Glu Leu Glu Glu
        755                 760                 765

Ile Pro Val Arg Glu Asn Ser Lys Gly Lys Arg Phe Thr Gly Ala Ser
    770                 775                 780

Glu Ser Leu Ile Asn Gln Ile Ser Arg Arg Tyr Asn Pro Ser Asp Ser
785                 790                 795                 800

Met Met Ser Thr Arg Lys Leu Lys Glu Pro Gln Asp Gly Ser Gly Phe
                805                 810                 815

Ser Lys Lys Pro Asp Leu Gln Phe Asn Lys Val Gln Arg Lys Ser Tyr
            820                 825                 830
```

-continued

```
Arg Lys Leu Lys Ala Thr Val Val Asn Val Thr Ser Glu Cys Pro Leu
            835                 840                 845

Asp Asp Val Tyr Asn Phe Ser Leu Asn Gly Ala Asp Glu Pro Val Ile
850                 855                 860

Lys Leu Gly Ile Gln Glu Phe Gln Ala Thr Thr Arg Glu Ala Ser Met
865                 870                 875                 880

Asp Asn Ser Leu Lys Leu Val Lys Asn His Asp Glu His Asp Pro Phe
                885                 890                 895

Leu Lys Thr Lys Asp Lys Arg Met Leu Ser Tyr Glu Lys Lys Thr Leu
            900                 905                 910

Leu Ser Asp Thr Glu Thr Glu Cys Gly Cys Asp Asp Ser Lys Thr Asp
            915                 920                 925

Ile Ser Trp Leu Lys Glu Pro Lys Thr Lys Arg Leu Met Asp Tyr Ser
            930                 935                 940

Arg Asn Lys Asn Thr Thr Lys Tyr Lys Ser Arg Lys Ser Arg Ser Ser
945                 950                 955                 960

Met Glu Lys Gly Gln Pro Arg Pro Thr Met Val Leu Asn Lys Asn Ser
                965                 970                 975

Met Lys Asn Asp Tyr Glu Val Val Val Asp Gly Arg Thr Arg Leu Pro
            980                 985                 990

Arg Arg Ala Thr Lys Thr Lys Lys Asn Tyr Lys Asp Leu Ser Thr Ser
            995                1000                1005

Glu Ser Glu Ser Glu Ser Glu Lys Glu Cys Ser Tyr Leu Phe Lys
        1010                1015                1020

Asp Lys Leu Pro Thr Lys Glu Glu Thr Ile His Ser Arg Ala Gln
        1025                1030                1035

Thr Lys Lys Leu Pro Glu Lys Gln Gln Lys Val Phe Asn Ser Glu
        1040                1045                1050

Ala Leu Lys Gly Gln Pro Ser Glu Glu Gln Lys Asn Ser Ser Arg
        1055                1060                1065

Leu Arg Glu Gly Arg Glu Asp Ser Leu Cys Leu Ser Ser Ala Ser
        1070                1075                1080

Val Ser Arg Ser Ser Ser Val Glu Val Met Arg Cys Thr Glu
        1085                1090                1095

Lys Ile Thr Glu Arg Asp Phe Thr Gln Asp Tyr Asp Tyr Ile Thr
        1100                1105                1110

Lys Ser Leu Ser Pro Tyr Pro Lys Ala Pro Ser Pro Glu Phe Leu
        1115                1120                1125

Asn Gly Asn Asn Ser Val Val Gly Arg Gly Gln Ser Pro Arg Ile
        1130                1135                1140

Ser Glu Thr Ser Ala Met Cys Val Arg Lys Ser Tyr Ser Pro Ala
        1145                1150                1155

Ser Gly Pro Pro Phe Ser Pro Arg His Thr Pro Thr Lys Asn Asn
        1160                1165                1170

Ser Val Val Asn Met Lys Lys Ala Asn Ser Val Ile Asn Asn Gln
        1175                1180                1185

Arg Thr Gln His Cys Asn Ser Tyr Ser Asp Val Ser Ser Asn Ser
        1190                1195                1200

Ser Glu Lys Leu Tyr Met Glu Pro Glu Ser Pro Glu Ser Cys Asp
        1205                1210                1215

Asn His Met Gln Asn Lys Arg Glu Gly Asn His Ala Ala Ser Pro
        1220                1225                1230

Leu Ser Leu Ser Ser Glu Lys Ile Glu Lys Met Trp Phe Asp Met
```

```
                    1235                  1240                 1245

Pro  Ser  Glu  Asn  Thr  His  Val  Ser  Gly  Pro  Ser  Gln  Arg  Gly  Ser
         1250                 1255                 1260

Lys  Arg  Arg  Met  Tyr  Leu  Glu  Asp  Asp  Glu  Leu  Ser  Asn  Ser  Asn
    1265                 1270                 1275

Glu  Ala  Glu  Val  Glu  Glu  Ala  Glu  Glu  Arg  Glu  His  Leu  Leu  Ser
1280                 1285                 1290

Lys  Lys  Arg  Cys  Gln  Trp  Glu  Asn  Ser  Asp  Gln  His  Thr  Phe  Lys
    1295                 1300                 1305

Thr  Ser  Leu  Ser  Thr  Pro  Asp  Phe  Ser  Val  Pro  Lys  Asp  Trp  Gln
    1310                 1315                 1320

Gln  Glu  Leu  Gln  Gly  Ala  Gly  Met  Phe  Tyr  Asp  Asn  Ile  Ser  Ser
    1325                 1330                 1335

Asp  Tyr  Lys  Arg  Lys  Thr  Asp  Ser  Gln  His  Lys  Ile  Met  Asp  Asp
    1340                 1345                 1350

Phe  Thr  Thr  Lys  Thr  Leu  Lys  Leu  Thr  Gln  Gln  His  Leu  Met  Ala
    1355                 1360                 1365

Met  Thr  Ser  Gln  Ala  Gln  Gly  Arg  Arg  Asp  Glu  Asn  Val  Glu  Lys
    1370                 1375                 1380

Phe  Gln  Val  Thr  Leu  Leu  Asp  Glu  Leu  Glu  Lys  Val  Glu  Lys  Asp
    1385                 1390                 1395

Ser  Gln  Thr  Leu  Arg  Asp  Leu  Glu  Lys  Glu  Leu  Val  Asp  Ile  Glu
    1400                 1405                 1410

Glu  Lys  Leu  Val  Gln  Lys  Met  Arg  Ala  Tyr  His  Arg  Cys  Glu  Arg
    1415                 1420                 1425

Glu  Arg  Phe  Arg  Val  Leu  Lys  Thr  Ser  Leu  Asp  Lys  Ser  Phe  Leu
    1430                 1435                 1440

Val  Tyr  Asn  Ser  Val  Tyr  Glu  Glu  Ser  Val  Phe  Thr  Ser  Glu  Met
    1445                 1450                 1455

Cys  Leu  Met  Lys  Ala  Asn  Met  Lys  Met  Leu  Gln  Asp  Lys  Leu  Leu
    1460                 1465                 1470

Lys  Glu  Met  His  Glu  Glu  Val  Leu  Asn  Ile  Arg  Arg  Gly  Leu
    1475                 1480                 1485

Gln  Ser  Leu  Phe  Lys  Ala  His  Glu  Gly  Asn  Asp  Ala
    1490                 1495                 1500

<210> SEQ ID NO 8
<211> LENGTH: 1505
<212> TYPE: PRT
<213> ORGANISM: Rattus norvegicus

<400> SEQUENCE: 8

Met  Pro  Val  Arg  Pro  Asp  Pro  Gln  Gln  Leu  Glu  Lys  Cys  Ile  Asp  Asp
1                  5                   10                  15

Ala  Leu  Arg  Lys  Asn  Asp  Phe  Lys  Pro  Leu  Val  Thr  Leu  Leu  Gln  Ile
              20                  25                  30

Asp  Ile  Cys  Glu  Asp  Val  Lys  Ile  Lys  Cys  Ser  Lys  Gln  Phe  Leu  Arg
         35                  40                  45

Lys  Leu  Asp  Asp  Leu  Ile  Cys  Arg  Glu  Leu  His  Lys  Lys  Asp  Ile  Gln
    50                  55                  60

Thr  Ile  Ser  Asn  Ile  Leu  Ile  Ser  Ile  Gly  Arg  Cys  Ser  Lys  Asn  Ile
65                  70                  75                  80

Phe  Ile  Leu  Gly  Gln  Thr  Gly  Leu  Gln  Thr  Met  Ile  Lys  Gln  Gly  Leu
              85                  90                  95

Val  Gln  Lys  Met  Val  Ser  Trp  Phe  Glu  Asn  Ser  Lys  Glu  Ile  Ile  Leu
```

-continued

```
                100                 105                 110
Ser Gln Arg Gln Ser Lys Asp Glu Ala Val Met Asn Met Ile Glu Asp
            115                 120                 125
Leu Phe Asp Leu Leu Met Val Val Tyr Asp Val Asn Asp Glu Gly Lys
        130                 135                 140
Asn Gln Val Leu Glu Ser Phe Ile Pro His Ile Cys Ala Leu Val Ile
145                 150                 155                 160
Asp Ser Arg Val Asn Phe Cys Ile Gln Gln Glu Ala Leu Lys Lys Met
                165                 170                 175
Asn Leu Met Leu Asp Arg Ile Pro Gln Asp Ala Asn Lys Ile Leu Cys
            180                 185                 190
Asn Gln Glu Ile Leu Thr Leu Met Ser Asn Met Gly Glu Arg Ile Leu
        195                 200                 205
Asp Val Gly Asp Tyr Glu Leu Gln Val Gly Ile Val Glu Ala Leu Cys
210                 215                 220
Arg Met Thr Thr Glu Lys Arg Arg Gln Glu Leu Ala Tyr Glu Trp Phe
225                 230                 235                 240
Ser Met Asp Phe Ile Ala Asn Ala Phe Lys Lys Ile Lys Asp Cys Glu
                245                 250                 255
Phe Glu Thr Asp Cys Arg Ile Phe Leu Asn Leu Val Asn Gly Met Leu
            260                 265                 270
Gly Asp Arg Arg Val Phe Thr Phe Pro Cys Leu Ser Ala Phe Leu
        275                 280                 285
Gly Lys Tyr Glu Leu Gln Ile Pro Ser Asp Glu Lys Leu Glu Glu Phe
        290                 295                 300
Trp Ile Asp Phe Asn Leu Gly Ser His Thr Leu Ser Phe Tyr Ile Ala
305                 310                 315                 320
Gly Asp Asp Asp His Gln Trp Glu Ala Val Thr Val Pro Glu Glu
                325                 330                 335
Lys Val Asp Met Tyr Asn Ile Glu Val Arg Ser Lys Leu Leu
            340                 345                 350
Thr Leu Thr Leu Lys Asn Ile Val Lys Ile Ser Lys Lys Glu Gly Lys
        355                 360                 365
Glu Leu Leu Leu Tyr Phe Asp Ala Ala Leu Glu Ile Thr Asn Val Thr
        370                 375                 380
Lys Lys Leu Phe Gly Gly Asn Lys Tyr Lys Glu Phe Thr Arg Lys Gln
385                 390                 395                 400
Asp Ile Ser Val Ala Lys Thr Ser Ile His Val Leu Phe Asp Ala Ser
                405                 410                 415
Gly Ser Gln Ile Leu Val Pro Glu Ser Gln Pro Ser Pro Val Lys Glu
            420                 425                 430
Asn Leu Ile His Leu Lys Glu Lys Ser Asn Leu Gln Lys Lys Leu Thr
        435                 440                 445
Asn Pro Leu Glu Pro Asp Asn Ser Ser Ser Gln Arg Asp Arg Lys Asn
        450                 455                 460
Ser Gln Asp Glu Ile Thr Thr Pro Ser Arg Lys Lys Met Ser Glu Ala
465                 470                 475                 480
Ser Met Ile Val Pro Asp Thr Asp Arg Tyr Thr Val Arg Ser Pro Ile
                485                 490                 495
Leu Leu Ile Asn Thr Ser Thr Pro Arg Arg Ser Arg Ala Pro Leu Gln
            500                 505                 510
Ala Ile His Ser Ala Glu Lys Ala Val Ser Lys Thr Ser Glu Ser Gly
        515                 520                 525
```

-continued

Val Asp Tyr Ala Val Ser Leu Lys Ser Arg Gln Ser Asp Gly Arg Asn
530                 535                 540

Arg Gly Asn Asn Arg Ala Asn His Asn Lys Thr Ala Thr Val Gln Asn
545                 550                 555                 560

Lys Gly His Glu His His Glu Ser Pro Asp Gln Thr Phe Asn Glu Ile
                565                 570                 575

Glu Glu Thr Leu Ser Asp Ala Tyr Ala Val Glu Lys Val Asp Lys Pro
            580                 585                 590

Val Leu Pro Gly Val Leu Asp Ile Ser Lys Asn Lys Ala His Ser Arg
        595                 600                 605

Trp Ala Cys Trp Thr Pro Val Thr Thr Ile Lys Leu Cys Asn Asn Gln
610                 615                 620

Arg Ser Cys Ala Leu Pro Gly Asp Thr Phe Thr Gln Asp Thr Gly Val
625                 630                 635                 640

Asn Lys Lys Cys Thr Lys Gln Lys Ser Val Ser Asp Asp Ser Glu
                645                 650                 655

Glu Thr Gln Arg Val Lys Tyr Ser Lys Asp Val Ile Lys Cys Asn Lys
                660                 665                 670

Ser Glu Glu Ala Glu Val Cys Glu Arg Asn Ile Gln Glu Gln Asn His
            675                 680                 685

Pro Lys Tyr Ser Gln Lys Lys Asn Thr Ala Asn Ala Lys Lys Asn Asp
        690                 695                 700

Trp His Ile Glu Ser Glu Thr Thr Tyr Lys Ser Val Leu Leu Asn Lys
705                 710                 715                 720

Thr Thr Glu Glu Ser Leu Ile Tyr Lys Lys Thr Cys Val Leu Ser Lys
                725                 730                 735

Asp Val Asn Thr Thr Ile Cys Asp Lys Ser Pro Ser Arg Lys Ser Met
                740                 745                 750

Arg Ser His Thr Lys Ser Arg Lys Glu Leu Met Ser Glu Val Thr Ser
            755                 760                 765

Cys Glu Leu Asp Glu Ile Pro Val Arg Glu Asn Ser Lys Gly Lys Arg
        770                 775                 780

Phe Thr Gly Thr Ala Glu Ser Leu Ile Asn Leu Ile Asn Lys Arg Tyr
785                 790                 795                 800

Asn Ser Ser Asp Asp Met Ile Ser Thr Arg Lys Leu Lys Glu Pro Arg
                805                 810                 815

Asp Gly Ser Gly Phe Ser Lys Lys Pro Glu Leu Gln Phe Asn Lys Val
            820                 825                 830

Gln Arg Lys Ser Tyr Arg Lys Leu Lys Thr Val Val Asn Val Thr Ser
        835                 840                 845

Glu Cys Pro Leu Asn Asp Val Tyr Asn Phe Ser Leu Asn Gly Ala Asp
850                 855                 860

Glu Pro Val Ile Lys Leu Gly Ile Gln Glu Phe Gln Ala Thr Thr Arg
865                 870                 875                 880

Glu Ala Ser Met Asp Asn Ser Ile Lys Leu Val Asp Val Arg Asn Arg
                885                 890                 895

Asp Glu Arg Asp Leu Ser Leu Lys Thr Lys Asp Glu Arg Ile Leu Ser
            900                 905                 910

His Glu Arg Lys Thr Leu Phe Ser Asp Thr Glu Thr Glu Cys Gly Trp
        915                 920                 925

Asp Asp Ser Lys Thr Asp Ile Ser Trp Leu Arg Lys Pro Lys Ser Lys
930                 935                 940

Arg Leu Met Asp Tyr Ser Arg Asn Lys Asn Thr Lys Lys Cys Lys Ser
945                 950                 955                 960

```
Ile Lys Ser Arg Ser Ser Thr Glu Lys Gly Gln Pro Arg Ser Thr Val
                965                 970                 975
Val Leu Ser Lys Asn Ile Ala Lys Asn Asp Tyr Glu Val Ile Val Asp
            980                 985                 990
Gly Arg Thr Arg Leu Pro Arg Arg Ala Thr Lys Thr Lys Lys Asn Tyr
        995                1000                1005
Lys Asp Leu Ser Thr Ser Gly Ser Glu Ser Glu Ser Glu Lys Glu
    1010                1015                1020
Ile Ser Tyr Leu Phe Lys Asp Lys Leu Pro Thr Lys Glu Glu Thr
    1025                1030                1035
Val His Ser Ser Ala Gln Thr Lys Lys Leu Pro Lys Lys Gln Gln
    1040                1045                1050
Lys Val Phe Asn Thr Glu Ala Leu Lys Gly Gln Pro Ser Glu Glu
    1055                1060                1065
Gln Lys Asn Ser Ser Thr Leu Arg Asn Gly Arg Glu Asp Ser Leu
    1070                1075                1080
Tyr Leu Ser Ser Ala Ser Val Ser Gly Ser Ser Ser Val Glu
    1085                1090                1095
Val Met Arg Cys Thr Glu Lys Ile Thr Glu Arg Asp Phe Thr Gln
    1100                1105                1110
Asp Tyr Asp Tyr Ile Thr Lys Ser Leu Ser Pro Tyr Pro Lys Ala
    1115                1120                1125
Ala Ser Pro Glu Phe Leu Asn Arg Ser Asn Arg Val Val Gly His
    1130                1135                1140
Gly Lys Ser Pro Arg Ile Ser Glu Thr Ser Ala Val Cys Val Arg
    1145                1150                1155
Lys Ser Cys Ser Pro Ala Ser Gly Leu Pro Phe Ser Pro Arg His
    1160                1165                1170
Thr Thr Lys Asn Asn Ser Val Met Asn Ile Lys Asn Thr Asn Ser
    1175                1180                1185
Val Ile Asn Asn Gln Arg Thr Gln His Cys Asn Ser Tyr Ser Asp
    1190                1195                1200
Val Ser Ser Asn Ser Ser Glu Lys Leu Tyr Met Glu Pro Glu Ser
    1205                1210                1215
Pro Asp Ser Cys Glu Asn His Val Gln Ser Lys Arg Glu Glu Asn
    1220                1225                1230
His Ala Ala Ser Pro Phe Ser Leu Ser Ser Glu Lys Ile Glu Lys
    1235                1240                1245
Ile Trp Phe Asp Met Pro Asn Asp Asn Thr His Val Ser Gly Pro
    1250                1255                1260
Ser Gln Arg Gly Ser Lys Arg Arg Met Tyr Leu Glu Glu Asp Glu
    1265                1270                1275
Leu Ser Asn Pro Ser Glu Ala Glu Val Gln Glu Ala Glu Glu Arg
    1280                1285                1290
Glu His Leu Val Ser Lys Lys Leu Cys Gln Arg Glu His Phe Asp
    1295                1300                1305
Gln His Thr Ser Glu Thr Ser Leu Ser Thr Pro Glu Phe Ser Val
    1310                1315                1320
Pro Lys Asp Trp Gln Gln Glu Leu Gln Gly Ala Gly Met Phe Tyr
    1325                1330                1335
Asp Asn Ile Asn Ser Asp Tyr Lys Arg Lys Thr Asp Thr Gln His
    1340                1345                1350
Lys Ile Met Asp Asp Phe Thr Thr Lys Thr Leu Lys Leu Thr Gln
```

-continued

```
              1355                1360                1365

Gln His Leu Leu Ala Met Ala Cys Gln Ala Arg Gly His Arg Asp
         1370                1375                1380

Glu Asn Ile Asp Lys Phe Gln Val Thr Leu Leu Asp Glu Leu Glu
         1385                1390                1395

Lys Val Glu Lys Asp Ser Gln Thr Leu Arg Asp Leu Glu Lys Glu
1400                1405                1410

Phe Val Asp Ile Glu Glu Lys Ile Val His Lys Met Arg Ala Phe
    1415                1420                1425

His Gln Ser Glu Arg Glu Arg Phe Arg Ala Leu Lys Thr Ser Leu
         1430                1435                1440

Asp Lys Ser Leu Leu Val Tyr Asn Ser Val Tyr Glu Glu Asn Val
    1445                1450                1455

Leu Thr Ser Glu Met Cys Leu Met Lys Ala Asn Met Lys Met Leu
    1460                1465                1470

Gln Asp Lys Leu Leu Lys Glu Met His Glu Glu Leu Leu Asn
    1475                1480                1485

Ile Arg Arg Gly Leu Glu Ser Leu Phe Lys Asp His Glu Gly Asn
    1490                1495                1500

Asn Ala
    1505

<210> SEQ ID NO 9
<211> LENGTH: 1079
<212> TYPE: PRT
<213> ORGANISM: Sus scrofa

<400> SEQUENCE: 9

Val Ala Trp Phe Glu Lys Ser Lys Glu Ile Ile Leu Ser Gln Gly Ser
1               5                   10                  15

Ser Lys Asp Glu Ala Val Ile Asn Met Ile Glu Asp Phe Phe Asp Leu
            20                  25                  30

Leu Met Val Ile His Asp Ile Asp Asp Glu Gly Lys Arg Gln Val Val
        35                  40                  45

Glu Ser Phe Ile Pro Arg Ile Cys Ala Leu Val Ile Asp Ser Arg Val
    50                  55                  60

Asn Ile Cys Val Gln Gln Glu Thr Leu Lys Lys Met Asn Ala Met Leu
65                  70                  75                  80

Asp Lys Met Pro Gln Asp Ala Arg Lys Ile Leu Phe Asn Gln Glu Met
                85                  90                  95

Leu Ile Leu Met Ser Ser Met Gly Glu Arg Ile Leu Asp Ala Gly Asp
            100                 105                 110

Tyr Asp Leu Gln Val Gly Ile Val Glu Ala Leu Cys Arg Met Thr Thr
        115                 120                 125

Glu Lys Gln Arg Gln Glu Leu Ala Cys Gln Trp Phe Ser Met Asp Phe
    130                 135                 140

Val Ala Asn Ala Phe Lys Gly Ile Lys Asp Ser Glu Phe Glu Thr Asp
145                 150                 155                 160

Cys Arg Met Phe Leu Asn Leu Val Asn Gly Ile Leu Gly Asp Lys Arg
                165                 170                 175

Arg Val Phe Thr Phe Pro Cys Leu Ser Ala Phe Leu Asp Lys Tyr Glu
            180                 185                 190

Leu Gln Ile Pro Ser Asp Glu Lys Leu Glu Asp Phe Trp Ile Asp Phe
        195                 200                 205

Asn Leu Gly Ser Gln Thr Leu Ser Phe Tyr Ile Ala Gly Asp Asn Asp
```

```
                210                 215                 220
Asp His Gln Trp Glu Ala Val Thr Val Pro Glu Glu Lys Val Gln Ile
225                 230                 235                 240

Tyr Ser Ile Glu Val Arg Asp Ser Lys Lys Leu Leu Thr Ile Ile Leu
                245                 250                 255

Lys Asp Thr Val Lys Ile Ser Lys Arg Lys Gly Lys Glu Leu Leu Leu
            260                 265                 270

Tyr Phe Asp Ala Ser Leu Glu Ile Thr Asn Val Thr Gln Lys Ile Phe
        275                 280                 285

Gly Ala Asn Lys Tyr Arg Glu Phe Ser Arg Lys Gln Gly Ile Ser Val
290                 295                 300

Ala Lys Thr Ser Val His Ile Leu Phe Asp Ala Ser Gly Ser Gln Ile
305                 310                 315                 320

Leu Val Pro Glu Ser Gln Ile Ser Pro Val Glu Leu Ser Thr Leu
                325                 330                 335

Lys Glu Lys Ala Asn Pro Gln Glu Glu Phe Val Lys Pro Pro Lys His
            340                 345                 350

Ile Lys Asn Ser Asn Lys Gly Asp Arg Lys His Gly Gln Pro Glu Ile
        355                 360                 365

Ile Thr Pro Ser Lys Arg Lys Met Ser Glu Ala Ser Met Ile Val Pro
370                 375                 380

Gly Ala Glu Arg Tyr Thr Val Arg Ser Pro Ile Leu Leu Ile Asn Thr
385                 390                 395                 400

Ser Thr Pro Gln Arg Gly Arg Ile Lys Pro Pro Leu Gln Met Thr Ser
                405                 410                 415

Ser Met Glu Lys Pro Gly Phe Ser Lys Thr Ser Glu Asn Gly Val Asp
            420                 425                 430

Asn Ala Val Ser Leu Lys Ser Arg Pro Cys Glu Glu Arg Asn Arg Glu
        435                 440                 445

Asp Asn Thr Asp Lys His Ile Lys Thr Lys Val Ile Glu Lys Ala Glu
450                 455                 460

Asn Lys Asp Ile Glu Tyr Pro Asn Gln Asn Phe Asn Glu Leu Gln Glu
465                 470                 475                 480

Ile Val Pro Asp Ser Gln Ala Val Gly Lys Ile Asp Lys Pro Val Leu
                485                 490                 495

Pro Gly Ile Leu Asp Asn Ile Cys Gly Asn Lys Met His Ser Lys Trp
            500                 505                 510

Ala Cys Trp Thr Pro Val Thr Asn Ile Lys Leu Cys Asn Asn Leu Arg
        515                 520                 525

Ala Ser Ser Ser Glu Asp Thr Phe Asn Gln Asp Ile Ile Ile Asn
530                 535                 540

Lys Asn Leu Thr Lys Lys Ser Ser Ser Met Ser Asp Asp Asn
545                 550                 555                 560

Ser Glu Glu Thr Ser Lys Val Gln Tyr Gly Lys Glu Leu Met Gln His
                565                 570                 575

Asn Lys Ile Asp Lys Ala Glu Ala Cys Lys Arg Asn Lys Gln
            580                 585                 590

Gln Gln Leu Asp His Ser Lys His Ser Glu Glu Lys Asn Thr Glu Asn
        595                 600                 605

Thr Lys Gln Asn Asp Trp Arg Ile Glu Ser Glu Thr Thr Phe Lys Ser
610                 615                 620

Val Leu Leu Asn Lys Thr Val Glu Glu Ser Val Ile Tyr Arg Lys Lys
625                 630                 635                 640
```

```
Tyr Thr Leu Ser Lys Asp Val Asn Thr Ala Ile Cys Asp Lys Ser Pro
            645                 650                 655

Ser Pro Arg Lys Asn Thr Lys Ser His Arg Lys Ser Gly Lys Arg Leu
        660                 665                 670

Thr Ser Glu Leu Asn Ser Trp Asp Leu Lys Gln Lys Glu Met Arg Glu
    675                 680                 685

Lys Ser Lys Gly Lys Gly Phe Asn Asp Ala Ala Glu Ser Leu Ile Ser
690                 695                 700

Gln Ile Asn Lys Arg Tyr Lys Pro Lys Asp Gly Thr Lys Ser Thr Arg
705                 710                 715                 720

Lys Leu Lys Glu Ser Leu Ile Asp Ser Gly Phe Ser Asn Lys Ser Asp
            725                 730                 735

Leu Gln Leu Arg Lys Glu Lys Val Gln Lys Ser Tyr Arg Gln Leu
        740                 745                 750

Lys Thr Thr Phe Val Asn Val Thr Ser Glu Cys Pro Leu Asn Asp Val
    755                 760                 765

Tyr Asn Phe Asn Leu Ser Gly Ala Asp Glu Pro Val Ile Lys Leu Gly
770                 775                 780

Ile Gln Glu Phe Gln Ala Thr Ala Arg Glu Ala Cys Val Asp Ser Thr
785                 790                 795                 800

Ile Thr Leu Val Gly Leu Arg Asn His Asp Glu Leu Glu Thr Ser Leu
            805                 810                 815

Lys Thr Lys Asp Lys Arg Thr Val Thr Asn His Lys Lys Thr Leu
        820                 825                 830

Phe Ser Asp Thr Asp Thr Glu Tyr Lys Cys Asp Ser Lys Thr Asp
    835                 840                 845

Ile Ser Trp Leu Arg Glu Ser Lys Ser Lys Pro Gln Leu Ile Gly Tyr
850                 855                 860

Ser Arg Asn Lys Asn Val Lys Lys His Lys Ser Gly Lys Ser Arg Ser
865                 870                 875                 880

Ser Leu Glu Arg Glu Gln Pro Arg Ser Lys Met Thr Pro Asp Lys Asn
            885                 890                 895

Ile Thr Lys Lys Val Asp Glu Thr Val Pro Asp Gly Arg Ile Arg Leu
        900                 905                 910

Pro Arg Arg Ala Ala Lys Thr Lys Asn Tyr Lys Asp Leu Ser Asn
    915                 920                 925

Ser Glu Ser Glu Ser Glu Gln Glu Phe Ser His Ser Phe Lys Glu Lys
930                 935                 940

Leu Leu Ile Lys Glu Asn Ile His Ser Arg Ser Lys Thr Met Lys Pro
945                 950                 955                 960

Pro Lys Lys Gln Asn Ser Phe Ser Ser Glu Met Gln Lys Asp Ile Ser
            965                 970                 975

Lys Glu Trp Lys Asn Ser Ser Leu Leu Lys Asp Thr Ile Arg Asp Asn
        980                 985                 990

Ser Leu Asp Lys Ser Pro Val Ser   Leu Ser Gly Ser Pro  Ser Ser Ile
    995                 1000                1005

Glu Val  Met Arg Cys Thr Glu  Lys Thr Thr Glu Arg  Asp Phe Thr
    1010                1015               1020

Gln Asp  Phe Asp Tyr Val Thr  Lys Ser Leu Ser Pro  Tyr Pro Lys
    1025                1030               1035

Thr Ser  Ser Pro Glu Ser Leu  Asn Ser Gly Val Glu  Ser Pro Ile
    1040                1045               1050

Asn Ser  Pro Asn Asn Ser Glu  Lys Asn Leu Leu Cys  Gly Gly Glu
    1055                1060               1065
```

Ser Cys Ser Pro Ile Pro Gln Ser Gly Phe Leu
            1070                1075

<210> SEQ ID NO 10
<211> LENGTH: 919
<212> TYPE: PRT
<213> ORGANISM: Xenopus tropicalis

<400> SEQUENCE: 10

Met His Pro Lys Gln Glu Ser Lys Leu Glu Ala Asn Ile Asp His Gly
1               5                   10                  15

Leu Arg Thr Lys Gly His Asp Leu Arg Pro Leu Lys Ser Phe Leu Leu
            20                  25                  30

Thr Glu Ser Cys Ala Gly Thr Ser Ile Lys Cys Ser Lys Phe Leu Leu
        35                  40                  45

Gly Lys Leu Asp Lys Leu Ile Cys Met Glu Leu Asp Gln Arg Glu Val
    50                  55                  60

Lys Asn Ala Leu Leu Val Leu Asn Val Ile Leu Lys Phe Ala Ser Cys
65                  70                  75                  80

Met Thr Leu Asn Asn Glu Glu Trp Leu Thr Ala Ser Ile Lys Gln Gly
                85                  90                  95

Leu Val Gln Lys Met Ile Ile Trp Leu Glu Lys Ser Thr Tyr Phe Leu
            100                 105                 110

Ala Tyr Ser Glu Lys Gln Lys Asn Glu Thr Val Leu Asn Phe Ala Glu
        115                 120                 125

Asp Phe Phe Asp Ile Val Met Leu Val His Asp His Ser Ser Glu Gly
    130                 135                 140

Lys Met Gln Ile Leu Glu His Phe Leu Val Arg Ala Cys Ser Leu Val
145                 150                 155                 160

Ser Asn Ala Ala Thr Asn Ile Phe Val Lys Gln Glu Val Val Arg Arg
                165                 170                 175

Leu Asn Leu Met Leu Asn Thr Met Pro Leu Val Ala Arg Lys Lys Ile
            180                 185                 190

Leu Ser Thr Glu Glu Met Thr Ser Ala Met Ala Ser Met Ala Lys Arg
        195                 200                 205

Ile Leu Asp Ala Gly Asp Phe Asp Leu Gln Val Ala Ile Thr Glu Ala
    210                 215                 220

Leu Cys Arg Met Thr Ser Glu Ala Gln Arg Glu Leu Thr Ser Gln Trp
225                 230                 235                 240

Phe Pro Met Glu Phe Ile Ala Glu Ala Phe Lys Arg Ile Lys Asp Ser
                245                 250                 255

Glu Phe Glu Thr Asp Cys Arg Lys Phe Leu Asn Leu Ile Asn Gly Ile
            260                 265                 270

Leu Gly Gly Lys Lys Ser Val Val Thr Leu Pro Cys Leu Ser Ala Tyr
        275                 280                 285

Leu Asp Asn His Lys Phe Gln Met Pro Cys Asp Glu Lys Leu Glu Glu
    290                 295                 300

Phe Trp Ile Asp Phe Asn Thr Gly Thr Gln Ser Ile Ser Phe Tyr Ile
305                 310                 315                 320

Ser Ala Gly Ala Ala Glu Glu His Gln Trp Asp Thr Val Cys Val Lys
                325                 330                 335

Asp Ser Asp Val Ile Val Tyr Ser Ile Ala Glu Val Asp Asn Asn Lys
            340                 345                 350

Leu Leu Thr Val Asp Leu Lys Ala Pro Ile Ala Ala Gly Gln Tyr Glu
        355                 360                 365

```
Gly Lys Gln Ile Arg Ile Tyr Phe Ser Cys Pro Leu Asp Ile Leu Ser
        370                 375                 380

Ala Ala Gln Arg Val Phe Ala Ala Gln Lys Asn Lys Asp Phe Ile Lys
385                 390                 395                 400

Lys Gln Thr Ala Ser Asp Ala Glu Thr Thr Val Arg Val Ile Phe Glu
                405                 410                 415

Glu Cys Arg Ser Gln Ile Leu Leu Ser Glu Ser Gln Gly Ser Asn Ser
                420                 425                 430

Ser Val Lys Pro Val Ala Glu Pro Asp Val Lys Asp Phe Ala Gly Lys
            435                 440                 445

Asn Gln Pro Pro Ser Ala Ala Ser Ser Leu Lys Gln Thr Thr Cys Asn
            450                 455                 460

His Glu His Asn Thr Asn Ser Leu Met Pro Thr Thr Pro Val Lys Val
465                 470                 475                 480

Lys Met Ser Glu Ser Ser Met Val Gly Ser Gly Leu Lys Ile Thr Asn
                485                 490                 495

Ile Ala Thr Asn Asn Pro Ala Ser Arg Arg Ile Arg Thr Lys Pro Pro
            500                 505                 510

Leu Glu Met Val Arg Pro Ala Glu Arg Asn Thr Val Pro Pro Asn Lys
            515                 520                 525

Ser Arg Gly Gly Ser Pro Cys Ser Asp Arg Thr Pro Gln Leu Pro Lys
530                 535                 540

His Lys Ser Ser Thr Asp Ala Ala Cys Thr Phe Gln Tyr Val Asn Lys
545                 550                 555                 560

Ala Pro Lys Asp Glu Leu Asn Glu Ile Val Pro Asp Thr Gln Tyr Cys
            565                 570                 575

Ala Thr Lys Asp Ser Ser Leu Leu Pro Gly Leu Thr Lys Arg Ser Val
            580                 585                 590

Asn Gln His Glu Arg Asn Arg Lys Gln Glu Asn Ser Gly Gly Phe Gly
            595                 600                 605

Asn Lys Ile Ser Val Ser Ser Val Cys Ile Ala Asn Gln Gly Lys Ile
            610                 615                 620

Ser Ser His Leu Val Lys Gln His Ser Asn Glu Ile Ser Thr Thr Pro
625                 630                 635                 640

Thr Lys Glu Met Ser Ala Arg Ser Ser Glu Ser Ser Ile Gln Lys His
                645                 650                 655

Cys Glu Lys His Leu Lys Glu Lys Pro Lys Glu Leu Ile Gln Ala Thr
                660                 665                 670

Asp Leu Leu Val Glu Asn Ile Arg Arg Lys Tyr Ala Arg Leu Thr Glu
            675                 680                 685

Glu Asp Lys Arg Glu Glu Asn Thr Phe Glu Arg Lys Asn Val Asp Lys
            690                 695                 700

His Pro Leu His Thr Asn Lys Asp Lys Asn Arg Thr Arg Gly Phe Asn
705                 710                 715                 720

Gln His Ser Pro Lys Asp Phe Ser Thr Thr Lys Lys Pro Trp Lys
            725                 730                 735

Asp Val Tyr Asp Phe Gln Phe Ser Ala Thr Asp Asn Pro Thr Ile Asn
            740                 745                 750

Leu Glu Val Ser Ala Pro Thr Val Ser Glu Arg Met Ser Ser Lys Ala
            755                 760                 765

Leu Ala Ile Gly Lys Lys Ser Thr Lys Asn Lys Gln Lys Gly Lys Thr
770                 775                 780

Gly Thr Glu Ile Lys Thr Lys Ala His Gln Arg His Leu Phe Ser Asp
```

```
                785                 790                 795                 800
Thr Glu Ser Glu Arg Gly Gly Asp Asp Thr Lys Ser Asn Leu Ser Trp
                    805                 810                 815

Leu Gln Glu Gln His Ser Lys Thr Lys Pro Pro Ile Ala Thr Tyr Arg
                820                 825                 830

Arg Gln Lys Ala Gln Lys Gln Glu Gln Thr Met Pro Tyr Lys Met
        835                 840                 845

Arg His Ile Thr Thr Asn Asn Ser Pro Glu Pro Lys Thr Gly Lys Lys
        850                 855                 860

Ser Tyr Asn Arg Ser Gly Gly Asn Lys His Asn Lys Leu Lys Arg Pro
865                 870                 875                 880

Cys Arg Thr Ala Ala Lys Ser Thr Asn Tyr Lys Asp Leu Ser Asn Ser
                885                 890                 895

Glu Ser Asp Ala Glu Val Pro Phe Ser Pro Pro Lys Arg Glu Glu Pro
                900                 905                 910

Val Arg Arg Arg Cys Leu Lys
        915

<210> SEQ ID NO 11
<211> LENGTH: 1530
<212> TYPE: PRT
<213> ORGANISM: Pan troglodytes
<220> FEATURE:
<221> NAME/KEY: misc_feature
<222> LOCATION: (1456)..(1459)
<223> OTHER INFORMATION: Xaa can be any naturally occurring amino acid

<400> SEQUENCE: 11

Met Pro Ile Arg Pro Asp Leu Gln Gln Leu Glu Lys Cys Ile Asp Asp
1               5                   10                  15

Ala Leu Arg Lys Asn Asp Phe Lys Pro Leu Lys Thr Leu Leu Gln Ile
                20                  25                  30

Asp Ile Cys Glu Asp Val Lys Ile Lys Cys Ser Lys Gln Phe Phe His
            35                  40                  45

Lys Val Asp Asn Leu Ile Cys Arg Glu Leu Asn Lys Glu Asp Ile His
        50                  55                  60

Asn Val Ser Ala Ile Leu Val Ser Val Gly Arg Cys Gly Lys Asn Ile
65                  70                  75                  80

Ser Val Leu Gly Gln Ala Gly Leu Leu Thr Met Ile Lys Gln Gly Leu
                85                  90                  95

Ile Gln Lys Met Val Ala Trp Phe Glu Lys Ser Lys Asp Ile Ile Gln
            100                 105                 110

Ser Gln Gly Asn Ser Lys Asp Glu Ala Val Leu Asn Met Ile Glu Asp
        115                 120                 125

Leu Val Asp Leu Leu Leu Val Ile His Asp Val Ser Asp Glu Gly Lys
    130                 135                 140

Lys Gln Val Val Glu Ser Phe Val Pro Arg Ile Cys Ser Leu Val Ile
145                 150                 155                 160

Asp Ser Arg Val Asn Ile Cys Ile Gln Gln Glu Ile Ile Lys Arg Met
                165                 170                 175

Asn Ala Met Leu Asp Lys Met Pro Gln Asp Ala Arg Lys Ile Leu Ser
            180                 185                 190

Asn Gln Glu Met Leu Ile Leu Met Ser Ser Met Gly Glu Arg Ile Leu
        195                 200                 205

Asp Ala Gly Asp Tyr Asp Leu Gln Val Gly Ile Val Glu Ala Leu Cys
    210                 215                 220
```

-continued

```
Arg Met Thr Thr Glu Lys Gln Arg Gln Glu Leu Ala His Gln Trp Phe
225                 230                 235                 240

Ser Met Asp Phe Ile Ala Lys Ala Phe Lys Arg Ile Lys Asp Ser Glu
                245                 250                 255

Phe Glu Thr Asp Cys Arg Ile Phe Leu Asn Leu Val Asn Gly Met Leu
            260                 265                 270

Gly Asp Lys Arg Arg Val Phe Thr Phe Pro Cys Leu Ser Ala Phe Leu
        275                 280                 285

Asp Lys Tyr Glu Leu Gln Ile Pro Ser Asp Glu Lys Leu Glu Glu Phe
    290                 295                 300

Trp Ile Asp Phe Asn Leu Gly Ser Gln Thr Leu Ser Phe Tyr Ile Ala
305                 310                 315                 320

Gly Asp Asn Asp Asp His Gln Trp Glu Ala Val Thr Val Pro Glu Glu
                325                 330                 335

Lys Val Gln Ile Tyr Ser Ile Glu Val Arg Glu Ser Lys Lys Leu Leu
            340                 345                 350

Thr Ile Ile Leu Lys Asn Thr Val Lys Ile Ser Lys Arg Glu Gly Lys
        355                 360                 365

Glu Leu Leu Leu Tyr Phe Asp Ala Ser Leu Glu Ile Thr Asn Val Thr
    370                 375                 380

Gln Lys Ile Phe Gly Ala Asn Lys His Arg Glu Ser Ile Arg Lys Gln
385                 390                 395                 400

Gly Ile Ser Val Ala Lys Thr Ser Leu His Ile Leu Phe Asp Ala Ser
                405                 410                 415

Gly Ser Gln Ile Leu Val Pro Glu Ser Gln Ile Ser Pro Val Gly Glu
            420                 425                 430

Glu Leu Val Ser Leu Lys Glu Lys Ser Lys Ser Pro Lys Glu Phe Ala
        435                 440                 445

Lys Pro Ser Lys Tyr Ile Lys Asn Ser Asp Lys Gly Asn Arg Asn Asn
    450                 455                 460

Ser Gln Leu Glu Lys Ile Thr Pro Ser Lys Arg Lys Met Ser Glu Ala
465                 470                 475                 480

Ser Met Ile Val Ser Gly Ala Asp Arg Tyr Thr Met Arg Ser Pro Val
                485                 490                 495

Leu Phe Ser Asn Thr Ser Ile Pro Pro Arg Arg Arg Ile Lys Pro
            500                 505                 510

Pro Leu Gln Met Met Ser Ser Ala Glu Lys Pro Ser Val Ser Gln Thr
        515                 520                 525

Ser Glu Asn Arg Val Asp Asn Ala Ala Ser Leu Lys Ser Arg Ser Ser
    530                 535                 540

Glu Glu Arg His Arg Arg Asp Asn Thr Asp Lys His Ile Lys Thr Ala
545                 550                 555                 560

Lys Cys Val Glu Asn Thr Glu Asn Lys Asn Val Glu Phe Pro Asn Gln
                565                 570                 575

Asn Phe Ser Glu Leu Gln Asp Val Ile Pro Asp Ser Gln Pro Val Glu
            580                 585                 590

Lys Arg Asp His Ala Ile Leu Pro Gly Val Leu Asp Asn Ile Cys Gly
        595                 600                 605

Asn Lys Ile His Ser Lys Trp Ala Cys Trp Thr Pro Val Thr Asn Ile
    610                 615                 620

Glu Leu Cys Asn Asn Gln Arg Ala Ser Thr Ser Ser Gly Asp Thr Leu
625                 630                 635                 640

Asn Gln Asp Ile Val Ile Asn Lys Lys Leu Thr Lys Gln Lys Ser Ser
                645                 650                 655
```

-continued

Ser Ser Ile Ser Asp His Asn Ser Glu Gly Thr Gly Lys Val Lys Tyr
            660                 665                 670

Lys Lys Glu Gln Thr Asp His Ile Lys Ile Asp Lys Ala Glu Val Glu
            675                 680                 685

Val Cys Lys Lys His Asn Gln Gln Asn His Pro Lys Tyr Ser Gly
690                 695                 700

Gln Lys Asn Thr Glu Asn Ala Lys Gln Ser Asp Trp Pro Val Glu Ser
705                 710                 715                 720

Glu Thr Thr Phe Lys Ser Val Leu Leu Asn Lys Thr Ile Glu Ser
            725                 730                 735

Leu Ile Tyr Lys Lys Tyr Ile Leu Ser Lys Asp Val Asn Thr Ala
            740                 745                 750

Thr Cys Asp Lys Asn Pro Ser Ala Ser Lys Asn Val Gln Ser His Arg
            755                 760                 765

Lys Ala Glu Lys Glu Leu Thr Ser Glu Leu Asp Ser Trp Asp Leu Lys
            770                 775                 780

Gln Lys Lys Met Arg Glu Lys Ser Lys Gly Lys Glu Phe Thr Asp Val
785                 790                 795                 800

Ala Glu Ser Leu Ile Ser Gln Ile Asn Lys Arg Tyr Lys Thr Lys Asp
            805                 810                 815

Asp Ile Lys Ser Thr Arg Lys Leu Lys Glu Ser Leu Ile Asn Ser Asp
            820                 825                 830

Phe Ser Asn Lys Pro Val Val Gln Leu Ser Lys Glu Lys Val Gln Lys
            835                 840                 845

Lys Ser Tyr Arg Lys Leu Lys Thr Thr Phe Val Asn Val Thr Ser Glu
850                 855                 860

Cys Pro Val Asn Asp Val Tyr Asn Phe Asn Leu Asn Gly Ala Asp Asp
865                 870                 875                 880

Pro Ile Ile Lys Leu Gly Ile Gln Glu Phe Gln Ala Thr Ala Lys Glu
            885                 890                 895

Ala Cys Ala Asp Arg Ser Ile Arg Leu Val Gly Pro Arg Asn His Asp
            900                 905                 910

Glu Leu Lys Ser Ser Val Lys Thr Lys Asp Lys Lys Ile Ile Thr Asn
            915                 920                 925

His Gln Lys Lys Asn Leu Phe Ser Asp Thr Glu Thr Glu Tyr Arg Cys
            930                 935                 940

Asp Asp Ser Lys Thr Asp Ile Ser Trp Leu Arg Glu Pro Lys Ser Lys
945                 950                 955                 960

Pro Gln Leu Ile Asp Tyr Ser Arg Asn Lys Asn Val Arg Asn His Lys
            965                 970                 975

Ser Gly Lys Ser Arg Ser Ser Leu Glu Lys Gly Gln Pro Ser Ser Lys
            980                 985                 990

Met Thr Pro Ser Lys Asn Ile Met Lys Lys Thr Asp Lys Thr Ile Pro
            995                 1000                1005

Glu Gly Arg Ile Arg Leu Pro Arg Lys Ala Thr Lys Thr Lys Lys
    1010                1015                1020

Asn Tyr Lys Asp Leu Ser Asn Ser Glu Ser Glu Cys Glu Gln Glu
    1025                1030                1035

Phe Ser His Ser Phe Lys Glu Asn Ile Pro Val Lys Glu Glu Asn
    1040                1045                1050

Ile His Ser Arg Met Lys Thr Val Lys Leu Pro Lys Lys Gln Gln
    1055                1060                1065

Lys Val Phe Cys Ala Glu Thr Glu Lys Glu Leu Ser Lys Gln Cys

```
              1070                1075                1080

Lys Asn Ser Ser Leu Leu Lys Asp Ala Ile Arg Asp Asn Cys Leu
        1085                1090                1095

Asp Leu Ser Pro Arg Ser Leu Ser Gly Ser Pro Ser Ser Ile Glu
        1100                1105                1110

Val Thr Arg Cys Ile Glu Lys Ile Thr Glu Lys Asp Phe Thr Gln
        1115                1120                1125

Asp Tyr Asp Cys Ile Thr Lys Ser Ile Ser Pro Tyr Pro Lys Thr
        1130                1135                1140

Ser Ser Leu Glu Ser Leu Asn Ser Asn Ser Gly Val Gly Gly Thr
        1145                1150                1155

Ile Lys Ser Pro Lys Asn Asn Glu Lys Asn Phe Leu Cys Ala Ser
        1160                1165                1170

Glu Ser Cys Ser Pro Ile Pro Arg Pro Leu Phe Leu Pro Arg His
        1175                1180                1185

Thr Pro Thr Lys Ser Asn Thr Ile Val Asn Arg Lys Lys Lys Ser
        1190                1195                1200

Ser Leu Val Leu Thr Gln Glu Thr Gln Asn Cys Asn Ser Tyr Ser
        1205                1210                1215

Asp Val Ser Ser Tyr Ser Ser Glu Glu Arg Phe Met Glu Ile Glu
        1220                1225                1230

Ser Pro His Ile Asn Glu Asn Tyr Ile Gln Ser Lys Arg Glu Glu
        1235                1240                1245

Ser His Leu Ala Ser Ser Leu Ser Lys Ser Ser Glu Gly Arg Glu
        1250                1255                1260

Lys Thr Trp Phe Asp Met Pro Cys Asp Ala Thr His Val Ser Gly
        1265                1270                1275

Pro Thr Gln His Leu Ser Arg Lys Arg Ile Tyr Ile Glu Asp Asn
        1280                1285                1290

Leu Ser Asn Ser Asn Glu Val Glu Met Glu Glu Lys Gly Glu Arg
        1295                1300                1305

Arg Ala Asn Leu Leu Pro Lys Lys Leu Cys Lys Ile Glu Asp Ala
        1310                1315                1320

Asp His His Ile His Lys Met Ser Glu Ser Val Ser Ser Leu Ser
        1325                1330                1335

Thr Asn Asp Phe Ser Ile Pro Trp Glu Thr Trp Arg Asn Glu Phe
        1340                1345                1350

Ala Gly Ile Glu Met Thr Tyr Glu Thr Tyr Glu Arg Leu Asn Ser
        1355                1360                1365

Glu Phe Lys Arg Arg Asn Asn Ile Arg His Lys Met Leu Ser Tyr
        1370                1375                1380

Phe Thr Thr Gln Ser Trp Lys Thr Ala Gln Gln His Leu Arg Thr
        1385                1390                1395

Ile Asn His Gln Ser Gln Asp Ser Arg Ile Lys Lys Leu Asp Lys
        1400                1405                1410

Phe Gln Phe Ile Ile Ile Glu Glu Leu Glu Asn Phe Glu Lys Asp
        1415                1420                1425

Ser Gln Ser Leu Lys Asp Leu Glu Lys Glu Phe Val Asp Phe Trp
        1430                1435                1440

Glu Lys Ile Phe Gln Met Phe Ser Ala Tyr Gln Lys Xaa Xaa Xaa
        1445                1450                1455

Xaa Arg Leu His Leu Leu Lys Thr Ser Leu Ala Lys Ser Val Phe
        1460                1465                1470
```

```
Cys Asn Thr Asp Asn Glu Glu Thr Val Phe Thr Ser Glu Met Cys
    1475                1480                1485

Leu Met Lys Glu Asp Met Lys Val Leu Gln Asp Arg Leu Leu Lys
    1490                1495                1500

Asp Met Leu Glu Glu Glu Leu Leu Asn Val Arg Arg Glu Leu Met
    1505                1510                1515

Ser Val Phe Met Ser His Glu Arg Asn Ala Asn Val
    1520                1525                1530

<210> SEQ ID NO 12
<211> LENGTH: 5497
<212> TYPE: DNA
<213> ORGANISM: Homo sapiens

<400> SEQUENCE: 12
atacacaatc atcatcttac tagttctctg tgttgctcgc taaccagtcc cccagttcag      60
tagactggag cccagagcct gcttacttgt caggtgttta ttttgtcttg ctttttttt     120 ttttttaaat gaagtcaaaa tgccaataag accagatctc cagcagttgg aaaaatgcat    180
tgatgatgct ttaagaaaaa atgatttcaa acctttgaaa acacttttgc aaattgatat    240
ttgtgaagat gtgaagatta atgcagcaa acagttttc cacaaggtgg acaacccttat     300 atgcagggaa cttaataaag aggatatcca caatgtttca gccatttttgg tttctgttgg    360 aagatgtggc aaaaatatca gtgtattggg gcaagctgga cttctaacga tgataaaaca    420
aggactaata caaagatgg ttgcctggtt tgaaaaatcc aaggacatta ttcagagtca     480
aggaaattca aaagatgaag ctgttctaaa tatgatagaa gacttagttg atcttctgct    540
ggtcatacat gatgtcagtg atgaaggtaa aaaacaagta gtggaaagtt tcgtacctcg    600
catttgttcc ctggttattg actcaagagt gaatatttgt attcagcaag agattataaa    660
aaaaatgaat gctatgcttg acaaaatgcc tcaagatgcc cggaaaatac tctctaacca    720
agaaatgtta attctcatga gtagtatggg agaaaggatt ttagatgctg agattatga     780 cttacaggta ggcattgtag aagctttgtg tagaatgacc acagaaaaac aaagacaaga    840
actggcacat cagtggtttt caatggattt tattgctaag gcatttaaaa gaattaagga    900
ctctgaattt gaaacagatt gcaggatatt tctcaacctt gtaaatggca tgcttggaga    960
caaaagaagg gtctttacat ttccttgttt atcagcattt cttgataaat atgagctgca   1020
aataccatca gatgaaaaac ttgaggaatt ttggattgat tttaatcttg ggagtcagac   1080
tctctcattc tacattgctg agataatga tgatcatcaa tgggaagcag ttactgtgcc    1140
agaggaaaaa gtacaaatat acagcattga agtgagagaa tcaaagaagc tactgacaat   1200
aattctgaaa aatacagtaa aaattagcaa agagaaggg aaagaattgc ttttgtattt    1260
tgacgcatca ctagaaatca ctaatgtaac tcaaaaaatt tttggtgcaa ctaaacatag   1320
ggaatctatc agaaaacaag gtatttcagt tgccaaaacg tcgctgcata cttttttga    1380 cgcaagtgga tcacagattc tagtgccaga aagtcaaatc tcaccagtcg agaagagct    1440 cgttagttta aaggaaaaat caaagtcccc aaaggaattt gctaaacctt caaaatatat   1500
caaaaacagt gacaaaggga atagaaataa tagtcagctt gagaaaacta ctcctagcaa   1560
aagaaaaatg tctgaagcat caatgattgt ttctggtgca gatagataca ctatgagaag   1620
tccagtgctt ttcagcaaca catcaatacc accacgaaga agaagaatta aaccaccact   1680
gcaaatgacg agctctgcag agaaacctag tgtttctcaa acatcagaaa atagagtgga   1740
taatgctgca tcactgaaat ctagatcatc agaaggaaga catagaagag ataatataga   1800
```

-continued

```
caaacatatc aaaactgcta agtgtgtaga aaacacagaa aataagaatg ttgaattccc    1860
aaaccaaaat tttagtgaac tccaggatgt tataccagat tcacaggcag cggaaaaaag    1920
agatcatact atattacctg gtgttttaga caacatctgt ggaaataaaa tacacagcaa    1980
atgggcatgt tggacacctg taacaaacat tgaactatgt aataaccaaa gagcaagtac    2040
ttcgtcagga gacacattga atcaagatat tgttataaat aaaaaactta ctaaacaaaa    2100
atcatcctct tcaatatctg atcataattc tgaaggaaca ggaaaagtga aatataagaa    2160
agaacaaacc gaccatatca aaatagataa agcagaagta gaagtttgca agaaacacaa    2220
tcagcaacaa aatcatccta aatattcagg gcagaaaaat actgaaaatg ccaagcagag    2280
tgattggcct gttgaatctg aaactacttt taaatcggtt ctcctaaata agacaattga    2340
agaatcgctg atatatagga agaaatacat attgtcaaaa gatgtgaata ctgctacttg    2400
cgataaaaat ccatctgcta gcaaaaatgt gcaaagtcat agaaaagcag agaaagaatt    2460
gacttctgag cttaattcct gggattcgaa acaaaaaaaa atgagagaaa agtcaaaagg    2520
gaaagaattt accaatgtag cagaatcctt gataagccaa atcaataaaa gatacaaaac    2580
aaaagatgac atcaagtcta caagaaaatt aaaggagtct ttgattaaca gtggtttttc    2640
aaacaaacct gttgtacaac tcagtaagga aaaagttcag aaaaaaagct acagaaaact    2700
gaagactacc tttgttaatg ttacttctga atgcccagtg aatgatgttt acaattttaa    2760
tttgaatgga gctgatgacc ctatcataaa acttggaatc aagagtttc aagctacagc    2820 taaagaagct tgtgcggata ggtcaattag attggtaggt ccaaggaatc atgatgaact    2880
taaatcttct gtcaaaacaa aagataaaaa aattataaca aatcatcaaa agaaaaatct    2940
gtttagtgat actgaaacag agtacagatg tgatgacagc aagactgata ttagctggct    3000
aagagaaccg aaatcaaaac cacagctaat agactatagc agaaataaaa atgtgaagaa    3060
tcataaaagt ggaaaatcaa gatcatcctt ggaaaaggga cagccaagct ctaaaatgac    3120
acccagtaaa aatatcacaa aaaagatgga caagacaatt ccggaaggaa gaatcagact    3180
tccacgaaaa gcaaccaaaa caaaaaaaaa ctataaagat ctctcaaatt cagaatcaga    3240
gtgtgaacaa gaattttcac attcatttaa agagaacata ccagtaaagg aggagaatat    3300
ccattccaga atgaaaacgg taaagctacc aaagaaacaa cagaaagtct tctgtgctga    3360
aacagaaaag gaactatcaa aacaatggaa aaactcatct ctactaaaag atgctatacg    3420
agataattgc cttgacttat ctcccagatc tttatctggc agtccatcat ctatagaagt    3480
aacgagatgt atagagaaaa taacagaaaa ggatttttact caggattatg actgcataac    3540
aaaatctata tcaccttatc caaaaacttc atcacttgaa tccttaaata gtaacagtgg    3600
agttggaggt acaataaagt cacccaaaaa caatgagaaa aacttcctgt gtgcaagtga    3660
aagttgttca ccaattccac gaccactgtt tttgcccaga catactccaa ctaagagtaa    3720
tactattgta aatagaaaaa aataagttc tctggtactt acacaagaaa cacaaaacag    3780
taacagctat tcagatgtaa gcagttatag ttcagaagaa cggtttatgg aaattgaatc    3840
tccacatatc aatgaaaatt atatacaaag caaagagag gaaagtcatt tagcatcttc    3900
attatccaag tctagtgaag gaagagagaa aacgtggttt gacatgccct gtgatgctac    3960
tcatgtatca ggccccaccc aacatcttag tcgcaaaaga atatatatag aagataatct    4020
aagtaattcc aatgaagtag aaatggaaga gaaaggagaa aggagagcaa acttgcttcc    4080
caaaaaactg tgtaaaattg aagatgcaga tcatcatatc cacaaaatgt ctgaaagtgt    4140
atcttcatta tcaacaaatg acttttctat tccttgggag acctggcaaa atgaatttgc    4200
```

```
agggatagag atgacttatg agacttacga gaggctcaat tcagaattta agagaaggaa    4260
taatatccga cataaaatgt tgagttattt tactacgcag tcttggaaaa cagctcagca    4320
acatctgaga acaatgaatc atcaaagtca ggactctagg attaaaaaac ttgataaatt    4380
ccaattcatt atcatagagg agctggagaa ttttgaaaaa gattcacagt ctttaaaaga    4440
tttggaaaag gaatttgtgg acttttggga aaagatattt cagaagttca gtgcatatca    4500
aaaaagcgaa caacagaggc ttcatctttt gaaaacttca ttggctaaaa gtgtcttctg    4560
taatactgat agtgaagaaa ctgttttac atccgagatg tgtttgatga agaagatat    4620 gaaagtgctg caagacaggc ttcttaagga catgctagaa gaggagcttc ttaatgtacg    4680
cagagaactg atgtcagtat tcatgtctca tgaaagaaat gctaatgtgt gaaatctagt    4740
ttttatcacc atactttatc taattattat tctctgtata taactgagga ataagaata    4800 gtcctacaaa gagaaaaata tacatgtcac cgaagcaagt gtacccttta taggaaccct    4860
caaattaaaa aaaaatgtct tttaatggat gagagggaac cactataaca tgagtccaag    4920
cccagaagac ttctgtctat acaatatttt tttttaattt tggagataaa gctttaaga    4980 aacttttga gttaattata ctcataaaat gagtttcttt aataaattaa atttattgt    5040 gtaaaatgta ttattacata aaatgtgttt ttgaatcaat gcagtttggg gatgaatata    5100
attaaaatat gtttaataac ttagaattca actaataaaa atttagccac acttacaagg    5160
gggaggaagt ccctagttta aaatgtataa ctgagtggta gatcagtact ttcagcacac    5220
tgttggaaac atttattcag atatggctct aatgtattag gaagcactaa atggcctaaa    5280
aaagctacta cattgcctaa atatgttaat tcaatataga agtcctattt cataaccagg    5340
ctgtttgaca aatacttta atctagtagt cattgtaata tcttgctaga ttaattata    5400 aaaatgagta tactttgat ttgcttttaa tgaagttgaa ataaatgctt atgtcacttg    5460
aataaatata aatcattata aaaaaaaaaa aaaaaa                              5497
```

<210> SEQ ID NO 13
<211> LENGTH: 5688
<212> TYPE: DNA
<213> ORGANISM: Mus musculus

<400> SEQUENCE: 13

```
atcacttccg gctgacccat cgtggacagg gcaggggtca tcggaagtgg ggcaaccgac      60
cgacccttcc cagaagcgct gcgtgtgcgc ccacagccta agtgtctgc gggtgtttgt     120 cttctcctat tcttaaatga gttcaaaatg ccagtgagac cagacctcca acagttagaa     180
aagtgtattg atgatgcttt gagaaaaaat gacttcaaac cttttgttggc acttttacaa     240 attgatattt gtgaagatgt gaagattaaa tgcagcaaac aattcctccg caagttggat     300
gacttaatat gcagggaact taataaaaag gatatccaaa ctgtttcaag catcttgata     360
tctattggaa gatgtagcaa gaatatcttt atattgggac aagctggact tcaaaccatg     420
ataaaacaag gattagtcca aagatggtt tcctggtttg aaaattccaa ggagattatt     480
ctaaatcaac aacaatcaaa agatgaagct gttatgaata tgatagaaga cttatttgat     540
cttttgatgg tcatatatga catcagtgat gaaggtaaaa accaagtatt ggaaagtttc     600
atacctcaaa tctgtgccct ggttattgat tcaagagtga attttttgcat tcagcaggag     660 gctttaaaaa aaatgaattt gatgcttgac agaatacctc aagatgccaa caaaatactt     720
tctaatcaag aaatgttaac tctcatgagt aatatgggag aaaggattt agatgtagga     780 gattatgaat tacaggtagg cattgtggaa gctttgtgta gaatgaccac agaaaaacgg     840
```

```
agacaagaac tggcatatga atggttttca atggacttta ttgctaatgc atttaaggaa    900
attaaagact gtgaatttga aacagattgc agaatatttc tcaacttggt aaatggcatt    960
cttggtgata aagaagggt ctatacattt ccttgcttgt cagcatttct tggtaaatat   1020
gagctgcaga taccatcaga tgaaaaactt gaggaattct ggatcgattt taatcttggg   1080
agccacactc tgtcattcta cattgctgga gatgaagaag atcaccaatg ggaagctgtc   1140
actgtacctg aagaaaaagt tcagatgtac aacattgaag tgagagaatc aaagaagcta   1200
ctgactctaa ctttgaaaaa tatagtaaaa attagtaaaa aagaaggaaa agagttactt   1260
ttttattttg atgaatcatt agaaatcacc aacgtgacta aaaaagtttt tggtggaaat   1320
aagtataagg aatttaccag aaaacaaggt atttcagttg ccaaaacatc tattcatgta   1380
cttttttgatg caagtggatc acagattcta gtaccagaaa gtcaaccatc tccagtcaaa   1440
gaaaacctca ttcatctaaa agagaaatcc gacatccaaa agaaacttgt aaaccctcta   1500
gaactaggca atagcagcag ccaggatgag atcactacac ctagcagaaa gaaaatgtct   1560
gaagcatcaa tgattgttcc tgatacagac agatacactg tgcgaagccc aatacttta   1620
atcaacacat caacaccgcg aagaagtagg gaaccactgc aagcaataaa ttctgtggag   1680
aaagctgttt ctaaaacatc agaaagtgga atggattatg ctgcgtcacc caaatctaga   1740
caatcagatg aagaaaaag atggaataat agagccaacc ataacaaaac tactgctgtc   1800
atacaaaaca aacaatacga ggataatgaa tccccagacc aaaatttcaa tgaaattgag   1860
gacactctct ctaatgtatc ttctgcagtg ggaaagtag acaagcctgt attgcctggt   1920
gttttagaca tctcaaaaaa tacaacacac tccagatggg catgttggac acctgtaaca   1980
actatcaaac tctgcaataa ccagagaagc cgtgctttac ctggagacac ttgtacccaa   2040
gatactggtg tcaacaaaaa atgcactaaa caaaaatcag tatcagatga tgattctgaa   2100
gaaacacaaa agggaaaata tagtaaagat gtaatcaagt gtaacaagtc agatgaagca   2160
gaattttgtg aaagaaacat tcaagaacaa atcatcccta atattcaca aaagaaaaat   2220
actgcaaatg caaagaagag tgattggcat attgaatctg aaactactta taaatctgta   2280
ctcctaaata agacaactga agaatctctc atctataaga agacatgtgt attgtcaaaa   2340
gatgtgaata ctactatctg tgataaaagc ccttctagaa aaagcaagag gaatcataca   2400
aaatcaagaa aggaactgat gtctgaactt acatcatgtg agctagaaga ataccagtg    2460
agagaaaatt caaaagggaa aagatttact ggtgcatcag aatccttgat aaaccaaatt   2520
agtaggagat ataaccccaag tgatagcatg atgtcaacaa gaaaactgaa ggagcctcag   2580
gatggcagtg atttttcaaa aaaacctgat ctgcagttca ataaggttca gagaaagagt   2640
tacaggaaac tgaaggcaac tgttgtcaat gttacttctg aatgtccact ggatgatgta   2700
tataatttca gcttgaatgg tgccgatgaa cctgttataa aacttggaat ccaagaattt   2760
caagctacaa ctagagaagc cagtatggat aattcattaa aattggtaaa gaatcatgat   2820
gaacatgacc cttttctcaa aacaaaagat aaaagaatgt aagttatga gaagaaaact    2880
ctcttaagtg acactgaaac cgaatgtgga tgtgatgaca gcaagactga cattagctgg   2940
ctaaaagaac caaaacaaa aagactaatg gattatagta gaaataaaaa cacaacaaaa   3000
tataaagta gaaaatcaag atcatccatg gaaaaggac aaccaagacc cacaatggta   3060
ctcaataaaa acagtatgaa aaatgattat gaagtagttg tagatgggag aaccagactt   3120
ccacgaagag caacaaaaac aaaaaaaaat tataaagatc tttcaacttc agaatcagaa   3180
tcagagagtg aaaaagaatg ttcatatttg tttaaagata aactgccaac aaaggaggag   3240
```

```
actatccatt ccagagccca aacaaagaaa ctgcccgaga acaacagaa agtcttcaat   3300 tcagaagcgc tgaaaggaca gccatcagaa gaacagaaaa actcctctcg gctgagagaa   3360
gggagagaag acagtctgtg cctgtcttct gcgtctgtgt ccaggagctc gtcctctgtg   3420
gaagtgatga gatgtacaga gaaaataaca gaaagggatt ttactcagga ttatgactat   3480
atcacaaaat ctcttttcacc ttatccaaaa gctccatcac ctgaattctt aaatggaaac   3540
aatagcgttg taggtcgggg acaatcaccc agaattagtg agaccagtgc aatgtgtgta   3600
agaaagagtt actcacctgc ttcaggaccg ccctttttcgc caagacacac tccgaccaag   3660
aataattctg ttgtgaatat gaaaaaagca aattcagtga taaataatca gagaacccaa   3720
cattgtaaca gctattcaga tgtaagcagt aatagctcag agaaacttta tatggaacct   3780
gaatctccag agagctgtga caaccatatg caaaacaaga gagagggaaa tcatgcagca   3840
tctccattat cattgtctag tgaaaaaata gagaaaatgt ggtttgacat gcccagtgaa   3900
aatactcatg tatcaggtcc cagtcaacgt ggtagcaaaa ggcggatgta cctagaagat   3960
gatgagctaa gtaattccaa tgaagcagaa gtagaagagg cagaagaaag ggaacatttg   4020
ctttccaaaa aacgatgtca atgggaaaat tctgaccagc acaccttcaa aacttcatta   4080
tcgacaccag atttttctgt tcctaaggac tggcaacaag agttacaagg tgctggaatg   4140
ttttatgata acatcagctc agactataaa aggaaaactg atagccaaca taaaatcatg   4200
gatgatttta ctacaaagac attgaaattg actcaacaac atctgatggc aatgacctct   4260
caagctcagg gacgcaggga tgaaaatgtt gagaaattcc aagtcactct cctagatgag   4320
ctggaaaaag ttgaaaaaga ctcacagact ttgcgagact tggagaaaga gcttgtggac   4380
atcgaggaaa agttagttca gaagatgagg gcatatcacc gatgtgagcg agagaggttt   4440
cgtgttttga aaacttcact ggataaaagt tttcttgtct ataattctgt ttatgaagag   4500
tctgttttta catctgagat gtgtttgatg aaagcaaaca tgaaaatgct acaagacaag   4560
ctacttaagg agatgcatga agaggaagtt ctcaacatac gcagaggact acagtcatta   4620
ttcaaggctc atgaaggaaa tgatgcatga aatctggctg ctgtcaatga attttatgat   4680 tagtttttttg tgtataaaata aagcactaat aaagtagctt tgcaaagatg catcatctaa   4740
gcacctctat tcttgtgtgc aagaacctcc cgactcaaat gttagagatg aaaaacatga   4800
ctccaaatgc agcttgtatg tcctatgagc aaacagtaaa aggagctgac tttccttgga   4860
tcatattttt atattaacta tgtctgtgaa agtagtgtct gtactaaagt atttatatat   4920
aaagtgtaat tttaaattaa tgcagttttg gaataaaata tactgaaatt tgcatgatgg   4980
tttgtaaata tacaagtatt aaaatattag caattctttg aaagaggaaa aggctctgct   5040
ttaagatctt taattgttag taccttcata ctttgagata tatagagtta cagtgcacta   5100
aaagtgttaa agtgacctaa agttatagct atttcataaa tattttatca cagtgtagaa   5160
gtcttaacta caaagcaggc tgcttgccat ttctttctaa gcacctggta ttcacctaat   5220
attttgttag attgtatttt aaataaatgc ttatttgagt aagtataatt actttacagt   5280
tactattatt gtgtttatg aaccatgact tacaagccac cttcagtcag acacttgaag   5340
gtaataccaa tctgaaggct gtagagtatt tgagcaatac cagcatttaa tattacagtg   5400
gtgaagtagt ttcttagtca agcacaaata cattcttggt gtattcaatt gacatcagct   5460
aagattttaa gatttatgag gaaaatgatg ggagtttcta gttttaagaa agagagagat   5520
tttacatttt attagccctt agatgaactg tgtgtacaac aaagaactgc taagattaat   5580
tttgtaactc ttgtttttttg agacatggtc tgtgtagacc tggctaaccct caaattcagt   5640
```

| | |
|---|---|
| tctgcctgca aacattaaag ccatgggccc aaacaaatgt ccttcaaa | 5688 |

<210> SEQ ID NO 14
<211> LENGTH: 4771
<212> TYPE: DNA
<213> ORGANISM: Rattus norvegicus

<400> SEQUENCE: 14

| | |
|---|---|
| cgttggctcc caggagactg aggaggcgcc ataacactcg acggcccttg ccggcggagg | 60 |
| tggtcgccag gtcccgggtg tcctggctgc aggtggcgca ggtctacggg agaccgtggt | 120 |
| gtctgtcctc tcctattctt aaatgaagtc aaaatgccag tgagaccaga cccccaacag | 180 |
| ttagaaaagt gtattgatga tgctttgaga aaaacgact tcaagccttt ggtgacactt | 240 |
| ttacaaattg atatttgtga agatgtgaag attaaatgca gcaaacaatt cctccgcaag | 300 |
| ttggatgact aatatgcag ggaacttcat aaaaaggata tccaaactat ttcaaacatc | 360 |
| ttgatatcta ttggaagatg tagcaagaat atctttatat tgggacaaac tggacttcaa | 420 |
| accatgataa acaaggatt agtccaaaag atggtttcct ggtttgaaaa ttccaaggag | 480 |
| attattctga gtcagcgaca atcaaaagat gaagctgtta tgaatatgat agaagactta | 540 |
| tttgatcttt tgatggtcgt atatgacgtc aatgatgaag gtaaaaacca agtattggaa | 600 |
| agtttcatac ctcacatctg tgccctggtt attgattcaa gagtgaattt ttgcattcag | 660 |
| caagaggctt taaaaaaaat gaatttgatg cttgacagaa tacctcaaga tgccaacaaa | 720 |
| atactttgta atcaagaaat attaactctc atgagtaata tgggagaaag gatttttagat | 780 |
| gtaggagatt atgaattaca ggtaggcatt gtggaagctt tgtgtagaat gactaccgaa | 840 |
| aaacggaggc aggagctggc atatgaatgg ttttcaatgg actttattgc taatgcattt | 900 |
| aagaaaatta aagactgtga atttgaaaca gattgcagaa tatttctcaa cttggtaaac | 960 |
| ggcatgctgg gtgacagaag aagggtcttt acatttcctt gcttgtcagc atttcttggt | 1020 |
| aaatatgagc tgcagatacc atcagatgaa aaacttgagg aattctggat tgattttaat | 1080 |
| ctcgggagcc acactctgtc attctacatt gctggagatg atgatgatca ccaatgggaa | 1140 |
| gctgtcactg tgcctgaaga aaaagttgat atgtacaaca ttgaagtgag agaatcaaag | 1200 |
| aagctactga ctctaacttt gaaaaatata gtaaaaatta gtaaaaaaga aggaaaagag | 1260 |
| ttactttttgt attttgatgc agcattagaa atcaccaatg tgactaaaaa acttttttggt | 1320 |
| ggaaataagt ataaggaatt taccagaaaa caagatattt cagttgccaa aacatccatt | 1380 |
| catgtacttt ttgatgcaag tggatcacag attctagtac cagaaagtca accatctcca | 1440 |
| gtcaaagaaa acctcattca tctaaaagag aaatctaacc tccaaaagaa acttacaaac | 1500 |
| cctctagaac cagacaacag cagcagccag cgcgacagga aaaacagcca ggatgagatc | 1560 |
| actacaccta gcagaaagaa aatgtctgaa gcatcaatga ttgttcccga tacagacaga | 1620 |
| tacactgtgc gaagtccaat actcttaatc aacacatcaa ccccgcgaag aagtagggca | 1680 |
| ccactgcaag caatacattc tgctgagaag gctgtttcta aaacatcaga aagtggagtg | 1740 |
| gattatgctg tgtcactcaa atctagacaa tctgatggaa gaaatagagg gaacaataga | 1800 |
| gccaatcata acaaaactgc tacagtacaa aacaaggac atgagcacca tgaatcccca | 1860 |
| gaccaaactt tcaatgaaat tgaggaaact ctctctgatg catatgcagt ggaaaaagta | 1920 |
| gacaagcctg tattacctgg tgttttagac atctcgaaaa ataaagcaca ttccagatgg | 1980 |
| gcatgttgga cacctgtaac aactatcaaa ctctgcaata accagagatc ctgtgctta | 2040 |
| ccaggagata cttttaccca agatactggt gtcaacaaaa aatgcactaa acaaaaatca | 2100 |

```
gtatctgatg atgattctga agaaacacaa agggtaaaat atagtaaaga tgtcatcaag    2160
tgtaacaagt cagaagaagc agaagtttgt gaaagaaaca ttcaagaaca aaatcatcct    2220
aaatattcac aaaagaaaaa tactgcaaat gcaaagaaga atgattggca tattgaatct    2280
gaaacaactt ataaatcagt actcctaaat aagacaactg aagaatcact catctataag    2340
aagacgtgtg tattgtcaaa agatgtgaat actactatct gtgataaaag cccttctaga    2400
aaaagcatga ggagccatac aaagtcaagg aaagaactga tgtctgaagt tacttcatgt    2460
gagctagatg aaataccagt gagagaaaat tcaaaaggga aaagatttac tggtacagca    2520
gaatccttga taaacctaat taataagagg tataactcaa gtgatgacat gatatcaaca    2580
agaaaactga aggagcctcg ggatggcagt gggttttcaa agaaacctga actgcagttc    2640
aataaggttc agagaaagag ttacagaaaa ctgaagactt tgttaatgt tacttctgaa     2700 tgtccactga atgatgtata aatttcagc ttgaatggag ccgatgagcc tgttataaaa      2760
cttggaatcc aagaatttca agctacaact agagaagcta gtatggataa ttcaataaaa    2820
ttggtagatg taaggaaccg tgatgaacgt gacctttctc tcaaaacaaa agatgaaaga    2880
atattaagtc atgagaggaa aactctcttc agtgacactg aaacagaatg tggttgggat    2940
gacagcaaga ctgacattag ctggctaagg aaaccaaaat caaaaagact aatggattat    3000
agtagaaata aaaacacaaa aaaatgtaaa agtataaaat caaggtcatc cacggaaaag    3060
ggacagccaa gatccacagt ggtactcagt aaaaacattg cgaaaatga ttatgaagta      3120 attgtagatg ggagaaccag acttccacga agagcaacaa aaacaaaaaa aaattacaaa    3180
gatctctcaa cttcaggatc agaatcagag agtgaaaaag aaatttcata tttgtttaaa    3240
gataaactac caacaaagga ggagactgtc cattccagcg cccaaacaaa gaaactgccc    3300
aagaaacaac agaaagtctt caatacagaa gcgctgaaag gacagccttc agaagaacag    3360
aaaaattcat ctacgctaag aaatgggaga gaagacagtc tgtacttgtc ttctgcatct    3420
gtgtctggga gctcgtcatc tgtggaagtg atgagatgta cagagaaaat aacagaaagg    3480 gatttactc aggattatga ctacatcaca aagtctcttt caccatatcc aaaagctgca     3540
tcacctgaat tcttaaacag aagcaataga gtggtaggtc atggaaaatc accaagaatt    3600
agtgagacca gtgcagtatg tgtgagaaag agttgctcac ctgcttcagg actgccttt     3660 tcgcccagac acacaaccaa gaataattct gttatgaata taaaaaatac aaattcagtg    3720
ataaataatc aaagaaccca acattgtaac agctattcag atgtaagcag taacagttca    3780
gagaaacttt atatggaacc cgaatctccg gatagctgtg aaaaccatgt gcaaagcaag    3840
agagaggaaa atcatgcagc ctctccatt tcattgtcta gtgaaaaaat agagaaaata     3900
tggtttgaca tgcccaatga caatactcat gtatcaggtc ccagtcaacg tggtagcaaa    3960
agacggatgt acctagaaga agatgagcta agtaatccca gtgaagcaga agtgcaagag    4020
gcagaagaaa gggaacattt ggtttccaaa aaactatgtc aaagggaaca tttcgatcag    4080
catacctctg aaacttcatt atcaacacca gagttttctg ttcctaagga ctggcaacag    4140
gagttacaag gtgctgggat gttttatgat aacatcaact cagattataa aaggaaaact    4200
gacacacaac ataaaatcat ggatgatttt actacaaaga cattgaaact gactcaacaa    4260
catctgttgg caatggcctg tcaagctcgg ggacacaggg atgaaaatat tgacaaattc    4320
caagtcactc tcctagatga gctggaaaaa gttgaaaaag actcacagac tttacgagac    4380
ttggagaaag agtttgtgga catcgaagaa aagatagttc acaagatgag ggcatttcac    4440
caaagtgagc gagaaaggtt tcgtgctttg aaaacttcat tggataaaag tttgcttgtc    4500
```

| | |
|---|---:|
| tataattctg tttatgaaga gaatgttctt acatctgaga tgtgtttgat gaaagcaaac | 4560 |
| atgaaaatgc tacaagacaa gctactgaag gagatgcatg aagaggaact tctcaacata | 4620 |
| cgcagaggac tggagtcatt attcaaggat catgaaggaa acaatgcatg aaatctggct | 4680 |
| gctgtcaaca cactttatct gattagtttt tgtgtatgaa tgaaaaaata ataaagtagc | 4740 |
| cttgcaaata tgaaaaaaaa aaaaaaaaa a | 4771 |

<210> SEQ ID NO 15
<211> LENGTH: 208621
<212> TYPE: DNA
<213> ORGANISM: Sus scrofa

<400> SEQUENCE: 15

| | |
|---|---:|
| gatccttaac ccactgagca aggccaggga ttgaacctgc gttcccatgg atcctagttg | 60 |
| ggttcattaa ctgctaagcc atgatgggaa ctcctcatgg tgtaaacttt taatttatat | 120 |
| tcctggtgct tgtgctgagt gcttgcttta tctcatttaa tcgataaaac atccttataa | 180 |
| gggacatggt attatagctt gggttctagg acacgggct cccaggttct cagagccgtg | 240 |
| aagggagtgg ctcttggcct tgcaggttca atgagtggtg aggtggaatt cacccaggaa | 300 |
| gaccagtatc ccagctttgg ctctgtacca cctcgacatg aaccgtaaat catggatctg | 360 |
| ccccttagt cggagagctt cagagaagat gacttaggtg acacagagaa ttttgttgca | 420 |
| agcggttttt tttgttttgt tttgttttgt tttgttttgt tttacatcta aagaaatccc | 480 |
| tgcaaaaatt caagacaccc aaatctctta aaaagctcct ggaattgatg tgcatctgat | 540 |
| tcgtgttcct tcaacttagc ggtagacaga gtcgccctgc ttggcagtgg cctcacgttc | 600 |
| tggagtggct ttcccaggag gagccttcat ggggcttggg gagaggtccc aggtgaagtt | 660 |
| acctgggttg gcagtgtcct catgcgttct tagaagctgg ggccggggcc ccttacaagt | 720 |
| tactgtgcaa acctatcttc cctttctgt ctttggtccc gagaccttct tacttggaag | 780 |
| atttgagatg atgtccccaa ggccggggga gcaggcagtc gtgtcagcgg gcggggtgtt | 840 |
| cgctctctcc tactcgttga agatgtccc aggccacctg gttcctctcc cagtcgctgc | 900 |
| gtggctgtgg ctgaccttgg accgaaatgc cccttactgc ccagaatttc catccggtcc | 960 |
| catcaggagg ggaaatgtgg atgctgcgtt tgtgtctgag cttcagcggg accccagccc | 1020 |
| cagaatcagt ggttccacct gcctggacca tcagcgggga cgtctcctcg tgtgcacctg | 1080 |
| tgcctgagag gtgacgagaa gggcagcagg ttccagcgtg aggaaagggg cggggctgaa | 1140 |
| atttggggat ggcacctata gatcacgaaa gggcactctt ccccaggcaa tgccaatcgt | 1200 |
| ggtccgtctt cgttcatttc gttccagaag gagatctaat tttaatttct attaggtcga | 1260 |
| tcggtacgaa attcccactt tgtgtagtttc gtgacagcca aactttggca aattcgaatg | 1320 |
| gctccattta gcacaacaaa ataatttaaa tctgaggaag aggccggtca gccctttgcg | 1380 |
| tggctcagtg ttttcaaaag gatgttgaca cggttcagcc gtacgtctct tgtgtgtggc | 1440 |
| gagcagctgt taatggttaa ggcgttgtgg ctgccctacg cgtggcctct tgtcaccaag | 1500 |
| agtctcctgc ctctccaagt ggcaggaatc tcattgcgag gccattcct gatctagata | 1560 |
| agaacccatc agatctcatg aaaatttaat gtgtcaaagt gtatagttgc atgagttttt | 1620 |
| tttttaataa actatttcat agcccttggt aacgccagat aaatacattg ataataagcc | 1680 |
| tcctccaggg gctgtggggt tgccaggtgg cccactagga tgacctctgc tctctctctt | 1740 |
| atttgtggct tttccttaaa ggaattcctg ccttttgttt ttcttcctca agtagatttc | 1800 |
| aagtttgaca gattctgggg gttttaactg gattttgtgc ttttttgcctg aaggatggag | 1860 |

```
tgacagccct gtgtgcacct tccctgggg ccacggttga cccacggtcc ccagctgagc   1920
ctcagtttgg gggtctttaa actggctttg ggggactcgt caggcttgcc caaatttggg   1980
tcttagtgat tggttcctct cccagtttca tcaggggcct ggctgaggtt gatatcaacc   2040
ttgtcacatg tcacaatcag ggaccccctag gtgacctgga gaggtccgtg acctgcctgt   2100
ggtcatggag ccagtatgac agggcgccac ccgccctccc tggcttcctc caggtcatct   2160
gatgagattg caaactcctt gaaagcaggg tgccgtgttg agacccaac agccacgctc    2220 aggagactag cacctctggc caccaagctc accatttctt tgggtgagcc ccgcacagag   2280
tgggccacac cctgccaagt ggagtggcca ttctgggtgc acagacgtgt caataaacac   2340
gattaccacc caggaggtac ccacgggctc acgtgcacag cccatggag actggagcag    2400 gtggagccgc ggcctctgag gtcccccaat ccctgtgctc tttgcttttg agaacactca   2460
ttgtgggcag tgccatgatg gtgtcttggg ccagcccac gggcgacaca cagctgaggg    2520
catccactga gcaaggggcc acgttctatg ttcccatatt tgtgcattta ggctgaccct   2580 gcccccgtc cagccagagt cctcaaggag tgtgcccagc aagagctctc gatctttctt    2640
tgatctgagg ataccggttc tcctgaattt tgttcgctgt gcatcccccc caccgccctg   2700
ccacccaccg ccccagatc tttaaaaagt cttgttctcc ttccaagtgt cttaggctct    2760
tgccctaatg gccacttctc ctaaaagcct cgaacctggc ccttgcagct tccagaaggc   2820
accacagatt tttttttttt ttcatttgtc tttggtgttt tgctttgggg agagaatatt   2880
cattctgtgg acaattaaag acttgataaa aagtgccttt tatgagtccc ttgaaaaccg   2940
tgagatgtgg gccggggtct gtggagtctt gcactcatgc aacagaaact tattgagtgc   3000
ttatggtgtg ccagacgctg tgatccagga aggccaggaa aaactggagc ctagaaaaac   3060
tgacagcgga gaaggcgggg ttgggagcta acgcttatta aacacagctc tgtgccttcc   3120
aggtgcgtca actcatttca tcctcacaag agctgttggc ggtgggtgct aacgtcaccc   3180
ccgtgtcacc tatgtcagga aaccgagcct cagagaggcg aagtgccttg cccgagtttt   3240
cagccattaa taagagctgg cattggcacc cagtctattc tggcctgtgg aagcccagcg   3300
cggcaatgct acagtccgct ttgtaggcta aacccacagt ggccactgct ctttcaaggg   3360
tccttcctga gcactgactg tgtgcgagat tctgccctgc ctgatggtgg tgggcaaggc   3420
atacctgtct ccctgccttg atggactgag tccacaagaa atcccatgca tccagcaatt   3480
tggatgctgt gtgagatgtg atatcagggg ctgatgatag aggggctcag cgtgcccaga   3540
gcgggacccc cagtcccgag ctgggactgg cttttgagag gaagtgaaat ttaagctgtg   3600
acccagagca ggagttggcc aggccaggag aagagtctta taaggaaag catgaataga    3660 attcctgaag caaaagaaaa aagatgctgc agaactaagt aagagccagt ctagttgggc   3720
gagtgatgag gtggcgagaa ggcaggacca daccccacgg ggagggcact ctgggcctct   3780
tgggctccct cctcagggca gcagatctgc acccaaaagt ttttgttttt gttttcttt    3840 agggccatac ctgcagcata tgaacattcc tagagtcaaa ttccgaggag tcaaatcaga   3900
attgggactg ccgccctacg ccacagctac agcaatgcca gatctgagcc acctctgtga   3960
cctatgctgc agctcagggc aacactggat ccctaaccca ctgagcaagg ccagggatcg   4020
aacccgcaac ctcatggttc ctagttggat tcgttaacca ctgcgccacg acgggaactc   4080
actagttggg ttcttaacct gcagagccac aataggaact cctgcaccca agaggttgtt   4140
tttttttttt tttttttttc tgcactcata gcatgcagaa gttccagga cagggatgga    4200 acctgagcta cagcagtgac aatgccaggt ctttaaccac ttggccacca ggaaactccc   4260
```

```
aagggaaatg cattgagccc tcacgaccct gggagaacaa tgtggacag acaggcagag      4320 tccccgctct caggggcttt gggttccagt agaacagcaa atggatacat acactgacag      4380
cggcagggag cagtgtgtac cccaaaggca gtgaaaaagg aggaagtggg ctgcgggagg      4440
tacaggaagg tagaggaagg aggggagggc tttggagaag aggagccagc aatgtggcaa      4500
agttggggga cagcattcca ggcggagggg acggcaggtg caaaggccct gagacagcaa      4560
caaactgggc atgctcaggg aacacagcag ggttagcgtg gctggaacag agggaatgag      4620
gaggagcagg tgcccattga ggcagagggg tcctcagggg tcttgggttt gatcccaaag      4680
gcgggagaag ccactagaag gttaggcagg ggatggagag gcctgatttt acttttgacc      4740
agccctcggc ttctgcgcgg ttaatggact ggggagcagc aagaatggaa gttggaattt      4800
ggggcgggga cctgagctcc tgacgtcacc tatgctccag aagatgggga attgacttga      4860 gcggggccg tggggagtgg agcccagatg ggcttgggag atgctgcaga gcaagcttgc      4920
tttgcggaag agcttctggt gggagggggt gagggccgca gcttatggca ggcagtcctg      4980
ggtcctgggt tccctcccga aatcagaaag accccgtgg ttctcagcca gctcacagaa      5040
ggacctgaat gaggatgcca gcaggcccta agcatctagg tttttctttc tctcttttt      5100 ttttggcagc tcaatgagct ataattcaca tattatccaa gtgacccacc cagagtgcac      5160
aattcaatgg cctttagttt attcacagcg ttaggccaca tttaccacaa ttcaacttta      5220
ggacactttc gttacctccc aaagaaacct cattcccatt aagtaacccc attttcccct      5280
cccccagccc ctggccacta ctaatccatt ttctgactct gcagatttac cgattctgaa      5340
tatttcactt aaatggactc ttaacaagaa gtgatctttt gtgactcgtt atttcacctg      5400
gcatcatgtt tttagggttt acccagaaac ctcctccctt tttatgacca ataatattc      5460 cactgagcag atgcaccacg tgctatgtat ctgtctgtgt gttgttggtg ttccctctgc      5520
tttttatgac gagggctgct gtgaacattc acaggcaagg tgcctggaca caagtgttca      5580
gtatttggcg tggaaaggga tacacccctg agtggagctg tcacctggta agtgggtttc      5640
actgggggaa gctgccggat ggttttctgg gcagccccct gtttctcatt cccaccagca      5700
gtgtgtcgat ggttctgatt tctcgcccac ccacccacac ttgtgactgt ccccagacac      5760
acccgggtcc acttacctga gcagttgccc acgatttata aaacaggtgc acaggatgg      5820 cacccgcccc ccccccgggg gggggcgtg accaggacgt ttatctgctt ccgagagtca      5880
gggtgacttg ggaccaggt cctcttgttc tctcctctcc cgccttccct tcgtcccact      5940
ggagggaagg acacgagctc tcagccttaa cttcatgtac ttaatggacg aggaaggaaa      6000
taatttctga ggccgagacc tgaggggtcc ccaaggactc tgttttgaca atgcacttaa      6060
acttccacga gggcatttgc ctgttggctg ggaactgtgg ccaaggacct ttcagcattt      6120
tatggttata aaaggatctc gagagtaatg actcttgaaa aaggcgtttc agtggggagg      6180
acggggatgc ctttgggtcc acagcctcgc tgaggtttgc aaaaggctgt cagacgagtt      6240
tcgcctttgg catcacactc tggtctaggc accctcgggg gcaggtgagc aacggagacg      6300
cggtgcagaa atccccttct cttggtatga ttcgaagccc actctacacc cagagctgtc      6360
gcccttgctg tgggatcctg gataagtcac tctgccttcc tggtctctgc ttgtctcttt      6420
gccacatggt tcctgatggc cgtgagctca gtgggctgg gagcccaggt aggcagtgag      6480
ctcgggtcag ccgtgagctt aggtagacaa tgagctcagg tgggctgaga gcccaggtgg      6540
gatgggagcc tggaaggct gggagctcag tgaggacagg cacgtctagt tttctggtca      6600
ccgtcacccc agcacctcac cagagtagca ggttgtctta gtctgggctt tttgcaaggt      6660
```

-continued

| | |
|---|---|
| gaccctgggg tgagggtttg agtggtctcc caggagacac tggttaaggg aacaggggca | 6720 |
| gccactcagg gaaggggaag gggaggccca ggcggagggt ggtcccaggc tgagtcctgc | 6780 |
| agagggcgct gcggcctgat cctgctcctc agaggctgag cccctcggag gggagggctg | 6840 |
| gatgctggct cctgtaaagc cagtcactgg ctcaggccgc caggccatgt tgacttcagc | 6900 |
| cctttcttct ctccacgctt gagggcaaag ggcaatgcat ccctgtgccc tccggggttg | 6960 |
| ggggtggggg gcagcgaggg tgcaggtttg ggccgtgaga ggcaagggca cacggaagcc | 7020 |
| gggtgaggcc acggccatgg tgaaggactc cagggcccag ggagaccgcg atggtgcctg | 7080 |
| cgggggggaca ggccccatcc tgcgtcctgt cctgatgggc cttgcaggac agggccgcca | 7140 |
| gcttcctcag tgtgcagttg gtatggtttt ccacgtgctc ggacaccagg agaacgtttc | 7200 |
| gattgtcagc tcaggtggtg cctccacgtg gccgtggttt gagccggggt gatgagtccc | 7260 |
| acagcgaaga cgctttgaaa tgtgtggtcc ctaacgagtt ttgcgtttag ggtgatggcg | 7320 |
| aggtttgcac cctgcatgag gctttctggt tttgtggctc tttcacacga gcatgaatcc | 7380 |
| cagtcctgat gtgtgtgtag gttcgtgttt ggcaccctga cccgccttct cccggacccc | 7440 |
| cgagtcctca ttctgcaaag ggctggatcg acacgtgaac agagaggcca cgcccggaag | 7500 |
| cgagtcagcg ctagatgcct ggggagcctg ctctgcccag tgtggacctg ctggggctgg | 7560 |
| agtcattgca tcgtatattc cccaggacac tgggtatcat cggctcgagg ccaggcacct | 7620 |
| ccgctcagat gcaggtgggc aggaaaccgg aaaaccttg gctcctcatt ccacctgcgc | 7680 |
| ttctgggtca gctttgcagg tttgccccca gcttgaggac gtgacaggga gcaccgctag | 7740 |
| gtcaggacat gccttggggt ttttaactgc tttggggttt ttaattgagg taaaagacac | 7800 |
| gtaacaggag ttcattcccc gggtggctca gcaggttaag aatccaatgt tgtctctgct | 7860 |
| gtggcttggg ttgcagctgt ggtgtgagtt cgacccctgg ccctagaact tccaaaaaaa | 7920 |
| aaagataaaa gacatgacat aaaattgagt gttttaacca ttttaaaggt acaattcagt | 7980 |
| ggcgtcaagt actttcacat gttgtgcgac cacccctccca ctctcattcc agaactttcc | 8040 |
| agcaccagat ggaaactcta ggctctttta gtgctccctg cccagccccc tctcccacca | 8100 |
| gccttgacaa ccacgaattc atgttctgtc gcagtggatt tacctattct gggcgtttca | 8160 |
| tgtaaacgga agcctgcggt atgtggcctt ttgtgactcc aggtggtagc gggccagtgc | 8220 |
| ttccctctca gggggtggaa acagtgcagc cactccggag aatggacggc atttccccaa | 8280 |
| aaagtgaaag aggaaagtca ggggaaggga gaaattaggg gtctgggatt aacagataca | 8340 |
| cgctattgtg tataaaataa tcaacaagga cctactgcgg agcgcaggga actctactca | 8400 |
| atatcttgta ataacctgta aagaatggct tcagttttgc taaatcactg tgctctgcac | 8460 |
| ctgaaactaa cacaacattg tcaatcaacc aaacttcatt taaaaaaaaa aaagtggagt | 8520 |
| ttcgttgtgg ctcagtggaa atggatctgt caagcattca tgaggatgca gtcaattcct | 8580 |
| ggccttgctc tgtgggttaa ggatctcgtg ttgtcgtgag ctgtcgtgtg ggtgacacac | 8640 |
| atggctcaga tctggcgtgg ctgtggctgt ggctgtggtg gaggctggca gctgcagctc | 8700 |
| tcattggacc cctagcctgg gaacctccat gtgccacagg tgcagcccta aaagaccaa | 8760 |
| aaaaaaaaaa aaagggggtg aaacctagag ctaccatagg acccagcgat ttcactccta | 8820 |
| ggtatattcc taaagaaact gaaagacgt gttcaaacac tcatatgtag atatctatgg | 8880 |
| ctcactgttc acaaccagca agatgtggaa acaaccaaat ggccatcaca gggcggatga | 8940 |
| acagataaat aagacgtggt ccattcgtac cgtggatttt ttccttttta aaaaagtatt | 9000 |
| taggagttcc cattgtggct cagcagtaac aacccaacta gtatccatga ggatgaggtt | 9060 |

```
tgatccctgg gctcactcag tgggttaagg atccggtgtt gctgtgagct gtggtgcagg   9120
ctggccgctg cagctctgat tcgaccccta gcccgggaac ttccatatgc tgcaggtgcg   9180
accctaaaaa taaaaagcaa aaaacacaaa tttattagtg cttgcttaac tcctgctgat   9240
gctctaaagc taccccaggg taccctcact ttcccaggaa ggctttcccg agtccggagg   9300
ccggtcctct tcctgcccac agaatcctcg ctaagtcttg gtcatcgtgc ctcgtccatc   9360
atccattcat tcaccgcttc cagagtatct cctggaaccc ctgtgagcca agcctgcatc   9420
tctccatcgg gcagaggtgg tgacgtcaga tcaactcagg gaggagcccg gtccctgcac   9480
agcgggcccg tgcctgggtc tcactgtggc tgagtgcgcc tccctgcgga ggagactgtg   9540
gcaccaaaac cctggggacc agaggaggca gctttgcaaa ggcagaaggg cacgggatct   9600
cccaggggcc acagagtgca ggggtccaga gatcagatgt gtgtagaagc tgaaggcccc   9660
cagggcctga gctgctggtg aggggagagg tcacgaggca tgaggaacca tgtgggaagt   9720
tcccggccta aggctcgaag ccaagtcaca gcagtgactg cagatgctta acctgcacca   9780
ccagggaact ccccacgtgg gatttaaatc caggtacaga cggaaggcac tggaggggtt   9840
tcggcagcta aggtggaggt aaggggccgc ggtgtgacat gattcagggg tagacattgc   9900
aggaacctga cagtgacgag ggcgaagagg gcgaccagga cagggtgtga ggcaggggag   9960
ggcggagtgg caaagtcacc ctgtcctaat tgcccagtca ctcgactgtt accacacccc   10020
accccaaatc ctgggactgg gtgggcaggg gccagctttc aggacagagt aggtgctcag   10080
ggagctggac tgaagtgagt cggtcagccc cgtgtgggtg cagtggggag tggcccctag   10140
tgtggctccc cagtggccca gcttgatgga ggatggtggc tgggaccggg cagtgggcat   10200
gcatctgcca ctggggaccc cagaggggc catcttccaa ccacagcagg aggtctttag   10260
ggatgttctg agcagacatg tgtcaactgc tccagagcag gttcccggga ctggtccgtc   10320
accagctggt gcttgtttcc agaaagcgtg cgctgtatgg acttgtgggc ttgtcccatc   10380
tccatctcgc tctgtcgctt ccgtgacagt taccagggcc gggacagggc ctgtggagaa   10440
gcaggagcca tggtgacagc agaattgcag acacttgcag atgtttgggc gtcacgtcct   10500
tggctcttgg gtgaaagttc tccgtgaggc atcacagctc agctgctgag gtggcagcgg   10560
gaagctgggc tggagaagca catcggatcc acgagggagg cccacgtggt acatgctgag   10620
acccgagcct tgttccagca ggataataaa ctccaggtgt cctggatgcg ctgccccagg   10680
caggggctgt gaacttgagc acagaagacc gggcagctcc tgtcaaacac ctgcagagcc   10740
cttgctgggc ctcccgggct gtgtttcagg gcctcaggag gcaggatata ggacgtgctt   10800
ggtctctgct tgtgacagga gagaaccttt gtgtcctgcc gcaagtcgct caccaaaggg   10860
aagggggctg taagcttaaa atatatttga tggcccgtct ctgggaaccc tccctcccag   10920
gcagtgagca ttaagctaag aaacctcctg accaggccct cctgtgaatg ctacaggga    10980 ggcagaaatg gacacctcct gtccaagaga ctgatgggaa ccaggaaatg gttaactttg   11040
cttcctcccc ttttcgtata aagaagcca  gaattctaac tcaggcaaaa cggttctttg   11100
ggacacgagt ccaccctctt gtctgccagc tttccgaata gtcactcttc cttgccccga   11160
tctcttagtt tattggcctg ttgtgccgta agcagtatga gcttggactc ggtaacatgc   11220
tctcctggtc aatttgccaa gatgcacatt taaactaatt ataaattgtg ctgaagattg   11280
ttgtggaaaa aaaacaagga aacataacag gtgggtatgg aggatgggc tgtgaggaat   11340 gagtaggagt tcatcaggga atagtgttac ctccagaggg tttggcctgg gaggcagccc   11400
tagggtggga gagagttgat gagtgaggag ccgaaagaga cagaactaga gcacagcagg   11460
```

```
tgaggggtgt ggcatgagat aagcagagac taggactctg gggtcacagc tggggttttg   11520
tgtttcatcc tagaagcccg ataggqtctt aagcagagaa gtgaggcaag gccctatttg   11580
ctaagggggg gccagggtta gtggaggcct ggaaaccagg gaggaagctg ctgagttggg   11640
tgggcagagt gatgctggcc gggagcccag agatgagaag tgggggtgaa ggtcagggct   11700
caggatcaga aaatgtcctt ttcctccctg tactttgtgg gatgtgtccc atggtgtgtt   11760
ttctctgacg acatcgccaa agggaccatt taaggcaggc aggagttggc aagggaccat   11820
gcctggacta aatcctcctg ccactggttt gtgtaaagaa agttttattt aaatatagcc   11880
ccgcccatta acttacggcg gctttcctat tgcagcggca gagttaggta attgtgacaa   11940
agattttctg gcggtccaag cccacgatat gcactactga agcccgagat ttctctctga   12000
cccattccag aaaatatttg cccatccgtg acctcagcga aatgagactg ggacacattt   12060
gcaaaagaca gatctcttgg ctcagactct tccagcactg aaaatgtgtt taattcctat   12120
gaaaaaatgc taacgtatgc atattttaa attaacattt gtacgtcctc aagctttgac   12180
tgacattatt taagaacctc gtcttgtact tgaggtttat aaagtcagtg ttggaacttg   12240
ggctttgaag atgttgcgcg atgttatttg tctaaattta tacgccgagg cgaaaatctc   12300
ccgatgcatt atttcactgt ttatcttctc tctgaaacac tcattttct cctctctgta   12360 aaataagatc tctaggcgga tgtctctaaa gccagctttt agtctttgca aagtctttgg   12420
cctgcttgca aaataatttt tgtgagagtt tgccgagttg cagatgaagc ccaatggcag   12480
caaagccaat ttcccagctt ctaccttttt ccttccctga tcctgttgtc tccatgtttc   12540
aactcctggt tccaaactcc gtgcagcatt tttggatcca cttgatttac agattggagc   12600
tgatttcact tggagaactg gccatatgtc tggcagacac cagccgccat tggcagaatt   12660
atggggttga tgcgaagcag atgggctttc tagttagatg tgctgttttt tccatgatac   12720
atatgaggaa aaaagaagcc actttagtaa tgtcttgatt ttttttccact ggtgtcggag   12780 gcataaaaga cacccatttta tctagtctta atttcagcat cattgctctg caggggqtag   12840 ccttagacag ctggaagagg cccagagact tgggaaatat tgaggcctga cttctgttaa   12900
tgacgcagag aatcctatta ccttgggaat acagttttg gggaagaggt ttttatattt   12960
ccaaaataaa tggtcactaa cgccatttag ctggagtaca ttcaaactgc ttaagctcag   13020
gtttattgct caaactccac ttgacagctt ttgtgtggtt attgctgcct gggaagcaag   13080
gtgtaaatag ggattggctg gtccatctgt ttaggagaag ctggccaagt ggctgaatgg   13140
gtttgcttgc tgcaggactt ctcagagcct ttactatgac aacacgtggc ggggctcttt   13200
ggggaaggct tttcgggtag atggtatctt cgcaaatgtc ttccttcaca agcctctcct   13260
gtgctagggt tccatgggac gtgcttgggg aaacactgaa gtcatgccca gatggtaagc   13320
ttccggtcag aggaccgggg ctccaatgcc agaccagtca cttgccagtc gtgtgactgt   13380
ccttctacgt gcccccacc ccacagcctc cacttcctaa atgtaaaacg gagctgaaaa   13440
tggaaatcct gcctccgaga ttgtttgctt ggaatgaaca cccgaaagaa tgtggtggcc   13500
tccccacaag cactgacaga tatgttctcc tatgatgcag cattcgttca attcacaggg   13560
ttccagggac tggttattcg cgctgaagct cagccagact ctcgtacttc cttctgtatg   13620
ttccttagca cctcgactaa tgaggaagga agaggaagga gatgccgtct gtttaggtgg   13680
cagccaggag aaataaatga tggggcactg tgagcccagg aagtcgctta ggaattacag   13740
ggatggctcg ctgtcaaggg gcacacaggt ggctcaggtc gttgttaata acctgcatt   13800 tgattccact tctgtggttg tatcacagat caaacgcttt cattcattct ctcctttgtt   13860
```

```
cattcacccc tgtgcccagc gcagtgctgg gccctgagga gggagagcct gctgcggggg   13920
ggtctctgcg tcttccaggc tgaaaaggca gcaatttttc catcccaggg ggtgtcagcg   13980
ttgccgggtt ctgatgatac actcacagag ctgtaggaaa gagtctgcag aatggctggg   14040
aatagggcca tgggtcttta ggaattcttt cctcccctt ttcagtaaat tcatccttct    14100
tcctacatcc ctgctccatc agcaaccagc ttcttcctgc attcagagca gtgtggttct   14160
ggggcgtggt ctcccctctt cctggaagct gtcccagggt ggcccagct ctgcttgggt    14220 ggattggctc tccccagaca tcctgcttct caggcctcac tccggaattt ccaggagaa    14280 gtagagaagg tcaaaccaag agtactttg tatctgggag actttacatc cattttgtaa    14340
atttggtttt ggagattcag acccatcagg tggggagtct atgaacacac ccagaaaaat   14400
cttcttagca gacggtcgtc aagccacatc tctcacagcg tggacacggg ccattggcct   14460
ttggacccca aatgccatga ttcgagtata tgtggctttg atcttcttct ccgcccatt    14520 cctccacctt cagcccatat cccagacgac cgcgcggtca tcgtctgctt gctgcaggga   14580
gtctaacggg gggagggggg ggaggacgag ggcttcggga gcaggtgtcc tgatttccag   14640
gcccgctctg tcacacgagc cgcgcgaccc gcgagaacgg gtccgcctct ctgcttccat   14700
tctcctcgtc ataatgtgag tgatgaagac aaggcctgat gggaacgagc cgattcatgt   14760
cgggtgctca gggcacagct tgtcacacag caagcgccca gcagatgctg ctgttgctga   14820
tgaccgtgac cgcaaaacaa cccttgccct gcttgactcc tccgtgtgag ttacaggccc   14880
gcataggcat caggtgaggg ctctgcccca gcatcgtctc tggttcctg cctcctttct    14940 ctgctgtccg catggtcctt gccctgctgt cctctctcag cgggcctcct agccttcagc   15000
ctcattcctc tgcagttggc acccgcatcg actgtctctg cagcccttc ctcagtgctg    15060 accatgtacc ccagtggtcc ccaggccctc aaggctcctc tggtggctgc acacggccct   15120
ccttggctgg gtcccaacct cccctccggc ctctccagcc caaaacccag agctccagcc   15180
taagggttct caggttcaag tacacagacc catgccagca aattcggaat gcctaggaca   15240
acacagcatt gctattttt ttttcattta tcggtatatt gattgatata tcaataataa    15300
cgtttcctct gttttaaaat ttttattgga gtagagctaa caatgctacg ttaatctcag   15360
gtgtacagca aagcgagtca gatatgtgta catataacat acaccccgt tctctttcag    15420 attccttttcc catgtaggct ctctcagagc gctgcgtaga ttttcccgtg ccacacagtg  15480
gctccctact tatctgcttt atctacagtt gcgtgtagat gccagtccca acctcccaat   15540
ttttccgtcc ttgcaacgtt tcccctttac taaccttaag tttagtttca aaatcattaa   15600
gtctatttct gttttgtgaa taagttcttt tgtatcattt ttaattaggt tccccttatt   15660
agtgatctcc tatgatgttt gccttctct cttagtgtga taacctctac gatgatgttt    15720
cctgttattt gtagtcaggg gtgatgctga caatgataat ttgtgtctag gtatttgtgt   15780
gtgtttgttg gccatcagtt ggcgccgttg aaatttggag tctcagtgtg catgccaggt   15840
ttatacatgg aggccgtaca gcttctgaac cttggagact gaggcattgg atctggctcc   15900
cctgcatcgt ttgttatctg ccaaacacca catgctttta tggtattta ctcaactcct    15960 actcaacctc caaggcccag ctccaatatt accctgaccc ccagtagcct tctgaatttt   16020
cccaccccag gcagggagaa tggcttcctc tgcagttgta atccctgtct gggttctttc   16080
tggtgattcc acacacctag attttctttg tggtcagttc accaggcagg agagtgtcca   16140
gtacctcttt ttttgttttg tttttgtttt tagctacacc caaggcctgt ggaagttcct   16200
gggccagggg acaaacctgc accacagcag ccacccgagc cactgcattg acaaggccag   16260
```

```
atccttaacc tgctgcacca ccagggaact ccaagcacct ctatgtgctg ccccatgcct    16320
ggcatggtgt ttggttcaca gaagatggtc actatgtgtt gctggatgtt tctttgggga    16380
cagggaagga ctcgtcaaag aaatagaagc cacgctctgt gatccacgtc cccacctctc    16440
gttttcctct ttcagagcct gtaaagcatg ctggagtcac ctccttgttc ccttcctcct    16500
ccgtaagcag gtgagcctca tgctgagcaa gacagcatgt cgcctgtgtt tactgctctg    16560
tgtcaaatgc agggcagccc tggcccacag cgggcctcag ctgatgcttg acgagtgaac    16620
ttgtgaatga acgtgtgaaa caaacaagcc taaagtcaca ttccagtatc gcctgataag    16680
gacagtgcct gtctgtccgg gaggccaagc cactcagcat gtggcatctg gaatctgag     16740 tgggggctgt ccttccattg tgttttagcc taggtgaccc agtgacatgg aaggagacag    16800
gggcaggaga gtggatagaa gacaaggaag cagaaatgcc cagtgtcact aaggtgaggg    16860
ctttggagtc agacggatgc gggagggact ggatcctggc tccagcactg cacctacct    16920 ctgcctccca aattcacagg tcaagcaggt gtttattcaa gtgccagtca agatgacagg    16980
gacccaggtg gacaagacag ccacccttcc tgtcctcaca cagcttaacc tttgttccag    17040
ggtggaagac agatgctaac catagataac acatcccagg gcactatctg agcgtgatga    17100
gagcaggatg gagggaacgt taggaatcag gagttggccc tgggccaggc atggaaatta    17160
gcccacaagt tccgtgacct tagccatgac agtggtgtcc ctcgctgtct tgttctagga    17220
gcacctaatt tgtaggtggg atccatcgat ggtggaagtc gatggggttg ccctggggg    17280 acaagtccac agactgcctc agaggggacc ggggagggt tgctgtggtc gagggaccag    17340
agatggcagg gagctaagcc ggcacccttta gctccagggt ggggcaccta ccccctcca    17400 tcatgggtgg gaggggggct cccgcctgcc ctataggtag gtggtgcctc ctcagcagat    17460
gtggaaaaca gttttcatta attaactgct aatgcctcac aggtggcaga ggtgcccctt    17520
caacttcgca cctccgagct gttccaaggc tggaggatc tgctgggtct gcacctgctg    17580
ggtgtgggaa ggtggttccc ccgccacggc cgagcagact cacaggctgg ggatccaggg    17640 aagcggcgt ccacgcagcc tcccttctgt ctgcatgaca cacacatagg ggtgcacaca    17700
cgccacccac aggtgtgcac acattcacat acagatacac cctctctcct agatacatgc    17760
ctgccgcgtt cacacccact ctccagggag gggcgggggc aggcgccagg gcacaggagg    17820 acccaccccca cctttgctgg tccggacccc caggcacagt ccgtggcacg cccatgccct    17880
tgagtaagtg gttcctttcc cggggcagca tctgttttga gtttctggc cttgggttct    17940 aagtcgcagc cctgaggaat cgcactggcc ctggctcga ggcgcctgca ggcagctggg    18000
ggcagagggc gcttcctccc atgggagcac tggaggcgca gttttcagac tgatggagcc    18060
tgtccccacc tgggcttggg gatcctcacg gcccctgaca gcaggccctg gggagtcact    18120
cagaactagg ggtctttctg gtcacgcact tcggatgttt ggtaaatgaa caaatcgggt    18180
catttgagct gaggagcccc aggggctccc tgctgaatgt tgaatcaagt tcaagccca    18240 gctacggccc tggcccctca tccactgcat tcttcctcca agcccttgac cccactcttc    18300
ctctgactgg caccttcgtc cctgcccag ctcctgtcta caccgccggc tccccgtcat    18360
ccaggcttct gctccaatag ctcctctcag agcagctttt cataacctct ctttacagtc    18420 agcccccgg gttccccaga ctccctgagc aggtgttggg ttccgtccgt ctgtcctgtg    18480
tggacgcacg caggtgtgtg caaacaccag ccatagatgt gatgggaaaa ataaggagag    18540
gaaggcagca gagaacgccg gggtgtgcag gctgattgtt ctcacccatc gtctgtcgcc    18600
tgcaggcaac tagaagcccc acaagggcag gcatttttct cttctgttca cctctgtaca    18660
```

```
ttctgctgga gcgattccca gcacgtggct ggtatcaata agttttgtt gaatgaatga    18720
atgaatggat ggatgaattc tctaagggag aatagcgggt gatttgttca ggagtgcccc    18780
gccctgccc caggctgtgt tgtgaggact caggcggcag aatgaggtgg gaaacccagg    18840
acctgctcca gccactaggg ggcagcgggg gggggcagg ggcagcggca gcggcagggc    18900
aggggcagtg ggaggcagca cattacagtg gtgacggtgg tgatggtgca agaggggag    18960
gggagatgag gaggggccg cactatccct tctgtccacc ttccatccgt tcagacaagc    19020
acttggaggt ccctgtccc cattccccca gcagagcggt ggcaaaagtg aggacacagg    19080
gagcagggaa gtggcctcaa cacttgagcc ccccatgatg agcaagggag acagggtgtg    19140
agcctggatg cctggttcta gcgcctgtgt tcccagcagc tcaccagact ggtttccatg    19200
gcgtgccata gacactaatg caaaatgatg gtgctaaagt gaagccgggg ctggggcaga    19260
ggtgaggtgg gcaggggttg ggagcagacc tcggagaccg tacaggcttg gccattaatt    19320
gacctttgtc caaaatgagg aaggaggcca tggggagtca ggaggaagtg atctgatcag    19380
attacgtttg taggggggtca tggggatgcc agttagaagg cttgtgtggg catctggtgt    19440
ggccgtgctg gtggcctgga ctaaagtgac agtgatgcag tggcagatgg agtgaggttc    19500
ggggtctgat ttgtggttta tttatgcgt tgttccttt tgctttggct gctaggaagc    19560
tcagagccac ctgtgtaccc atgtggagtc tctaaccca gaggctgtgg tcctgtccag    19620
acgccccttc ctctggactt cctcaggcac tcatttatc ttggtgggca tgtttccgta    19680
cccaaccttt gtggcgcgag atgagggcta accaagcag tgacaaagcc gccttgtccc    19740
cgtgcacatc tccagggatc ttcgtcttta tcttcagacc agccggaagc ttgggggggac    19800
ctggccagtt cttcccctt tgtgccaaaa ttgcctccag gacggccagc cttcctgggg    19860
ccatgtggca gccatgtggc actggcagtc ccgctcccat ctggcgtccg tgggcggagg    19920
aaggaaagaa ggggataata acacggggta aacagtctct ggggagagaa gggccgtctg    19980
caggctgcac gcctggtgtg tggagctggg gacctgcgac cggtccttgg acctccccga    20040
gtccctcgcc cgaacttcct ggttcctact gggtgctggc cactgggtc acagctgaac    20100
acaagatgga gcgtgtcact ggcttaggag tctcgctggt ctgctgtctc tgtaagaagt    20160
cctcgcacga gactcctccg ggctgtctgt ctgcacaggg gaggggcttg ctgtgtggac    20220
gctgcagacc cagcctgggt gtacccaagg cgcagttctt aaccactggg agagggtggc    20280
cgcacaccct gggtggctgg gatggcctgt gctgtgtccc attccctcat gtcctgccct    20340
gcctggtaca gtcatataat caccctagaa gcagcttagg gctgcgagag ggagtcaggc    20400
tgcccagagc cagcatttcc tagctccgat agccgacaga atggctctga gcctcagtgt    20460
gctcatctgt aaaatgggta taactgtctc caccgcatag attcctgtg agggtacaac    20520
acagtggtaa ctggcccaga caagcagtg actaatttca ttccagaata attattgtat    20580
catgtatata atataaatta acgcaatgaa aatgtctacc agggagttcc cgtcatggcg    20640
cagtggttaa cgaatctgac taggaaccat gaggttgcgg gtttgatccc catcctcgct    20700
cagtggctta aggatccagc attgccgtga gctgtggtgt aggtcgcaga cgtggctcgg    20760
atcccacgtt gctgtggctc tggcgtaggc tggcggctac agctccgatt cgatccctag    20820
cctgggaacc tcccatatgc cgtgagagtg gcccaagaaa tggcaaaaag acaaaaaaaa    20880
tagaaaaaaa gaaaagtcca ccaaaaggta ccctgccga tggggcatgt taattagtgt    20940
ggctatacag ttttttgttg ttctttgttt ttctcatttt ttagagtttt attgaggcgt    21000
tcccattttg gctcagcagt aatgaacctg actagtatcc atgaggatgc gggttcaatc    21060
```

```
cccggccttg ctcattgggt taaggatctg gtgtggctgt ggctgtggtg tgggccggca    21120
gctgcagctc tgcttttgact cctcgccagg gaatgtgcca tgggtgtggc cctaaagaga   21180
caaaaacaaa acaaaaaaag ttttattttt attttttaaaa tgttaaaatt ttaattacat   21240
tttatttaat aaatattaaa taaatttatg tttatttttaa aaataaattt aaaagtaaag   21300
tttggatttt attttcaaaa cactatcatt gatttacaat tttaaaacag atgatatgac    21360
ttcgcagggg ttgtaacata ctatcgagaa actgtgtgtt ctgtatgttt gcctatggtc    21420
acacagactc ttccactcac ccctagggat caggtggagt gattatttta ctgaggtgga   21480
aactgagggt ccgaggggct gagtggccta agctgctgag agatgcagcc ctttgtaagt   21540
cagaccacgt ggggcattgg gcggggtctg acggtgacca gccatcccag gtccagtccc   21600
ctgccggccg gggccctcct tcagcctggt cctcgctcgc tccagctcgg ctcttcctgc    21660
gtccttgggt ctctgtgggg cttcttggct cgagagggac tcaggcttcc ggcccttctt    21720
cccaggcagc agcaggtgaa tgaacccacc gggcgtggag ctgagcgtgt gctggacctg    21780
accccacgga gcccccggct ttggaaggtc actggtggcc ccaggacagg ggagtcacgt    21840
cgggtcccca gggcccctg tgggctcggt agcactgacc cctccctggg cttcgtcttc     21900
cagatgagac ggaacaaacc ccccggcgc gctccgagta tctggtctca gggattcgaa    21960
ctccgcccgc gaggaggagc agcaaactgg ccaccctggg caggatcttc aaaccctgga    22020
agtggcggaa aaagaaaaat gaaaaactga agcagacgac gtcgggtgag cagcggggac   22080
ggggcctgct gtttgccctc ccgcgggtcc cctgcgggtc cctggtgggg gcgggtcagc    22140
accaggcaca cctggagccc actccccgcc cagaccctca ggggcccacg agtcaccctg   22200
gatcccgtta gacacccaga atccgggtca gtgctggccc caggcctgag actcagcttg    22260
taacgacctc ccctcgctga ccacagagta gaaagtgccc agcaccccgg catctggacc    22320 ctcccctcgaa gggcccacca ctccacccc accccggct gatgccaagg gccctcggtt     22380
tggcctcagc accctgcggc ttctcctact ggggcctcct catccccatg ccctcccta    22440 aacgatccag aagcttctct cactcacctc cagctgcagc cttacacccc accagtccca   22500
gctctctggg gggttgggtt atgacaggtg gtacccttgc ctctacccct cgaggtccat    22560
gtcaggaact ctggccatga ggccgagcca gtcactgagc ctggggtaac tgtgcctgaa    22620
ctggctacga gagtgaaaat cgacccagca caattccaac catccaaagc ctgagaagca    22680
cccctctcgc cagcgccctg accaccccgg ggacaggaag tgggctctgc gatgggcagc   22740
cgctccaggg tccagcagca gtgggtcgtg gggctggggt ttgggtccag ctccaaggac   22800
agggtgccct tgatgaagag gaggtcagtg tcctgagagg ccaaccccag ggagcagcat    22860
cctagctccc ccaggcctat atccacggcc ggaaagaatt agtgagaggg ctgccgtgtg   22920
gagggagccc tgggccttgg ggacctgtcc tgtgagcgcc cgtctcaggc tgttgcctct    22980 ggcggtccccc ggagtcccta ttcccttccc agccttgaag aagcacagat gccagggcgc   23040
agaggatggc agaggcaaag ccagtggggg cgggggtgg gggctgcttc ttatagcagc     23100
agctggtcct ccactcacac ttttaatgt tttatgaaat cacgtgtttc actacccaaa     23160
aaggtgattg acaaattctc caagtcaaga atgaaagcag aacaagcact gttattcagt    23220
gaatctcgtg aggcccctgc gtgccaggca cagagcaggt ggggggccca ggtcccgccc    23280
acagagcttt ctgccaggtg ggggctcagg ccacagacaa gcaaacacgt ggacgagctc   23340
gtgagataga ccttccctg gcaggctgtg gaggaggag tcagcaggtg ctggggtggg     23400
ggggtgggtg agggtgggtg ttgccttggg ttgcgtggcc tgagaggacc caggtgagaa    23460
```

```
ggtgacactg agctgaccct taattggccc ccctggggaa aagcatcgca gcagcaggaa    23520
cagccatgcg gacgcactga gttggggaag gctcaccttt gcgccagtga aaggctccag    23580
gggctggggc agcatgacct ctgtgacctt ggggaacccc gatattctct gggccatggg    23640
attggaaggg gagctgcatg ctctcaggac cctgtgcccc tggccccttg accctgggct    23700
gtggggagca ccctgtgagt tcatcgggat gctgggacc ctgccagggg gtgagtgtca     23760
ccaggttaat cccggcaggg tccccaactt caggttcctt atcaagtatt tggaagactg    23820
gaaacggtgc tgtgttttat ttatttattc taagccattc ccctcccctc caagtgcggg    23880
atattattta tttcagcata tcaaatcctg gatttcacag gcttccttgg ctagggtgag    23940
atgaagtcaa taagaagatg gtttagagaa aaaaaatgat gcaggagttc ccgtcgtggt    24000
gcagtggtta atacatccga ctaggaacca tgaggttgtg ggttcgatcc ctgcccttgc    24060
tcagtgggtt aacgatccgg tgttaccgtg agctgtggtg taggttgtag acgcggctcc    24120
catcccgcgt tgctgtggct ctggtgtagg ccggtggcta cagctccgat tcaaccctta    24180
cttagcctag gaacctccat atgccatggg agcagcccaa gaaatggcaa aaagacaaaa    24240
aaaaaaaaaa aaagatgcag acaggggttt gggcgcgggg ggactggccg ataccacaga    24300
gatggctttc agaagcctgc agtctgggac gtggcatctg gtccctgctg gctctggggc    24360
gtggcctggg cggtggggca tgtccctgag atgcgggcag cagccctggc ccctgcctct    24420
tccagtagct ggggtgtgtc caagtcactg gggtgagtcc aagtcccgca tcggagccgg    24480
cccctgtgag tgccacccag tgctggctgg acgacgcggc ccctcagttc taggaccttc    24540
accctcgttc tgctcacctc tgttttcaga ctagacggca gtcctttgct cacctcccaa    24600 agccaggggtt ccacttctca gttttatcca cacttctggc gcctggaaac tggattggaa    24660
attggactca gaaaggaaat tatgccccct ttgtccccaa atgtcatctc tctgatgttt    24720
gggttttccc attcacccct cagatggcag cgtaaacacc ctcaggggtg ccctccccac    24780
cccaccccca cctccgccct gtgccttcct gcttgaggcc acttgcctgc ttgttgatgt    24840
ttgtcatctg ctccatgcac catcctcccc gaggctggca cacagtaggt gctcagtaaa    24900
tgtttctgaa taaacgaaat aacttcagtc cccttgcctg tttgtcctca gccactagac    24960

tttaagctcc accggccggg ccactctttc ttttcccatc ccaacccgcg ccgggcagag    25020
agctcccacg cgtgcctgac ccaggcccct tggcgaccca ggcttgtagc caggactttg    25080
catcttttaa agggaggatc tgagggatga cggttcatat ttggaaagtg gattctactg    25140
gaggcaggta gttttctgga tggttaggag aagaaggagc ttgtcaagcg gagtgagccc    25200
gccccaggag gggagaggca ggggcggagg gcgaggtgct ggggcccaaa gggctattct    25260
gaaggaggaa tgagaaggct cagcacattg aggacggtgg agggggtggg ggcctggcct    25320
ccatcctgtt tatctgggga attcttggaa agcacgaacg tggggttcat gggaggagcc    25380

tcccgtgcca tagttgtgca gaagcctgat ctgtggacag gтgтgaagggт ggccaggatg    25440 tagttaacga acaataatag agccacaaaa gagcatcccg gggtattggg gacagagaga    25500
ggatgcagtc ctgggctgga acatgaaggg atttctgcag gggatgggac gggcgctgga    25560
agaggctgag cagaggccgt cgtacggggc tccсттттcag gtgcgtcatg gcaaccatca    25620
ccctaaacca tactcccctt ccgccctgct ttccgctggt accggcagaa ttgttcaggg    25680
agggagctcg ggatacctga ccgcgcgcca cacacacaca cacacatg cacatgcaca      25740 cacccggtgg ccccctaacc tgcggtcacc tgccacttg ctgccctctc cctgacctgg    25800
aggtggcatt ggtgggctc aggcagggcc acacggcacc tctgcccgtg actcacctga    25860
```

```
tgtttgtgtg tcctgcagcc ttggagaaga agatggccgg caggcagggg cgggacgacc   25920
tcatcaagaa agggctgctg gagatgatgg agcagggtga gtggggccgg ggcaggaggg   25980
ctggagcgca gggctgggcg tctgacgggg cccaggaagc ccactggcgg ggaggggag   26040 gtggaagagt ccagatgtgg cagctggacc tgaaagaggc ctgcatgcct agagaaacgc   26100
cccaagtgag gacccggggc tcagccccca ggcctctgag gaccattggt gagtctaagc   26160
tcagctactc ccaggctggg tgtggatgga gctggtggtg agtcctgatt cctctgaggt   26220
ggtagcactg cctcttggtt tttttggtat tcatattttc agcgtagatt tgggggagtt   26280
actcatcccc cattttcccc tagtcccggg gctgccgttt attaagcatc agtgatgaga   26340
ttatatgcca ggtgctgagc cgggcgggcg ctctactcac ctccacccct tcgtcgtcac   26400
agcctccttg ggactggggg tggtgttact ccccgtttcc aggtgaggga tgtgagggtc   26460
tgggaggtgg ctgtcctagt cgcgcagctg gaggacccag aggctgtgtg gactctggtc   26520
cagagacctt aatcaccgca gtacgggccc acctggggtg gcctctttgc gaaacaccag   26580
gttttatcgc tggcacagtg aattttcaga attctcgagt tccctcatct ccctctcttg   26640
gggacggtgt gaggcgcggg ctcgggtcct gatgctcacc cttcctgctt tctagttctc   26700
tgagtctctg aagcgtgggg acgggagcgg gtatcaggaa acctccatac tgcttataag   26760 tctctggga gctgaaccaa gcacttgctc ctgattgaag aaagctggcc tcccagagcc   26820
acaggtcccc gaggacacga gaataaacgg gaattcccat ctcccttaag cctgcgaata   26880
tcactagtgt ctttgtgatt ttccaggtat cagaaactgg ggaggagcc cctggagtca   26940 gtgacccag atttataaca caggccctcc gaagtcctcc ctctcctta gcttcaaagg   27000 gaaagtcagc tgctgatgct gttttcggag gaaaactatg tgggaaattg cttagggtat   27060
gaatcaaact ttgcctgtaa aaaaaacaaa aacaaccttt ggtgtcaagt cctgtgacct   27120
tcagatggtc aaggtcccgg cctgactctg gggtttggag gaatgtcatg gctgggatgg   27180
aaatcggact gttttaattt ggacgggaca gaaaaactcc caactgcggc cttttgaata   27240
cctagccaac aaactttccc ttaaatcttg gggaaggagg agggaaacaa agcaatatga   27300
aggcctgttt atcatctatt tattttagag cctcacccaa aacacatgga ggtgcccagg   27360
ctagggggcg aatcggagct gcagctgctg gccgacacca cggccacagc aatgccagat   27420
ccaagccaca tctgtaacct atgccacggc ttgtggcagc tccagatcct taacccactg   27480
agcaaggcca gggatggaac ccgcatcctc atggatgctg gtcaggttct taacccacca   27540
agccacaatg ggaactccta tcatctattt tttaaaaata ttattgacgt tcctgtcatg   27600
gctcagtggt caatgaatcc gactaggaac cacgaggttg caggttcgat ccctgacctc   27660
gctcagtggg ttaaggatcc catgttgcca tgagctgtgg tgtaggtccc agaagcggct   27720
cagatcctgc atggctgtgg catacccggt ggctccagct ctgattcgac ccctagcctg   27780
ggaacctcca tatgccacgg gtgcggccct gaaaagacaa taaataaata aataaatata   27840
ttattttgct gaggaaagag ttactaaaga catggctttg attcccttga taaggaggct   27900
ggtgagtcat ttaagggag aacttccagg agaaggcag tttgccttcc ctcatctccg   27960
catcatggca aaacaatgtt gcctgacagc ctgagcagcg agccagcagt caaattgatg   28020
gggtgggcgc ggggccgagg tgccggggc cagctctcct ggcttccgtg aggctggtgg   28080
gaggtctcat gccagcccgc ctgcggtctt gcgctagatg ggggtcagcg agccttttt   28140 ggagagagcc agacagtggg tattttcggc ttagatggcc gtcctgtgct gtaatcaggc   28200
aaaaactgcc acagacacta cttgaaggag tgggcgtggc tgggttccag gaccactta   28260
```

-continued

```
tttagggacg ttgaaatttg aatttcatat cactttcctg tgtcgtcagt tattagtttc    28320
ctttcaattt tttccccacc attgaaagag gtaaaccccc tttgaaactc cacgctctag    28380
gaaacaggtg gcggctggat gaggccaggg tgtaggttgc caaccccgac gttagatgat    28440
ttttctcttg ctcagtgatt atggaccagg agctcgaggg gcctgaacca gtctctttgc    28500
tcaggaacgg acagcacgct cgttaatggt tctcccccaa ttttattgag cacatgctat    28560
gggccagggt ctgtgttagc tgctgaggat gcggtgagca aatactttc tcccaggact    28620 catagtctgg tgaggaacaa gccttaaaca tcccacaaac aaatgtaaga ccacagctga    28680
gatcagtgtg gcgcaggaga ggcacctgca aaacaggagt tggggccccg acctggtcag    28740
ggccttgggt cgggtggggg agggtggtga ggctggcgtg ggtctgaagg caggaggagc    28800
caataggctt ctctcagaac ttgccagcat caggatcacc tgggcagctc ttgcgtcaaa    28860
ggcgctgggg gtggggccca ggcatcatac tttataagcc tccccagctg cttccaactt    28920
tggtgccacg gaggttgaga agcggaggga gccggtgagc tgggggtgg gagcagcccg    28980 cgtgcatccc tgcttctccc tgcaaggtgg acagagccag gaaaactaga ctccccagga    29040
aggaagcggc tgggtgacaa agcctcctct ggggctgtgg gggcccagga cagccacagg    29100
gtgcgtgggc agggtgcctg cccagggcat cgctgcagtg ggggtggggg gtgttagaag    29160
cagggcagca gggattgccc ctgggaaggg ccctggggag ggagagggg cagggaggtg    29220 ggctcaccac ccacgtggac cccaggggc tttactgcgt gtattccctc caacaggcag    29280
acagacagcg ataagaggag ttgtgaaatg tttgatcaca ggctccttgc agggttgttt    29340
ccttcctgca tttgctcaga aaatgccttt tctctctggg ggtgaagtca aagctctagg    29400
tccgtcctgt ccctcatttg tcctggtgtt gggaccgcag ggttcctgct gggtgcgtag    29460
caatccgtgg ccttgggagt tggtccttgg tttggattca gaaatcgccc acctgggctg    29520
gacatctttg tggccaggag cgccccctg tggccggccg ccctccgtcc ccgctgagcc    29580
tgtacttcac acccagtgaa gcccctggcg gctcagtgag cctccagctg tgaccgataa    29640
cctaggggct cagagcagcc cccgcaggcc agggcccgg accctcccag agctgcccgg    29700
agtcctccac agccccagga cctcacactt gaacttcctt ggccaggaca cacctgggaa    29760
gggcctctgc ccagcgcagg tgtgcacaca gacacgccct ggagtcagtc ccctggagtt    29820
tgcccacaat gcagtcagga gccagccctg gacgagcct gtgggagagc ccacgtcccc    29880
gggcacccct ctctagggg cacccctctc caggggtgt gttatcttgt gatgctctga    29940
acacgtgttt tatgaactcc tctgacctct cctctggttt ctgagagtcc ggccatccgc    30000
cgggcccagg aaggaccctg tgtgtggtgg gagatgggac cagctctgcc cgggaacggg    30060
cagctgctga cctttctcct cactccgcct tcactgctct ggctggtgac acatctgtga    30120
caggcaaggg ccggtgtccc acccctcca tagggtcccc gacccagaca ggctgcttga    30180
gggcagaagc ttgcccgttt ctctgtccac atgccctgtg tgctcctaaa ggacttcccg    30240
catcctctgt gtgtatctgc ctggcacagt cttcagtgat ttaaggaatt gcattctctg    30300
tcgttggaca taagaggaag ttgttagcct ggcgctgtgt tcagtgacct gagagacttg    30360
aggtctctct ccttggggaa gctggcagtg acaaatcgtg tcagtctggt ttctgtgtgg    30420
cagaaacgct gggagcagcg tgtgtgtctg tatgtgtgtc tacgtgcatg cttgtacacg    30480
catgtgtgtg tttgcacagt gcatgtgcac gcatgtgtgt gcatgtctgg ggcacgtccc    30540
cttccctctc accatggctg ctctgggtat aaccctggca tctggcttgt gtgccccct    30600 gccgccctcg ggggagaagg gcctggaggg agggccgacc gtctgtgaga ggcgcagggg    30660
```

```
accagctgcc cacagctccc ccgccccgcc agcgttgctt agcaacgacc ctgccacggg    30720
gctattttgg gaaccgtaag ttttcattga aggtgattat gagccgcagc ccaggaaagt    30780
ccagcaagtc cactaaggtg ggaagcgggt ggaggaatcc agaaaccctg ggtgttttgc    30840
caagcctggg gcagggagcg ggcgggcgca ggggaggag gctggggacc ttccggcctt    30900
tcaggctctg atcacttgat ggaggggagg atggagacgc cgttataagt atcgacatca    30960
ttattagtaa tcaccagcag caaatgacct gcccccttcta agacctggtg tccccgcctt    31020
taaagggcgg gtagcagtct ctcctaaggc cgtggagagc tgtccactca gctgggacag    31080
cgccgtgcgc tgtctccggc tcatgcatgg gtgctggctg tcaccccagc cacgaaaggc    31140
cgtgtgagcc agtggcacag acggtcacag ctgtgtgtca ggatgggtaa gctagttgtg    31200
agaaagggcg aagaagttgc tgagcgtggt ggcctctgat cgggttcaca gggtgaattc    31260
tcttgacttg tgtctcagtc ttttcctggg tcaggactgg tgggctgctg gtcaaatcag    31320
gcccaggacc tgttttttgta gagcccttcg agctaagaag aggtttggac cttcaaggat    31380
tttataaaac tgaaaaatcg ggtgttcccg ttgtggttca gtgggttaag aacccgacat    31440
agtgtctgtg aggatgtggg taggatccct ggcattgctc cgtgagttaa ggatcccgcg    31500
ttgccgtgag ctgtggtgta ggttggcagc tgtggctccg attcgacccc ccagcctgag    31560
gacttccacg tgccgcctta aaaggtggt ggggaggggt tctcagggtg tataggagca    31620
aaaggtctac cacaccgggc ctggggtggc gtcctggcca ggaagtcact ttgtgtgaat    31680
gaaaagcagg aaggagggag tctggcctgg ctgacagctg gatttctttg cagacgctga    31740
gagcaaagca ggcagccctg atggaggccc ccgagctgcg cagagcgaac cttccacgcc    31800
caggcaggag cccctgactt cagaggaagc ccagccggga agcccttcag ccgctgggac    31860
agaccaggct tccctggatg aaccgctgtc ctcggaaacc cattcagatg atgcaggtac    31920
tggctggctc ctggagttga gctgttccca ggatggcatc gggcctgggt ggtgactggg    31980
gtccctggtc caggctgtgc agcagctctg gcagaagact gtcccagag gtgcagccac    32040 accccctggtt ccgagccctg ccgcgctcca ctgtgtggct gagtttcaag gtttgctggg    32100
cgttctccct cagcatcttc ccaagtcggg cagggctgtg gatagaggtg ctaacagatg    32160
ggcacaggtg acttaccacc aaccttcctc ccaggacgtc tttgcttgtt ctcttgggac    32220
ttctgaccaa ggaaatgctc tctaaagggg ccctgtccag tgggagcatc tttgctaccc    32280
caaggccaca gggcaggatg gaggcagggg gcctccccgg tggcctgact ccctagggga    32340
tggctgcccc tccagagggc agcctgtctc cctgggccac cctggggctg gcagtgctgg    32400
tggtggcgcg gccagcctac tcctcacctt ctctgccagg tgtgcctggc acatgcccga    32460
agcctcattc ctccctctgg caaatggggg aagaatggtc tgtctggggt tatctgcagg    32520
gtgcgaggag ccccaggtgg tgtctgctgc gttgaatgat tcttggtgag ggcggtggag    32580
gccgaggtgg tggttctagt ggagttgaat tgaacagaca gttgccgcag tgaagcagga    32640
ggagagagaa ggagagaggg atggtgggaa ctaactgtgg ccccaccaca gaaacctacc    32700
tgtaggtgct ttgaaacacc cacccgtgca ccctctgacc tgttagcttc cacagaattc    32760
ccccgggaga ccttgtggtc cagcaggaac cctgttccct cataaaacca aagctataaa    32820 tatcccagc atggggctg ggacgtgaac tgggttccca cagcatggag caggggagtt    32880
agggcctctg gggtcagctc tctggcttca gagctgggga cagggacagc tgtgctcggc    32940
ccctgcttct ccagaggagg ctccctccta tgcttccccc gctgccccat ccacggcact    33000
ctctggctta gcaggcacct gccaagagct gtgctctgct ctctctaggg gtggctgtga    33060
```

```
gtctccagtc tcagtctcac cccagcttgg agacgtgata ggagtttggg atccaagagc   33120
tgtatttctt gggacagtcc tggccttttcc cgcagaggtc cactcggcac gcctgtgtcc   33180
ccgtgggctg tgtcatcaga cttcagggca gtggttggcg ggttcttgtc gcccacctgt   33240
ggttctagca gccgagctgc tctctgtcca ccagcttggt gggggatgga ttcttgggtc   33300
caggcttggc ttttttgagat cacacatttg tattggagct cccgctgtgg caccacagga   33360
ttggcagtgt ctgcgcagcg ccaggacgca ggtttggtcc ccagcccagc atggcaggtt   33420
aaaggatcca ccatcattgc cgtagctgca gcataggtcg caactacagc tcaggtctga   33480
tccctggacc aggaattgca catgttacgg tgcagcccaa tgtgaaaaat aaaaacaaaa   33540
accaaattaa ggacttttcc caaggtggga catgcttttg ggtctggggt catgatggta   33600
gtgtgtctga aactgtcttc ccagagggat tgggggggga gcaaacctgg tggcccctag   33660
agccgagtcc acggcagccc agctggtgcg aagggatgag aggaattgtc ggcacagaga   33720
tggagggata gagcaggctg gacggggggag ggacccttgt tggacccgtg tgagactggg   33780
agcagtaaat atcattgact ttgtggctca gaaggtctca cctccaccaa gtagcacaga   33840
aggagccaca gagcatgtgc cgaggaagag tgagggctgg gtgccagtgg tctttcatca   33900
caaagagcct acaggctgca ttttggtgga ctgtggttgg cttgggaaca agagggtcg    33960 ggggacttgg gcagagctga aggtttatag atgtggacag gcctgggcag accagcccctt  34020 ccctgagcca cactgggggtt tgccctgtaa gagcaccggc tggtgggcgg ggcaaggcct  34080
gggggagtga gaccctggtc ggagtgtggt cggcgtgtgg tccatggtaa cacagtgacg   34140
ctcatccctc acctgggctc ttccttccct cctgcccagt gtggtcctga cccccagggt   34200
gtgagaggtg atgttttgtg ggtggtacat gcaaacaact taaacacctt catagtgatg   34260
cttatttcca ttaattagag caagtggtac gggtttctca ttcaggccaa tgatagcttc   34320
ttaataaaca aattgaagta agaagtagga ctgtaagtac agcagacaga aatatacaga   34380
gggccgggca gtggccagta tccagagcag ggctgatggt ctccttagcg ctgcagttag   34440
tgtattagca gctagtgatg cttagcacac tgctgatgac aacaagagcc agcatgcaca   34500 gcccctttgtg tgcaggacac tgttcaaagg gctccatgta catttcacca tggaaacccc   34560
cccaagacga tcgatgctct ggccccgtct tgctcatgag gagctcaagg tgcacaggtt   34620
aagcatctca cccaagggaa cagaattggg gaactgacag cagcatatgg tctttgacat   34680
caggctggcc cgagtttcag attgaccga actcctcgcg aagccgtgtg accatggaca   34740
agccacgcag cctctctgaa cctgcctcac caactaaatg gggatcatgc cctaccctgc   34800
tcttggggtt gctaaaattg aaccacttgg ttgtgacccg cgctgagtgc gcagagagcg   34860
tttgctgctg cagctgagga cccttgtcac cgtctttatc atcatcatca tcactttcgt   34920
catcgtcatc atggaaaagc agccctggaa ggagggcgat gcattaactc catatttggc   34980
tgcccacaca cgcccccctag gggccatgcc tctctctgcg tgtgctgggg ctgagggtgc   35040
acctgcattt tgctcttgag ctgggacacc cccaccccca cccacgggc ctcttgcagc    35100 cctgcagcag gaacactgat catgacttcg gctccgagtc tccgctgaga agcctgacct   35160
ggagcaaagc cccttccgtg agggagcgct tgtaatctaa tgcagagatt ttaaactcac   35220
cgttgaaaac tgaagtttaa acatcaggag ctttcacaaa aatccacatg tgcaactagc   35280
tgcttttctt taaaaatttt tgttttctta cggtatggtt gatttacagt gctccttcaa   35340
tttctgctgt ccggcaaagt gacccagcca tacatatacc tatatacaca cattcttttt   35400
ttttgttttt gtatcatctt ccatcatgtt ctagcccaag agattggaca taggtccctg   35460
```

```
ggctgtacgg taagactcca tcgcttgtcc attctaaatg gagtagtttg cgtctaccaa   35520
ccccaaactc ccagccctct ccctgtctcc cccttcccc tggcaaacac acgtcggttc    35580
tccgtgccca tgatctggtt ctgttctgta gagaagattg tctgtgccat atcttagatt   35640
ccacgtataa gcgatatcat ggaatatttg tttttctgtc tgacttcact tagtatgaga   35700
gtctctagtt ccatccacgc tgctgtaaat ggcattgttt tgtcctttt gtgaccgagt    35760 agtattccac tgtgcatata taccacagct tctttttttt ttgtctcttt tccttttcca   35820
gggccactcc cgcagcatat ggaggttccc aggctagggg tcgaattgga gctgtagcca   35880
tcggcctgcg ccagagccac agcaacacgg gatccgagcc gcgtctgcaa cctacaccac   35940
agctcacggc aacgccggat ccttaaccca ctgagcaagg gcagggatcg aacccgcaac   36000
ctcatggttt ctagtcggat tcgttaacca ctgtgccatg acgggaactc caatatacca   36060
cagcttctta atccattcat ctggctagct gttttttcaac caccagagtc caggcccacc   36120
tacgcagcca cggtctctcg gagcaaggcg aggtccctcc cttcgggggt cttacccccc   36180
agtgcctgcc tggcccattg ggtgtgagct ggccatccct tccatggcag gaaagagcct   36240
ggctctagga gccaacccct gtgctgcact gggctgctgc ttccgggcgc cccacactgt   36300
ggagtggggt tttgtttta gcttttgctt tttagggcca cacccaaggc atatggaggt   36360
tcccaggcta ggggtcaaat cagagctgta gccgccagcc tacaccacag ccacagcaat   36420
gctgcatctg agctatgtgt gcgaccctga ccacagctca cggcaacatt ggatccttaa   36480
cccactgagc aaggccaggg atcgaacctt cagcctcatg gttattagtc agatccgttt   36540
ccgtgttata tctaatgatg gcaaacatct cggtaggaaa cgtggtcaga ctatgaccat   36600 ggttttctt gatcctctgt ttgcgttcag tgatttgggt tgactttggg gtgatttgtg    36660
tttggggtgc ttgctggttt tgtcctcttg gtgtggcatc aaccacagaa cttgccctaa   36720
aaagcccagg agggtttgtt gttttgatgt taagtgggac aggatcccgt tcagggtgtc   36780
tgtcgggcag aggctgagct ctgggcttcc caagagtgtt ctcattaaaa ggaaaagtgg   36840
ccttcagtga gcatgttctc cctatgcaat attatcttag ccctgctttg ggttttgctt   36900
ttgttttgag atgagaaagc aggagcccag agaggttaag tcacttgccc gaagccacag   36960
agcatataag cggtaaagct gggatttgtt cttaactta acactctaca gcccaaacta    37020
gagccaagct tttctctgct tctggaatgc tctggaatgt ggcttgtttc tgcagtcttg   37080
aagatggtta gcaaattgca ggctacaggt cagacccagc ccacctgtgt ctgtatgacc   37140
agctcaagtg tgttggcacc gtaagcctgg ggaccatgca gagatggccc cctccttgcc   37200
cccagcctct gcctcccagc tggtgccaca cttgaccaat gtccagggtc tgtgctggtc   37260
ccacctacac ctgggatttg gctgtgggca cctgctgggc tctgagctgt ggaacctcct   37320
tgcaggaatc atccagggcc agccatccat gagatcaagg acttggggt gtccctgggg    37380 tgggatgaca ctgaccacgg cacctccagc ccaccagctc cctcctccag gctggtctct   37440
ctgggtctca gaatgtgtcc agtgggtggt cactgggtgt taaggcgagc ccacccagca   37500
ctacacccca gcaggaaagg ccttggctgg ctggagctc agttgatgag cagcgacctc    37560
tgctggccag ggcaggacag gacaaccccg agggatccta aatgttggag caccacaaag   37620
ctgactctgg cttcttcagc gttaaaataa aatttgacat agcacttgag acttttaaca   37680
gatgttagca tttcagtttt gacaagattc tgaaatgcaa aggcagctgc accgtcacat   37740
ggcactcgcg tgagatgtgg aggaagatgt agataagaaa gaaatggaaa caccaggttc   37800
ccagaccagg gaccctcag acaggttggg gtgtgagggg tcagtgtgtg ggtttggagg    37860
```

-continued

```
aggggcattg gaggagggg ctgatgtgag ttcctgggtc ctggggctct cagagcagag   37920
ggtagggcct ccacactcca cctggggctg gttggtgggg gggccaccat ggggctgtta   37980
gaagcttacc ctgccatctc tctggttgaa ggggtgtggc tgtgaccacc aactcaggct   38040
caaacccaga gttgccctgt ccactacctg catggagatt tgaatgaatg aagactaaat   38100
aaaatgaaaa atccagctcc ccacttgcac cagccacttt ccaggtgctc cttggccagt   38160
gtggctagtg gctgcccta aagagcgag aggacacatc tccatcatgt cagggctact   38220
gggcagcact gagggtgaga cgtggccaca catccacttt ggtgcaaagc cagtggagtt   38280
ggctggcttg gccagccctt ccagagtttt ctgcatcaag cagggacctt ataacctgca   38340
atgccaaagc cctttacagg aaaagtttgc catcccctca tttagagtgg acttagggca   38400
tcatgggcag aaggggaaga gcttgaaggc cttgctgagg tccaggggag gctgtggcag   38460
ctgacactgg gagaacaggc aaaaggacgg tatttctgag aaatattttg gaggcagagt   38520
gcccaggatt tatctatgca ttagatccaa gagtcaggtc tgaggtggag agggcaggag   38580
gggaatggag catggggtcc agtctggctg gaccgctgag gggatggggg accatgtaga   38640
aagtctggtg acagtggggc tctgtcttgg tcaaagccat gtccacagct cctggaaggg   38700
tgcctggacc ccataattgt tcagggaccc ttgtggatgg atgaatggat ggacggatgg   38760
atggatggag aagtgagaga gaagaggaac tggggagggc tttctcatgg gaaatcaaga   38820
gatgcgtttg catgtgtttt attttgatta tttgacctcc tgacggaagt gtcaaagtgg   38880
ccagtgatgg atgtgtctgg agttctgagg aagggtcaag ggtcgacaga gatgggattg   38940
gttctgaagc cagaggactg actggatgag agaattggat gagagaatta atgagagag   39000
tgagccaatg ggaggagca ccaagggcgg gtcctgggc ggcccagcgg gagcctgaga   39060
ggggctgagc aggagtggta ggggtaccgg gggatgtggt ttccagaagc actagaggaa   39120
ggtactggcc tggacagatg gagggacttt gctgccacag agccaagtgg accagccctg   39180
gctgacgcag gtgtgggaac gcggatccac ggctgccctg tctccctgtt caccctttcgc  39240
gtggaactat tcagcccttt ggacagttat aggcaccttg ccaggaaaa aggcagtctt   39300
ttggaacatg gatgcatttt tcttcatct taggtcaagg gttctcggcc ttggcagtat   39360
tgatatttgg ggccagagaa ttctttgcct gtaagagccc agttcaaaca ctgcccactt   39420
tgtccagact cccaggtcca tggggggaga ccaaggccca gtgggagcaa ctggcctgtc   39480
tgggtttcca gggtagcagg acccagactt gttccaagag cctgtgtcac agctgcgcgt   39540
ctcaccgtgg gcctcccttg ccaagcagac accgcaacgc atccccatgg aaatctaagt   39600
agtgtctgcc tcaagcaggg gctctcggcc gtgggcattc tgccccccag gggcagtagc   39660
tggagaccgt tttggtggtc acactggcat ctggcagata gaacccaggc ttgctgctat   39720
gtatcgtata ggcagagatt tatctggaag gagaggaaag tgcatccatg cttcaaacca   39780
cagctcttag ccctgaggat aatgtgcaaa gtgccgaaga gtccagacct cccctccgtg   39840
gcctccatca atctccctgc cttggaatgg gcagaatcgg gcatgttacc caaatatttg   39900
tgtagatgag gaaaccgggc ctcacagagg tggagactaa ggcgcttgtc tagaaatgag   39960
tcagtcatca cagaggaaaa ggatgggtgg aggtgggaga cgggtgtgtc agcgggccat   40020
tcctgtgcca gccttccccc caaaaccttg acattgggga cctactgatg cccaggggag   40080
ggatactgag cctgtcctga gcactgcgag ctcacgccgg ccctgtgcct ggtgcttctg   40140
gctgcaggct tggctgctga gggcctgggt ctggagcgt ggcctctgaa gggtcggggt   40200
ccactgcctg gcactgattt gcaggaaccg ggagccaaca gagtcacagg acaggtgccc   40260
```

```
acatggagaa aaagagcctc tgcacacgca caaggaaacc acacaaccgc ttttacctgg   40320
aagcaccaaa tgtttgcttt aatgttatca tttgtgcaaa acgtattaac caagtctcag   40380
tggtggactc ttagaagtta caggttgcag ttcataggcc ataacaatag tcttagagtc   40440 tagggggtctt tgaaaaattc ctatgaacaa gtaacccttc tgaggacggt tttattatta   40500
ctcgtaggag taataataat aaaaccagag tgtttccggg tgcgtgtctt tgctggacag   40560
aagagtaagg agcccactct catgcctgtt ctcagctcag actgagacct gccatctgcc   40620
gtgggcgggc agggggcgtt tcttagatcc ttttcatcgg gatttgggag gagccctttg   40680
aaggcaaggg ctgcatttcc atgagtatca cgagggagag gacctggcct gagaggtctt   40740
gaacttccaa cgtggatgat ggaatcacag aaatggtgat gagccctggg acccgcggga   40800
cgtgcaggcg tccttctccc aagcttggta ggaccgggag cgggtggcct cagtcagcac   40860
cacggacagc gccatctctt tggtcaggca ccagccgcgt tccctgactg atggatgaac   40920
ctgtcaggct gttcctaggg gttgttggta tcttcccctt gggtggttgc aaagataaaa   40980
tgagattaag tggggccagg gccttgccag ggccaggcac ctggggctgc tccaagaggg   41040
caggaaggct ggggtcccaa ggtgaggatg ggaggccacc cctcttttg cgtcaggtg   41100 gaaggaaggg tgtgttgggg cccataggtt tgtgtctgag gccccccgc ccctgccccc   41160 agcccagttt ccctgtaaag ctggaggtga ggtggcctgg gaggggagt gagaagctgg   41220 acagagaaga gccatggatg tattttcctt tgcatccatg gaaggaaagg gacagaagag   41280
ggtttgacgc agagtggctg caggatggag cagagcccag ggccctgagg gtgtggtcct   41340
gggatggcca ggacgggggc ttctgtgtca ctttcttctg cagcactgtg cctcggcagg   41400
gactggcaga tggaggcttc atccagaggt gggactttcc cagtggggca gaggacttgg   41460
gggtactggt gaggtggttg ttgctgcggt ggatggtgga acttgagctg gataaagaga   41520 gaagggaaa ggagagggct gatggttgg gagaaggcgc aggtgacagg ctgaagtggg   41580
ggtggagcag tgccccagga ggtggaggca ctgttctaga tgagcctgca ccaggcgagg   41640
ggacggggct cggggggctc aaagctgaac ctccctgatc ctcccctgcc actcacctgt   41700
cttgctcgcc tggggcagtg atgttgaaaa gcaggcgtgt aaagtcaata gctgcccaac   41760
ttgagggtct gcgacatgcc aggcacacat ctcatggttg cttcttcttc ttcttcttct   41820
tcttcttttt tttttttttg tcttttaggg ctacaccca tggcatatgg aagttcctag   41880
gctaggggtc tattccgggt ctaattggag ctacagctgc cagcctacac cacagccaca   41940
gcaacacggg atccaaggag tgtctgcaac ctacaccaca gccacggcaa tgccggatcc   42000 ttaacccct gagcgaggcc agggatcgaa cctccaactt catggttcct agtcaggttg   42060
gtttccgctg cactgcgata ggaactcctc attgtcactt cttagttaaa cctcccagcc   42120
atcctgtgag ggactcttgt tcgcctgacg tcatccgtga caaatggtga cacaggagtt   42180
tagtaactta tccaaggtcc cagggtgagc tcagggacca attggagtct gattccaaag   42240
cctgtgtttg tgaccagctg cccaggtgag gtgggagctt cagtgacacc tgttgagtgg   42300
aaaagggaca gaatcccctc cactggcgca cctcccctccc ccttccgcct ccgtcgtcct   42360
ctctctgctt ctgatgtatc tgttgacagc ggaattcaca agtgtcatgt ccatgggcca   42420
ggccaccccc tgtactcagc tctgcaataa caaccccacc caaccaaggc ccttgcagtc   42480
ctcacaccca ccccaagcgt gtctcaactc tcttgccttt gaaccagcca agacgtcatc   42540
agcatccaga ggtgacgaag cagacgccgc cggcagccgc ccacctgcca tggacgagcc   42600
gtctcaagcc ttagctgggc ccgatgccct ggacagtcct cccagacccc tggacagatc   42660
```

```
catgggccag cttcccagcc ctccgctgct gcccaccccg ccacccaagg caggctccac   42720
agcctcaaga agcaccccag gtgggtccgc ctgcatcccc cttcctgccc tccatccatc   42780
cgtgcctccc accagccctg ctgggcctgt gaccaggact tcagactcac acctgcccct   42840
ctgggtccag gaacctaagg acatcagggg gattttctga cgcgtcaccc actggtctgg   42900
ggactgaact aggagtgcga ggggacaggc gggtcatgag cttggactt tggcctggat    42960 cgcttagagc tgagatattt tttgtgattg atttaatttt cttaggggg aaaggtttgc     43020 ttcggcaagt ggacgctagg tggcagcaga aaggagaaa gccctcact tgggcttaac      43080 tggggcccaa ggggacagag gccacaggct gagtctccct ggggcccccc atcggagaca   43140
gccgagcggc cccccgcccg agagcttcct caccccactc tccacccaaa tcccacttgc   43200
agacttgctt tgctgggcct gcatgatatt taatacttaa aagaaaatgt gtggccacat   43260
ttaaaatata tcaaaacata tttaaatatt aaacatatta catatgttta aggggtggcc   43320
tgcggacccc tgggccttgt catcattagc ccagaccttg tctgaagggg gatgggagag   43380
ccatggtcag aaagctcctg ctgggcaagg cacagggtgg gaggcagacg tgaatgagga   43440
agcagagggg cccctgtggt ccaggctggg ccaggcctct ggaggacttg tggcttcggg    43500
gagccaagtt cgtagcagag aaatgggaag gagggcttca ggcgcctgag accttgcagg   43560
gagctgtggg tactaatgtc tgcagctcag gggtcacgag gacggatcgg aactgctcat   43620
ggctggaccc cttctccggc tctggggaca aggaggcctc atgcagcatc acagggttgt   43680
gtgagtgggc tcacctggcc acgagccctg cattctcttt gcttacgggc tcctatcttt    43740
cagcaaagcc ccacttccct gcttccaaag acttatattc ttttttataa agttatttta   43800
ttttatggcc tcattcccag caggatatat ggacattccc aggccaggga ttaaattgga   43860
gccatagttg ggcaacacca gatccttgaa cccactgtgc tgggccattg attgaaccct   43920
tgcctctaca gccacctgat ctgctgcagt ttgattctta acccactctg ccacagcagg   43980
aactcaagac ttatgctcgt gtttgtcctt ctcccacccc aggccaggcc acgctcttcc    44040
aaggctctgg cgggaagaat actgacccte cgctccgagg acagctttcc acgcccacgg   44100
ggtctccgca tctccccacc gtccaccggc cgctgccccc cagccgcgtg atcgaggagc    44160
tgcatagggc gctggccacc aagcaccgcc aggacaggtg aggcccctct cctggcaggg   44220
ggtcctgtgt gcccaaattc ccactggggc ccagcctcgt gggggtcacc tatgcagtta   44280
tgggggtgcc cgctctgggt gggcttaatg ctgtgcagtc acagtcttga aattctcagt   44340
ttttgagcaa gaagctcacg ttttcatctt gtaccggact ctgcagctgg tctgtagctg   44400
gtctcggctg ccacattcca gtgggtca gctgggagga gtgcactgtg aggacaagcc      44460
acaaacccca cgtgtcccct ggaccatccg ggtcaggtg ggagcctcct gagggagcca    44520
atagtgaggg agttgtagat gtcgcgttgt ccccggactc tgccggcttt gggtttgcat   44580
caggcaggag cacaggtaag cctgctgtga tgctgcctct aagtcctcat ctcctgtgcc   44640
tcacagccct gaggacaggt gagtccttgg agggccaaac agataatgca acacacgtgc   44700
ggcttggcaa atattgctc aaataaaagc cctcttcagt tcttaggaaa tcctggctct     44760
gagcgtttgc tgcactaagt gttggtggat tttattccat acccgtctgc cattcaagac   44820
agcatgttct cagtgccatt tgccttggcc tccaagccgt gtgctcctct ggagcttcta   44880
gcccagtgta ccggctgtac ctacttggga gctgtctctg cggcccctgc tataaacctg   44940
atataagccc ccgagtcaac tccgcacggt tgcctgggga agctggacca ctgacaatgt   45000
gacctgcctt tctgattcag tttccaagga cgggacagta aagggtcccc gaagaagcgt   45060
```

```
gtggatgtcc ggctgtccag gacgtccagt gtggagcggg gcaaggagcg ggaggaggct    45120
tggagcttcg atggggcctc cgacgtcaag cgggccgccg ccaaggagtc cgaggagaac    45180
aaggagaact tgctgatgaa ttccgagctc aaggacgacc tgcttttgta tcaggacgaa    45240
gaggcgctga acgactccat cgtctccggt gagtgcaggg cggatcccgg ccgtgggaac    45300
ttctcgccgg aggcaccacg cccacgtcga ggggtgctt ctgtagctag catgtggggg    45360
ggggtggagg gacaccctct ctgtccgtga acagggcgtc agcaggcggg cacggggcac    45420
aattagccag ggaccgaggg agctggtttt attctgatca ttgcatattt tcatgtgtgt    45480
tcgaaccaac aaaagtggct cagctatcga ctaagacatc gtggcgtggg gatgacgtgt    45540
cagatggtgg cagggggggc cctgagatgg ccagtgttgg aagatgtggc caaagatgct    45600
catagaggga gatgaggtgg ggccgatgcc agtggccatc tcagaaatac acaaacctgc    45660
tgtgtctgct ttgctcgggg ccacatctgc acgaggccct tagaggcctg gtctgtcctc    45720
acagtgtcct caagatcaga gggattgctc tgccctaccc gtgaggacct ggggctcagg    45780
gaggcagagc gttgtagacc ccccgtgatg aatgtaaaag gaactcagcc ctggtgtggg    45840
ctgtgctgag ctgcatccct tgcaaaggtc aaggacggat gtggccataa agccttgtgg    45900 cgggggggtgg tgattgtccc cgagcgaggg gttcctagaa gcatctcgtg gtgaccatca    45960
ccacattggg cagaggtctg ggtggaggct ctggggaact tgcctgctgc tcgtgccagg    46020
tggggaaggg gatggcattg accctgccct ggctggtatg acggggcac aggcagtggg    46080 cactgtgccc aggtgggcag accgggaccc ccggattaga cactgacctt ggctgtcacc    46140
ctgcccggga ccttgcatac gtctgggcct ttcccgccct ggtctggtga agctcttctg    46200
gaagagcagg tgacagtgct tccaactggg tctgttgctg aaattcagcc tctgtctgcc    46260
agtgtcaaat agacgcagag acagagcttt gggtgaaggt gaaaaaggta actttattgc    46320
tttgccagga aaaggggcca tagcaggcta atgccttata gattgtgccc ccgttggagg    46380
gggttaggag gtggttttat agtttgggc gtggaaaata gggccacacg taaggatcac    46440
gttgaggcaa gcttgccttg tcttccaaag ctggtgttta gtggcccag gactggttct    46500 ggtggttctc ctccttccgg gaatgaagat gcttcatcac gtagttcttc cattgtgggg    46560
ctggggtttc gttctgcaga aaggctcaaa ggtactgtta tctatattcc ttgaggagac    46620
accaggacct gtcccaaggc tgcgctcttg tctctgacgg ctcctccctg gtctctgcat    46680 cccctcccctt ccctgaagag caactgccct ttggaactca gggaaggtca cggaggctga    46740
ggcttattcc ctaaaaacaa gaaacgaggg acacagaaag acttgtgtgc ccaggagccc    46800
cacagggctc tgctcggttg caggtcttca tggcagaaac gccaagccag tcattggcca    46860
agaagccctg gacatctagg aagaggcttc tgaagcctgt gtgttcccca aacttatctg    46920
gccccggggc tttcccttaa acacccatca gcctcctgca ggacaggtgg cgtgggacac    46980
acctgagagt ggctggtgga ggcagggatc tcgggctgga gcaggtgcct aaacatcggg    47040
accagtgatg ctgagggctg gagggttctc tgccgtgggg ctgccctgag ctttgcaggg    47100
tgtttggcct ctacccgcca gactgcgctc cctccagctc tagggagggg tccttcctgc    47160
ctcttccagc tgctgtggct gcaggtggtc cttgccttga ggctacgtcc ctgctgccct    47220
cttcacattg ctgtccctgt cctcttgcta ataaggacac tctcactggg ttaaggaccc    47280
atccgcataa tcctgcatga tcctcatttt gagttcctta tcttaattac atctgcaaaa    47340
gcaaattaca tctttttttt tttcccttcag agaaggtact ttcccaggtt cccagtgcac    47400
tctttggggt cactcttctc tctcccctgt cactcctgat ggtgtaccat gttcctcttg    47460
```

```
ttgagccaag gtcaccsctg gggcctttca tggcccccca gccccatccc tgggtcctcg    47520
gcagcagggc cagtccactg cctcagcggg agctcccatg ggaaggtgcc ctgctctgtc    47580
cctgcagcct gggtaggtcc cctgcctcgc tccctcctca gagatcagat caaccatccc    47640
tcagagctcg acgcagtcgc aatttcaccc tgattttgt tattatttct ctgttgtccg     47700
tctccctcta aaccatcaat tattcgatga tgatggatca tctgacatgt gtgtttgacg    47760
gctgtccgga tggggacgg tggccttcg tccacacagt gcctggttct aaggaagagt     47820
caggaagtag cttctggata atataatggc tgtgattctg tctgccgatc tgatgggtcc    47880
ctggtgaggt cccccagccc acgtgctcca aggtgtcacc ccatagacgc agcatgtcca    47940
cctggggtct cagacgtgtc gctgacctga ggtctctggc tctgagctct tgatctttgc    48000
ttccaaaacc aaattgtcct tgtgaacaag ggccctgacc ctctgggccc cgggccacct    48060
cacccctctc ttggctttgc acctgacgca cagacggctc ttcctcaggg aaatctggcc    48120
atttctcctc tgctccatcc tctcctgccc agagtcagcc tcccacgggc cccctgccac    48180
caccaaggcc cctgttgtag cccctccctc cagacgccac ccctcgcttg tgtccctcca    48240
gcggcttcct gaaggctgaa acgccacttc ccaccaggac ctgggtggcc tgtccctgtc    48300
acccaggctt atctccttcc aagctccttg ggacccagcc atgggccctc tgtgctcctt    48360
acacacacca accacagtcc acccaccact gggctctcgt gcccacccag gaagaggtgt    48420
gtgtggctgc accgtgttta aaacaccgct tcctccgaga agccaacagg cctaagcgag    48480
tgacgccccc ctcacacggc tctgcagccc ctccctctcg ttgcatcccc tgagacgccc    48540
ctgaggtcag gggcttcacc aggcagctcc cgctttgtct gcagtccccg cttcagtgct    48600
gctacgtgta caataaaggt cagttaggaa agactgggtg tccccggggg attaaaggag    48660
gggtgattgt ggcctcagat ggaggagcag catatgatgt ctcccagggt gtgggccaaa    48720
cacgcatctc ttgttatttg tctcctaaaa cctggagttt gacgacagtg acaggagcag    48780
gagagtagaa ctcattctag aaactcgctg ttgtggccct gccctggctc ccctggacgg    48840
cgctgggctg tgcttatggt atttgcaaac cccagcaaag ccacctctcc tcctgggcct    48900
tccttgcgta ccagcctctg gggtcaaggt caaggtcaag ggctcacaac cagccctaag    48960
atcatcctgt ggagcgcccg gcccactgca cagtcaggcg ggtctggaga tcgagtcccg    49020
acaccccgg cctggcccct gccaactgca gctgaggcca gggtgcaggg tctggggcc     49080
ccaaacccct ggaaccccaa gtagaaactg aggtctttgc ttttatcaca ttctcataag    49140
tgtccggaac tccctccaag ttgtgaattt ctggaacaaa atgcttggag gagaaaacgc    49200
aatgctggtt ctggagaaag cgtacagatc tcacttagg gggaaaacca gtcatagtgg     49260
gagaagccca tacaagtatt ttgccccggta ggagagtagc acagatccgt ttttcttggc    49320
ttttctcgag ttcagacccc ctcccaccat ggcggatggc accttatttg tagatcgctg    49380
gggtgcgacc tacaaataaa agaagtagaa acacgcccgg cagcagcttc atcagttgtc    49440
aatcttagaa actgcactgg tgtttcttat ttatttatcc tcataactca ctgtccccgg    49500
agcctttgca ggtggtgtcc catccatcac gaacccccca ggacgttttc attagcatct    49560
cattaccctg aattctctag aagcagcagc tactttaggg tgtgatttct ggagctgatg    49620
gaagccccac ccaaggcaga tctgccctgg catcggctgg aagcttgtcc tgtaggatcc    49680
tgttgcagtg acaaatgtat ttgtttcagt ctagggctga cagtggattt ccatgcaggg    49740
caaagacaat gtcttgatca atacagcgtc acaggccgtg tgtttccgcc tcgagctggc    49800
tgccccggct tgccgtgtgc acacacactc ccccaatatg cgtgctcagt acctgccagc    49860
```

```
acatagggca cctttgtggg catgcgtggt cagcgccagg aagaaacagg acactgggga   49920
ccttctcaag tccatcaaag gtgattcttt acaagatttt gttttttcaga gcaatttaag   49980 tccatagcaa attaagactc aatacagaca tcccctggcc ccgcaactgc aaagcctgga   50040
cacagcgtca cccaaagctc ataactgaca ttagggttta ttctcggtgt tggagggtct   50100
gtgtgtttgg acaaatgtat aaggaggtgt ccatccttgt atagtgtcag agagagaatt   50160
ttccgggtct tagcagtccc ctgggctctg cctgtcaccc cattcgtcac cccaacccct   50220
ggcaaccact gatcttctta ctgtctctgt agttttgcct tttctaaagg gtcacacttg   50280
gaaccatcca gtaggtaggg ggctttcctt ccctcaggac taggcatttg tgttcctgcc   50340
atgccaccac atggctggat aacccgtctg gttttttttcc ttttttttct gccggtttca   50400
ctgagatata atcaagacat aacactgtaa atttaaggta tacagcataa tgttttttcac   50460 ttaggtagta tcctcaaatc atgaccacag taagtacagt aaaaatttat catctcatat   50520
agatacacct ggtattttga ttttcaaaga aatagaaaaa ttattttttc ctagggatga   50580
gaactcttac gatttactct ttttttcattt tttacttttt tgtcttttgt cttttttgggg   50640 ccgcacctgc agcatctgga ggttcccaaa ctagggtct aatcagaact acgccagagc   50700
catagcaacg ccagatctga gccgtgtctg tgacgtacac cacagctcac agcaacactg   50760
gatccttaac ccactgagca aggccagggg tcaaacccac aacctcatgg ttcctcatcg   50820
gatttgttcc tgctgcacca caacagaaac tccctcgatt tactcttta aaactttctc   50880 tctctctctc ttttttttt tttttttttt ttttgtcttt ttagggctgc acccacggca   50940
tacggaggtt cctaggctgg ggtcaaattg gagctgtagc tgccggcctc taccacagcc   51000
acagcaacgc gggatccttg ccccactgaa tgaggccagg ggtcgaactg agtcctcatg   51060
gatcctcgtc agattcgtgt ccgctgagcc atggcgggaa ctccaggacc ttcatatgta   51120
acatacaaca gtgtgaactg ttttgatcac gttgttcatg acatcccgt gctcggctgt   51180 tttgttggtg gaagcttgga cctttttgact gccttcatcc aatccctacc accccctctg   51240
gtcaccacaa accagatctc ctttttcaatg cgtttgtttg tctttggagt ataattgccc   51300
tacactactc tgttagttcc tgttacacaa cacagtcatt tgatacgtct atgcatttca   51360
aagcgatcgc cgcagtaagt ctagtccct ctgctatcat acggagaaat tatatcatta   51420
ttggctctat tccccacacg ccacgtttct gacccacgac tcatttattt tttgactgga   51480
ggtttgcacc tcctaatctc cacctattcc tctcccccc acccgcctcc cttctttttg   51540
atggagacta gtatcccact gttgacacct gccccacctt ctgcattcct tcacctatta   51600
gaggacctct ccgttgtttc ttagtcttgg caactacgaa tacatctgct ctaaacatcc   51660
atgtgcaggt ttttgtgtgg ctgtaagttc tcaactctat tgggaaaata ccagaaggca   51720
attgttggat cacgtgggaa gagtatattt agttttgtaa aagaaatcca gtcttccaaa   51780
gtggctgcac catttacccc ccctccccgc caccggccgt gacagttcct gtggctccac   51840
attctcgcca gcatctggag ttgtcagtgt tctgggattt gaccatattc attctaagag   51900
gtgtgcagtg gtgtccccctt gttgtttaa tttgcatgac atatactatg gagctacagt   51960
tactggccta caccacagcc acagcaacgc aggatctgag ccacatcttc aacctacacc   52020
acagctcaca gcaacgccag aatccttaac ccactgagcg aggccaggga tcaaacctgc   52080
agcttcatgg ttactaggca gattcatttc tgctgcaccg caaagggaac tcctgttttt   52140
aatttcaaat tccatttgtt tattgttggt ataatggaga gcaattggct tttgtatgtt   52200
aaccttgtat cctacaacct ttatgtaaat cactaattag ttctgggagt ttttcattga   52260
```

```
ttccttagga ttttctacat agacgtttgt gtcatctgca agcaaagaca cgtttatgtt   52320
ttctttctca ctctgcctac cttttatttc cttttcttct cttattgcat gaactacttc   52380
ttccagtatg atgttgaaaa ggagtgatgg agaagaaaga catcttgcct tgttcctgat   52440
cttagtaaga aagctctgag tgtctcacct ttacatgtga ggttaactag aggttttgt    52500 agatattcct tatcaaggtg aggaagttcc tctctattga cagtttacag aggagttccc   52560
attgtggctc agtgataatg aacccaacta gtatcatgcg gatgtggatt caatctgcct   52620
cactcagtgg attagggatc tggcattgcc atgagctgtg gtgtaggtca gcagctgcag   52680
ctccaatttg acccctagcc ttggaaactc catatgctgt gggtgtggcc ctaaaaagca   52740
ataaaacaaa caaacaaaaa cagtttacta aggtgattct tttaaatgga ggtaacatta   52800
taacacatgg gtttcacata gacaacatta tactttatt tctgtctaca ttacagcatg    52860
ctcaccaccc aaaatttaga ttctagccat caccatgcag ttgaccctct gtgtccattt   52920
tacttcctcc ccattctcat ctggtaacca ctgctctgct ctctgtatct acattttggt   52980
ttggtttggt ttatttttgt tgttgttttt tatgttgcac atatgagtga tttcatatgg   53040
tatttgtctt tttttgtcac atttatctca cttttgcataa tatcctccat atccattcat   53100
acccttccaa atggcaggat tttacctttt tttttatgac tgagtaggtt ctggtgtgta   53160
tatgtgtgtg tgtgtgtgta tacatgtgta tatatatgta catatatcta tatatgtata   53220
cacacatatg tatacccccaa cttctttatc cttcatttgt tgtctacaca tcttggtact   53280
gtaaataata ctatgaagaa cacaggaggg cattatctt tttgaattag tgttttgta     53340 ttcttcagat acataaccag aagtagcata gctggattgt atggtagttc tcttcttatt   53400
tctttgaggg ttctccatac tgttttccat agtggctgca ccaatttaca ttctcaccaa   53460
caatgcacaa gggttcccct tcttcacatc ctcgctaacg tttgttattt cttgcttttc   53520
tgataatagc cattctgata ggcatgaagt gatatttat tgtggttttg atttgcattt    53580
ctctaataat tagtgatgtt gaacatcttt ttatggtcct gttggccatc tgtgtgtctt   53640
tttagaaaaa tgtctattca gatcttctgc gcattttttt taaattgctc aatgaatttt   53700
attacattta tagttgtaca acgatcatca caaccaaatt ttatagcatt tccattccaa   53760
acctgcagcg cctctcccca ccccccaacc tgtctcattt ggaaacaagt ttttcaaagt   53820
ctgagtcagt atctgttctg caaagaagtt cattgtgtcc ttttttttaga ttccacatgt  53880 aagtgatagt atttgatggt gtttcaccat ctgactgact tcaattagca tgttaatttc   53940
taggtccatc catgttgctg caaatgccat tatttctttc cttttaatgg ctaagtaata   54000
ttctgttgtg tataggtacc acatcttctt tatccactcc tctcaatgga cattcaggtt   54060
gcttccatat cttggctatt atatatagtg ctacaatgaa cactgaaata catgtatctt   54120
ctcaagtcat gttttttttt tttttttct ggatagatgc ccaggagtgg gactgctgga    54180
tcaaatggta attctatttt tagtttcctg aggaatcttc atattgtttt ccacagtgat   54240
tgcaccaatt tacatcccca ccaacagtgt aatagggttc ccttttctcc acaccctctc   54300
cagcacttat tgtttgtaga cttttggatg gcagccattc tggctggtgt gaggtggtac   54360
ctcatagtgg ttttgatttg catttctcta ataatgagtg atgttgaaca tcttttcatg   54420
tgtttgtttt ttggttttgg ttttggtttt tgctttttta tttgttttg ttttttgtttt    54480 ttggccatct gtatgtcttc attggagaat tgtctattta gatcttctgc ccatttttt    54540 tgatggggtt gtgggttttt tttttggta ttgagctgca gaaggtgttt ataaattta     54600 gagattgatc ccttgtcagt cgcttcattt gcaaatattt tctcccattc tgtgggttgt   54660
```

```
cttttcattt tgttcagggt ttcttttgct gtgcagaaac tattaagttt aattaagtcc   54720
catttgtttt tattatcttt actctaggag gtggatctga gaagatgttg ctgtggttta   54780
tgtcggagag tgtttggtct atgttttcct caaagaattt tctagtatct ggtcttatat   54840
ttaggtcttt aatccatttt gagtttattt ttgtgtatgg tgtcaggaag tgttctaatt   54900
tcattctttt acatgtggct gtccagtttc cccagtacca tttattgaag gggctgtctt   54960
ttctccattg tatattcttg cctcctttgt catagataag ttgactgtag gtgtgtgggt   55020
tttattctgg gctttctatc ctgttccact gatctatatt tctgtctttg tgccagtacc   55080
atacagtttt gatgattgtt gcttttgtag tatagtctga agtctgggag cctgattcct   55140
ccagctccat ttttcttttt caggatgtat ttggctattc agggtctttt gtgcttccaa   55200
acaaacttta aaatatttgt tctagttctg tgaaaaatgt tcttggtaat ttgaactgaa   55260
tcattagatt gccttgggta gtatagtcat tttgatgata ttgatccttc cagtccaaga   55320
gcatggtatg tctttccatc tagttgtgtc atctttgatt tctttcatca gtggctaata   55380
attttcagag tacaggtctt ttgtctcttt agataggttt attcctaagt attctatttt   55440 atttatttt gttttgtttt gttttttggt ctatttttag ggacgtaccc atagcatatg    55500
gagattccct ggctaggggt ccaatcagag ctgtagctgc tggccttcac cacagccaca   55560
gccacccagt atttgagccg catctgtggc ctacaccaca gctcatggca atgcaagatc   55620
ctcaacccac tgagcgcatc ttcatgaatg ctagttgggt tcattaactg ctgagccaca   55680
gtgggaactc ctaagtattt tattcttttt gatgcagtgg taaatggaat tgtttcccta   55740
atttctcttt ctgatatttt gttgttagtg tgtggaaatg cagttgattt ttgtgtatta   55800
attttgtatc ctgtgactgc caaattcatg gatgagctct aatagttttc tggtagagtc   55860
tttaggattc tctaggtata ttatcatgtc atctgcaaat agtgatagtt ttacttcttc   55920 cttttccaatt tcgattcctt ttatttcttt ttcttctctg attgccgtgg ctaggacttc   55980
caaaactatg ttgaagggta gtggcgagag cagacatcct tgtcttgttc ctgatttcag   56040
tgggaattct ttcagctttt caccattgag aatgatgtta gctgtaggtt tgtcatatat   56100
ggcctttatt atgttgaggt tggttccctc tatgcccact ttctgaaggg ttttttataag  56160 aaatgggcat tagaacttcc caccatggca cagcggaaac aaatctgact aggaaccatg   56220
aggttgcagg tccaatctct ggccttgctc agtgggtaag gatccggggt tgccatgagc   56280
tgtggtgtaa gtcacagacg tggctcagat ccctcattgc tcgctccaat tagacccta    56340 gcctgggaac ctctatatgc tgtctgtgca gccctcaaaa agacaaaaaa aaaaaaaaa    56400 aaaaaagaat gttggatttt gtcaaaggct ttgtctgcat ctattgagaa ggtcataagg   56460
tttttattct tcagtttgtt aatgtggtgt attacactga ttgatttgcg gagattgaag   56520
agtccttgca tccctgggat aaatcccact tgatcatgat gtacaatcct tttaatgtat   56580
tgttggattt ggtttgatag tattttgttg aggattttg cgtctgtgtt catcagtgaa     56640
aatggcctgt aattttcttt tttgtggta tccttgtctg gttttggtat cagggtgatg    56700
gtggcttcag agaatgagtt tgggagtgtt ccttcctctg caattttttg gaataatttc   56760
agaaagatag gtgttagctc ttctctaaat gtttgataga atttgcctgt gaagccatct   56820
ggtcctgact tttgtttgat ggaagttttt aaatacacagt ttaaatttca gtacttgtgt  56880
ttgatctatt catattttct atattgtctt agtttagtct tggaagattg tacttttcta   56940
agaatttgtc catttgttct atgttgatca tttttattggc atatagttgc ttatagtagt  57000
ctcttatgat cctttgtatt tttgtgatgc ctgttgtaac ttctcctttt tcatttctaa   57060
```

```
ttttattgat tgaaacctc tctcttcttt tcttgatgag tctggctaag ggtttatcaa    57120 tttgttgat cttttcaaag aaccagattt tagtttcatt aatcttttca actgttttca    57180
tttctactca aatacttatg attactttcc ttctgctaac tttgggtttt gtctgttctt    57240
ctttagttgc tttaggtgta gagttaggtt atttgagctt ttccttgatt ctttaggtag    57300
gattttattg ctataaactt ccctcttaaa actgcttttg ctgcatccca taggttttgt    57360
actgttgtat ctttgttgtc atttgcttct aggtgttttt taatttcttc tttgatttct    57420
tcagtgagcc attggttgtt tagtagtgtg ttgtttattc gccacatgtt tctgtttttt    57480 gaagttttt tctggttgtt gattttcagt catatagcat tgtggtcaaa aaagatgat    57540 tgataagatt tcaattttt taaatttatc aaggcttgat ttgtggccca gaatgtgatc    57600
tatcccaaag aatgttccat gtgcacttga gaagaatgtg tactctgctg cttttgatg    57660 gaatgttcta taaatatctg gtccaatgca tcatttaaag ctgtgtttcc ttgttgattg    57720
tctatatagg tgatctgtcc attgctataa gtggggtgtt aaagtctgcc tctgttattg    57780
ttttgttgtc aatttctcct tgttagcagt tgccttatat attgtggtga tcctatgttg    57840
ggtgcatata tatttaaaat tgttacatct tcttcttgga ttgatccttt gatcattatg    57900
taatgtcctt ccttgtctct taaaatattc tttatttcaa ggtctatttt gtttgagtat    57960
tgctactcca gctttctttc aattcccatt tgtgcggaat attttcttcc atcctctcac    58020
tttaaatttg tatacgtccc tagaagtgaa gtgggtctct tgaagacaac atatatatat    58080
gggtcttgtt ttttaatcta ttcaacagtc tatgtcttt ggttgggggtt tagtccattt    58140 acatttaagg taattactga tatgtatgtt cttattgcca ttttatgaat tgctttggat    58200 ttgttttgt tgctctttt tcttctcttg ttctctcctc ttgtggtttg atgactatct    58260
ttagtgttgt atttgaattg attttctta tttgtgtgtg tatcagttgt aaatttttgg    58320
tttgccgtta cactgaagtt ttgatatagg agtctgtgtg tgtgtgtgtg tgtgtgtgta    58380
tgagattgtt ttaagttgtt ggcctcttaa ctgcaagtgc atctccagtg tcctgcattt    58440
gtaccctcct cttctcacaa tttctgattt tggtagtgta attgtacatg gatagttttcc   58500 tatctttact gtatatatgt cttactggt gagccttatc atttgtggta ttttttgttc   58560
tagttgtagc ctttttttt ctgcctaaag aagttccttt ggtatttgat gtaaagctgg    58620
tttagtgttg ctgaattctc tcagcttttg cttatctgta aagcttttga tttctccttc    58680
aaatctgaat gacagacctg ctgcgtaaag taatcttggt tggaggtttt tttcctttca    58740
tcacattaag tatatcatgc cactcccttc tggcctgaag agtttctgct gaaaatctg    58800 ctgataacct tattggggtt cccttgtgtg ctatttgttt cttttctcta gctgctttca    58860
gtacattccc tttgtctta attttgatca gtttgattaa tatgtgtctt gggtgttcc    58920 tccttgggtt tattttatat ggtactcgtt gcacttcctg gatttgagtg agtggttccc    58980
ttcccatgtt aggaagttttt tggctattat ctcttggaat atttttttctg tccctttctc    59040 tctctctctt ctccttctgg tactcctata atgtggatgt tgatgcattt aacgttgtcc    59100
cagagttctc tgagactctc ttcatttctt ttcaatcttt tttctctttt ctgttctgca    59160
tccgtaattt ccactagtct gtcctccatc ttgcttattc attcttttgc ctcctatatt    59220
ctactgttgg ttgcttctaa tgaatttttt atttcagtta ttgtatttg catcactgct    59280 tgcttaagtt ttaaatcttg tatttctttg ctcagtgttt gctgtaaatt atcaatctttt   59340 gcctccagtt tatttccagt gtcttgcatc acccttcagca tcatcagtct aaagttttt    59400 cctggaggtc gataatctcc agatcactta gatgtttttc tgggtttttt tctttctccc    59460
```

```
ttatctgagc tacagctcat tttcattttt ataggtctttt ggtgtggtgt ctttttgcag   59520
ataagtgagt taaagcatct cttacttctg gtatctgccc tccttctggc cgaagttggt   59580
atgggcttac tgtaagctcc ctgatgaagg gactgctacc cgcccactgg tagttggagc   59640
tgattcctat ccttctggtg ggtggggctt tgtctctggg tgagattaga ggctggctgt   59700
gtgcctgggg gtctttgggc agcctgttta ctaatggatg gggctgtgat cccacctgga   59760
ttattgttgg gcctggggct tctcagtgct gatgggtggg gccagatttt cccaaaatgg   59820
ccacctctag aggaacactc actgatgaat attcccaaaa gctttgcctg caatgtcctt   59880
cccccacgag gagccacagt caccccctgt tttcccagga gatcctccaa gaactgcagt   59940
caggtctgac tcaggttcct atgaagcctc tgctttgtcc tgagacccag tgcacatgaa   60000
agtctgtgtg cacctttcaa gaatggggtc tctgtttccc acaatcccct ggagctccta   60060
ggcacagtcc ccaatggcct tcaatgccag atgctctggg ggctctttct tccaatgcca   60120
gatccccagg catggggact tgatatgggg ttcagaactc tcactcttgt aggtgagtct   60180
ctgtgaacca gttactttcc agtctgtggg cttcccacct gggagggatt gcttatatca   60240
tgtaatcacc cctcctacct tctgatgtgg ctgctctgtc ttctggagta ggatatcttt   60300
ttgaaagttt ccagtccatt tggttgaagg ttgttcagca tttggttgta attttgttgt   60360
ttttatgaga gaaggtgagc tcctgtcctt ctattctgtc atcttaatcc catctcttct   60420
gcccattttc tcaatcaggt tttgtgtttc ggagttgttg tgttgtatgt gttcttcata   60480
tgttttggat attaaccccct attggatata tgattaacac atatcttctc tcattggata   60540
ggttgtcttt tagttttttt gatagttccc tttgctgtgc agaagttttt tagtttgatg   60600
tagccctatt tgtttatttt tgcttttgtt tcccatgctt gaggagacat atacagaacg   60660
atattgctaa gacttattta agaagagcaa ccttcttatg tttccttcta ggagttttat   60720
gcttacatgt cttatgttca agtctccaat ctattttgag ttagttttttg tgtatggtat   60780 gaaatagtga tttttctctc attctttgca tgtggctatc cagttttctc agctccattt   60840
attgaatgga gctatccttt gtctatagta tagggtttgc tctttggtta taaattaatt   60900
gtccatgtgt gtgggtatat ttctgggctc gcaattctgt tctttttttg atctatggac   60960 ctgttttttct gccaataccg tgttgttttg atgactatag ctttgtaatc tattttgaaa   61020
acaggcagta tgatatatcc agctttattc ttttttctca gatttgatttt ctcaggtatg   61080 tgtgatcttt tgttgttcca tataaattta aaaatttttt gattctattt ctgtgaaaag   61140
tgtcattggg attttgatag ggattacact gaatctgtac actactttag gtaatatgga   61200 cttttttaaca atgttaattc ttttagtcca gtgagaacgg agtatcttta tctttttttt   61260
tttcactttt tttgaattaa tgtatagttg gtttacaatg ttgtgccaat ttctgctgta   61320
cagcaaagca acccagtcac atatgtatgt atatacacat gtgcgtatat atatgcatta   61380
cctttcttat attacctccc atcatggtct atcccaagag actagatata gttccctgtg   61440
ctctacagta gggactcatt gcttatccat tctaaatgta atagtttgca tctactaagc   61500
ctaaacttcc aatccatctc attctctcac ttctggcaac cacaagtctg gagaacagag   61560
tatctttctt tcttcccttt ttttttttccc ccttttttagg gccacacttg cagtatatgg   61620
aagttcttag gctaggggtt gaattggagc tgcagctgca agcctatgcc acagccacag   61680
caacatggga tctgagcagc atctgcagcc tacaccacag ctcaccacaa tgctggatcc   61740
ccaacccact gcaaggccag ggattgaacc tgcatcctcg tggatactag cctcatttgt   61800
ttgcactgcg ccacattgga aactcccaga gtatctattt ctttgtgact ctgcagttta   61860
```

```
tttccacaat gtcttgtatt tttcagttta caggtctttc actttcttgg ttaagtttct    61920
tcctagattt ttttttgcag caattgtaaa cagaattgta aattttctc tctgcttact     61980
tattgttagt gtatagcaat gcgatagatt ttaatgtatt gattttatac cctgcaactt    62040
ctctgtaatt ctttattatt ttgagtagtt ttttagtgga gtctttggag ctttctatat    62100
ataaaattat gtcatctgca gaacagtgac agttttactt cttcctttcc aatttggatg    62160
tctttcattt cttttttctta cctaatttat ctggctagga cttccaatac tatgttgaac   62220
aagagtggtg agagtggacc tccttgcttg ttcctaatct tagagtgata actttcagtt    62280
ttccactgtt gagtatgatg ttagctgtgg gcttgtcacc tgtgattgct attaggttga    62340
ggtacattcc ttccacaccc attttattga gaatttttat cataaattgt tgttgaattt    62400
ttatcataaa ttgttgaata ttgtcatatg cttggtcata tgattttat ccctcatttt     62460
attaatgtag tatgttgtat tgattgactc tgtggatatt ggaccatcct tgcatccctg    62520
gaataaaccc cacttgatca tggtgtatgc tcttttttaat gtatcattgt gttcagtttg   62580
ctaatatttc attaagggtt tttgcgtcta tgctcaccag atatattggc ttgtagtgtg    62640
tgtgtgagtg tgtgtgtgtg ttgtctggtt ttggtataag aatgatgttg atcttgtaaa    62700
atgagttagg aaacattcca acctcttcaa ttttttgaaa gagttgagaa ggatagataa    62760
taaaatcttt gaatatttgc taggattcac ctatgaagct gtatgcccct ggacttttt     62820
tttagaggaa attttatta ctctttcaat ttccttacta gttattagtg tattcagatt     62880
ttctacttct tcatgattca gtcttggaag tttgtttgct tctaagaatt ttcccatttt    62940
tttctaggtt gcccaattta ttgagtgtac agctattcct agtattgtct cataattctt    63000
tgcatttctg tgatattcat tgttatttct cctctttcgt ttctgagttt attcgtcaga    63060
gcattctctc ttttaataa tgagtctacc tataggtttg tcagtttatt tatttttcaa     63120
aaaaccagct cttagtttca ttcatctttt ctgttatctt ttagtctcta tttagttatt    63180
tcttctctaa tttttgttat ttcctcccgt ttactgacat tgggctttgt tcttttttttt  63240
ctgtttcctt taggtataaa gttagattgt ttatttgata gttcattgtt tcctgaggtg    63300
ggcctgtatt gctataaatt tccctcttaa taccactttt gctgtacctc ataaattttg    63360
gtatgccata ttttcatttg tctccaggta ttcttttatt tcttaatttc tttttttttt    63420
tttttttttt ttttttttgg tgacccagtt gtatggcgtg taatagcata ttgttcagcc    63480
tccacgtgtt tgtgacttct ccagcttttct tcttgtagtt gagtttttgt ttcagaacgt   63540
cgtggtcaga aaagatgctt gatatcaatc ttttttaaatt tgccttgttt tgtgtcccag   63600
tacatgaccc ctctctcctc gagcatgttc catgtgcact gtgggagaat gtgaattctt    63660
ctgcatttgg atagactgtt ctgcacaaat atgtaaaatc catatagtct aatgtttcat    63720
ttaaggccac ttccttattg acattccgtc tggatgatct gtccagagat gtaaatggga    63780
tgttaactgc tgttgtgttg ctgtcaattt ctccctttag gtcagttaat aattgcttca    63840
cgtatttggg tgctcctgtg ttaggtgcat actcgttaat aacttttata tcttttgct    63900
gaattgtccc cttatccttt atataatatc tgtatttgtc tcctgttgcc ttttgggct    63960
tgaagtctgt tttgtctgat ataaatatgg ctatatcccc tttctttcga gctggtattt    64020
tcttgtagaa tcatcttcca tgctccgact ttgatcctat atttgtcttt agagctgagg   64080
tgtgtctcct ggaggcagca tatagttggt tcttgttttc gtttgtttgt ttgttttta    64140
aacacagcca gccactctgt gtcttttgat tggtaagttc agtccattta catttagggt    64200
gattactgat aaatgagaac ttagtaaaag cattttgttt gtttctttgc tttctggtag    64260
```

```
ctctgtatcg ccactgtttc ttttctttg tgtttctctt cttttggctt ggtaattttc   64320
tatggcactt ttttggtttc ttcttttatt actttgtgtc tctgctccag atttatgctt   64380
tatgctttct atgatgtttg tttaaaacat atcatagata aaactgtcct ttttctgctg   64440
ataacatctt atcttcattt gcctatatga tttctctcct ttcctcttc ccttttatgt   64500 ttttattgtc tcaaatgatc ccttttatg gttgtgagtt tgttaccaaa gtgaagtgta    64560 gttattttc ctacttttt cctctttgac tttttcctg tagtacatgt ttaaaaacct     64620
attttgatcg atagttgcaa tttctgatat tgtctgttac tacttactc aaatatttgt    64680 gtacttttgc cttttttag gtagaaaagc tcctttcaat atggcttata aggcaggcct    64740
agtacagaag ttatgactcc ttcagctttt gtttgtttcg gaaaacctttt accttccttc   64800 acacctgaag gataacttgg ctggatggac taatctggg tgacagtttt tatctttcag    64860
cctttggaga atgtcttcct actccctcct gggccgtggg gctcctgatg ggcagtctgc   64920
tgatggcctg gtaggggctc cttcagagat taccctcctt ttcccttggc tgcctttaaa   64980
gttttctttg ttggagttcc cattgtggct cagtggtaac aaacctgact agcatctatg   65040
aggacgcagg ttcagtccct ggccctgctc agtgggttaa ggatccagca ttgccatgag   65100
ctgtggtaga tgtcatagac atggctcaga tcgtaagtgg ctgtggtgta ggctggggct   65160
gtagctctga attgaccccg agtctgggaa cttgcatatg ccacaggtgc agccctaaaa   65220
agaaaagaaa aaaaaaaaa ctttgtcatt gatttgtgac agttttgata taatgtcttg    65280
gagacggtct tcttgcattg aggcagttag gtgttctctc agcttcctga acttgtgtat   65340
ctggttcctt ccccagggtt gggatgttct cagattttct ttaaacaatc ggtctgctcc   65400
cctttgcgtc tcttcccttc tggattacct gttatcctaa tattgctctt cctaaaaagt   65460
catactgttc tcacagtttc ctcattttta aagatgtgct cccacctctt ctccctgaat   65520
gatgtccaga tgtccgtcat caagtccact aattctgttt gaggtggtct gctctatttc   65580
cagcactttg tgtcgtattc ttcatctggt tttctcagtt atacacctcc ctaatttcca   65640
tttggttctc ttctcgagtt tcaatttctt tggtaaagta ttccttctgc tcttcagttt   65700
tcttctcgaa tttgttgagc tgccttttctg agcttttctt gtggctcatg tgtttttttc   65760
ctgacagcta ttttgaattc tctatcagtt tgataacact atgctgtgac ttcgagtttg   65820
gcttctagaa aactgtcatt ttcttttctgt ggcacagtgt ttctgattgt tcctggtgca   65880
tttgaagcag tgagcaccat tcaactttag gtaaagctttt tcttttttac agttgtacct   65940
gtggcatatg gaatttccca ggctcgaggt caaattggat ctgtagctgc cggcctacac   66000
cacagccacg gcaacaccag atccaaacca cacctgcaac ctgcgctgca gcttgcagca   66060
acactgaatg tttaacccaa tgaacgagac cagggatcta acgcacatcc tcatggatac   66120
tagtcgctga gccacgctgg gaactccaaa gcttttttat tttttaaact tggttctaac   66180
tgttcaacag gttagaaatc agaggacttt cttttctctt ccagcaggtg gtgctgtggc   66240
acaggttcta acagttcaac aggttagaaa gcagaggcgc ttcttttcat ttccagcagg   66300
tggtgctgtg gcacaagttt ttggtgtctc ttacctgagg tcgcatttga gaactgggac   66360
tttgcaacct ccaccctgta cccttcttgc cccaactgtg tgtccggagt ccttggtgcc   66420
ttgctgctgc tgacctccaa gccccgcca tctgtcccca tcaggctgt gccccacgcc    66480 ctgccactcc cttgcccagc tctgtgctct ctctccagga ctgtcctcac ggctgccccc   66540
gtgtaagtgc acgggctcaa gtcttcaccc ctggcgccag tgctcaccca ggctgaggc    66600 ttacatgtcc actgcccact gcttgtgccc ctgtagaggg cccactgacc cacaacccag   66660
```

```
gaaacccgcc caaccgccga ggtccccact ctcaatgtct tcgccacgtt tcgagacact   66720
gaagccacag ccgtccctct ttccgctctg tcctcatcac acacccgttt gttcatccag   66780
aaaatattag tcacaccgtg tgtcgggcac gggggaaagt gatgggtggg aggggtact    66840 tgtccccaag actcggtctg tggctgcatt tatgaggatc actgtccttt acagaagggg   66900
tcagccactg ctgcttctgg cctgggcaga acaagggtag ctgcccttct cctaaaccag   66960
ctataaaacc actgtgtagg ggcgatgagc agcaagcagt gtggactgtt gaccaggaa    67020 gtcgagggga cacacagagt gagccccaca gtggccgtcc agcttgctgc ctggagcctc   67080
ttcccagaga gggtgcaggg aggtggcccc cgagcagagg ggtggccaca tcttccatga   67140
ggcagattgc aacatggaag cagctggagt ttgtaggaca ggtcctgggg ctgtgggaa    67200 gagggcccag aagttccggt ggacactcag ctggccgagg gctgggtgtg tctgggaagg   67260
tgggattccc ggagattaag cagcagtcac ctgtaggagt gagggaggaa ggtgacgcca   67320
gaagccaggt atgctgggat ccggcccagc ccgcggagag acctcgctga gcacccggac   67380
catacgctga accccccagaa aggtcgggcc tcgggagtaa ggagctggcc gtggagtaga  67440
cgaccacgat caaaaccgaa atagacctgc tgtccttgtg aacatgttct gggcgctaag   67500
gaccgggatg aatgaacaga tggagaatct tagcagagaa ccagaaagca gaaagagggg  67560
ccaaatgccg attctagaat taaaaagcat aatgtctgga atgaaaaatc cacggtgggt  67620
taaagatggc cccacagtgt ccctgcttgt gctgggacag ctatcagggc tcttgacaca   67680
gggcccctgc agccaggcgg gggcatcctt gccctgcctc ttctctctcg ggcaccccac   67740
gccttcatcc tcctcctcct cctccaagcc tcgtgtgccc ccgccctgg ccctcccctc    67800 cctgggttct aggatggctg gtctggacat gcagtttcag aggggggtgtg gctgcattgg  67860 cgccatgggg atacgcttct ttgcagctaa ggctttgtgc atctctgcag ttttgtcttc   67920
aggataaatt ccaaagtgtg actaattgag aaaaagatct cgtgctgtgt gtattttaa    67980 ctccggagcc tctcactcag ccttctgttc ctctttacac gcggtcccct gtgagggtcc   68040
ctccctcttc ccaagagggc actcaagcct gtggttctgg aagcagcggc gcagcgatgg   68100
tccagggtgg actggggcga ggagcacctg tctgcaccta gaatacatgg cgacgtggc    68160 tcagcgatgc tcccacgtcc agggatggag cattcatccc acatgagtat gggggtgttc   68220
gtttatgtgc agggaagtcc aggaaggagg gcagtccctg aggttttggc taaaagagca   68280
agaagcagct ttaaccggga cccgcaggtg atgggattac gccacgtcca ctctcgggga   68340
ttatgtgcag ccgttgttgg aaagagctgg ctccggtccg cttttcgaagc tcgtgagtga  68400 gccagctcac tgccctgctg ggcgtggtgt gttccctcgg tgctgtaatt ggaaatgtca   68460
gttgttaatg gcagagaaat aggtctggaa ggaaatagcc ggaacctcag gagtggtttc   68520 ctctggggt gagatgtggg cggggaaagg ggttcttttc atctcgatgc tgccgctggg    68580
catccgttgt ctgcactgag tgcattgttc ctgtagcgga ggcagagatc aaacctctct   68640
gagcccgaag gcagccacct ggggctctgc gctccctgca cttggggcag ctcccacctc   68700
ggggaactta accttccctc tcttcacgtt gctggcgagg caggcgggca gatcccgccg   68760
ctggggccag tctgctctgg tagagggagc ccccggtaca tggaagaatg gtctaatgac   68820
atggtttttt tccttttttaa cgtttgttaa tttggcaaat tacatcgact gcttctcaaa   68880
tgataaactg ccttgcctcc cagttggttg ggactgttac catgtttcta aattattggg   68940
ctcgatctgc tacaatttta tttagggtgt tatgtccaca ttcacgaggg ctcttcatct   69000
tcgggatctt ctctggtttt gacatcacgg taaattctag cttcatgaca cgcgttttaa   69060
```

-continued

```
cgtctttcct tcttttcaat tttccgaaat catttgtata gaattggaat tatttacatc  69120
ttacatgctt catagaattc atcagtgcat ccatcttgcc cggctggggt tttttctttc  69180
gacgggggaa gcgttttttca gtagaaattg taattcttta gtacagatgg ttctatttta  69240
gttacatgtt tcttctaaag tgagtcttgg aagttgatgt tgaatcacat ggagatatgg  69300
cccctccttc ctgacactgg tagtgtgtgt gtgtgtgtgt gtgtgtgtgt gtgtgtgtgt  69360
gtgtgtgtgt gtttcttcct ccccttctca ccgttgcctc cttacttccc cggtgagcct  69420
gcctggagtt ttatctgtct tacgactgtc ctccaagtat tcactttat tgctcctctg  69480
ttttcagttc catcagtttc tactctggtc tacatttctt ctcttctcct tcgttggttt  69540
taattcactt tttattttct agtttcttaa gatggattct gaggtcagtg atttgagagt  69600
cttcttttt ttctcacata ggcatttgat gctgtaaatt ttccctaaca tcattttgat  69660
aagctgtatt tttttttct ttttcttta gggctgcacc tgcagcatgt gcaagttccc  69720
aggctagggg tcaaatcaga gctacagctg ctggcctcca gcacagccac agcaacccca  69780
gaacccagcc acatctgtga ccacagctca cagcaacact ggatccttaa cccactgagc  69840
agctccaggg atcgaaccca catcctcata gatactaatc agtgtcgtta ccactgagcc  69900
acagcaggaa ctctataagc tgtattttt ttttttacc tcaaaatact ttctaatttc  69960
ccttttggtt tcttcttggg atggggtgat tcggaattta aaattttagt ttccaaatta  70020
tatgggtata tttctagaac tcttttggtt attggtttcc catgtaattc cactctggtc  70080
gaagaacata cttggtatgg ctcgagtcct gtttaattta ttgagacttg ttttatggcc  70140
tcgagcatgg tctgtcttgg taaatgttgc atgtgttctt ttgtgggtag acaacacccc  70200
actaactatt aatcggacca catcgctcgg tagtgttgtt tcggcttcct cagccttgca  70260
cgttttctgt cgtcgtatca gtcacttacg gagaggtctg aaatcgccag ctgcagctct  70320
ctccgtctgc tgcttctctc cgttccgtga gttcttcttc ttggattcca tcatcttcag  70380
aggtgtgtga acacttaggg ttgttctgtc ttcccgacgc aggtgtccct ctggcatttg  70440
gaatgaccct ctttgtcccc gagaagcatc tttgctccgg aatctacctg gtctgacacg  70500
gaaataccac ttccgctttc tcttgattcg tcactcgtct tgtacgtttc atcgatgtgc  70560
tgcttttat ttcgagcgca tgcttttaa cagcacacag tctgctcttg cttttttgtc  70620
catcctgaga accctggcct tcggttaaga tgctctggct gttcacactt catgcgatca  70680
tggatttcat taggtttaag tccaaccctg tccatggcct agaaactcac tagaggcagc  70740
aagctgggtg atcatagggc tcaacctgtc ctggctcaag gatcgtcatc ctttccagtg  70800
tcatcaaaac tgttgtctcg tatattttga cttcgtttg ttttatttgt gggcgggaaa  70860
ctcagcgtgt atcactctgt cttcgtcaga agtagacatc aaagtcaccc cttttgcttt  70920
ggagccaagc tctcagagca cgtcccttct ctggaaggag ctgtgttctg atgtgacgtg  70980
tccccaggag ggactctctt caggtccag ctcagaggct gcttcctcca ggaagccttc  71040
cttgatggtg acctcaagcc cccttcccca cgtggcctat tcgctcttcc ctgctgtgtg  71100
caattcagca gacatttccc gagtttgttc aggggaagaa tgagcaaggc agagtcttct  71160
ctatggatga gctcatcaga tttgtttttcc tccatcgcgc gaaaatgttt cgagcttgga  71220
taatgactgc ggttagggaa gagccacaca aacagacaat taggatgcgt tgggaggatg  71280
agcaagagga acacacatga caagtttcag atcattccag gtgcttgttt tcacgtctgc  71340
ctccctcccc tgagcgagct cagcggggtg tgcctcctgg tttctgctct tggggccag  71400
gtgtgtgaca ggcgcattat agatggtgcc ttactgaact tagcagatcc gtgaggtcac  71460
```

```
agccaagggt ggatgccggg gtcagccctg ggtgtgcata ttggctctgt cgcttaacct   71520
gttggcactt cagcaggaaa agaggagctc agttgtggga agggctgagt ttgagatgcc   71580
tcatggggac cctaggggag acctcctgaa gggagcagaa gatgtggtgc agattcagga   71640
gagaggacat ggctagagag ggagattcgg agcccgcagc agtggacttg tagtgtcatg   71700
ggctggagat cccctagaaa gcaagtgtgg acagaggggt ttgagaactg agtcctgggt   71760
gcacccacat ccagagggga ggtgatgaag agccagcgga cggctgagat gtggccatgg   71820
aggtgggagg acgctggcca gtgtggtgcg tggggagaga gaagggagcc tttcacaagg   71880
aagagcgtgg atgttctgag tcccacccct gctggtgggt cggcctgggt ggagcccggg   71940
agcctgcccc ccacttggtg aggtggagcc cgagccctga ggtcagcagc tgtctgggct   72000
gcgctgggtc ctgggagaag agccagcatt gcccaccctg cctcctgagc cctgtgcact   72060
ggaaaatctc tccagcattg gctgcacttg aactggctct gctaacatca aggtcttcct   72120
tttaattgac tgaattttt gccctgtgca ttgcttttta ttggcttttg ccgggaaaga   72180
actctccagt ctattgagca agactggtgt caagaaatat gagggtcctg cgccgttacc   72240
gttctggagc aatgcccctg ggagagggcc cttcccgccg ggccagctct gggtcagacc   72300
caaagcaggc agcctcgcag tggggacctg agggttccag tgacaggtca gaggcctgtt   72360
cccttccctc tgggggcttc caggcccctg gtcttcatga gagagcagac tgcttcagcg   72420
ctgccacagg gctggagaga ggggcaggcg gctggacgga gcaacaccct cttactgaaa   72480
ttcagcctac tttttcttga gttaattaat actccctgtg ctgcagccct ggggttactt   72540
cacagagttc tgaaaagag cccgataatt tttgcagttt ccttgttgaa tcgtgcagtg   72600
acttcttcac cctctctcca caaagttcct tctttttctt ttctgttttt ttggttttg   72660 ggggcatcct gcggcatatg gaagttcccg ggtcagggat cagatcggag ccacagccac   72720
agcaacgccg catcctcaac ccactgtgcc gggcccatg gaacctgcgt cccagcgctg   72780
gagacgctgc ccatcctgtt acaccacagc gggaatccag ttcgttcttt ttaaataatt   72840 acttttttatc caaggaaact gtgtttatga taaaaaaaaa taaagtacgg acaaccaagc   72900
ttaataagta aaatcaattc ctggcgtttc tgttgccagt ttataagact atatattctt   72960
acaatatgag atgcaagcac atatacaggt atgctgatat gcatcttata catccttcct   73020
acaagttgct tctcttagca acatgtcctg aatgtctttt tgtccctcag tggcgtatgc   73080
accatcgttc ttcttagtcc gcaattctca gatgatacag aatcaccttc tgtgaacaag   73140
ggctgtcttg ttggccgttc cggctgttta atttttcct ttcataaata aggctggatg   73200
aacatactat gtgttggggt gcttgtcgcc tttgttttgg gaggcagact cttagaagtg   73260
tggtttctgg gccacagca tgtttggggg agcatctggg gagagggtgg tctgctccct   73320
gcccctgggg acaggaagtt tcctggcccc cgtttctcag cttgtaccca tcctgcctgt   73380
ggtagacgtg tgctctgggt cacgtgctca tttaggttaa ttctgtcatg tgggtagaag   73440
tgctgttcaa gttcatgcaa aagccctcat tttaagttat ttgtctggaa atgtcctttt   73500
ctggctttta agtagcaaaa cctagtaacc tgatgcctcg ggaagactga cagcccagga   73560
gttttctttc ttttttcttt ttttttttt ttttttttt ttgcttttt agggctgaac   73620 ctgcagcata tggaagttcc caggctgag tccatttgga actgcagctg ccggcctaca   73680
tctcagccca cagcaatgcc agatccctga cccctgagc gagacccggg atcgaacccc   73740
atcctcatgg acactggtcg ggtttgtagc tgctgagcca tgatgggagc gccccaggag   73800 cttttcagtgt ggccctactg ggtgctcatg ttgtggtcac agaggctgga ttaataagca   73860
```

-continued

```
gaggagaatt ccttgctctg agcccagagg cttcatgcgg gatgaattct cattacctct   73920
ggaaacctct ggtggaagga tcttttctcgc ttaagaacaa gtatgattag agtgtgtaag   73980
ggcaagcctg agacatttgc agtgggctta aggatgttct ttatcaaaag ctaaaaagat   74040
taaaccacac ccagtgtagt gttatggtga cgctattaca cgcgtccgaa aatggcaatc   74100
cctctcgcca cacatcagac ccttgacatc cacaagggat ttgtcccccg agaacttcga   74160
gagccccacc cactcccaaa cgccggctta gcttcccgtt tcccccagaa catgcgggag   74220
agaccaactg aacaatgcat gtggctgctt caagcttttt atgactctat aaacacagca   74280
ttctgatcgt ttagaatgct attaaaacaa aatcaggctg gagcccttgc tgaaatggtt   74340
ttggggggtca ctattttttct cttttctctat aaaacacagc aaacaggttc atatgagaaa   74400
tccaagcctc agttgagtcc aactgttttgt ttttttttttt ttttccggtc tttttgccat   74460
ttcttgggcc gctcccacag catatggagg ttcccaggct aggggtcgaa tcggagcttg   74520
tagccgctga cctacgccag agccacagca acacgggatc tgagccgcgt ctgcaaccta   74580
caccacagct cacggcaacg ccggatggtt aacccactga gcaagggcag gggtcgaacc   74640
cacaacctca tggttcctgg taggattcgt taaccactgt gccacgatgg gaactccccca   74700
agtccaactg ttaatatctt tatggcaaat tcctgctcaa ctggcaggtt agagacatac   74760
ttcttgctgt gtattctgca tcccacacaa actgactttc ttggggagtc gttttttcttg   74820
tgaaatgaag tttgcctcca cctgcgtgca tggccctgtt ggatggtggt ttgggcccca   74880
agatttaaac ccaaccccta gtcaaccggc aaaaccccac cctgcaaaac cgcaaccgac   74940
cttatacttt ggagtttctc gccagttgtc atctgcactt ggtggcgggg ttgtcggggg   75000
gggggcacgt cgggactccc tcattcgaaa aactcagagc catctcctgg caccctggag   75060
aatgaccctc ctctgcccgc gaatgcagcc aaccccatt tctgctcaaa ccaatataag   75120
catcgttcct tgagatctta cacgcgccct gatgtccctt ggctgattct gggcgtgtgg   75180
agagatgagg tcaatgtcag cctcaccata ttccttgata acctgcaatg tcagcactgt   75240
tcctggacca gcagaacaga ctcttgttgg actcaaaggc tagtggagga gacgaatgat   75300
caactcgcga gggagaaaga gaccagatga ggggagaatt cgtagggcgg gtgatggtga   75360
ctggagaatc gcttgggctg ttgagaacag ggttcaaggc cagcggcggg gctcaggagg   75420
tggccagccc cggtggtgca aacggagcag ggtggcgggc gatggaaaga caacggtgct   75480
gagatcctga gttgggatgt tccaggcgcg aaaggagacc cgcatggcgg ggggtggggg   75540
gcagtggggg gaggcgggag ggagagtcgg ggggagggcc gctatgggta aagttaactg   75600
taattttttta tctgaacgtg gacacttttg aaagaaaaat ggaccctattg atagtcaccc   75660
tgggcaatag gtgccaacca ggtctgtccc tggagacccc agatgcataa ttgatccccc   75720
acccgtggca ggcgtggctg cgggtggggg gctttaggaa ggcaggcgca ttgcccacca   75780
ttcgctggag gcaccacagc tgctggacct gcccctggcg ttcaggtcca gattctgtcc   75840
tgcggcgggg ggtgggggggc tacactgaca gccagcgcct cactgacacc tgtttttctct   75900
ctgcctctga acggctctct taggaaccct gccgaggaaa tgcaagaagg agctgctggc   75960
agtgaagctg aggaaccggc ccagcaagca ggaactagaa gacagaaaca tcttccccag   76020
gaggacggac gaggagaggc aggaaatccg gcagcagatt gaactgaagc tctccaagta   76080
agtagcctgt gtagacacgg gcagaggctg aggccagacc cctctgccac cccacccttc   76140
ccgcccgtg acgtccccg cccgccatca ccactgtcag tgctggggac cagacggttc   76200
ttcgctgtgg gccccgtcca tggcgctgtc ggatgctggg cagcctccct ggcctccgca   76260
```

```
ccttatgtcc cctgtgacag cctacgctgt ccccagacat ggctgaatgc ccctgggggc    76320
cagtgggaaa gcagtggaca cagaaatctc ataaggcctg cgtttgggcc aagccccggg    76380
gctgccggtg ctgctggtct ctggccgcac ctggaggaac ggatctcccg ggcttggcgc    76440
tgctgctgtt tgggtgactc tgtgattggg tggcctgtgt gtggcgggat atttagcagc    76500
gtctctggcc tctaccctag agatgctcat ccccccgcc agctgtgaca accaagtgta     76560
tcgtaattgc caagtgtccc ctggggtggg ggtggacccg tggccttacc tccccgggtc    76620
ttagttttct catctataaa gcgctccggt cgttgtgagt ttgggggat tcggtaagga     76680 aggcacattg cagggctctg cgcacagta ggggtgcagg aaccccccagg ctggtggtg     76740 gctgggagg cccagggccg gtccttgcag cccctcctcc tgcctcggct cggctcggct    76800
cgcgtggtga gggtgcccac ggcccagacg gctgtcaagg tgcctgtggt tacctgtggc    76860
tttgaaccca gaacaggcct cccccagac ctgggtcaga ctcggcggg gcaggatttg     76920 agtgaatccc ctgatttcca cggggttggg gaccttctcc ctttggacct tcttagcccg    76980
atggcagtga gattgtcgga cccaccaagc acttatccgc ctgcatctgg tccctcaaca    77040
aaggctgatt ttactcgcat gaggagcggg cgccgaggcg ctgctggaga taggctgcgg    77100
ggagcgaggc tgaccgcgcc tgagagcgcg ggttccggga gagcaggctc agacctcttc    77160
tgtgcggctg gtacccactc tggggctcgg tacagatgag atgctggaac acaggcagca    77220
cagccggggg cagtaggaag ggcagggcca aggaagccag cacagtactg gggccccagc    77280
gcggaggtca ggccctgcca caggcgtgac ctctcagagc tcccctgcag aaaaggctgg    77340
ggacaagcat ttcctaaagg gatgtcccac ctagtgtgac gtccgccgtc agggtgaacg    77400
ggctctccat ggtcaaggga gttagggaaa ccatcgcaca agcggtttat ttgctgctgg    77460
acttgtcaga acctttaatg tgattaaacc cccatggttc tgcaagaggg ggtgtgggac    77520
tttgtcctgt aactgtgaga tctttcctcc tctggcacct cgggtaccttg gggccccttg   77580 tggggaggtg ccactgtagt cacaaaggtg tgggaggaac ctgagggtgc tgggaccgcc    77640
cactttgcag ccacgtgggg tgtgtcacac ctggcgttgg cccctggtcc ccactgcagc    77700
tggaggggtc cttggtgggc tgtgggggt ctgcatggac ccctgtggcc agacctcgcc    77760
cacactgggc aggatggtgc ttggatttct cagggagttg ctggtgcagt gcaaggagtg    77820
tgtgaccttg ggccagggga gatgacgggc agcatctcaa cgtcctaggg tgacgtgggg    77880
gactcggtgc caccaccaca atcaggacta tgatggctga tgcttcaagg tggccctgtc    77940
agcctctgcc tgtgagcaag gccccagtt ctggtctgga ccacaggctg ccgtgatggc     78000
ttctggtcag ggtgggacag gaccccggga gtgcagtccc agcactggct gacgactggt    78060
agcgcctgcc tctctctgga cccccagatc cggcatgaaa agtgaagaac aggagaatca    78120
gtgcttcccc aacagtagtc actgcggagg taccaagaag aagctatagg gtctatagag    78180
ccccagggac ccaataacgt tcattttcct aagtcagcat tgccttgtgt tcagtcatcc    78240
aaatccatgg tcatcctggg tctgatgctc ttagttttt gttgttgttg tttttaaat     78300 aaagaagaag agctggtctt cttgtctgtc cacctgggta ttctgaagct caaaggaaaa    78360
gccacaggga aaggggcat cgttaataaa gcttcctgcc tacctgctgg agtcatgatg     78420
gatggtctgt ttggatcctc tctgtcacct ccacctcttt gtaaacttcc cctttctttt    78480
cactggtaca caggccatct gctgaataac agtgacatgc caggacacta gggctcacaa    78540
catttgtgta tgcttcaggc atgccttgat ccaggtgctg tacatggcat tgactggaat    78600
ttctctattg ctgtttctgg actctgcttt gctctgtatg gattcactct cttgactgtc    78660
```

```
ccattccacg tccttgcctg ggaagctcca ggcttacata ggagcagcag aaagataagt   78720
actctttcct cctcaggaaa agctccagga tcgagtctga ttcaattgcc cgggggcagg   78780
cacccagtcc ttaatcaatc accttggccc aaggggatgc aaggggctgt tggccaagtt   78840
tggatcacat gctggtccct aagcccatcc catggccaag gggatgtgct ggccctccag   78900
gcttagtgtc ttacggtatc cttgttgtca tcaggtggct ggcatatgcc ttccccagag   78960
gctgggttct ctgtctcttg tttctagtga gattgaagtt ccttttttctt tttttttta    79020 atttttattt tgacttctag ggccgcacct gtggcttatg ggagttccct ggttaggggt   79080
cgaatcagag ctgcagctgc cagcctacac caccgccaca gcagcacagg atctgagcca   79140
catctgtgac ctacactgca gcttgcacca atgcaggatc cttaacccac tgagcaaggc   79200
cagggatcga acccgcaacc tcatggttcc tagctggatt tgttaaccac tgcgccacga   79260
cgggaactcc tctttttctg cgtttatttc ttttggttt cttctgttct ttttatatac    79320
tttacctggt tcttctttct cgtgatgatt ttaggagttt actctggaaa ttgcagcttc   79380
cagtcctttc cagtctgtgc gattcccctc tcctctgtct tctgggctca gtactgtcag   79440
gtgcttctgg ctttcctttg ctgtgcaagt ggtttcattg ttaagttcat caggttgtca   79500
atcagatact tcaggtgtcc ccagactttt cctgtgaaag accagagact gaatatttcc   79560
ggctctgggg actccactgc gtctgctatg accacacaac tctgttgttg ccctgacgca   79620
gccaaagcca acacgtggtg agtgggtaca gctgtgaaac catacgaaca cgagcagcgg   79680
cccaatggtg acaaaattcc acagcccga tgcgctatgg ttcacactat tgttcgtgt    79740 tttaaaacat ctttccctgt ccagaagcca aaaaaaaccc ttacttttac ctgcattact   79800
tttgcagtta tcttctaacc atgccggtcg agaatggttt tctatttgct aaacaaacca   79860
agttctcttt caaaatagaa tattgagtga actaagaaa aattaggaat tcccgttgtg    79920
gctcagcgga cacaaatctg gctagcatcc atgaggatgc aggtctgatc cctggcctcg   79980
ctcagtgagt taaaggatcc ggggtggccg tgagctgtgg tgtgtgtagg tcacaggctc   80040
aactcgaatc tggtaatgct gtggctgtgg tgtaggccgg cagctgcagc tcggatttga   80100
cccctagtct gggaacctcc atatgccgtg ggcgtggccc taaaatgaaa gaaaaacatt   80160
gtagtacatg tgattcaaga aaaacaaaat tatccccatg acgcttgata tcagacaact   80220
ctggggacca cacctgcct cccagggcag agggaggtgg gcgaaggtgg ggtgaccgga    80280
agccacggcc gagggtctcc cagggcccct catgaagagg ttcccagagc acagacccct   80340
ggtctggatt tcctccatca ctcactgagt ctgtaactaa ttttaaaccc tgggctggaa   80400
cgtggtggct ccttggacgt gtgtcatcgt gttgaaaagc ggaaacgtat ccccagaatc   80460
aggcacggag agttccgtgg ttgggaaatc gcgtcccagg atggcagttt gtttccctgc   80520
agacgaggct taattggatc ctttgtcttt gctttgcctc ctttcagaga ttcttctgcc   80580
atcacttgct gaataattca gcctctggtt gccatggtga cgcaccatcc accgtatcct   80640
caaatgcagt tggcgttttt ggtttgttta ttttttttaat ctccagacct ttactgtttg   80700
tctttggggc gcctctaggg cttttctgcc gcagggtca cagggtcccc tgagtctttg    80760
tgctggccct gcggattcat gtgccggtgg agtcagcgtg gcggactata gccccggtg    80820 actgtcgccg ccttttctgta caggagccca actcaccttt accgcccgtg agatgtacc    80880 tacagagtgt tactgaccta aggttctgtg cctggaaaat tactggaaca ctcccaacct   80940
actgtgcgcc caccactcaa gggaaaccca taaggatgtc tgacagcttt cttcttgttg   81000
ttattaaggg tttcaagggt ccagcattat aattcagcat ctgagtgcac tgcaaaggga   81060
```

```
tcagatgaca gcttttactt ttaagtgcag agctcgggcg gtagcagtaa gttttgcttc   81120 cttttcctttg tgtcatcttc acaggcaccg atagagtagg tgttgtcatt gtctctggtt   81180
atacggacga gaaaacgaag gcttgatgag acagggtaag gaacttgccc aggatcacac   81240
agctcacgga ctgggaatca ggccgcgggc ggtccccgag agcaccaggc ggggccgcag   81300 gtgcagggg tcctgggagg tggcctccgt gcctggcgta tctgagtctc tgctttgcat    81360
tttctcttct tggtgtggct tccatcaggg cgcagtcagg cctccggcca acactctggg   81420
cctcagagcg aaatacctca cgtctttaac cctgtagtta gggaaaacat ccagagaggg   81480
gccgtcggcc ggccacgggc tttggggaaa tgtagacggg cgggttcgaa tcccagcctt   81540
tccgtcacag ccctgtgggc ttgggccagc accgccacct ctgaatctcg ccctggcccg   81600
gacaccgtgc ttggcagcac cttcctccca gggccctttg gaaggttcca ggtcagtccc   81660
tgcacgacag gtagaagtgc atccccacag gaggtgctca gaggggcaga gcagctgctg   81720
tatggtccct tgtcacctga gcaggggcgc aggccgccca gcaggccagg ctaggtcagt   81780
gagctgcgcc tggagggcca aggagtgtaa gcatagctgt taatgatgat acgttgtgct   81840
tatccgtgac cgtggtgtca tctgcctgga gacagtggag ggatgcacga accttctatt   81900
aaatctccct tgggtgcccc ctgcccgggg acgacatcgt ggaagctgat taatgctcag   81960
cggtggtgtc ctccaggagc tgggagctgg catatgttaa atgatcctcg agctggtcct   82020
ttcgtacagg gtgttctgct gcatccagaa caggctgcca ccattcaggg ctccaggaaa   82080
acacaaattc ctaggggggg aaaaaaaaag gttgtgtgct gctgctccca tccccgtgc   82140 ttgctttgga atctgcagaa tcttgaggag aaggctcgat gcctctgagc atggcgtgga   82200
ggctgacatg ccttataagc acagggctgg ctggctggac cgagccttag tctggtactt   82260
tctttcagct gaagtcccag gaaaaccggg gccgagagca gggtctccgt tctgcggatg   82320
cagagttttg aaaaatacag aaaccttagt tggcctgggc tttgcaggaa aaaaagtga   82380 ctcagttgct agaaaggaag ccactgcttt aggaagtttt gagccttcat tgcacagcgt   82440
ggaagattgc ctcataacag attccgataa ataattcgcc aatttcccta ttcccgacct   82500
gcagtgctgg gtaggagccc agcttatcct gggtggctgg aatccaacct tgtaggcatc   82560
atctaagagg gacagaaaag cgaagttatt aaaaatggtc gctgctaaca tttatttcat   82620
gccttctggg taccagcttc ctgctatgtg ctctgtgcat cttacctcct cgggcttt    82680 cgagagccct ccagggtgga tgctcttaac ggtgggccg ggggtagctg ctcatctgaa    82740
ccacaccact tcccacacct gagtgcccat ccagatcacc agggagcgtg aaaacacaga   82800
ttcccagacc acgcgccaat cccgtgaata ggaatctgta ttttaacaga acccttctct   82860
cctgtgtcac tgctgcctcc tgtccccttc ttcatgacct gtcttctgag cctcaggatc   82920
aaaacaaact atttctgtgg aacagatgcc acagaatagt tagcgtctta aggagaatgc   82980
acgtttggta gttaagtttg tttctgattt tgccttgccc accaggaagc tcagagccaa   83040
gtgtacctct acctgttgca gctgggttgt gtcatttggg ctgtgtgtct gtgtttgacc   83100
ttctgttgta cgaccttggc cttcatttcc tcaactcttt tctttttttg gaaagaggaa   83160
gtctcatatt tattgatcat gccacgtaat aattctttca cttacgttgc attccatagt   83220
gtagctctcc ggaagctctg gtagtattct ttttgtaaat tgaagtatag ttgatttacc   83280
acattgtgtt aattttcggt gtacagcctg gtgattctgt attttgcag atcatactcc    83340 attataggtt gttacaagat agtgggggata attcccgtgtg ccacacagta ggtccttgca  83400
gtttatctgc tttatgtata tattagtgtg tatctgtgaa cccccccaatt tgtctctgcc   83460
```

```
cttctccctc tcccccttg gtaaccacaa gtttgttttc tatgtctggg agtctgtttc    83520
tgctttgtaa atacagtcat ttctattatt ttttacttct tatttatttt tatttattac    83580
tattattatt attttgtctt tctaaggctg taccagcagc atatggaagt tcccaggcta    83640
ggagtcgaat tggggctgta gccaccggcc taccccacag ccacagcaat ggcagttctg    83700
agccgcatct gcgacctaca ccacagctca cagcaacacc ggatccttaa cccactgagc    83760
aaggctaggg accgaacctg cgtcctcacg gatactggtc agattcattg actgagccac    83820
gatgggaact tctgtattat tttctagatt ccacatataa gtggtatcat atagtgcttg    83880
tctttctctc tctgacttat ttcactaagc attaataatc tctagaagtt cccgtcgtgg    83940
agcagtggtt aacgaatccg actaggaacc atgaggttgc gggttcgatc tctgcccttg    84000
ctcagtgggt taaggatccg gcattgccgt gagctgtggt gtaggttgca gatgcggctc    84060
agatcccgcg ttgctgtggc tgtgatgtag gcgggtggct acagctctga ttggacccct    84120
agcctgggaa cctccatatg ccgtgagagc ggcccaagaa atggcaaaaa gacaaaaaaa    84180
ttaaaaaatt aaaaaatctc taggtccatc tacactgctg ccaatgtcag tacttcattc    84240
tttttatggc tgaataatac tccagagtgt gtgtgtgtgt gtgtgtgtgt ggacacatca    84300
catcttacgt cttctcaagc catttatctg ttgatggaca agtaggttgc ttcccagtct    84360
tgtgtcatgt atcttttga attggagttt ttgccacatg cccaggagta ggaatgctgg    84420
atcatatggt agttctcttt tttgttttt aagagacctc tgtactgttc atagtggctg    84480
caccaattta cattcccacc aacagagtag gagggtcccc ttttctccac gccctctcta    84540
atactgattg tttgtggact tttaattaat ggccattcgg actggtgtga ggtgatacct    84600
cattgtggtt ttgatttgcg tttctctaaa aattagcagt gttcgagagt tcctgccgtg    84660
gctcagtggt aacgaacccg actagcatcc atgagaacac agatttgatc cctggcctca    84720
ctcagtgggt tccggacctg gtattgccgt gagctgtggt ataggttgca gatgtggctt    84780
ggatctggca tggccgtggc tgtggtgtag accagcagct gcagctccaa tttgaccct    84840 agcctaggaa cctccatatg ccgtgggcat ggtgctcaaa agaccaacaa aaatcgaata    84900
aaaacagcaa catcaagcat cttctcatgt gcctgttgcc catctgcacg tcgtctttgg    84960
agaaagtcta ttgacgtctt ccgcccattt tttggttggg ttgtttgatt tttttgatat    85020
tgagttgtat gagctgttgg tatagtttgg gtgttaactc cctgtcagcc gtatcatttg    85080
caaatatttc ttccagttct gtgtgttgtc ttctcatttt gttgatggtt tcctttgctg    85140
tgccaacgat tttaattagg tcccatttgt ttctttctgc ctttattcct tttgccttag    85200
gagacagacc caagaaaata gtgctatgac gtatatctaa gagggttctg cttacattct    85260
cttctaggag ttttatggtt tcaggtctta aaattaggcc tttacaccat tttgagttta    85320
tttttgtata cgtccagtga gggagtgttc taatctcctt aacttacaag tggctgtcca    85380
gttttcccag caccacttgc tgaaaatgct cttttcccta ttgtgtattc ttgcctcctt    85440
tgtcatagat taattgactt taggggggtca gtttgtttct gggctctcac ttctattcca    85500
ttgacctatg tgccagtgcc atactggttc tattactgta gctttgtagt atagtctgaa    85560
gtctagcagg ttatgcctcc aggttggttc ttttgcttg ggattgcttt aatttgttca    85620
actcttaatt ttgtctttgc aatacatcat ttcaaatcca tttctagatg ttaactttaa    85680
aaatgtgagt agccattcct gtggtggctc agcaggttaa gaacccgact ggcatccctg    85740
aagatgcggg ttgatccttg gtctcactca gtggatgaag gatccggcat tgccgtgagc    85800
tgtggtgtag gtggcagatg caacctggat ctggcattgc tgtggctgta atgtaggcag    85860
```

```
ctccgatttg acccctagcc tgggaacttt catatgctgt gggtgtggac ctaaaaagac   85920
aaaaaaaaaa tgtgagtaaa tatatatata tatatatttt aatggagccc ctcttcacac   85980
acctgagcga tttcgccacc tcacatcatg tcagaagggc tttctctgct tccacgaagt   86040
atttgaatgt tggtttttaa cagtggcctg gtgtgtaggg agtggacaga cattctatag   86100
ctttgcttct ccctccctca atcagcagac ttttagtcct gctgcaaaat ctttactttt   86160
aaaatcaaac tacatgcaat gcttatttcc atgcatcagt gggttttttc ctttctgtgg   86220
attatttata tgagccacag ttccaaaatg caaaaaagaa gaggaagaaa aatgcactga   86280
attagacaat gtcatcattc aagaatgaag cccagtgttc agcagaaacc ggcagatcac   86340
tgggcaaaaa cagcctggaa ttcctggtgc aagaggaagg gggcgaaatt tctaaacaaa   86400
tatatgaaaa taattcaact tcactggtaa gtgcaggtat taagaattca tagtaacagg   86460
agttcccgtt gtggctcagc agtaacgaac ctgactggta tccatgagga tgcaggttcg   86520
atccctggcc tccctcagtg ggttaaggat ccggtgttgc cgtgagctgt ggtataaggc   86580
gcagatgtgg ctcagattcc atgtggctgt ggcgtaggcc ggcagctgta tctccagtga   86640 gaccccctagc ctgggaccct ccgtatgcta tgggtgcggc cctaaaaaga cagaaagaaa   86700 aaaagaatt cgtagtaaca gggaactttt catcccccat taaaaatgac aataaaactt   86760
ttaattatta attttccttt atacgtcact aatataaata ctgataatgg actgaaaaca   86820
ccctgccctg gcgggtggtg ctttacctgc catcctctgc tggcagccag gtgactcaaa   86880
ataatgggac agaggaagag ccaggatgac agtctgcaca gattaaccaa cccttttttg   86940
cgcttctggg agttatgcta tggaatttag aggaaggtca gtgttgtgat ggtaacacag   87000
agcccagcgg tggactttgc tcgtgcacgg tcggcagctt ctgcttggcg gaggggggtg   87060
gcggccaggc cacttgggga acagacacgg atgcccctgt taactttgcg agcctccccg   87120
gttctttgct ttcgggacct cgtggagaga tgggaagtcc tgtcagtatc agatggtacc   87180
tgggctgctt ctgcccggag atgctgttct cgacacatca cacccaccca gccgatgagg   87240
tcgacagcct ttcacccaat tggaggtgag gccgtgggaa ccactgcaaa tgccttggcg   87300
caaggcaccc actgctgagt gggtcgggat ccagcactgc cctggagcag ggtccccgga   87360
gcaggttgat ctgggcctgg ccgggctgcg tggccctggg aaggtcctta actgcctgtc   87420
tcctcccagc tcccctgggg gggcaccttt gagcacctgc ccctctgagc ctctgccagt   87480
ggccccagtg ctgtcgccca ctcgaccttt gcctgtgccc ccccatcact catggcctcg   87540
tggggacaag gccttgctgt ggtggggtct cagcccgcgc accccttttag tgtctgtggg   87600 gggaagggtc aggacacagc gtgacagcca agagcctcca tccctggctg ggctgtcggt   87660
ggggcaggtc tgttttgagt cctgcggatg gaatatgctg agactgtttc cggagaagct   87720
gtcactcggg ctgtgaaggg gacgtggcgc tgggctagct gggggtgggt ttggtccctc   87780
tgggcctttg ttctgcggca catttgtacc caaacctgtg cagacaatgg ctctcacttt   87840
tcagaagtgt cctttggcca agttcaggcc agttgaggtg gggagccagc ttccgacgcc   87900
aggtttcgtg acactgtgaa ttgcagcagt gaatcgtgaa ggttgacccT gacctctggc   87960
ggggacccag ctgctcgtgt ctccagcctg ttgctgcgtt ggtcagggac ggtcctcctc   88020
cccgctttgc agaggagggg gccgggcggt gaagcgggt cccagcgtct gttaggagcc   88080
tccagaccat gggttccagg gcccccccgc tcccctgccg aggagcatcc tgtgctcatc   88140
ttgcacacag gggcagaggg cacatgatga gctacagccc aatctgatgt ctttctttct   88200 ttcttttttag attataggac ttcggttgac tcagattgtt gtgttggttt caggtgcaca   88260
```

```
gcaaagtgaa tcagttatat acacccatgg atccattctt ttttcagatt ctttccccac   88320
attggttatt acagaatatt gaagagagtt ccctgtgctg tacagcaggt cctcattggt   88380
tacctatttt atatattgta gcatgtaaat cgttaatccc aaactcctac tttagccctg   88440
tccctgtgtt cccctttggt aagcaaaagt ttgctttcga atctgtgag tctgtttctg    88500 tttggtaaat aagctctttt gtatcatttt taaaattaga tcccacatat aggtgatatc   88560
atgtggtgtt tgtcttctg tgactgatgg acttcactta gtatgagagt ctctagttcc    88620
atccaggttg ctgcaaatgg cattattgtg ttcttttta tggctgagta gtattccatt    88680
gggtatatgt accacatctt cttcatcgac tcctctgtca atggacattt cagttgctcc   88740
atgtcttggc tcttgtgaat agtgctgaaa ggagcatcgg ggcgtcagtc cagtttctgg   88800
tgcttcagaa ctaactagaa ggtaacctct acatccttca ctggttcttt gtctgctgca   88860
gcatgggcag ccctagagcc ttccctctgt gttctgcatc ttgtggggcc ttgtaagcgc   88920
agcacggccc ccaccccac ccccgatgcc cacgttgcag cctctgagga cgcagcacat    88980 ggcacccta aatcagggct ggcacagctg ctgccgactg tgctcgggta ataacagcta    89040
ttaccgccac ccttagaatt ccttggagat actgcctcct tcctacccca cgtcttgtgc   89100
acggttgctg tgacacaagg caatgctgta aacgactttc cgggaaggtc gtgactgcag   89160
gagagcagcc ggcttcctct gtgccccctg ggggcacagc ccccagtcac agacttccct   89220
tcctgtggga gcacaggggc tgggggttgg ggagtggcgg tgcatctaga tcacccactg   89280
tgcctgataa aatacgcacc aaagtaaata caaaccagac gcagaagtgg agggctcggg   89340
agggagggtt aatccagcag gagggaggcc gagctggggg tgcaggccgc acaggggtg    89400 ccatggagca cggtttggac ggctggcctc acaggtggca gtgcaggtgt caggctggag   89460
tgcaaggatg tcccagacag aggggccaca agagcctacc acggcctgcc ctgcattgcc   89520
cctcagagaa caaggcgggg ctgagaaggg cggcctggga ggcgggtggg ctccgcaggg   89580
ccgggtgctg ggctctccct gctctccatc cgcactcagc tgcctctggt cattcagggc   89640
tcagctcgtg tcacctcggc agaagggcct tcctcgatgc ccctgtcctc cccaggggcc   89700
tggcctcaca ccagctccct ctgcatctcg tcatcccctg ctgtctgcgt gacactttct   89760
gctgcctgag gtcacccttt tggatcccctt tctgtgcctc gtcagggtct gtctgctgct   89820
agagcctgcc tgtgtccttc atccgatgtg ccctggtgcc gtttattccc attttttgagc  89880 agccgcttga gaaataggcc taaatggtga atagacatgt ctggcctcta ctgagaagca   89940
gcgagggtcc ctggaggggt catgcgcagg ggcgtggcag aggggggcca cccggcctgc   90000 acgtggggc tcaggtgggg acctgctggg ggcaggtgac agtggacttg gaagtgctgc    90060
aggaaaggca tgtcatcagg tggccctgag gctggagagg gtggactcgg ccgctggggg   90120
aggacgagga gcaggacccc cgggtgagga cttgaggagg tggcctggtc gggcggagcc   90180
ggtatgctgg gcacagggga gggggctcag gaggaaggga gggaggcgtg gcggaagct    90240 tctgtgtcca gacccttgtt ggcgtgtctc tggcacatcc acgactctgg cgccgttagc   90300
ggcggtccga tccacaaacg gggcgcgcgt cgactgcgtg gaggatggca gatacaggca   90360
gtgccggctc aagaccaaag gcagtgaaga cccagcatgg agttttacgg ggtcctgtgg   90420
gtccttttat catggggtca tttcctaccc cagtgttctc cctcggacct cacatcacag   90480
ctgcagaagg agacggggtg gccggctgtt ttcttggcga cagagcaggt ttaataagcc   90540
ccgtccatct aaggaaacag ggcagcgtta aatgcaaccc cccggaggac gtgagatcca   90600 ctttttctcgg ttctgcaagc ccgcagggtt caagctgtgg gacgttgttg atgctgggct   90660
```

-continued

```
ggcccatcag gggccaggct tctgtttagg acaagggaca ggctgagacc tttctcacat    90720
gctgaggagg agccgggcca gggctccccc acttagggg tggagtctcg cagccgggct    90780
ggggctgcag tccgtggggc ccagctggac agagtcaggc cgggtctgcg gagagaggct    90840
cgtggttact gaacagccat ccatgaggaa ggcacacgct gttctcccgg cctcagcccg    90900
gctgcacgac gagaaccctc agagggctga actcaatgtc ctggtacgtg aaggtacctt    90960
gtcctgctca gtctctgaag tgaccagtgg ggcaacttcc agagggatgt tcagacagta    91020
gacggaagaa ccaagatgag taatgagagg acgaataact cattatgccc gagatgatct    91080
tgaacagaaa actaatagca gggcccctgc ggcaggaaga agcacagctg tgctcgaggc    91140
gggaggtgcg ggtgtaggta taacagcctc tcactttaca gcgaaccctc agtctgcaaa    91200
gtggatggtt acgcctgtga ttgtgcacct ttggggactg ggaatttaag aatttgatgg    91260
aagccttaat aaaactgggt ataataatat ctcccatgat ttctggaatt ttgccacttg    91320
tctagtgcag tctgcacgtg taaggactgg tggctctccc ttcctgagtg gtgggtctga    91380
cacctcccgt tttgcatgcg aggaaactga ggctcgggat tgctggtggc cagtgagtag    91440 ctggcaagg acgtgaactg ccgagctcag agtcattctc tcagtaccca ctgcctgagg    91500
tagcctgctc tgtaactcct tgaggctggt ccggttcaga accactgaat tgtttgtatg    91560
accctccacc tgtgcagtag ttgttccttg aaggaaggat cttacttgtt cagtttttatc    91620 tgcagtgccc accacagtgc ctggtgcaag gtaggcgccc agctaacaac tgctgaatgg    91680
atgggttact tggatgaata gatggagatt gagagatggg tggttgggag gttagttaga    91740
tggatgggtt ggcagatgga gaggtgggta gatggacagt taagtggttg caatgttgga    91800
tggatgggtg gatggatatg tgggtgggtg gatgggtggg tagatggaag gatgtgtgga    91860
tggttggatg gaaggacgga tggatagatg gatgatgtgt ggatgtacag atggatgtgg    91920
ggatagacag atggatgggt ggatggatgg aagaatggat gtgtgatgaa tggatatata    91980
ggtggatgga taggtggatg gatggatgtg tggatggatg gatagatgga tgggtgggtg    92040
gatggataga tggatgggtg ggtggatgga tggatagatg gatgggtggg tggatggatg    92100
gatagatgga tgggtgggtg gatggatggg tggatggatg ggtgggtgga tggatagatg    92160
gatgggtggg tggatgaatg gatagatgga tgggtgagtg gatggaagga tgtgtggatg    92220
gttggatgga aggacggatg gatagatgga tgatgtgtgg atgtacagat ggatgtgggg    92280
atagacagat ggatgggtgg atggatggaa gaatggatgt gtgatgaatg gatatatagg    92340
tggatggata ggtggatgga tgatgtgtg atggatgga tagatggatg ggtgggtgga    92400
tggatggata gatggatggg tgggtggatg gatggataga tggatgggtg ggtggatgga    92460
tggatagatg ggtggatgga tgggtgggtg gatggatggg tgggtggatg gatggatgga    92520
tggatggatg ggtgggtgga tggatgggtg gatggatggg tgggtggatg gatagatgga    92580
tgggtgggtg gatgaatgga tagatggatg cgtgggtgga tggatagatg gatgggtggg    92640
tggatgaatg gatagatgga tgggtggatg gatggatgga tggatggatg ggtgggtgga    92700
tggatggatg gatggatggg tgggtggatg gatagatgga tgggtgggtg gatgaatgga    92760
tagatggatg ggtgggtgga tggatagatg gatgggtggg tggatgaatg gatagatgga    92820
tgggtgggtg gatggataga tggatgggtg ggtggatgaa tggatagatg gatgggtggg    92880
tggatggata gatggatggg tgggtggatg gatagatgga tgggtgggtg gatggatgga    92940
tagatggatg ggtgggtgga tggatagatg gatgggtggg tggatgaatg gatagatgga    93000
tgggtgggtg gatggataga tggatgggtg ggtggatgga tagatggatg ggtgggtgga    93060
```

```
tggatggatg gatgggtggg tggatggatg gatgggcagg cagatgatta gatgatcaca    93120
tagttaaatg aataggtaga tgggtatata gcgttggata aatggatggt tatatgaaca    93180
ccacggtaca caaggcagag ggtagggtac agtcagtaag aatgtagtta aacaaagtag    93240
atgtgctttg aataaatgtc ttcctgtggg tagtagagtc ttaagatacc tgatttatcc    93300
accaatttca ggtagatctt tcaaggcgta tttgtgggta atgtgaactt acagatctat    93360
ggtgagtgtt gctaatttgg gggttttttct gtctctggga tgcatctagg ccagggactg    93420
aatgttcctc ctgttgcatc atggctctct ggccagctgc ccagacgggg ctacctccag    93480
gctacaggtc ccctggctct ttgggagggg taccgcccaa ctccccttc tccatccggg    93540 gaaggctggt ggatgttgaa gctcccaaag cttcctgagc actttcgtgg ggagaggaga    93600
ggagctctcc ctggatggcg atggctccag aaggacactg gcctgtcctc acagctcatt    93660
tccgagtagg actcacaagc tcaaatgctc tgagagtgac ttggggcagg tgggaactgt    93720
ggcaggttgg ggcatgcacg tccttgcggc aggggccacc tgccgttcag caactgtggg    93780
tgtcacctct gcagatgcca gatccgtgtg ggcagggttt tctaacagaa actggaaatg    93840
tttattttga tgccaaattt ccttcattta aatgttggaa gccactcac attttacaaa     93900 cagaaagggt gaaccccata aaacatgttt gtgggctgta tttggcctgg ggggggtggt    93960
caccatttgt cacctgtgat acaacaaagt cacttgtttt atgagaagct caatcttgtc    94020
tgtgctgaga acggggactt ttgactgcgg aatgaacgta gggaaaacaa tgggtcagac    94080
tctgaatcga tggtccccag tggaaacatc acgacccagg actgggacca tcagtgccct    94140
gtgcagcccg gtgcatcctt tctcttcctc tggcctctga ggtgctgctc aggaagagct    94200
tgtgtgtgac ccccgcccct ggctctgacc ttgatccaag gaagcatctc tgtggcggtg    94260
aaagtgcgga ctctgggcag ggaaccttgg ttcctgtccc agctctgctg ttttccagct    94320
gtgtgaccac aggcaggtga cctccctgac atgtgcctca cggtcctctt ctgtagaatg    94380
ggggtaatta caacagagcc catctcctag ggctgcggaa aggacgcaaa gagacaagac    94440
acataaatgc ctagaattgt gcccggcagg gaggaagcac gagggaataa aacaaataca    94500
tgtgagatct gtggggcgg gaaatttgtt ccaatagttt gagatagaat atccacacca    94560
tacgattcac cctttcaaag tatgtgatcc agggctctag tttatccatg gagtcgtgcg    94620
tccatcacta cagtctgttt tgggacattt ttgtcactcc caaaggagc cgctcacccc    94680 tttgccgtat ctctgatccc tagcacctgg gccacatggt cactcagtaa ttctccagct    94740
cctgttgcaa ggacggaggg aggtaccctg tgcaaagagc cacggccaca gtttagcctc    94800
atcatccttt tcttcatctt tgtcgtcacc gacgtgaaca tctttctgag catcttcatc    94860
actgtcaccg tcttcgtcaa catcttctct gtccttctct tctttgtctc tgtccgtctg    94920
tcttcttcat tgttgtcctt agttccttcg ttatcttctt tgccgtcgtc ttggcaacgt    94980
cttcatccat gtctttgtgg tcatcaccat tatcttcgcg gtccctcttt gatacaaagt    95040
gagcacttag gagacactgg ctcttcactc cgtggggacc agcggcccca cttccaggac    95100
aatgacgccc acgtctgacg ttgggtcagg agcttcaggc tgattcctgc ctccaggga    95160 agggagcctc caaagaggtg gcaggttgag ggtggggtgg ggccaggacc tttctgaccc    95220
tgcaggtccg gctcaggacc cgcccagtgc agtgacggtt gggtaccagc gacccctcag    95280
tggggatgtg caggacacag ctctctacaa ccctcttgag aggattttga gatcccagga    95340
gcagggagtc tttgtgttta gcggttcctc tgctttcttg cctttttggg tgaagcagat    95400
gtgcctggct gactcccact ggcctccagg gagtccaggg catcttcctg gggctttcag    95460
```

```
tctccctctg tttagaagcc tcggagcaca ctgaggtccg tctggtctat cagataaccc   95520
cgcgcccggg acctcagctg ggtacagccc cctgctccac tgcgggagtg agtgccttga   95580
gtactgcgta gcctccaagg tcaagaggca tctggggctt atttagctga ggtttcaagg   95640
atccgttgct aaacacaaaa gggatccgtg gggcggggct gtgagcaggc cctgtggggt   95700
ctgtggggag ggcaagacaa gaccccgacc ctggagggag gggctcggtg gccctgcgag   95760
gctgcggagg tgggcgaggc agctccagcg gtaggtcttg ctgcctgctt ttagatggaa   95820
gtacctgggc aacagaaaac agcgcttcca agtcaggaaa agtttgccaa aatcggagcc   95880
ttagaggaca tgaatataag tcttggtcct tgatggagag cgtgctgtgc agaggggag    95940 gggcagtggg gggggagggc tccgtgaccc ccccgtgggt agtgctcagg cccctcgctg   96000
gtgtctattg aagtggcgca agctcctggc cttcccgtcc ttcgtggggt cggctgctct   96060
ttgtttctct tggttacttg ggagtctgtc aaggaaagta cagcatgttt tgtgagaaaa   96120
ggcaaaacaa caaacccct  tcggtaccaa taaaacacag atcccatgca caggggagca   96180
ggtggcctgg cagatttgag ctcacctggc tgagggaacc caggcacatg gccccatctg   96240
cctgagctgt gaagtgggta tgtgacacct gccagcttta cccagagtca gggcttttcc   96300
cctctgagtg agtagttgtc atagcagtag cgctgtggta gcaaacattt attaaatctg   96360
tgttgtgtgc caaggactgc gctttgtgta tttgccgaag cccaagatgt aaatgctatt   96420
attaggtgta tttcataggc tacagaaatg gtggctcaga gaggtcaggc aagatgttca   96480
aagtcataca actagtatgt catggagcta agatttgacc caggcaggcc ggttctggac   96540
actgggccta aaggcatcct gctttgttga atggttgcag acatacaagc ctggcttggt   96600
tattccacag tcatcgagga cccaggcttc tttctatctt cctgctcagc tatcctcacg   96660
ttggcattta ccctctatgg tcccaggtgg ctgcgggagc acctgacatc acattcaggt   96720
tccgagggtg cacagatccc agctgagtca gctcttccaa aagacccttc tcagaggctt   96780
tcagcacacc tctccctaca gctccttggt cagaacctct tcatgtggcc acgcttcgtt   96840
agaaaagagg ctttcctgaa cagaatccac tttctgatgc taccaaagaa gagagagtgg   96900
aggattgggt aggaaaccag cagtctctgc tacgtaggtg ctcaagttaa ttttgtgttg   96960
agttagcctg aagcaagaaa ggaaggaagg agcaaacaga tggacaagtg aagaaaaac    97020 cctgtgtctg tgagatgaga gccagcgatt ccctgggcag tctggtccga gaagcctgtg   97080
tggagccctg ataggctctg ggaggtttat aagtgcctca tgttcctgtc cagtgctggg   97140
cccagggact tgggcaggtg gcgggaagct gggaaagggg aggaggggac agagctgcaa   97200
ggggcccctg gagtgatgag gacagacaca gctgtcccct cctcagtggt accttcacct   97260
caggacggta cagttcaagg acagacactt cctgggcaat ctctgtgtgc cacctgcagc   97320
ccagggcact gggggtggag gaaggaacca ggtggatgca ggagctgcct tcaggaccgg   97380
gggatggggg aaggtcacct aagagagggt gtgatacctg tggcctgggg gaggggatg    97440 caggaagtag cacaccttgg tgcagagggc gctatccgtc cagcgtcccc cttcccaccc   97500
ccaggcagct cctcacctcc cctgtctggg ccggcgaggc gcaagctccc tggtagcact   97560
gatggagttc cggggcctgt ggaaattatt tggtgtgtag gctggtgccc tatccttta    97620 aaaatcgagg cagtgttaag tggaatttgt gcttctcttg gccctggtat ttccttgccc   97680
agtatttgct tgtttcctgg aggagcccgg gagcccccaa gccctgggga agcgacactg   97740
gggaagtgtc agaggaggga ggggatggcc agggcctggc acgcagcagg tgctccatgt   97800
ttggggacca gaaatcaaat catcccgatg ccaggggcca ggcaatggga agcattatat   97860
```

```
attactttca ttttccaaat ctgaataagg gactgattta cgtgcaaaaa caaatggtgt   97920
gtctccctcc caccctgtct cggcccagag gctgccgctg gccgtgggct gtttgcagcc   97980
actcagaggc ggtgttacac aagcagccat aagcacaccg gtaactagtg tgctcggggg   98040
aggtgacgcc cgtgagggag gggcctggag tcccctcctc caagggcaac aacaaagcca   98100
gtcagaagaa gaaattaaaa tgcgatttgt tcgagctcag aacacttaat tttaacctgt   98160
cattgagatg tgccttaact tgggcttctt ctgctgggaa accaaagact tttccctgca   98220
gaaggaccaa cagttagtgt tcttccttgc ttgagacaaa cgctggttct ttgcagagga   98280
gtgagaagga gacacttggc agcagtcgcg cacagagtcc ttccagagac ggagccctgc   98340
tgtctacacg ctcctctccc acactcacgc ggacagctgg gttccaacat ctagccttta   98400
ctgccttcaa agcagtccat ttggttattg tagaaatatg ttttctttttt ccatccacat   98460 tgagtcattc catccctgtg tgtaaagtct gattagatca cctgatacag gcacaggtcc   98520
acctggcgca cgtagctggg gaagaaggga cccacgcccg acaggtgcac aggtcaccac   98580
gggaacagat ggcacggggc gggggctgcc ttgccacgcg tgcgtgctcc gcgggtctgg   98640
ttcgccagaa ggaccgggag ggtcagttaa tctggggtca ggtaagtgga ggtaacagga   98700
cagcactcct cccacgggac tgtcatcctc atttagggag gaggctgcgt ctgagacgac   98760
agcggtccag agccgggggg aggtgtctct caagggattt attgcaaggt gttggtggcg   98820
gtggctgtgg ggctggctat gcaggtctgg catcgatggg acaggccgtt aggaagggct   98880
ggaactccct ggtagggacc gaggctgctg tccacaggca gaagtgcctc ttcattcagg   98940
gagccccagc cctgctcgtg aggtccttct cctgattgga ccaggcccac cagaccattg   99000
gtgacaatgc cccacactta aagtcacctg gttatggatg ttaatcacat ccacctttac   99060
cccagtacct agatgagtga ttgattgaag aacaggggat gaggcctctc cgggtggaca   99120
gataacacaa gatccggtgc tggaggtgaa ggataggcct ctctttccag cttgaggtct   99180
tcccagagga ggtgaggtat ctgcccagga gcccagggct taggccagct gttcctgtgg   99240
cccctggtga gcctggggag cttcgtgtgt cctgtcactg tgaccggatg tctgtgtttt   99300
tgggccaggc cccggtgtcc tgcagtcaag gacacctcct gagcagggaa gacttgcccc   99360
gctccaccca ctcagctttc tgtgtcccct ggacactcat acagaaggat ccagagccgt   99420
gggaaggacc tgaacctgca tcctgggtgt acagcggaca cgccgagggg tttggtggag   99480
tttggtcaca gtctgaattc tccccaaatg cacgtgccgg ggaaattgat ggaaatggac   99540
gtgccttgtt tcattcagaa ctttaccaag aaccacgcat tttgggaaac agctcccgtg   99600
tggctgcatt gctagtggtg tgcgaatcac cggaaggacc ctggtccctc cgtgctggtg   99660
gctgaggtca tcgtggtgac cgtgtggacg ccttttgcccc gtcgcctgat gtgctctggt   99720
ctgaacaccc gtgtgtggac tgtgtgttat tgggttaaaa cgccctgcct tcctcctgcg   99780
cgttacagct gagcatcaca ttgacttttt tttttttttt tttgtctttt tgccatttct   99840
tgggccgctc ccgtggcata tggaggttcc caggctaggg gtccaatcgg agctgtagcc   99900
accggcctac gccagagcca cagcaacgcg ggatccgagc cgcgtctgcg acctacacca   99960
cagctcacgg caatgccgga tccttaaccc actgagcaag ggcagggacc gaacccgcaa  100020
cctcatggtt cctagttgga attgttaacc actgcgcccg acgggaactc ccacattggc  100080
ttttaaaact tgtgcacgtg ggtgggttgc agtaaaggga cgggatgcaa tactcgatgt  100140 aaggggggtgt aggtggctgt gcccgagggg gccggtgtaa gcagctcggt gtgggggcca  100200
cggggcacag agttggggga tgggtgtcca cggactcgct ggcctcgcgg ccctggactt  100260
```

```
tgtcctgagt tcactgggga tcccagattc gagctctttg tgggactggg gatatgtttc    100320
agaaggtcca cacgtggctg tgggggcagc aggatgccga gggcccctgg aggctggtgg    100380
cctgggtcag gcggtggggg gatggggagg cagatggaca agtgaggtgt cgacgcctgg    100440
gaccccacag acttggagac tcctcgggc tgggagtggg cagtgggagg ggcagagggt     100500
ggttctgggg tgagtgtgtg gacgacggcc agcctctgag gcggaccctg gacgatgagg    100560
aaggggacga ggtggggatg gggtgcgagg cagctttgga cgagcacatc ttgagtgccg    100620
gggtcacaag atgctgtgac gggggcggct gcacttcccc aggcaaggcc tccacgggct    100680
gatcattcgt cccagggcgg aggcggctga ggctgggggc ggctgctgtt ccctgacgtg    100740
gacaagctct gctcttggag cccccggccc atctctgggc tttccatggc tttgtctccg    100800
catcacatcc tggagaggcc ccctcccttc cctgaccctc tctcccaggg ccgcccactt    100860
gtccctggtg gcccctgcc ctgacagcgc ccatcgggtc agaggagcca ccctctgttc     100920
acgattcgcg agcccacgc ccagcacagt ctggcacagt ctcccctgat gatggggaga     100980
cgttgccccg ctgggggaat ccctgcccgg cggggactcc cgccttcctt ggtgactcaa    101040
ggctggcggt ggagccggat cggtgttccc aggaaggagc tcccaaaata gccggcgtcc    101100
ccgtgggcgg ggagctgtct gttctgcagc tgcggcttct ctctccagga aggcgttttg    101160
ccttgtttga cgggattgct tctcagctca gttcttgctt gatgctgagt tgatttgaga    101220
tgtttattgg agccccgcgg ggatgaggga gacctggggc ccatgagccg aggggggacag   101280
agctggctgc ggatctggag ccagacaggc cattcctccc gtgtccccgg aattacctgc    101340
agcctcggag ccctaccagg tctgcagtcc tgagaggcgg agaggggtgt gcaaagggcg    101400
attcagaaac gggccatatg ccaggcacct agcttggcac ttcttgggcc atgtcgccat    101460
cctcacggca agcccaagag gtgacagttg tcatcagccc atttggggag agacaggaga    101520
aatacaggga gtaacagggt cgggatggag ggtcttgagt gacggccaa gatgtgggcc      101580
cccgcccat ggtgttggcc tcgccaccaa agcactttc ggggcaaggt gagccacctg       101640
gagcccaggc tcaggaggcc tggggtgggg ggggtggaac aggggacaa gccttggcca      101700
aggtgggagg agtcacctgg aggggtgact catggagggt gtcgtccccc ccgccccac      101760
gccccccacc atagccggct tccagggtga ggtgggggat gggaagcatc ctcacagggt    101820
gagtcccctg tgctgcagg tcctccccac ctgaggtgag ggctgggccc tgcgcagact     101880
ccaagcagct gatggggaga ggtgagctca cagaggtcaa gggtcacatg gtgagacggg    101940
gcttccctg ttgatcagga actgtttggc aaggacctcg gtttgggct ttcgttggtt      102000
ttctaactcc ctgtgctcat cagtcgacgg cagggacgga ggccggggtc agggggaggc    102060
ttagcgagtc ggggtccggg gagagcctgg gctttcgggc tgatcgctgg cctctgctct    102120
ccactgcact gccaccttag agagctttcg cgatgaagag agaaccatgg caagagtgct    102180
gaagctggag ctttgcgtgg cggcccatga gatgggagtt tgcaattccc gcgacacagt    102240
gtcccaccta gtggatggaa ggtggctgga cagcaaggac agaagaaagt cactgaaaac    102300
aggggtcacc aggctcgtga aagccttgtg cctgtggta ctgggagggg ggtgcctggt     102360
ggcactgttc ccagcaccct cctggcacca gcccctcagc agtggcaggc cgcgtggccc    102420
tggttcttga agcccttga tcacagctgg ggggctgggg gtgcaggatg gggtggcggt     102480
tctccctgac ggagaagccc agcagctgga tgctcccctg ggacactcag ccagggccat    102540
ctgtccccg ctgacctcag aaaggagatc aagacctgct ttctccttgg gccaccctcc     102600
caccatgcca ggcactccag ggaacttggg ccacctgccc cacgtgtgtc tgggaggcag    102660
```

```
aaggggtcct tgggacaagg agaggttccc tccctcagga gcctggtccc acaggtgaca 102720
tagaagaaga gggtccctg gggccagccg tgaggatgac aaggagccag gcgcccctc 102780 agcccagacg ctgttccact ccagcctttg ctctgtatct tcaagggcag ccagaaagct 102840
gatgttttaa agtgagaact ccctgttgat taatatttgc ttcatattcg tgttttaaaa 102900
gtatggcgtg agccaaaaat gcaactgctt gctggatttg gaccagcgca ccagtgggtc 102960
tggtagccag cctgtccccc atgccagctg gccgagtgag tgtctgatgg aggaggaggg 103020
gctgtctgac agagggaggt ctgggtgggt gtctgatggg gactttctgg ggatcctgg 103080 ctggcaggga ggctaccagc agggtggtga gggtggctct gttggctgag tgaggctgga 103140
cgagacctgg cgagggatat aaatgctgac agtcaggaca ccaccaccca cttgtgcgcc 103200
agcctccgcc ttgtcttagt ttctccaccc cctccgcacc cctggggtcc ctggggcagg 103260
ggaggagcag gggattggag gctcatgtgg gagggtggta tcctctgtca ccctgctggc 103320
ccggggccga gctgggactt gaattcagac tctgcctgtg tcgtggcctc ggtgctggtc 103380
caggggatgg gaatttgcag cctgacagat gtggatggta caaccgcttc accgcatctc 103440
cttcagcccc ctcggggcat cctggtcacc cagctggcgg tggcctcctg gctccccgc 103500 cctccaccgt gcctcctctt tcgtctccat ctgctcgctg accaagctct ccgtcctcag 103560
tcatgtccca cgttcagagc acaggggttgg gtgtggcgtt cggccgtcac cacagactgg 103620
ctcagaggag acacaggagg gcaggggagc ctctttgggc tggttctcct ctcccgacag 103680 ctggggggccc tgactacgac acacacccac actgcacagg gacccaggt gccatgaccc 103740 catcctgtcc tgtccccggt ggcccatgcc tttacctcct gctcaggtcc ccagggcctg 103800
tccggtgtgc tcctgctgcc cgcctctgtc cctgcctctc ctgggggcac aggccgggac 103860
caggctgggg gacaggcagg agcctctctc taccctggtc tccttccctg gtgtggctcc 103920
cacacccaca cggcgctgtg attggctgcc acactcctgc tttctcagcg gggagagtca 103980
gaaatagact gtggcttccc cagttccagg aggcaccaga gcagcagttt ctgaatcagg 104040
ggtgggagcg gctgtgggcg gagccgggga atccctcggg cgctggactg aggctgcccc 104100
gccccgcctc tcctgaggct ccaccccacc cgcctgaggc tccgcccct caccaccaaa 104160 gcccagcccc tggggctgtg gggctgggtc tctgcaggtc ctggagaacc ccttgctgct 104220
gaggctccaa agcaggggttg ctgtggctgc acacgcctcg ggagggaga gaagccggcg 104280 tccatttgct cctctcgtca ggctctggga tctacgcaga gaatgagacc tggtcccaca 104340
ggtgacacag gtgccagtgt ggattctcca ctttggcctc ctgagcccct atggcctcat 104400
ctgtaaagtg ggtataatcc cacgtgctgt ccgcttggat atgagggttg tcgttcatca 104460
ctcctgcttt gggaagaccc agccccacat ggagagcgag ccgagtctcg ggtagcaaat 104520
ggatggaata ttgtgtttaa tgtatattta gttcagtgtg tattaatttg gagctggcag 104580
tgttcttact ctagagccag tatctttgcc ttgcctcgaa catttcacag gccccttgat 104640
ggctcacggg cctgtggcac ctgtgcttgt ctgatgtccc cctccaagt ggctctatat 104700 ctcctggtgg taggttctgc actgttcttc cctggacagc agtctggaag agtctagaag 104760
tgctcccaca ggcaaatcca gtcctggcct gccctcacgc catcctgccc cgcctgctcc 104820
ccacccttga gagccttccc ggcttctctg gaaagaaacc cagacctcag cagggcctgc 104880
aggttgggtg ggtcctgccc caggagcagc acccgtcacc gcaggagtcc tgagctcagg 104940 accctttgcac acgctcttcc ttcccgctc ggcttagccc tccccactgg agcctgtgct 105000
ccctgaggac agggctgggc cgcaccacag catcaggggcc gggcaggttc tcaggtgctc 105060
```

```
actaatatct gactgggagg gtcaggttaa ctcacattag accttctcag cctcatacag   105120
gggggtgtct gcacagtagg ggcaagtcca gactcaccgc acacccaccc cccatgacta   105180
gggtcccaca gggaggtgct cgggctggcg gtcctctcgt ccagcctctc tgggtagaga   105240
gacagttggt gccaagccgg ccggctgtgc tctggtggca gctacagacc tacagggctt   105300
tgaccagagg ataccccttt ctgcttcgtt cagaggtgct ccgaggatcc gctgtggccc   105360
cgcagtggga agtaggactc ggcaccaggc ttgccagctg cataggtttt gagggtgaga   105420
tgtccgcact ttgctgagac gtgtgacttg gacaaaatgg ctttctggga actcagccca   105480
tgatcagctg acaacccaca ggtttggttt tctcaagaca tttttgaaga aactactgtc   105540
ccaggccagc atggtaacgg tgggtttgtg cgttttctct caatgccctc ggctctgtga   105600
gggtctattg ctagacagtt tggaagagaa gtgggatccc agcaataaaa agcctctctg   105660
ggggcagagt gagtggaggc ttggtgttgg tttcaggttt gagggatgc gtggccttgg    105720
tgctcaggtg gccctgcggg cacccggctg gccaggtggc accagtaggc acctggctct   105780
gcacccgtg tggattctcc acacctccgc ccaaagggtc ctcttccaga gcttggctt    105840
gcccactcct cccagctgtc cccaacccag ccagtgagca aataggagac acagtccaga   105900
gatgggacct ccctgtggct gtggcgggct cctcctcttc ctgctgggtc cccatggcaa   105960
tgcaccccca agtgccccag cccatcactc agcttccaca gcccaccttt tgtttcctcc   106020
tggccttgac cactccctgg gttgttctgg tttgtttact gtttgtctgc ttcctcttta   106080
gagggtgact ttccaaggc agggaccact gcgtcctggg atttagaaca gtgcctggca   106140
cagagcacgt gctccatggt cacatattga gtgagtggca ttgggggggt ggggttgac   106200
caggctgagg cacccaccc aaagagctgg gtttatgccc tttgcttggg agggagctgg   106260
aggttctggc ccttggtccc agccaggagt tgtgtttttt gttttgttt ttggagggga   106320
ggtaggttca gcccccagca gacatccaga tgagatgtta atcaaccacc caccagccag   106380
cagacacaca aaaccccccaa aggagcagac ggcacactgt cgctttgagt gtggagggag   106440
gagcagctga gccctggggc cgccctgggc tttgtgctgg gacagggtta taaataggag   106500
acaagtatt ctggaggtga caaccgcttt gggcagagt attacggcc cacattgtgg     106560
ccccattcaa atgctcagcc tggtgtctct gcgctgaggc taaaggatcc ggaagtggga   106620
aggtttctgg cttggcccca aagacaacat tattggagtt acaaaaataa ttggagcttg   106680
gcttaatt tggctaatta tgcctccctc tcctgacaag ccttttattt atttatgtgt    106740
tgtttttttt ttcttttga ctgcgtcctc caactccctc cctgagaagc catttcaaag    106800
gaaatgataa tttgtcttcc tatctcgcaa accgtgtgtg tctcttgggc tggtgggacg   106860
gcaggcggga gccgtgggcg tggcaggcgg gagccgtggg cgtggctggc agctgtgggc   106920
gtggccgggc tcgcgctctc ggcccaggag attccgggcc tggattggct gcgctcgctc   106980
cctcctggcg gtgctccctg cgggtagagg caggagctcc ctccatcacc ccgcagctgg   107040
cgggtgtcca ctgaggctga acggggcaga aacaggacca gggccggagc ccgtgtctgg   107100
ggcgctggga tacggaagcg ggagtctcgc ccgcccgccc ctccctccgc ccgcgagcag   107160
gggaccgtct cccgggtgga gctcctgctg ctcctacgcc gctggggag ccgtccagcc    107220
ccgcgggctg gcagcagatc tggacatgaa gagctgcccg tccagggggg gcgcggggac   107280
tgccccagcc gcccggtgac ggagggcccc ctccctcccg cgtggaggtc tgactcgcca   107340
gcaagaggca gccaccggag gaggctcccc ttccctctcg cttttgggga ggtgctcttc   107400
aggggggtgcg ccagccacct ctgaccctcg cagacccagg gcggaattcg ccggcagcca   107460
```

```
ccatggtgca aaatgtaatt ctagtgtttt tccgcagacg gctgagccaa agacccgccg   107520
tggaggaact ggagagaaga aacatcctga aacgtgagta gcgggtgacc ccctagggct   107580
ctcctcaaga gtgctgatgc tcaggttgct gcaggatccc agcgtgggcg gtgggcggtg   107640
cagtgactcc ggtccttcgg ctgagccctc ctgtgtgtct gagctgccca ggaatctgaa   107700
agcaaccccg gggaaagttg aaacacccag aagcatccca tttaaaattg agagggaaaa   107760
aaaaaaaaaa aagactctct tggcatggta aagatgtcc ctacttcagc gttatctaat    107820
gagtcagccc cataggtcta agggagatga ttctgtatcc tttcgcaggc tgggtctcag   107880
caggtttccc tggcagtttg gacagggtt tctgatggcc gcagtcacca caggcaggtg    107940
tggacaaggg atgaactcac cccttagcgg ttacacctgg ggaatcaaat agccccaagg   108000
aagcgagaaa ccttggggaa tgttgccggt ggctttcaac tccacagtgt gatgcgattc   108060
cagaccaccc ccccccaccc cccccccccc cgccccagc cttctgggct tctccagtta    108120
ggtgtgtggt tgtgaccagt gctgagcatc actgtccagg aagaacccc gaagtgtaga    108180
gagcactgtt ccatctcatt aaagccattg atgagtcggg tggtaaaacc cttgcagaag   108240
tgttttcgca gatacttctt atgtatctgg tcaatgcatt tcagctttcg agacattttg   108300
tatgaaaagt gtcttctaag gcctgtattt ttgaactatt ttcctttccc tcctctcttt   108360
atgatggatg gacactgcag acattctctg agcttgggtt tcattgcatg ccatctttc    108420
tacaaagagg gtcccgaggc tgagctgtca gaaagtgggt gccagggccc ctgctccagg   108480
tgtggagccc taacccattc ctctgcccag caccttcatt aactgcctag aaatcccctc   108540
tctgtccacc gttggaaata cttaaaccct aagatccaga attcttggtt ttattgtttt   108600
aatttaaaat tatagttgat ttacactgtt gtgtcaattt ctgctgaaca gcgaagtgac   108660
ccagtcctac atgtatatac attctttttc tcatattatc ttccatcctg ttctatcgca   108720
tgagattggc tatagttccc tgggctgtgc aggaggacct cattgcttat ccatttaaa    108780
tggaatagtt cacatgttta atttttaaa cctaggatac ggcgactgct gttctatttt    108840
acccaaacta ggccacatct gaggatttaa agaaaagctt ttcattgata acaatcttca   108900
gcacgtgagc ggatacaaaa gtcaagctat ttgtgacaca tatttgaatt ttaaaaaatg   108960
aagtcactta cgatggaaag cgcctaagtc tgatgcccct gaagaaaatc taagacttga   109020
gtggggcaag ttcacgcccc tcagcctggc ctgccgccca gagtgggcag aggcttttct   109080
cctgggaacc gttcctccca tccgtgggga cccctctct gctctggtgg atggccagga    109140
cccccagccg gtcagtgccc ctaagggagt tagtcttggc acagaagccc tgggagcagg   109200
gtggggcctg gcgggcagag gtggcaggtg gtcccgggat ggacagagct cgcttctgcg   109260
cacagaagag gcaggaaaac aagccccgcc aaccccact gcagcccga catcccttcc     109320
tcaccacctg gccaggcggg tccatccctg gtcggacgcc tcggtgcccc gggcagcagc   109380
gcctgagaat ttcgctggat agtggtgggc ggtgctttgg tttggttttg tgccgggaga   109440
agcgaaggga ggaactgtgt gagatgccgc ccagggcgtc atcctcgcag gcccttgacc   109500
caggctcatg ctccatggtg gcgtctgctt ttcatcagtt cttaggctgt cagcacattg   109560
tatttgctcc ctttaagtgg ggagctcatg actaacgcca tcctgtcggg ggaacacgca   109620
gagctgggcc tgcgtgttga tggagacaag agcgtaagac agagcggccc tgtacctgtg   109680
atgacactaa aaatgatcct gtggcattgg gcccacgcta tgccaggcct cggactcagc   109740
gcgtccggtc ctcattcagt ccttggagca cagtcgccag ctttgctcgg cgtccccatt   109800
tccctagtga ggcagctcgg actccgggag gtaataggac tttttatcag gcgtctcggc   109860
```

```
acagggaaag gaaccgcagt tcacgcccat gtgtcctgga ttagactcag gcacactcta  109920
atcactgtct caggagcaat agtgcaggtc tgatgattta cagaagatgc acgtgtgact  109980
gtcccagctc ctgccactat ttctggaaaa tctgggcgtg gaggctgtgg tcatggctcc  110040
cttgttttgc acaaggcacc gtgttttccg ggtctgggag ttagacatcc cgaacccagc  110100
actgagtggc gctcagagag tctgtagctt aacatctcag gagggacttc taagagttgg  110160
tgccccacca agcgcctggc ccggagacga tcctaccaga cactttcaaa gatcagctct  110220
ccaaagcccg tgctgtgccc gtgtgccctt gtcatgcaga tggtacccat gattttaaaa  110280
aaggaaagat ctgatcttgt ttccgtgttt tcacatgagg gctgtactgg gggtttgttc  110340
gtggcctatt tttgagaact ctgaagaatt agtttcatat cattgtttga atccctcatg  110400
gttgcccag gtggtacttt catcactttt ttctaattgt atcatcagct ttctgattag  110460
agcttataac tgtggtttct tctggctttt cacttggatt aagaccccag gacataacag  110520
ggtttggttt cctttcttaa aacagccaaa tgtaagctgc atcttccgtc ttaacgaaag  110580
ttacagaaga gtacgatggc taagtataca aagcacctag ataccaaacc ccccaggcgc  110640
acaaatgtta ggagtgtttt aaatagaggc agacatgtga acttatgtta actgcaagga  110700
gcaggcttcc cctttctcaa acctggcggt gtgtctagga gtgctgacag acgaagtcct  110760
tttcctagga gtggaatgct gggtcccctc cagggacctg aggctttatt tagcaacaga  110820
gagccagaaa taggacatcc attatctcgt atcccagggc agagcctaca ttttacacta  110880
cagctcagca ttctgctcca ttttttagcta caaagtgtag gtgtgagcac ggcttgaatg  110940
ttaatagcca cactcaccaa gcaaagccaa ttttggcgaa agatcctcgg ggtcccttga  111000
aaggcagctc acgtgtcttg cttctgcagt ggagaggcag ctgggttccc gggtatgttt  111060
cgagttgaaa tatattctga aaatacgcat tccaggcaag catatgctgc ccacaatctg  111120
aaatgggtgt ttcttatctt acgttggttg gctgaaagca tgtgtgccta ttacgtggaa  111180
aagggggga aaggcagtga cagttctatt aatattcatt tactcattca catatacgaa  111240
gatattatat atgtgtatct agctcatcct aaatctgttt ttgtttgcca tctatgttcc  111300
tagatgtaaa tacacacaga gagagagttg attagaggga gagggagaga gagagcgagc  111360
tttttcctgg ttctcctgca aataaatgcc caacaacaat cgatgcggtt atttctgacc  111420
cagaggaagc ggggatgctg gcaaagcgtc cacatacaag gctttctgtg tgacagtgag  111480
gccacggtct cccgagcagt gatgggcaaa gtggggaaaa acaaagtgat gtggacaaaa  111540
gcgtcttcta cgtcgtgtcc ttcgtcctcc accccccagca tccaggtttt gaggacactt  111600
cctgctaaag agaagaaagt ctcaacctgc ttcttccttt tcttttcttt gttttgtttt  111660
gctttaattt ttcacagaaa ggaatgatca acggagcag gaagaaagaa gagaaatcaa  111720
gcaaagattg acaagaaagg tactatcatt gaagcacctg attccggacg attcgaggga  111780
gaaagctgct tctgcagcgg tcgggatggg cgatgcaggc cctcactctg tgagggcagg  111840
tgccaggaat tcactcacca gacgccagga gagcagggcc ttttgccacg tcctggcatg  111900
taactgacat gcctgccaat agtgtcctcg cctggcaccc gagcccgcgg ccctgatgac  111960
acttcgcttt gtttccaggg ggtgagctct ttacacagtt cctgggcaca gcgcccggac  112020
agcagagctg ccctttcctt tgggacactg gttacctcac tctgtctaga agctctggat  112080
ggcagaacat tttattagcc tcaaggattt gtatcggggg gtctctagta gttaagtcaa  112140
tcaaaatgga ctgtggccaa ataggtagc aactccataa gcgctgatct ccttctaaag  112200
ccctgcccat ctctaaatcc aggtgttctg gtgttgccct ttttctactg tgttctccaa  112260
```

```
ttattactat tctaacaatt attattctat taataataat tctattaatt attattatta    112320
ttattgtcct acttgaagtt catggagtgt cttcctgagc ttgacttatg agtaccagta    112380
gtatttagca ttttaacttt ctctacctttt ttcgtaaaag cttccctaat gatagcagaa   112440
aagaagccgc tgctactgta aaatctttcc taagttcatt cacctatggt tccttgagct    112500
gtgctgtgaa cagggcactg ctgggctcct ggagcttagg gtccagagaa gaggtgctga    112560
gggcaggggc ctggaataga agaggtgtac tttaaacccc tcatacttga ggttttttgc    112620
atcagggttc catttcacag cttcaggtg ctttaagaat gctaatttgg cacgggacac     112680
ctgacagtgg tgatctttta ttttttcagct taatcagaga cccacggttg atgaactgag   112740
agacagaaaa attctgatac gattcagtga ttacgtggag gtggcaaagg cacaagacta    112800
tgacagacgg gccgacaagc cctggacgag actgtcggca gcagacaagg taccgagcag    112860
gccggtctgt gccgccgggg tgggtcggtg tgaaaggagc agagcgcgtc ctgccagcag    112920
gtttctatcc ttggtgggca ctgtccactg ttgtggtcga ggctgtgcct tcccagatgc    112980
tggctttgta aatacaagct ggcggtaggg acatgcttttc acctggggga cactttgcct   113040
ttagggactc tggcagtggc tggggacagt cttggtggtc agcagtggtg gtcgctgctg    113100
gtgtctagtg agtggagccc aggggtgccg ctcccccctg tggcaatgca caggatagcc    113160 gccccaccc cgagactgtt gaggacgtga aactctggcc tgggtgcgag tcacagtagg     113220
caggtgggca aaaagagct ggacaacatg ggtttacaca aagcgagcca cagccgggtg    113280
ggggaaggga ggagatggga gaagccttca ggctgcaggt ggaggcggct ctggactcgg    113340
tcctgggctg gtcccgttttg aggtgtccct ggggatcctg agcagtctca accaaagggc   113400
caggaggaga gcaaggggt tgcgggggg tgaggctatg gggtgaagca gagggaatta    113460 acatcccta gcccgtacac tcccccgtac tggacccagc ctgccaggcg ttatttcact    113520
taatcctcag caacatccca aagagagagg tgttgtcatt atccctgcag aggtgaccag    113580
gagaggctgg gggagtagtc ttgaccgtgg gcaaacgcta ttgaccagca gaacttaaac    113640
ccaggaacgt ctgttggcag agtctgtcct gccttcctgc ctctggtgat tttcagaacc    113700
tcaaagcctt taggaagagg aactattata catccagcca atacatttgc aggattttct    113760
cattgttcct cctccttcat atgctgagtg tgagtctgga gctttttaagt gaacacacac    113820 gggcatagca tcagcttgga gaagtccaga caggctgtag ttggaccaac tcagttaccc    113880
ttggcgaggg gcttggaggg gcccgggcac gggggagagg gtgggcctct ttggtggcag    113940
gcctggtgac gatgggcgta gcctgcccct gacattctgg aggcagagtc tttccttgcc    114000
ctgaaggctg atgttttttg tctccctgg tcctggaggg tttatctgag agaagcacac     114060 gatgaagtg ggcgttggga agctggaggc gggccagggg agaggccccg gatgggcggc     114120
gatgcgcgtc tcacccacag gcaaccggga ggttcttttt caaaatgcag aacataaacc    114180
tgcagtgacg tcagaatgac ttcttcctac attgtctagt tgcagagttc caagtaattt    114240
caccaaaagc tgaagtttgc tcgttgtctt gaggcttggg gctcttagaa agcaggacca    114300
tcagaataag gagtgacgtt cagctttttgg tgacgatagc cccgcattta tctatttatt    114360
acgtatcgtg gctgggtggg gagggctggt atcttccctc ttgggcacag cagataaatt    114420
ccctgaacac ttcctgaata ccagccatgc actagctcgg tgggactgta aacatgagca    114480
agtaagagtc ggaatgctga acaaaaagct tttctgcctg tcgcaccagc accgaagtca    114540
acatgtgttc gaagtggctg tccatccgca gccatgacac cagtttcctc tgctaatgtt    114600
gtaatgttct gaaaaatgat atgctggttt tcaattccag gcagcgattc gtaaagaact    114660
```

```
gaatgaatac aaaagcaatg aaatggaagt acacgcctca agcaagcacc tgacaaggtc    114720
agatttctat ttgtatgaag ttcgtgatac ttacaatatg gtgtttattt aaaaggaaaa    114780
ttaacatgcc acaaagaact atgtgttcac gttaaaaaaa aaaaaattca gtatctctgc    114840
agagaactgt attgaacaga cagaaggcac ctcaattaaa agctctgttc gctccctgg     114900 tttctcgtag ggctcggtgg aaggtggttt taggaggaca ctgctacgca gatcactggt    114960
tatctgagca gttagtgtat atttaaggaa atgagcctca aagcactgaa agtaatttgc    115020
ctgtgtgttt aattccccctt tgctaacgtc cagaactctc tcgtttatga gctccctgat   115080
tcattgatac gtagaggagt ggtgtgaaac aaccctctcc attcctgttt tcccaccttta   115140 tttaaatctg tattcatttc tttaacacaa gctaatgctc cctcgaagct cttccaaaga    115200
gctggtgttt ccccggcaaa tgtttgaatg acgctgtgcg ccgttcttgg cactgagaat    115260
acaactacag ataagatcaa ggaggtcctt gtcatcatgg ggcttatgtg ccagtggggc    115320
tgtgctggct gatgcctctg taatcgaggc gtttcacatg aggggaacat ccactctgcc    115380
cacgtgaccg tagcagcgat ggggtgtctt gctgatcatg acctgctcac tggctgcatg    115440
ttctttcagc atctccctct gtccgtggcc gtgacagtca ggatggtgtg aggttctcac    115500
acccttttaa tcccaagggg tggccgtgat gccataagcc ttcaactgca gctgctgctt    115560
cgtcatctct cccttggtct gatgatgctt gggccccaga tacaaagaga aaggacggtc    115620
tgaatggaga tactgccttc agctaaaaga acggattccc tccctttcc gtttgtcaca     115680 aagtggccac tgcaattgtt atttaaaaga tctactctgg agttcctgtg gtggcttagc    115740
ggaaacagat ctgactagca tttatgagga cacaggttcg atccctgggc ttgctcagtg    115800
ggttaaggat ccggtgttgt ggctgtggtg taggccagca gctagagctc taattcagcc    115860
cctagcttgg gaacttccat atgttgtggg tgcggcccta aaaaaaaaaa aaaaaaaaa     115920 aagattaact ctgcaagcac aatgaggttg tagaacagaa accaggtctc acaagatagt    115980
tttactttga ctatttcaag ggaggaagag gaggttgatg ggcaagaaaa aaacgaggca    116040
agtatatagt ttgtttaaaa acgtttaagg gttttcccct actttggggt aggaataaat    116100
catcttattt ttgagtgttc aaaacgctga aaaatgttta ggaaataaac attctcctta    116160
aaacattttt taatgttcag tctatgtttt taaaaagag atataattgc taccattcta     116220
tgtatggtga tagcaaatat ttaatacacc ttcttattct ttagatgttt actaaagaca    116280
tgtattttct ctcataagtc cttgataact ttcttagaag atggaacttt aagagagagc    116340
ccaaaacgta gacatcagga catataagat ttttgtgcta ccacagttta gcacttaatg    116400 ccaacttta ccagaacagt atttttagtc atatgaggtt ttcttaagca tatgggacat     116460
taccacaaac acattaccag ttctttaagt gcaaaactat aactctactg tattatccaa    116520
taatttgctt tattaatcag ttcattactt ccactgattt agtgaagccc tggtctttct    116580
gtgtactcaa gggcttaatg ggctgttttc agacgaagtt ttaggtagtc ttaagaattc    116640
agtgtctagg agttcccttc gtggcacagt ggttaatgaa tctgactaga aaccttgagg    116700
ttttgggtcc gattcctggc cttgctcagt gggttaacga tccggcgttg ccgtgagctg    116760
tggtgtaggt tgcagacgcg gctcggatcc cgcgttgctg tggctgtgac ataggccggc    116820
agctacggct ccgattggac ccctagcctg ggaatctcca tatgtcatgg gagtggccct    116880
agaaaagcca aaaagacaaa aaaaaaaaaa aagaattcag tgtctactat tcacaagagc    116940
caagaagaca tggaagcaac caaaatgtgc attgacagag gagtggatta agaagacgtg    117000
gtacatgtat acaacgggat accactccgt cataaaaaaa agaaggaata atgccatttg    117060
```

```
cagcaacaca gatgcaactt cagattatca taccaagtga agtaagtcag agaaagacaa    117120
ataccatata atatcactta tacgtagaat ctaaaacatg gcacaaatga atctatctac    117180
agaacagaaa cagactcaca atcgtggaga acagacttgt ggttgccaag gggagggccg    117240
agggagtggg atggactggg agtttgtggt tcgtggatgc aaactctcac atttagactg    117300
gataagcaat gaggtcctgc tatacagcac agggaacgat acccagtctc tcgcgttgac    117360
cgtgatggaa gatcacataa gggaatgagc tgggtcactt tgctgcacag cagaaattgg    117420
cacaacattg taaatcaact gtacttcaaa aaaaagaag aattcaggct ctagttcccg     117480
aacaggtggc cccaccatta ctttaaccca aacaggtcca tcctcatctt ttacctgttg    117540
gacttctgag acgcttgtaa tggcaacagc attatttgtg gaagattttg gcagtgttaa    117600
cgtaggaatg tgtaaccttc aattcatttt ctctttgtga tttctagatt ccacaggcca    117660
tagagatttt cttctgagaa gaattgtgtt taattttga taccaacact gaacattcat    117720
cagggaactt tcctgacgct catgaccacc tgctgtgttt gcgaaggagc aggaccacag    117780
gcaggtgaaa tgtgggtcgc tctcacctgt aagaggagga agcgggggac ggcctccact    117840
ctctggtgtc tgaggagtgt gaacagttgg ggtcgataca gcccccagga actctcccag    117900
aagaaaactc agttttgctt tgcagctctg cggtgcgaag gaggacgcgg tgtgcatgtg    117960
caggtcaccg ccgaggctct gagtgccgga cgagtgacgc agcgtcgtca gtaccatgtg    118020
gccgagacgt ttttattctg atcacgatta atttgagact ctttaagttc ctgttataca    118080
aaatgattta ctgtattata cttttctttt tttttatata atgtctaaca aaaatacagc    118140
tgcgacattt tgattcctgt taattttgtt ctttcattaa atgactactt attgcaggaa    118200
attaatctgg ccagtacagt ttcttgggggt tggggtgtga gatgttttta gcacaggggt    118260
ctgtgaaaca agtccaattt tattacttt gagccatcag aagccaacca catcaaagag    118320
cattcaaacg ttttgtgtat tttgtttgt aaattctgtt agtatatgtg atttcgtgcc    118380
ctggaaaatc aaagtattct tttcaagtga agtttatgga ttattgagta atgaacctag    118440
aaataagtga tagcttgttg aaaaagtctg ccaagatgaa aattatgcct tatttaagag    118500
tattttgaag ttcgcatttg cagacagtat taaaaacgca ttataagaag cagaggttta    118560
aatggaggtg cgatcgtaaa gaggaaattt ccctcctcca gcacaaaaag gtaaaaagta    118620
atcttgcaca aagggggaaa gtaagttaaa taaaaataaa tattccaagt aaatatgttt    118680
tggcttggcc tttgagtaag tgtcctcgag aatgagccca ccctctctgc tggtccatcc    118740
aggcagcgag cacagtgcgt ggactttggg acctgggccc caatcccagc tctgcacctt    118800
gcagcgagat attttatttcc tccgcaggaa catctccccg ccccccccaac acggctgtaa    118860
tctttgaatg agatgaagga ggtcaggtgc cagcgcagtg gccagcacat tctcagcctg    118920
accaggtggc cctggagcag ctgaatgtcc ctgtgacttc tcaccgcaca tgttacctca    118980
ttgccttccg tgacctttcc tgttccgctg ctttaaggct gcgatgggtc agctgcccat    119040
ggaaactgct cagcctttga ggtagcactt tgtgctgagg gacttatgac cagtcctggg    119100
tgctagacaa cctactgtga gttgaactgg ggtctttag aagaaatcac tgcatggtag    119160
aaaaagtcca gctctacctc ttacttgctg tataaccttt tgtgaattgt ttgacttctc    119220
tgagcctcag tttctgtgtc tgaaatgaga tgatttctaa atcctttcta accagaagtc    119280
aatcccttaa ttttataagc atttatgtgt atgcatatat actgtgtatt taatgtatat    119340
ttatatgtgt ggactctatt ttatacgagc cgttacttgt tgccaatcaa ccccctcaaa    119400
tactgatttt ctactttaag ctacgtatta gcagctccct attttatatt ttattcaatt    119460
```

```
taaaataata tttggagcca gactagggaa aagatttcac tctcctgtac aaatatccac    119520
ataactactt actatgaagc aaagcaaaga aaaggcctcc cttattctag aaaccaccct    119580
ggcccctaaa gcaaaaagat tcagtggtta agaaataact gcacctatag ttagagataa    119640
cctgatggat gggacacatg cttaggtttt tttcccaagt acagacccat agctaataaa    119700
tacatttgaa aataaagtac aagataccaa agaaggtttt ggctgggtcc agccccaaag    119760
gttctatgat attatagaac cagaagacat tttcattgta atcaaaatgt ttgcaataac    119820
agctaacttc taccactgta ttttttattaa tcttgaatta ttctaaattt tatttctgta    119880
tttcatgtcc ttagcaggtg tcatagaggt caagataaac taaaactatg tgttaagtag    119940
gtatgtctac tctgcaccta ctaagagtgt gtaatcctgc actaaatacg ttgatgacat    120000
ggcatctcac atctctctca tccagttagc tggaggaaca acattaaaaa gcagttcgta    120060
aatcacatgg tactggtgat atgcatgcat aaatttacat atgtcgtata aatttgaaga    120120
gaaagtttat atactgagga gcctgaagac ttagaaaaaa caatcctaca gagttgccgt    120180
tgtggctcag tgggttggga atccaaccgc agcagctcag ccgctgtgaa ggcacaggtt    120240
tgacccccag gccgacctca tgggttaaag gatctggcat tgccacggct gccgcttgga    120300
tttagtcttt gacccaggac cttccatatg ctgcaggtat gaccattaaa aagaaaattc    120360
tgccttcttg ttcagtaaca gatataggat ctgaattatc aacactcttc atgactagta    120420
gtagtcattg atggagtttt taacgcactg atttttataaa tcatttaaca aaatatgatt    120480
attaaagtaa caacattaag tcattaaaga gattgttttt aaggagttta aaagatttaa    120540
aaaacttact tggtaatttg gtgagaagaa attgagttat gtcctgaagc atcaagtttt    120600
aagccagtct gatgggggaa tgctgcattg tatgactttg taaaaagtac attttttaaaa   120660
attcaaaggg gttttgaatt tatgtaatgt tttggacaca tggatttaaa aaagcaccta    120720
acatcaagag gtccaccttg tggaaatata tggtaattac aagtctaaat ttatatttga    120780
ggtgtgtgaa gtcagtgttc tttgacagca aactcaagtc cagaaatgca aaattctaat    120840
taaaatgact agtctcacat gattcgtctt tatttaccca gattttttgtc cagaagtttt   120900
tcagtttttc atatgaaagc agtttcagaa gatgctcata cacaactgaa tatattgaaa    120960
gtcaggctga atatcggaaa atattttaaa atagtgaatt actataaatt acatttcttc    121020
atttttggc aaacgtattg ataatgatgg tgttaggaac ttatcgctag ttcatattta     121080
gacaaacgat atttattaga ctgaacagcg gaagagctac ctgttaccag ttctatgaaa    121140
acagaacggg cattctcttg tgggacacgc tgggttaaca cccaccccg cccaaaaaag     121200
aagaatagca atattttata tttggagtaa taaaaaaact tttaagtctt tatctcaact    121260
gtaaatctct tcaaggatg tgagcaggga aactaaaaat tacattgtct tgactgtgag     121320
cagttataca tgctgataat ttaaaaatt gaaaatatgc tgttacacat gcatcattac     121380
tttcgaaacg caactgattc tccttttttca aaggcacacg tgctgaaaat gtggccacga   121440
tacaggtgtg tgccctgaac aactggtctg caccgcatgg tccactccct gcttcccacc    121500
ccgagagttc ctgggttatg ctggtgactc caggtgtggc agagcacagg ctcaggaagg    121560
acttaactcc ttgctccaat ctttgcagtc caagttaggt gggtttgttg ctcagcattc    121620
tatcttgggt gtttaatcac cgcaccagat tcttccatgc ttactcccgt tttcatgcaa    121680
cctattagtg agcctgaact cacgtctgag agctgtgact gggctcattg cccataggtg    121740
acggtgcaga gcggaagac ctacccggag caaccgctga gcttcacgct aggcaggccc     121800
tgaggtcagg ggtggcagcc ctcatccccc tggactgcca gggtgaccaa gaatcaagaa    121860
```

```
gtagctgagg gcccagtgta ctgtccactc gaggacctcc cgtgcattta tggagtcagg   121920
actgggcggc atttaggtct cttcagtcgc gtctgtaggt ttggcattta tggttctgcc   121980
cagctgtact aacgctgcaa aacgttctct ctctccgtct tttccccgtg ttcttttgga   122040
acagtgacca ctgtaccgct ccgtttggtc gaggaagtgt ggcagacctg taccagtagg   122100
gtgtgaaact gtgatctagg taagaattgg atgtcattag caacaatgat tgtttatttt   122160
ttgatatgct tggcacagga aaatcaaaac gtgttaatta acacaaccat aaacccttcc   122220
caatgcaatc ttgatttaaa ccactatgtc ttttaagtag taagataaat tgaagaatac   122280
attttgtact taagaacaga gaggtctagg agttccagtt gtggtgcagt gggttcatga   122340
tccagcttgt ctctggggct ttaccggttc aatgcctggc ccagcacaat aggttaagga   122400
tcttgcattg ctgtagctat ggcataggtg gcagatgcag ctcagatttg attcctggcc   122460
aaggaacttc catatggtga gggtgccact gaaggagaaa aaaaaaaaaa ggaacagaga   122520
tttgatcttc aaactgtttc ttctaagcta ggggtcttgc aagctatagc ccacagacca   122580
aatctggcct gcctcccttt tttttaatgg tctgcgagct aagaatggtc cttacatttt   122640
taaatggtta catttgacgt gtttatatta gtttctacat gatctcctca agtttacctt   122700
ttggtccaca aagcctaaaa catttaccat atagcccttt aaaagacagt ttgcctgctc   122760
ctgctctaaa aacttttttt aaagtgtaag taaatatata atagaaaatg ttgaattatg   122820
cagaacaaat agctaacttt tgtttctaag taagcttaaa attttttaaca tcaaatctgt   122880
ttcagggagt tccattgtgg ctcagcggaa acgaacctga ctagtaccca tgaggatgcg   122940
ggtttgatcc ctggcctcgc tcagtgggtt aaggatctga cattgctgtg agctgtggtg   123000
gaggtcccag acacagctta cttagatctg gcgtcgctgt ggcataggct gcagctccaa   123060
ttcgacccct agcctgggaa cttccacatg cgtggcccta aaagaaaaa  aatctgtttc   123120
attttcagac tcattataag ctcacatgac agtagctgtg tgacatgcag agaaggcaca   123180
tcgagtcagg taaataataa agggctaagt gatattaaag aattattttc tcactgtgac   123240
aacccactgc tccagcttcc tttcatttaa aattattgct atcatagcat aaaccaaaat   123300
taaattgtct actgttcaag atggtataac atacagatct cattgaacac atctgcattc   123360
ctgaaagaca accggattat ttccctctag atgttgtttt agaatatttc catgggcttt   123420
ttggacctaa tttaaaaaaa aaaaaaacag taagcaagca ttacaaatgt agcgtctttg   123480
gcagtgaagc ctgtgcacat ttgatttgcc tgcatactct tcaaaggcac gaatgaaagg   123540
aaatctgatg ctgaacgacg gctttaaaac agagatctaa aagcccaaaa gggccacaga   123600
gacctcattt tattagtttt tcttttttagg gctgcatctg cagcatatgg aagttcccag   123660
gccaggcatc aaattcgagc tgcagctgca acctgcacca caacttatgg caatgccaga   123720
tccttaaccc cccgcgtgaa gattggcatt gaacctgctt cctcatggac actgtgtcag   123780
cttcttaacc cactgagcca taatgggaac tcctagatct cattttttaag tacaaggaaa   123840
gggttctttt cttacctctg catgtagagc taagtacagt gtatgtcata tactagacac   123900
tcaaatggct atttgactaa tactctgtta tcaattttaa tagaaatgcc aacactatgc   123960
aagatttgag gatctgaggg ttttaggagg cacattggcc ctctccaaac gtagcaaatt   124020
tctacctaga aatactacat ttgttcaatc atttattcac tgtgcaggtc aacttttcca   124080
ggcactcgtt ttaggaagta gaacctagac aaaccaggct cttgttccca tagaatttac   124140
aggggtgata ccaaaaaatg ctgtatgata gagggtgata attgcattaa taggattgtg   124200
aaggaagtcc tttctaaaga attactattt aaatgggaac ctgaagaaga gtaagagttc   124260
```

```
ccaggaaaat tgaatcacat aaacaaagac tctaaaactg gaataaggag ttctgttgtg    124320
gctcagttca tgatgtggtt cattgctcag aggtcatgaa cctgactagt acccatgagg    124380
acacggattc aatccccggc ctcgctcagt gggttaagga tctggcgttg ctgtgaactg    124440
tggtgtaggt caaaaatgtg gcttggctct ggcattgctg tggctgcggt gtaggccagt    124500
ggttacagct ctgattcaac ccctagcctg ggaacttcct tatgcctcag gtgcggccct    124560
aaaaagacaa ataaataaat aaaataaaac aaaacagaaa taatactggt taaggaacaa    124620
ggcttgaagt atatgtacaa gaggagagga gtaagaagaa ggaagagtga gaaacgaggc    124680
agaggccagc tcacatccac ctgtgggggc catgtgctat aaaacttaca ttttaagggc    124740
acaggaaacc cctggagagg ttctgtgttg ctgctggttt ttttttttt tttttttag    124800 ttcaggtgaa atgcagataa catgaaagag tacagttcaa tggcattgaa tatacccaca    124860
gagtcataca accaccacat ctctctagtt ccgaaacgtt ttcacacctg aagaggaccc    124920
catgctctca aggtggctac tccccactgt cccctttcca aacatctcct ctgctttctg    124980
tttacaagga ttcacacagt ctggatagtg catgtaaact gaatcacaca acatgttacc    125040
ttccgtgtct acttctttca cttagcataa tacatcggag gttcatccac tgtaataaga    125100
atcaatactt ctctcctttt ttggctgaaa acattccag tgcatagaca gactacttgt    125160
ttgttggcca cacccatggc atgtggacgt tcctgggcca gggatggaac ctgagttgct    125220
gcagtgacga tgctggctcc ttaacccact gcaccaccag ggaaaagcac cactacatac    125280
gtacttagct gatggccgtt tgggctgtct ccccctgttg gctattatga acagtgcact    125340
tgtgaacatt cttgtacaaa agtatttgtt gaatatgttt ttaattctta cgggcgtatg    125400
acgaaaagtg gaatcatacg gtaatttctt ctttaatttt ctgaggaacc accaaactat    125460
tttccatagt ggctgcatta ttttacattc tcttagaaat gcacacgttt tccaattcct    125520
gaacagtctt gccgatcttt agtgttttt gattctagcc atcctagtgg gtataaaggg    125580
acatcagtat tgttttggtt ttcattttcc taatgattaa tggtgctcag tatatgttca    125640
tgtgtttgtt ggtcatttgt gtatcttctc tggagaaggg tttatccaag tcctttgccc    125700 attttcagt cagatttttt tgtcactttg ttgaactgta agaattctct gtatattctg    125760
gatactagac tctacagatg gatcatttgt aaatatttta tcccattcta caggttgttc    125820 tctttactt ttataaaagt attctttgat gcacagaagt tttttttttt tattttgatg    125880
aagtacaatt tacacttttt aatgttgttt cttgtttcat tttgtttttt tcttttttgg    125940
ccgccctgca tggcatatgg agttcatggg cctgggtcag atctgagctg cagttgtgac    126000
ctacaccaca gccgtggcaa gtccagatcc tttaacccac tgagctgggc caggaattga    126060
acctgtgtcc cagcgctcta gagacaccac ttattccatt gcactaaagt gggagctcct    126120
gttgttggtg ttttggtgt catatctaag actccattgc caaatctaag gtcgtgaaga    126180
tttgctccta tgtttttcc taagagtttt atagttttaa ctcttttagg ttcttgatcc    126240
atttaaagtc aatttttaca tttggtttaa ggtaagggca tccagcttta tgttttgca    126300 tgtggctata tggttgtccc aaaaccattt gttgaagaaa ctgttatttc cccatcaaat    126360
ggccttggca ccttttgatga aactcgactg accatagcta aataggttca tttctagaat    126420
ctcagttcta ttccatttgt ctttatgtct atccttatgt aggtactata ctgtgtgttt    126480
tgtgggtttt ttggttttgg ttttggtttt ttccttctta gggctgcacc cgtggcatat    126540
ggaagttccc aggctaaggg tggaatcaga gctacagctg ccagcctacg ccatagccac    126600
agcaacgtca gatccaagcc acgtctctga catacaccat agctcactga gtgaggccaa    126660
```

```
ggatcacacc acatcctcat gggtactagt caggtttgtt accactgagc caccatggga   126720
actcctggta ttatactgtt ttaatttagc tttgtagtaa gtatgaaatt gggaactgtg   126780
agtcctccaa ctttattatt cttttttaa gattgttttg ctctgttggg tctcttacat    126840
ttccatgtga ttttttagg accggctttt ttcatttccg tagaaaggac ttggaatttt    126900
gtgagagact gcattaaatc tgtagcttgg ttcagaatat tgccattttg accgtattaa   126960
gtctaacaat cacgtgggat gtcttccac ttgtttggga cttctttaat gtccttcagc    127020
aatgttttgt agttttcagt gttcagatct ttcaactcct tcataaaatg tactcccttc   127080
gatatgctgc tggacttggc ttcccagaat ttcgttgagg attttgcatg catattctac   127140
tggtctgtaa ttttcttttc ttgtgatgtc tctatctgac tttgggagca aggtaatgct   127200
ggcctcgaat gagttaggaa tgctccctcc tcttctgttt tctggaagca tttgagaagg   127260
gctggttaat tctgaaaatg tttggtagaa ttctgtcttg ggaggttttt aattactgat   127320
taaatctctt gttataaatc tgttcagatt ttctgctgct tcttgagtca gttttttgtag  127380 attgtgtttt taggcatttta tccatttaat gtgagttatc taatttgttg gcatacagtt  127440
gtccatagaa ttctcttaga agcctttcta tttctctaac atcagtagta atgttcccag   127500
ttttcatttc tgcttttaga cattttagtc ttctattgat cgtaatctga caagtcagtc   127560
aggtttatca attttcttga tctcttcaat gaaccaacct ttggttatat tgattttctg   127620 ttgttttct attctctttt attttattt ttttattt tagtcttttt gctatttctt        127680
tggggccgct cccacggcat atggaggttc ccaggctagg ggtctaatcg gagctgtagc   127740
caccggccta cgccagggcc acagcaacgc gggatccgag ccacgtctgc aacctacacc   127800
acagctcacg gcaacgccgg atccttaacc cactgagcaa gggcagggac tgaacccgca   127860
acctcatggt tccagtcgg attcgttaac cactgcgcca cgacgggaat gccgtccttt     127920 ttttttttt tttttttgg tctattctct tttaaaaagc tttactatct attatttcct      127980
tccttctgac agctttgggt atagcttttt ctagttcttt aaagttaggt gattgagatt   128040
tccatcactt ttaatgtata taatgtaca gctataaata tctctgagca ttgcttttcag    128100 taagtttcat cttcatttgt tccaaagtat ctttttttt aaaaaatctt tttccttttt    128160
ttaatggctg tacctgtggt atatggaagt tcccaggcta ggggttaaat tggaactgta   128220
gctgccagcc tggccatagc cacagccact gccggatccg agctgcacct gcgacctacc   128280
ccacaggtgg cggcaatgct ggatccttaa cccactgagt gaagccaggg attgaacctg   128340
catccttacg gacacaatgt ttggtttctt aacccactga gccacaacag gaactcccca   128400
aagtatcttc caatttccct tgtgatttct tctttgactc actagttact tatgaatgtg   128460
ctgtcactgg agagttttac ataagggagt cacaagctgg gtatatgatt tacgatttaa   128520
caagactata ctggctgcta tgtgaatcag gggttgtaaa aaggggagca cgagtgctgg   128580
gaagcaattt agcagctgtt gccattgtct ctgtgagtca atgatgtaaa taaacactgt   128640
caaaggtgag tgatggcaag aaagtatatg gacctacttt ggcggtaaaa tctgcaggac   128700
ttatcagcta actggccaaa ggaaaaggaa caatcaggaa atgcttctag gtttgggctt    128760
gaatagttgg gtggatagaa gggcatttac tgagatggaa gtacaggttt atttttttct   128820
tcggtggcga aacgctgag agagaaaaga gaggtgtttt gagaacagct gtttattgaa    128880
ctgtcaataa aacaatgtat atgacatgct aatgttcaaa gtcagaatgt ttctacacgt   128940
gggagttagc aagacaacga cagttactgc atgggaccaa atgaaattac ccaagagaaa   129000
gtgcagacta aagagacgtg acagactaag aggtaaaagg ggaacgagac aagaaagagt   129060
```

```
ggaaaacatg tgccagccaa aggttttaag tgtggaatgg cactgcgaag cttaagacga    129120
caggtaagat ttgataaaat ggacgactgg tgattttgac aaaagctgta gggacaggag    129180
ttcccgtcgt ggcacagtgg ttaacaaatc ctactaggaa ccatgaggtt ttgggttgga    129240
tccctggcct tgctcagtgg gttaaggatc cggtgttgct gtgagctgtg gtgtaggtca    129300
cagacgcagc tcggatcccg cggttcgctg tgggtctggc gtaagccggc ggctacggct    129360
ccgattggac ccctaacctg ggaacctcca tatgccatgg gagtggccct aaaaaaggca    129420 aaagccaac aaaaaaaaaa aaaaaaaaa aaagctgtag ggacaaaaag tgggactggg     129480
gcaaataggt agtgtgtaag ttgagacagt acctaaagaa cattcttttg atatggtctg    129540
tgtaaaggag catagatgat ctcacggggg ggcagtaagt aaaggggaac ttgatgttaa    129600 catcttttt tttttttttt tagtaaatgt gggctataca caccggtaag agaagtcata    129660
gacaacaggc ttcagaaggg ggattacagt gtcctgaaat aatgagtcta atttgccact    129720
ggaacatgtg agaaatcagg aagtgccggt attgatgcag gcaagctgtc agaggagatg    129780
aggaaagtag aaggtaaggc cacctcctaa aaggcaatga attaagggat gaggtactga    129840
tgtacagtaa caccctggaa atggggcaaa atcaattaag acagaataag ggttgctgag    129900
caatgctttg tagccactgg aaatatgcag tcacagattc taaccttgat tatatgctat    129960
ttctcgagtg atgtgcgcat tgaggggtct gaaccagtgg gtaaagttga agacaggaca    130020
gagggcaaga gagtattatt ttggcctaag gactctagaa tcggtgaggg gcatggcaag    130080
acagtggtag agtaagcatc cgggctcctc tgaaaagcag gttggggagt tcctgctgtg    130140
gctcagcaga aacgaatctt gactggcaac catgaggatg caggctccat ccttggcctc    130200
cctcgctcag tgggttaagg atccagcttt gccgtgaact gtggtgtagg tcactgacac    130260
agctcagatc ttgcgtcact gtggctgtga tggagcattg ctgtagctcc aatttgaccc    130320
cttgactggg aacctccgta tgtcacgggt gcggccctaa aaagacaaaa aaataaaaa     130380 agcagttgga gtgatcatgt cagaagtgag agtcagtgcc caacttttgg ttatgacaag    130440
gtcaaaggag gcagatttaa agagctgaga agaagtagga acctggggttg gatcggagtc    130500 ttctaagtct ggccatgggt gaggtaaact ggggaaatgt gtcatgatgg gactgcttct    130560
caagtctcac aaggcaacgt ggagttacaa ctgctggtcg tatttaaaat tacagcagtt    130620
tttaaaaata ctgccactat tgcttgaaat agaatcccga tgctaacaac agaataaagc    130680
tgaagtatgt aggatttccc tttgcttatt cagactgaga agccactttc accactgttt    130740 ttcgttttt ttgtttttt tttttaagg gttgctctca tggtatatgg aggttcccag       130800
gctagaggtc aaatcggaac tgtagcttcc agcctatgcc acagctcacg gcaacgccgg    130860
atcctcaacc tactgagcga ggtcaggaat cgaacccaca acctcatggt tcctagtcgg    130920
attcgtttcc actgtgccac aatgggaact cctggttttc gttttttgacc atgcccttgg    130980 catgtggaat ttctggggcc agggactgaa gccatgtcac agcagtgtcc tcagccacac    131040
cagcgacaac accagatccg tacccactga gcctccaggg aactcctttc cactgtactg    131100
aaatactggc agtattcaaa tactctgcta ccattaagca ggttaagtga tagtgtgtga    131160
ggctgtgtgg taatactgtg gatgtctgac tggagaagga tgttttgttt gatccaatgt    131220
tcataaacta gaaaagagt gattcataaa ataactgtaa tatccaagtg acagagcatt     131280
tatttcaact ttattataca attaaactgt attatttcat aaattaatct agcaaaatat    131340
tattacaaag aacactaggg cttaaaaagt acttgtcaaa acagcctgct tatgagttaa    131400
taatgtctcc acctagaatt aaaatgtttc gataacaaag taaccatctt aggctacttt    131460
```

```
gtgccttcta gcataatgga gctgaagcag aacaaatata ctctccaaca gtatcctcaa  131520
agtactgatt tacactcagg taagtatttt aaatcaaatg ttctatgtgt cactaaaatt  131580
tttaatagtt gtagtatatt ctgaactagt aaataaattt tattaataat ttatatctgt  131640
agttaaaact tatttaaaat atatgataaa ttttagtttg ttaaagaaat aactagtttt  131700
gagtacagtt aactcagtaa tattgtctca tgcaagtatt accataaaaa caattccttt  131760
gactgtttgg cttcccaaaa ctttctttaa aaaaagcagt actgtataga caagactttg  131820
gggctcggag tatgttaaag tgattatagg gtcttttta tccataaaat gacatttctt  131880
tgaatttgga ggttcctaca aaggtgctct tgccagggtg acatatattt tctccttgta  131940
gagctacttt gggtatttcc tcagttatac acaaatattg gataaaacct gttgatagca  132000
actagacatc acacattgtt tcttcatga gccatgaata atgactttag ccctctgcgc  132060
acattaagaa gctcctcttc ttgctatggc caagaaaaaa agacagattt taaattatca  132120
ctgtaaaact atcaaataaa ataggaaaaa aatcaagatg ttatgaataa atatactgtg  132180
tatcagtgtc caatctccca ggatatattc ctagctatct acagaattat gtgctcatca  132240
ctgatgtttt agatgatcaa ttgagagaag accttcagac ttaaatccca aatccacaaa  132300
atttatttt ttcatttaaa tattaaatct atactccaga aaataatttc agtaagggtc  132360
agtccagtta gattacttgc ttcaagctaa gctggctaag ccacaacatc ctgctcctct  132420
actatttcag catactgagg tgctattaaa atttactagg tgcattaata ctaatacttt  132480
agaggggatg tttaaagtt aacctaaaat tcctccatct tggagaaaac accaaaggca  132540
tgctcacttg gaaaagcacc ttaaagcacc ctcccctctc ccaatcttag tgtacttttc  132600
ccagaatgca gttagttgct ggtctactag actttgcaaa gtcagcttat tttatcccca  132660
cgtctaagta gatgaagcct tgttgtccaa gtaatcaata attctttcta ggtaactctg  132720
cctgacacat catctccttc agaagccaca acaggacaga ggtctgctac agtgcacact  132780
gctaagatac atacaaataa atcattcttc tagctaattt taaaattttc aaattgacct  132840
ctccttttc cttaggaggg actctttatt tgtttagttt tttagggcca tacccacagc  132900
atatagagag tcccaggcta ggggtgaaa aggatctgta gctgctggct gacaccacag  132960
ctcatggcca cgttggattc ttaacccact gagcaaggcc agggatagaa cctgggggct  133020
catggatgcc agtcagattc gtttaccgct gagctacgat gggaactcct tggactcaat  133080
atttaaatca cccctgttat tctactataa atttgctccc attttaattt aaagaactta  133140
cagtactaga agaaccctaa tggggctaaa actgccttct ctgaatccga aaacaaagaa  133200
agaagaaaag cctatggaag aaattcccat ttaaatatgt aaaagcatga ctgattattc  133260
catttgaaaa atccaaacta gatagttgac ttaccatttc cttaagaagc ctgtcttgta  133320
tcatttcat gttttctttc attgaacaca tctgtgaata agtaattttc cccatgaaat  133380
ttactataaa gttttcacag caaaaagact gaccaatagt gagcgattat atataaaaat  133440
ataaaattga tacctcagaa gtaaaaatag tttcttcata atcagtattg tagaagacat  133500
tcttgttcaa cgaagctttt aaaaggtgaa gccttaacaa gtaaaataat gaagtcacct  133560
ttgaagttac cttttgtatt tcactttaac aaattacgtt gctatatgta tataattaca  133620
tatgtataat atataattta gctcataata aaaaaaaatc cagtgttata gatgccaatc  133680
attaagaatg tcacactaac ctctgctgtt cacttttttg ataggcactg aacttctgaa  133740
atatcttctc ccaaaagccc taaatttcaa aatacaaaat tagttatact ttaattatga  133800
ctaaaaatta acacttgaaa gaatatactc tatttctact attcctaatt taaataaaca  133860
```

```
actcagctgc atgctaagaa tattcagatt catacactct tttagacaaa aagaatgtat    133920
caaaggtatt catcaactat ctgcatattt ttatggaagt atagtgactt acacagtttt    133980
aggtgtacag cagagtgatt cagtttttta taggttttcc attataagtt attacaagat    134040
attaaatgca gttccctgtg ctatatgtag tttctggttc atctatttta tatatagtat    134100
ggtatatctg ttaatcccaa attcccaatt tatccctccc cccattataa acttaaatct    134160
gtattttaag tgtgtgtgta agaaattaac taaaaactta agataaaata agttatcttt    134220
taaaaatgaa acacaagttt aaaacaggtt ttcctgagtg tagctcttta aaaataattt    134280
taaagcctca ttttaaact cttaaaagca caaaccacta attccttctc caaatctttt    134340
aaggactgtg aatctttttc aaaattctcc agctccttta tgatgatgaa ttggaatttg    134400
tcaagttttt tgattctagt aaagaaacaa aatgagattt ttttcaaaat gatagcactc    134460
agaataccca gcacttataa tatttcagaa gggattttca gtacagacct atactcctga    134520
atctgatgat tcattgtttt tatatgttgt tgagctgttt tccaagaatg cttcgtaaaa    134580
taatccatta ttttgtggcg gatctgaaaa atactcattt ttaacttgaa aaaaatcttt    134640
acaaaataat aatctaacca agattatatt aagaccaaag cctttctat gaaatataaa    134700 cgactaagaa gaacttagca aagtgaaaaa ttgaaaactc agtgatttaa agtgaagggt    134760
taataaataa gctcagtcag agcacggcct ggttctacca ggaacgctct ggctgagagt    134820
tgaactggca attaatcatt ttcataacta catcacattc tatagtattt acaaaatgct    134880
ggttaataca attttttttt ttttaggagt gcagcctaag agtcacactc aaaattattt    134940
attactattt ttcataaaaa cattttcaca tctagccaca gataagtaac agaatatatg    135000
aatcagggct tctctgttag gctagattaa atcacagcaa aataaatata tacgctctta    135060
aataatttca ggttttaccc ctgaagataa gaaaaataat ttcaggttta cccttgaaga    135120
taagaaaaag aaaaggaaga gatatggctg ataacctgtg caaaaagaac tgtctgtcct    135180
aaataaagac atgtgagaag atgggtggag aaaaataataa aattattttc gaaagcattt    135240
ttgcaaacat cacctcacaa gcctcagtaa caaaggatac ataagtacag agctggtgaa    135300
acaaaatgaa atggatttct ctggctgagg ttgctcatcc tttacactt attatgtacc    135360 ctcactagca atcacttctg tgagataaat gtattgatta aaaagaccag gcatgaaaag    135420
aaaattgttc caaaaaataa agaaaaataa gctaagagtc aaaatattaa attgaaaagg    135480
aagataggac aaagagacag aacccacaga agaagaatac agagaatgca cagattttag    135540
aagacaaact tggctcatga gataaaaggt tttttttgcc taggaatcat gccagttttc    135600
accagcacac gaagaaagct gagttcatga atggatgttt tgttgccaag agttcacact    135660
gatagtctag cagaaagtgt ggcatactgt catattattg gttataagtt gtaaatcatg    135720
atttaaaaat gacaactcac atgaactttc ctcctaaatt ctgtattgag ctgctcatac    135780
atcattccga catctgacat ttcatttccc cagttctccc caggaataga aaagtcattt    135840
gttgataatg gagatatact ttcagacact aaaaaatgaa gacaatcaac taaaattaag    135900
atatgcattg ttagatattt agccttttg tcatgaggcc aagaacaaaa tctcttattt    135960
tcagattctc tacataatct aagtattatg aaatcaaagg cagactattt tttttttttt    136020
ttgtcttttt agggccgcac ctgtggcata tggaggttct caggctaagg gttgaattga    136080
agctgtagct ggccgtccta taccacagcc acagcaatgc cagactgagc ctcgtctgcg    136140
acctacacca cagctcatgg caacgccaga tccttaaccc tttgagcaag gcctgggatc    136200
gaacctacat cctcatggat ggcagtcaga ttcacttctg ctaatccatg acaggaacgc    136260
```

```
ctatatttt  taatttaaaa  tattttgagg  aatcccgtca  tgactcagtg  gtaacaaact  136320
gactagtatc  cattaggatt  caggtttgat  ccctggcctc  actcagagag  ttaaagatct  136380
ggcattgctg  agagctgtgt  tgcaggttgc  agaatcggct  tggatcccaa  gttgctgtag  136440
gccggcagct  acacctccaa  ttcgacccct  agcctgagaa  aacttccata  tgctgcagat  136500
gccgccataa  aagcaaaaaa  taaaataaat  aaaatatttt  gacttataaa  taaaaaagtc  136560
ttttagcatg  ggtattaagt  tcaaaacagg  taacattaaa  atggaacata  tttggactgt  136620
tttttaaaac  cagttttaa  ctacttccat  attagtaact  caagtattta  gtatttacca  136680
gtaaattctc  tagtaaaact  tataagtggt  aatcagtgat  agaatgatga  gagaaatgta  136740
tgagtaagac  cctcagtata  atattattca  gataaagtga  actgcgtaat  aaagcaccat  136800
ccttgggttt  atccaatgtc  gttacaaagg  aatttgtctt  gtgaatggag  tcactcaaga  136860
tctaagaaac  caccttcgac  agtaactgaa  ttttgacaga  ggcatttgat  ctacctacct  136920
ttgtaagttt  gaaaatccgt  accttcactt  ttagataatt  ttttgggaag  caagcttgct  136980
ctttcctcct  ctctctctcc  caatgctact  tcatcagaat  tactcagatc  cttttctatg  137040
tacattcgtt  tccgactaac  atgtagtgta  gggccttagg  aacagtttaa  aagtaatgaa  137100
taaagctaca  atcttaattt  aaaacaccta  atattttctt  gcttttatca  aaaaaaaggc  137160
atttgcttca  gttatttgta  tagttttagg  cacctgtgca  ttaaattcta  ctgtatttt  137220
ttcattttca  ctaaaattgc  aataactaaa  ttgaataatg  gtatgattta  aagtatatag  137280
ctcctttaga  tgagacatca  ccatagtatt  tcagtaatta  atacgttttt  aaaaagcaag  137340
tctatgacta  caaacctgat  ccatgagtgg  agtcacaggg  caggccaccc  catattttct  137400
ctcttccttc  actagccatg  gagagtggag  atgctgaatg  actttcctaa  aatttattag  137460
aaattggaaa  aaattctata  agtactcttg  gattcatctc  ctacttccaa  attcgtatta  137520
tgattttgat  ttcttttgagt  caggatatgg  gaggccgtag  aaactgaaag  tctaaactac  137580
tttttcacgc  tctattttta  acgtctttgt  cctctaacct  tgtttcactg  ctccaataca  137640
caagtctctt  tgttccagtc  aaatcagtct  ttttccttt  tttttttaa  atcttttgt  137700
cttttaggg   ctacacctcc  agcatacgga  ggttccccgg  ctaggggttt  aatcagaact  137760
gcagctgcag  gcctacacca  cagccacagc  aaacaggatc  caagctgcag  ctgtgaccta  137820
caccacagct  cacagcaatg  ctggatcctt  aacctactga  gcgaggccag  ggatggaccc  137880
tgcgtcctca  tggatgctac  tcatgttcat  taaccactgg  gccacgacgg  gaactcccag  137940
tcttttcct   tttttagaaa  aatgtatgtc  tacttccagt  tcccttgtg   gacttaggtt  138000
actgttcttt  ctccattcag  ccggatatat  gaacctaccc  actccagtcc  agatcaaatc  138060
ccagcccact  tcaaactgtg  aaattctgcc  ttaactttct  gtattttata  ggtcattaaa  138120
atcttttata  gaggaaaaaa  ggtcaaccaa  actcctgtat  aatcatgaaa  ctataaagtc  138180
ctgattatga  atatgtaagc  tagtggttaa  cagtgacagc  ctatttaaga  ccttctcatt  138240
ttaaaaattt  caactttttt  ttgtctttta  tcttttagg   gctgcaccca  tggcatatgg  138300
aggttcccag  gctaggggtc  gaatcagagt  gtagctgctg  gcctatgcca  cagccacagc  138360
aatgccagat  ccgagctgca  tctgcaaact  acaccaaagc  tcacagcaac  accggatcct  138420
taacccactg  agcgaggcca  gggtttgtac  ctgcaacctc  atcgttccta  gttggatttg  138480
tttccactgt  gccatgatgg  gaactcccct  caactttttt  ttccatgatc  aaaccatcct  138540
aaatatttta  aacatcacat  ttttagacaa  ctgaaaaata  ctaaattatt  ataaccatta  138600
ttaaaggccc  ataatctgat  tcttataaga  accacctag   tttaagtaaa  gtctgatggc  138660
```

```
cacataacac atatactctc cttaacttta aatatgattt tcatatttgg aggttcaatt   138720
tccatacatt ttttctgaac tataactgct taatctgaat agctactgca attttgtgtt   138780
tcttacgaaa ggacactctt ctctcagtat ctgtggaggg ggattgcctt caggacccct   138840
tgcaaatacc acaatccact gatgttcatg tcccatgtgt aaaacagtga tctgcaattg   138900
actgaattca ctgttgggca aatccacaga tgtggaatcc atggatatgg agagtcaact   138960
gcatcacaaa gtttatattg tttcttttac agtagtattc ttaactgggc aatgaacaag   139020
acatacagaa atccagagga aattagaaaa ctaagaaaag aaaaacacaa tagtaaacca   139080
aaactagcta aattttaaga gaataattga tttgctgcta aaactcaaac atattcctaa   139140
ttgaaaaaaa gcacttaaca cctaaaatat taatttgata acaagtatcc accaaaacct   139200
atagataagc atgcatgcta gcacagtatc aattaaacac tgttccaagg gtcatggtca   139260
acttaaaaat gaaacgtca tgaagtataa ggactggaac agaaaaatgc aaaaaatata   139320
catacattgt ttttttctt accaaaaagc ctgattgtgg aattggtgag caactttctc   139380
ctccacacag taagttttc tcactgttat tgggtgaatt tattggactt tcaactccac   139440
tgtttaagga ttcaggtgat gaagttttg gataaggtga tagtgatttt gttacatagt   139500
caaaatcttg agtaaaatct ctttcggtcg ttttctctgt acctatattg cctcatgaaa   139560
cagaaagaaa aagagatgac aggtgttatc attgatattt actttagaaa cagtatgatt   139620
aatttaaatt ctaaaaaata gtaatttacc aagtcctcaa atcctagctg tacttaggat   139680
aaactttcaa taaattaaga tcaaattata tgtaaaatat tttaataaga cttttaaaat   139740
actaatggct tgatttaaaa tgtaactgta ggagttcctg tcgtggcgca gtggttaacg   139800
aatccaacta ggagccatga ggttgcgggt tcgatccctg ccttgctca gtgggttaag   139860 gatccggcgt tgccatgagc tgtgatgtag gtcacagacg cggctcggat cccgcgttgc   139920
tgtggctctg gtgtaggctg ttggcaccgc tctgataaga cccctagcct gggaacctcc   139980
atataccacg gatgtggctc taaaaagaca aaacaaaaac aaaaacttcc taacatttag   140040
taaagcttca gtgtcataac agtttactta gcaaagacca agttactagc attaactagt   140100
ttaaaaataa agttttgact actgaaaatc ttaaatacac ccctcaaaat tagtcttcaa   140160
attatatttc cacatagttg taacagaaaa ttactaaata ttcaactaaa gaaaaaaaat   140220
gatactgaca tctcattact tctatagatg atggactccc agataaagat acaggagatt   140280
tgtcaaggct attatctctt atagtatctt ttagtagaga tgagttttc cattcttttg   140340 atatatcctt ttgcatttcg gaagagaagg aattctgttt ctttggcggc ttcatggttt   140400
tgcttctgga atggatattc tcctaaatgt attggtaata tacaaattat atttgaatac   140460
aaataattta tacttgaaca cacaaaataa tttaattaaa ctacactgaa atctttacta   140520
aatgctttat accactacat acaggcaaaa taggagcctc aaatgagtag agaaagactt   140580
taaaagtaaa attgttggag ttcccgtcat ggagtggtgg aaatgaatcc gactaggaac   140640
catgaggttg agggttcaat ccctggcctt gctcagtggg ttaagaatct ggtgttgcag   140700
tgagctgtgg tatggttcgc agatgtggct cagatctggc attgctatga ctgtgcggtg   140760 tagacccta gcctgggaac ctccatatgc tgcgggtgcg gccctaaaaa gaaaaaaaa   140820 attgtttatg gccacaccca cggcatatgt aagttcctgg gccagggggt ctaatccaag   140880
ccccagctgt gacctaggcc acagatgtag caataccaga tccttttaac ccactgagcc   140940
aggaaatcga acctgtgcag ccagagacac cacctgctac accatagtgg gaactccgtg   141000
aaagaccttc taatatacta gaaagcacat gacaaattca caggaaaata taaacataga   141060
```

```
ttataataaa tatcctaata gatacaaata aaatgctata acagttgaaa gattattttc    141120
agtttaggga aatgagaaag agttcctagg tttcctgtta ctcaacatgc tcaggagttt    141180
gtaaaggaag atggcatgct gagaatgtgg aggactactg atgggagaag agaagcaagg    141240 cttttgtttgg gaaccacagg ttattttatt ttattttgc ttcttagggt cacacccgag    141300
gcatagagaa gttcccaggc taagagtcaa gttggagctg tagcccccga cctacaccac    141360
agccaaagca acatggggcc caagctgtgt cttcgaccga caccacagct cacgacaatg    141420
ccggctcctt aacccactga gtgagggcag ggatcaaacc cgcaacctca tggttaccag    141480
tgggattccg ctgtaccaca aagggaactc caagggagtc acaggttatc ctatctgact    141540
gttacagctc tgggtatata ccggggaaac aagaaaataa gcttggaaag gcatttgatg    141600
cgctgaatgt ctatttggat attttcaggg ttcttctttg aaggttaaag tgagcgagga    141660
ctgcgcaaga tgtacctaac taaatgtata gtagattaaa ttaagaactg atagaaaatg    141720
tgaaaagtta caaagtcctt aaggtcttcc agataagagg cgacaggggg atatggaggt    141780
ttaatgattt aaaatgggaa cagtgtaatg caataattgc agagacctac ctctactgcc    141840
tctcttttga gttcaaacct tttttaaaaa atttttcaac acttcctagc tgtgtgacct    141900
tgggcaagtt ccttcatctc tctgagcctc aattttctca tttgcaaaat gagatgtcaa    141960
taatagtaat agtcacctat gatacttaag atattttaag aaattagcac ctggcacatt    142020
ataagcacta tattctttca ctttgttaaa aaagctttca agctagggta tgtctataat    142080
attaagatgt aaggaagaag tcaggaatga acaacggtgg ggcagtgtat gggaagaagc    142140
tcacatccag tcatttttact ttcattcaag aaaaagatcc acggcttccc aacagtgtac    142200
tttcttgaag cataaattttg aaaagaccaa gtacttctct aattcaaaga tattatctta    142260
aagttataat tttactagtg ctttgtaaca caccaattta ttacaaattt taacattata    142320
tggcctaagg ctcaatttca gaagattaaa tcttaaaaga agtgatgaaa taaatcttat    142380 attttttacaa aaatatatac actatttaat attttaagaa gctgttagaa attattaatc    142440
tgaattgaat ctatttacct ttattagcaa tttctcttta aatgaatgtg aaaattcttg    142500
ttcactctct gattctgaat ttgagagatc tttataattt ttttttggttt ttgctgctct    142560 tcgtggaagt ctgattctcc catctggaac tgtttcatcg acctttttgg tgatgttttt    142620
gtcgggtgtc tttaggagaa aaattcctga atatattaga tcaatatttt gagatacaag    142680
ctatctgcta taaaattggc accatgacaa aatatgcatg aatatttgta ggaataaaaa    142740
gattcctgat caatacttt aaaatgacta gattttatct ttccaaatac attctttatc    142800 acttttttaat ccttatcatt aaagctctga gatgtcttat atatattacc taactttagt    142860
aagacagaga gaaaggaaaa gatagcaaaa atacccataa ccacagaata aaatagactt    142920
aaaacaggcc agcttcaaaa aggcagaagt aagtgtgcaa agttttgaac aattatggaa    142980
aataaggaac tgataacaaa gataaaaatta tgagatgaca aatgatattt ttcatgcacag    143040 aaaaataatt taaaagggat gtttgaggag ttcctgtcgt ggtgcagtgg ttaacaaatc    143100
cgactaggaa ccatgaggtt gagggttcaa tccctggcct tgctcagtgg gttgaggatc    143160
cgtcgttgct gtgagctgtg gtgtaggttg cagacgtggc tcagatcccg agctgctgtg    143220
gccctggcgt aggccgtcgg cttacagctc caattcgacc cctagcctgg gaacctccat    143280
atgccacagg agcggcccta gaaaagacaa aaagataaaa aaaaaaaaa aaaaaaaaa    143340 aaaagggat gtttgaacac aaacttcctg gttttaccat tttagatctt ggttgttccc    143400
tttccaaaga tgatcctgta atttaagaaa ataaggttaa aattttcaaa tagataagtg    143460
```

```
acattaaaca attattaaac aatttctgca tataagttaa tatcacaaaa gcaacaagac   143520
tgcatggtta tttttgatat cttttcctct ctctctgtct tacaaaagtt aggaatatat   143580
atcagacctc ttagtcactt gctcttaaaa gttttacttc agagatatat atccctaaac   143640
aatacaatga actttataaa acagtattat gtcatattcc atgatttgct ttatttttca   143700
tccatcatct taagatttag ccatcttaat gagagtagct tcagtcccta ttccgttttt   143760
ttcatttcca gcacaactgc tactttctaa atattctctg aagcctaaga tttgggatta   143820
tccaagctaa ggaaggaaca gagctctcgt agaaggtcc ttcgatcctg gcaataagcc   143880
agctcgtact tactgactga ctcatcattc agccgtttaa acaaaacaat tcagggagtt   143940
ccattttaag agtaattact gactacagtc ttctaacttt actaattcct caagatttct   144000
gtgttataaa tgtctttact tgtacatctt cccattgtaa gcttgctgag agtatgtgaa   144060
tctaatcctg tttctccttg tctttcaaag tctacaccct gactagaccc agccacatct   144120
gtcagcattt tcccacaagt ctgagctacg ttccaacccc tccaatactg cacttcctga   144180
gttcgtatgt cacttgtact gtcactttta tatatgataa cgcttttgct tctcttcctc   144240
atgtatatga ttgaactctc atctgtttcc aagaatcagc ctcatttcaa attacaagcc   144300
caaattaatt tccatgtctc tattttact tcttttctt tttagggcca cacctgcagc   144360
ataaggaagt tcctaggctc gaggttgaat tagagcgaca gctgccagcc catgtcacag   144420
acacagcaac atgcgatctg agtcgcatct gcaatcctat gccacagcct gcagcagtgc   144480
tggatcttta acccactgag tgaggccggg gattgaacct gcatcctcat ggataccagt   144540
cgggttctta acccagtgag ctataacagg aactatttt acttttttta aagccatcat   144600
ttcttccccc aactccaaga ggccactaac aattatttt atcctgaaat aaaataagaa   144660
gtgattccct taaatataaa agttaagggt tatcgtatct tctttgaaaa taaaatacat   144720
aaaatctttg ttttaataac cattaaaact gatgttaagc tatgaaaacg gtcattatgt   144780
ctagcccaaa ctccatactt caaactctta tccaactact tcaagagatt caccagagaa   144840
agtagaatat ttaggctggg aaaacatttt gtggaggatt taggcaaagt atttctgtaa   144900
gaaaattgtt tacctttcaa taaatttgta ttgcatctat tagaattcct aaaagtatgt   144960
gtattggatg tggcagggag tagggtgttg tccaaggttt gattttgttt agggtgttag   145020
gttcatgagt acttaacaca tattcacaat tagccaaata accaaacagt aggctaggag   145080
ttgacaaatg accagagtgt gtcatgaacc aaagattatg atcaatcata ctttatgtcc   145140
ctgagatccc aatgaaaata aaatttaaat ataaccatat tgccaaaaat aataaaacaa   145200
aaaaataaaa accactgtag tgctttggtg tatttgcttt catactttt ttcctattca   145260 taaggatatg tagttataaa cactatctac acacaaaaat atattcaacc aacaaagcat   145320
ttcatatagc tgaaatggta aaaccatgag cagcatttct ctataaaagt gatttcttac   145380
ttgatttccc acttttatgt ttcttcacat ttttatttct gctgtagcct attaactgtg   145440
gtttcgattt tgattctctt agccagctaa tatcagtttt gctgtcatca catttgtatt   145500
ctgtgtcagt atcactaaag agagtttct tcttatgatt tgttacagtc tattaaaaaa   145560
aaaaaacaat ccttgtaaga gatgaagaca tctgtcttaa tatatgtcat gcaaagaata   145620
tgtcatagca ccccccccc caaaaaaaac cccaccaaaa taatgaaaaa actaacttgc   145680 catttttag cgtgctaatc tatctggcat taaggacctt tccaacagtc actcagaaat   145740
ccagatcaga gattgagatt tatattttgc tgccaatgtt gctgtaaatc aagctaaaac   145800
agctcacttc cacagagaca taacttaata gcactgaaga gagtaactac agttgttaca   145860
```

```
tattactaga tgattacaaa tagctcagac accataagaa aagacaattg gaacatggat  145920
atttcctaca attaaaaaaa tgacccaaat atttttgttt ccaattctgt gataatcttg  145980
ggcattgaaa aattatatac tgattttaat agacatattg ggatattaaa acttactcgt  146040
ttatctttgg ttttgagaga agtttcaagt tcatcatgat tccttaaacc taccctggaa  146100
caaaaatatg cattcatttt aatctcaatt acttgtgttc ttaaagtagc atacaatggg  146160
acacttgggt ttcctgccta aactctttac taactcccta taactgtg gccaagtcac  146220 ttgttctgac ttctatttat tataaaataa ggttagatca acaactatc aagttttttc  146280 agttttatca tctgagttat gcaactaata ttaaaagtgt acagaatctc tagattactt  146340
ttagaatggt gaaataagag aatcctaaag gtgtattcat gacattcagt aacattttta  146400
ttcactcttt tcatatgtta aaactctca aagtgggagg aattatttaa gaaaagtaac  146460
aactgataaa agtatatttt aaacaaaccc atctgattat aataaaaata cctacaatgt  146520
tattgtacta tccacgcagg cttctctagc tgtagcttga aattcctgga tctatattgt  146580 gaaaagcat taaaaatttt tcttagtgtt aaaaaaaatt aaagaaata agcatgaaaa  146640 atctcatcac attcaacaga agatgtgaca ataaaattaa gctttgaaaa agtttaataa  146700
tataaactat accaaaacca aaatgagtat tattttatat ttaatttaaa aaaattttta  146760
aggagttccc gtcgtggctc agtgcttaat gaatccgact aggagccatg aggttgcggg  146820
tttgatccct gcccttgctc agtgggttaa ggatccagcg ttgccatgag ctgtgatgta  146880
ggttgcagac gcagctcgga tcccgcgttg ctgtggctct ggtgtaggcc cgtagctaca  146940
gctccgattt gaccctagc ctgggaacct ccatatgccg caggagtggt cctagaaaag  147000
gcaaaaagac acacacacac acaaaaattt taagagtaat tattttaaat ctgttgcatc  147060
agtaaggaaa gtagttttct tgatgcctct attactcatt tttctctact ttggtatagt  147120
gggagaaaga aaagatttga atgaaaacca aatataccta cgttggtatc aaataaattt  147180
tgaggaattt agtaatataa atattttaaa gcatatctat aagaggatga aaataaaaag  147240
gcatactcta gtaactgcat ggtaaatata aaataactac ttatttctag cttaccccaa  147300
gttttataac aggctcatca gctccactca aattaaaatt gtaaacatca ttcctgtaaa  147360
gatgagaaga aatattaact ccattataca taaataaatt tatttttttc aaacatgagg  147420
aaaactttaa gctttataaa aagttactta caatgggcat tcagaagtaa cattaacaaa  147480
agtagtcttc aattgtctgt aacttttttt ctgaaccttt tcctaaatac aaaagaaatt  147540
tacataaaac cattcaaact tgtacagtat gatatgtggt aaacagatac cgtgcaatta  147600
aatttcatat attatctact tgtgttttca tcaatataaa ttttatactt gtaaagtttt  147660
ccttaaacat ccacactttt aaaaatattg aagactggag ttgccatcgt ggctcagtgg  147720
ttaacaaatc cgactaggaa ccatgaggtt gcagggtcca tccctggcct cgctcagtgg  147780
cttaaggatc cagcgttgct gtgagctgtg gtgtaggtca cagacttggc tcagatgcca  147840
cgttgctgtg gctgtggtgt aggccatcgg ctacagctcc aattagaccc ctagcctggg  147900
aacctccata tgccgcaggt gtggcctag aagacaaaaa aagacaaaaa aagacaaaaa  147960
aaaaaaaaaa attgaagact taagtatcta ctgagaacaa atattgtaa atcaaataca  148020 aaataaaaat aagatgctta tatctttaat atttattgac aatatatagg taaatgaccc  148080
cactggtata ctacaggcta aatcttagtg atgctaggat cacaaaacaa gcatgcttct  148140 actttttac caccccacct ccccgactct catttgtttt aaaactctta aatagaaaaa  148200
ctttgggaga ggctactatt tatgtaaaat atcatgcgaa aaagtcaaaa ttctgtcaat  148260
```

```
caaatagtat gattagggga aaatatgtgt aaggttattc ctatagcata ttgttcaaag    148320
tatattcaat ctgatcaaaa agtaggcaga gaataagcta aataaaattt taacatatta    148380
aatgaataat tgttattaaa ataatttaac tacaattaca aaatgactac tgatcagaaa    148440
taattagaag tctaatttaa tatctggaga ttggaaatac taaactaaaa tattcatttt    148500
aggtgatatt catctccagt tttattactt cttttggcta ctttataata aaattctttg    148560
cattattcca aaaataatgc tattccaaaa agtttatccc ttaatatatt actcctctga    148620
tcatttatct cgcttattct ttccattatg attttttacca gtgtttagat acctttgctc    148680
aattcatctt ctgcatgcca gtgtgtgcta ggtatttaca aaagatacaa aaatgagcaa    148740
agatattaaa gaaggtgcag aaatgagaaa aggtcttata taggatacaa agatgattct    148800
aaacagctgc attctagaag aggacagaag agagaaaaaa ggaactccaa ctgtgaataa    148860
aatatcaaaa ataaggtata aagacattgt tgcatagatt cagagttctt gtccatttgg    148920
attttgagtc aggacacctt agaaagtttt tataaagaag gcagactctt aacaaagact    148980
tgcaaggagg aatgaagttc tgacaacgag aaaagagggt gaaagaacct ggtaactcac    149040
tcttaatttc ttttcaaagg ggggaagaaa aaaataaact taggaaagac acatcaggga    149100
atctcaagtt atttcgtttc agctaaaaaa gacatgtcta aggaagtagt tttaggaaat    149160
aagacatact tttaggaggt ctagggagcc agcctacgtt cccacttaat tcaataagga    149220
acagagacca aaggaggatt tgaacaaga gagtgacagg attgaagcta tgtgctttac    149280
aaagtccaaa agctagtact gaaagtaatg aatggattgg cacaaagaaa cactagcagt    149340
gaaaagaatt acataaaggt gaacctaata tgtcttccca cagaaaagaa actcatggac    149400
atgaacagac ttgtggttgc caaggggaa ggggagggag tgggacggac tgggaatttg    149460
gggttaatag atgcaaacta ttgcctttgg aatgggtaaa caatgacatc ctgctgtata    149520
gcactgggaa ctatatctag tcacttaaga tggagcatga taatgtgaga aaaaaagaa    149580 tgtatatata tatatgtgtg actgggtcac cttgctgaac agtagaaaat tgacataaca    149640
ctgtaaacca gctataatgg aaaaaataa aaatcattaa aaggaaaaaa aaggtaaatt    149700
catatataaa ttttaaactt ctgtacaata gagcaaaagc ataacaaca aaagaaaaga    149760 attacataaa ggcaattgta aaaatccagg gatgagaaat tagaactcaa aaaaacagga    149820
gttggcacaa gcagaagagg gaagatgcga gaggaattc ctgagggcaa acctcaaaac    149880
ttgaaattaa ttggagataa ctatgaagaa taaagcaaag ataactgata tttaaagcct    149940
gtatgaatag taaatgtttt taacaaaaac aaacaaagaa aaaaacccc aaaaaaacaa    150000 aggacttaag gagtttcctc atggttcagt gggtaaagga tctggcacat tgtcactgtt    150060
gtggctctgg ttacagctgt ggcacaggtt cagtccctga ccctgtaact tccacatgcc    150120
atgggtgtag ccccaatttt ctttttttta ataggggact taataatttt actgtcagga    150180
gagatggagt aagctagaaa aaaaaaatgg tactgaatca tgtaccgaaa agtaaaaata    150240
acacacatac acataaaaga ggcattttct ttgaaaagta gaacagaaag ttaggggcta    150300
ttttgagtac ttgccactaa aagttgtcag ttatttaaca caattatcaa tatgttgaaa    150360
acattaaata tacttccatt ctactattat tctattttag tgtttacagt caaatatcat    150420
aaagtttgac tacacatctg gtgtagttaa atagatgaaa cctacctttc tgagctgtag    150480
atcagacttg tttgaaaaac cactataaaa aaggttttgt caaaattaaa aaagtgaata    150540
tcagtagaat gttttttcata aaagccagtg tatataaggt aaaacatatt tgggtcacta    150600
agtccacatt caatatgcta caaataactg aaatgacggt actagtccag tattttttgca    150660
```

```
ccttcatcca tagccaacag ttcaataata gttaagtcta agttgaatca tttatgcagc   150720
aggaggtgcc aagcaatata agatgaatgg ttctgccata agagtatttt ttttcatgcc   150780
atttaaggcc agaattaatt taaacaccaa ctggcagcct acaaggagat acttctcaat   150840
aaaagaaaat cttcagaaag actgcaaaca aggaatctac atttactatt atgaaatagc   150900
taaggagttc ccgttgtggt gcaggggaaa tgaatctgac taggaaccat gaggttgcgg   150960
gtttgattaa ggatctggca ttgccgtgag ctgtggtgta ggtcgcagac atggctcaga   151020
tcctgcgtgg ctgtggcata ggccagcagc tgtagctccg attagacccc tagcctggga   151080
acctccctat gccgagggtt cggccctaaa aagcaaaaac aaaacaaaac aaaacaaaac   151140
aaaaaaacaa aaaaaaccac cctcacctca gctcatttac atttcatact ttattaaata   151200
atatatttaa aatatttagt tttactcatc actaggctca ataaataaaa ttttgaaaat   151260
atctatatac taaagattta tttctgaaat gttatgctgc atcaatatgg tcttttgat    151320 actttataaa atgtactcag atattagaat aatttcaaat tgagttccct ttatgtataa   151380
tttgaacaga tactatttat aaaagtaacc aagcaactgt attctctaat ggaaagttaa   151440
gttatttaaa cacatgttta aaaactaact gtaaaactat gtaaataat  ttatttgtat   151500 ctgtcaaaac atattaattt ctaaaattta agaacatacc tgtcaattaa agactccttt   151560
aattttcttg tagactttgt gccatccttt ggtttgtatc tcttattaat ctgacttatc   151620
aatgattcgg ctgcatcatt aaatcctttc ccttttgact tttctctctg aaacagttta   151680
caagttacat aaaaactgtt aaccttgaaa ggtaaaaaaa ggctgaaaag aaaatttgag   151740
aaaaatctag ttctgtaaaa taagtgcaaa gagaaataaa gggggtcaga aattttttta   151800
aagaaattat ttaataaaca cttgggcttt gttttgcagt aaaacaactt ataagttttt   151860
ttaacataca gaactgtgca gggtgctctg ttttttttaa agtttctatc catgggaaaa   151920
aaattattaa aaaactgaag gaaccaaaag ttggctcttt gaaatgctca ataaaattga   151980
taagcctcta gccaagttaa ttaagaaaaa aaagaaatta ctagtatcag aaatgaaaga   152040
gaggttagca ttattgatca catgaataat aaatcacaaa gaattttaaa acacattatga  152100 acaactctat gctcattaat ttgataacct agattaaaag gaccaattcc ttgaaggaca   152160
agttttacta aaactgacac agggagaaat aaatcatcta attaggatta taaatattaa   152220
ataaacttaa tgaataaaat tttttttggt cttttagggc tgcatctgca gtatatgaa    152280 gttcccaggc taggggctga attggagctg tagctgccag cctacaccac agccacagca   152340
atgccagatc tgagccacgt ttgcaaccta cactgcagct caaggatact acaccacaac   152400
tcacagatcc ttaacccact tagcaaggcc agggatcaaa cccatgtcct tgtggatact   152460
ggtcgggttt gttaccgctg agccacaaca ggaacaccaa ttgaataata cctgtcaaaa   152520
cagaaagcac caggcccaaa gaggctgagt tttagcaaac atttacagac gaattataca   152580
atttttcaca accctttcaga agatagaagc aaagggaata cttcctaatt cattctatga   152640
agtcaatgta tcctaataac aaaatcaaag acattacaag aaaggaggac tgtagaccac   152700
tatctctcat aaatataaat gcaaaaccct caacaaaaat attaacaaat cggaggtacc   152760
atcatggcac agtggttaac gaatccgact aggaaccatg aggttgcagg tttgatccct   152820
ggccttgctc agtgggttaa ggatctgcca ttgccgtgag ctgtggtgtg ggtcgaagac   152880
tctgctccaa tcccatgttg ctgtggctct ggcataggcc ggtggctaca gctccaattc   152940
gactcctagc ctgggaacct ccatatgccg cgggagaggc cctagaaaag acaaaaagac   153000
aaaaaaaaaa aaaaaaatta acaaatcaaa tccaataatg tataaaacaa gaattatgta   153060
```

```
tcatgactat gagaaattaa ttccaggcat gcaatgttga ttcaacattt gaaaatcaac  153120
taatataatc caggctaaga aagaaaaatt acaagatcat atcaatatat gcacaaaagc  153180
atttcacaga atccaatacc catttgtgat aacaattcgc agaaaactag aaatagagag  153240
gaatgtcctc aatctgataa ataacatctg caacaaaatc atagctaatg gagaggaacc  153300
agatactttc ccaggaatat cagaaacaag gaagggatgc ctgctttcac tacttctaat  153360
caacatcatt ctagaagtct tactaattcc gtaagacatg aaaagtaaat acactgtata  153420
catattggga aggaaggaat aaaactattt cttcacagat gagatcactg tctatgtaga  153480
aaatctcgaa gaatcaaaaa aaatatccct ggaactaaaa tacaattaca gcacaactga  153540
ggggtaaaga gtttatatac agaagtcaat cgccttctta taaatcagta atgaacaact  153600
cgaatctgaa attacattcc acttacatta gcgccctccc taaaatgaaa tatttagcta  153660
taaacctaac aaaacatgta gaacatctgt ttgggaaaaa catgactgat gaaaaatctt  153720
aaaaaatgga gagaggatcc atgttcatgg ataaggaggc tcaatactgt caagatgtca  153780 ggtcttttcca cttgatctaa aagtcagtgt aatcccaaag tcccagcaag ttattctgtg  153840
gttaacgaca aaatgactct aaagttcaca tggagaagta agagaccctg agtgccaaa  153900 caatattaaa ggagaataaa gttggaggat tgaccctact ttaagactta ataaaaagat  153960
attaataatc aatatagtgt ggtattggtg aaggaataga caaatagaat ggaacaaaac  154020
agagggcccc aaataggtcc acataaatac ataagaacaa aggcaataca atcttgaaaa  154080
gttggtcttc tcaacaaatg gtgttggtga gctcccgctg tggcacaagg gatccctgg  154140 cctggaagct ccatatactg tggggcagcc aaaaatgatc aaaaaaaaa aaagctaaaa  154200 aaaccaaatg gtgtcacaac atcaccgtgc cctgcccaga tctttcaccc ttcacaacaa  154260
ttacctcaaa atggataata gacctacatg taaaatgcaa actataaaac taatataaaa  154320
tctaggtaaa cttgagtttg gcaatgcatt tttacataca acaccaaaag caccatcaat  154380
gaaagaaaaa aattgctaag aattcattca ttaggagttc ccgtcgtggc gcagtggtta  154440
acgaatccaa ctaggaacca tgaggttgcg ggttcggtcc ctgcccttgc tcagtgggtt  154500
gacgatccga agttgccgtg agctgtggtg taggttgcag acgcggctcg gatcccgcgt  154560
tgctgtggct ctggcgtagg ctggcggcta cagctccgat tcaaccccta gcctgggaac  154620
ctccatatgc ctcgggagcg gcccaagaaa tggcaaaaag acaaaaaaaa aaaaaaaaa  154680 aaaagaattc attcgttaaa attaaacatt tctggagttc ctattgtggc acagtggaaa  154740
tgaatccgac taggaaccat gaggttgtgg gttcgatccc tggcctcgct cagtaggtta  154800
aggacctggt gttgcatgag ctgtggtata ggttgcagac acggcttgga tctggcattg  154860
tgtggctgtg gcacaggctg gcagctacag ctctgattta gacccctagc ctgggaacct  154920
ccatatgctg cggggtggc cttaaagaaa agcccaaaaa aaaaaaaaa aaaaaaaaa  154980 agtaaacaat aatatactta atgccccaga gcggttcatt taaacatggt taaaatggag  155040
ttcctactgc ggcacaacag gatcggcagc atctctgaag tgctgggatg cacgtttgat  155100
cttggcacaa tggttaagg atccaacgtt gctgcagctg gggcaaagga acttcatatg  155160
ccacgaggtg accaaaaaag aaaaaaaag aaaaaaatt taaatttctg ctctgcaaaa  155220
gatactgttt agagaatgaa agaaaggat acagattggg agaaaacata tgcaaaatac  155280
atatctgata aagaactcat atccaaaaca cacaaagaat ggttgaaact caacaattag  155340
aaaacaaccc aattaaaaat tgggcaaaag atctgaacag acaattcacc aaagaagata  155400
tacatatggt aaataaaaac atgaaaagat gctcaacacc atctgtcatt tgggaattgc  155460
```

```
aaattaaaac agcaatgaga taccaccaag catccctaag aatggctaaa atccaaaaca   155520
ccgacaacac caaatactgg aaaggatagc cgatcaatag gaactctccc attcattgct   155580
actgaaatgg aaaaatggtg cagacacttt ttccactttt ggaagacagg cagtttcttt   155640
tctttttttt tttgccttttt ctaggcccgc tcccgcagca tatggaggtt cccagaattg   155700
gagctgtagc cgctggccta tgccagagcc acagcaactc gggatctgag cagagtcttc   155760
gacccacacc acagctcatg gcaacgccgg atccttaacc cactgagcaa ggccagggac   155820
cgaacccgca acctcatggt tcctagcagg attcgttaac cactgcacca agatgggaac   155880
tcccgaagac aggcagtttc ttacaaaact aaaaatactc ttatcatatg accctgctcc   155940 ttggtattt cccaaatgag ttgaaagttt atgtccacac aaaacctgca cacgaatgtt   156000
tttggaggca ttattcataa ctgtcaaaac agggaaacac caagatgtcc ttactgatgg   156060
atgaacaaat attggtacat ccatacaatg aactcagcgt tttaaaaaaa aaaaaaaaaa   156120
aaaaaaaagg tagttcccgt tgaggctcag cagattatga atctgactaa tatctatgaa   156180
gatgtgggtt cgatccctgg ccttgctcag tggcttaagg atctagtgtt gccatgagct   156240
ctggtgtaag tcacagacat ggcttggatt tggtgttgct gtggctgtgg cacaggccag   156300
cagctgcagc tccaacttga cccctagcct gggaactttc atatgccaca ggtgtgcccc   156360 taaaagaaa aaaaaaaag ctattgagcc acgaaaacac atggaggaac agtcaatgca   156420
cactgctaag ggaaaaagc caatctgaaa agactgcatg tatgattcca actttatggc   156480
attctagaaa aggcaaaacc atggagatag taaaagatca gtgacagcca ggagtttggc   156540
agaggaggag gaagtaaagg agggatggag cacaggggaa tctgggggtg gtgaaactaa   156600
tatgcatgat attgtaaggg tggataccctg ttatacatct gtcaaaacac agcagaaaga   156660
gggatctaaa atgtaactat ggaatagagt taatatgtca caggggctca tcattttatt   156720
cggaacaaat gcagcactaa tgtaagatgt taatgacagg ggaaactggg atgatggaaa   156780
ggggtatatg ggaactctct gggtagctgt agacctcaaa tgcttttgaa aaattctatt   156840
acttttttta atgaaagac tgcaaagtag gaattattat ctgcatagct ttaaataatt   156900
tggttaaaag aaaacttgat gacactctta aagatatgag ttctcttgat tttagctttt   156960
ctttttttct gggaatcagg catatgaggt ttttaaaatt aggacaaaaa caacaaataa   157020
aacctgacat aaaattact ttttaaccat ttttaagttc atatatatat ttttttttg    157080 gtctttttt tttttctagg gccacttccc gcagcatgtg gaggttccca ggccaggggt   157140
ctgatcagaa ctgcagccgc tggcctatgc cagagccaca gcaactcggg atccgagcca   157200
cgtctgcgac ctacaccaca gctcatggca atgccggatc ctttatccac tgagcaaggc   157260
cagggaccga acccacaacc tcatggttcc tagttggatt cgttaaccac tgcgccacga   157320
cgacaggaac ttccaagatc atatgttttt atttatgata gataataagt tattacttct   157380
tatcccttct tttttttttt tttgtcttt gttgctatt cttgggctgc tcccgcggca   157440
tatggaggtt cccaggctag gggtcgaatc agagctgcag ccaccagcct acgccagagc   157500
cacagcaacg cgggatccga gccgcatctg caacctacac cacagctcac ggcaacgccg   157560
gatcattaac ccactgagca agggcaggga ccgaacccgc aacctcatgg ttcctagttg   157620
gattcgttaa ccactgcgcc acgacgcacag gaactcccaa gatcatatgt ttttatttat   157680
gatagataat aagttattac ttcttatccc ttcttgagat taccagaaca aaagattac    157740 cagaagaaag ggagggtata cttgccttga taaaaacaaa cctcccttaa aacagtgtat   157800
cattaagaac ttagacataa ctggagtcaa tgtggaaaat ctgtacccttt gaaacacaaa   157860
```

```
ggtcctattt ctcttgattt atccagtgat cagaaagaca ggaccaggat ttcctgttgt  157920
ggctcagcag taatgacccc aaccagtatc catgaggatg caggtttgat ccttgacccc  157980
tctcagtgag ttaaggatct ggtattgctg tgagcttcaa tgtaggtcac ggacgcggct  158040
tggatctggt gtggctgtgg ctcaggccag cagctgcagc tctgatttga cccttagcct  158100
gggaacttcc atatgccaca aatgtggccc taaaaaaaag accaaaaaaa aaaaaaaaaa  158160
aaaaaaaaaa aaaaagaca ggaagacaag accagacaga tgacagatga ctagcttaga  158220
ggagagtgat ccatgaatga gagtggcagg aaatcctgca taataaaaaa gggagtcaca  158280
ctattaaaag agtgaaaaga acttccgaat acaggaagtt gatttaaaaa aaatcagagc  158340
acagcttaga aaagatgatt aagagtctgt gctctcatga agaaatgatg gctagatgag  158400
aaaaattctg tagaatgatt ctaaattcca agaaaacag tttaaaatta aaatcgaagg  158460
gcagatcagc attcagacaa aaacaatgtt acttccactg gatctgaagg aactaaatag  158520
cagtttaagc ctagaataaa gaatagtaca ctaaaaacca agaaaaagt gacccaacag  158580 gatctgctta aaaagaaag ttgcaaaatt aggaagaaaa ggtaaattgc aggttaaaaa  158640
caaagagtaa gtagcctggt caagataaac gaaataatgt ctacatacaa gtgaaaaatt  158700
acctattaaa tattttactt gcacactaag atgctccaat atatgaacat tttcactgcc  158760
tcctaggtgt taagaagacg acaaatgaaa atgaaggcct gtgaaacctg gatcttctag  158820
ggcatagaga aaagggactg cattattgcc agtggatatg tattttataa gattttcatt  158880 tttccatta tatagtgttc tgtcaattc tactctacag gaaaatgacc cagtcataca  158940
tatataatac attcttttc tctcattatt ctccatcaca tttcgtcaca agtgaccaga  159000
catagttgcc cttgttatgc agcaggatcc cattgcctat ccattccaaa ggcaagagtt  159060
tgcatctatt aagcccaaat tcccagtccc tcctagtccc tccccctccc tatgggcaac  159120
catagtctgt tctccaagtc catgattttc ttttctgtgg aaaggttaat ttgtgccata  159180
cattagattc cagatacaaa tgaagtcata cggtgtttgt cttttctga cttacttcac  159240 tcagtatgaa agtatctagt tccatccata ttgctgcaaa tggcattatt ttgttctttt  159300
tatggctgag tagtcgtcca ttgtgtatat atacatcttc ttagtctgtc gatggacatt  159360
taagttgttt ccatgtcttg gctgttgtga atagcgctgc aatgaacata ggggtatatg  159420
tatcttgttc aagggaagtt ttgtccagac atatgcccaa gagtgggatt gctgggtcat  159480
gtggtagttc tatatttagc tttccgaggt acctccatac tgttctccat agtggttgta  159540
ccaatttaca ttcccaccaa cgtgcaggag ggttctctt tctccacgcc ctctccagca  159600
tgtgttattt gttgacttgt taatgatggc cattctgact aatgtgaggt ggtatctcga  159660
tgtagttttg atttgcattt ctcaaataat cagtgatgtt gagcattttt tcacgtgcct  159720
gttggccatc tgtatatcct cttcagagaa atgtctgttc aggtctttg cccattttc  159780 aattggattg ttggcttttt tgctgttgag tttataaact gtttgtatat tttagagatt  159840
aagcccttgt cagttgcatc ctttgaaact atattttctc ccattctgta agttgtcttg  159900 tttttttgt tttttatgg tttccttgc tgtgcaaaag cttgtcagtt tgattaggcc  159960
ccattgcttt tgttttcgct tttatttctg ttgctttggg agactgacct gagaaaacat  160020
ttgttaaggt tgatatcaga ggatgttttg cttatgttct cttctgggag tttgatggtg  160080
tctcgtctta catttaagtc tttaagccat tttgagtttg gttttttttt gtgtgtgcat  160140
ggtgttaggg tgtgttccag tttcactgac ttacatgtga ctgtccagtt ctcccagcac  160200
catttgctga aaagactgtc ttttagccat tttatattct tgcctccttt gtcgaagatt  160260
```

```
aattgaccat aggtgtctgg gtttatttct gggttctctg ttctgttcca ttggtctgta   160320
tgtctgtttt ggtaccagta ccacactgtc ttgatgactg tggctttgta atattgccta   160380
aagtctggga gagtgatgcc tcctgcttgg ttttttgttct tgagattgct gtggcaattc  160440
tggatctttt gtggttccat ataaattttc ggactgtttg ttctagttct gtgaaaaatg   160500
tcatgggtaa tttgatatggg attgcactga atctgtagat tgccttgggt agtatggcca  160560
tttttacaat attaatttttt ccaactcagg agcatggaat atctttccat ttctttgcat  160620
cctcttttat agttctcagc atgtaagtct ttcaccttcc tgtcaggttt attcctaggt   160680
atttaatttt gggggggtgta attttaaaag gcattatatt tttgttttcc ttctctgta   160740 tttcattgtt agtatacaga aatgtgactg atttctgaat gttaatctta tatcctgcta   160800
cttggctgaa tttgttgatc agtttgagta gtttttgtgt ggcgtcctta gggtttccta   160860
tgtatagtat catgtcatct gcacacagtg acactttttac ctcttctctt ccaatttgga  160920
taccttttgt ttcttttgtt tgttgattgc tgtggctagg actttcaata catgttgaat   160980
aaaagtggtg aggtgggcat ccttgtctag ttccagattt tcgtgggtag gctttcagct   161040
tttctccatt gagtagtata tttgctctgg gtttgtcata aacagcttct gttatattaa   161100
ggtatgtgcc ctctataccc actttggtaa aagttttgat catgaatgga tgttgggctt   161160
ggtcggatgc ttttttctgca tctactgaga tgatcatgtg gttttttgact ttccttttgt  161220 taatgtggtg tatgacattg attgatttgc gtacgttgaa ccgtccttgt gaacctgggc   161280
tgaatcccac ttggtcgtgg tgtgtgatct ttcttctatg ttgttggatt cagttggcta   161340
aaattttgtt gagaattttt gagtctatat tcatcagaga tattggcata tcatcttctt   161400
tttggggagt atctttgtct ggttttttggta ttagggtgat ggtggcttca gagagtcctt  161460
gggagtgctc ctcctccttc aacctttcag aaaaattcaa gaaagatggg ttataagttc   161520
tttgtatatt tggcagaatt cgcctgtgaa gccatctggt cctggacttt tgtttatagg   161580
gaatgttttt attacatact ctgtttcagt tctaacgatc agtctattca attgatttct   161640
tcttgattca gttttggcgg gctgtatgcc tctacaaagt tgtccatttc ttccaggttg   161700
tcaaattggt tggcatataa ttgttcatcg tattctctta tggtgttttg tatctctgca   161760
gtatctgttg agttttctgc cttttgattt cttgttttct ttgatttctt tctctctttg   161820
gtgagtctgg ccagagcttt gtcaattgtt tacccttttca aagaaccagc tcttggtttt   161880 atcgatttttt tcgattgttt cttgaatctc tattttgtga tttccttcct tctgctgatt   161940
tgggttttgt ttgttctttt tctaattctt tttaggtggt aagttaagtt gttgatttga   162000 gattttttctt cttttctgag gaaggcctgt attgcaatga acttccctct aagcaccact   162060
tttgtggcat cccatagatt ttgaatggtt ctgttttctt tatcatctct ctggaggtat   162120 ttttttaattt cccttttttat ttcctctttg acccactggt tttttagtag catgttattt   162180
agttttcatg tagtcagttt tttctcatat cttgtcctgc ggttgatttc tagcttcatg   162240
ccattgtggt cagagaagat acctgaaatg atctctagac tcttaagttt gttggttagt   162300
tttgtggccc agtatgtggt caatctttga gtatgttcca tgtgcacttg aaaagatgta   162360
cattatgatt attttggatg taatgacctg aatatgtcta ttgtgccact taggatcttt   162420
gttgctttat tgattttctc tgcagaggat ctgtccattg acgtgagtgg ggtattaaag   162480
tctcctactc ttaattatat tcccatcaat ttctcctttt atatctgtta gtatttgttg   162540
tatgtacctg ggtgctccta cgttaggggc atatatattg acaatcctaa taccctattc   162600
ttgaatggat cctttatca ttaaatgctg tccttctttg tctttatggc ctttgtttta   162660
```

```
aagtctattt tgtctgatat gagttttgca acttctgctt tcctgtcttt cccattggca  162720
tgaaatatct tttcccatct cctcactttc aatttatatt gtgtcctgtg ccctaaggtg  162780
agtctcttgt agacagcata ttgtaggccc ttgcttttt atccactctg ccacactatg  162840
tcttttgatg aagcattcag tccattgaca tttaaggtaa ttattgataa atgcgtattt  162900
actgccattc gaaaccttgt tttccagttg attctatgtt tctcttttgt tcctttcttt  162960
ttttggttgg atgatttcct tggaaatgta ctctgattag aaaaatctta atctgcatct  163020
tgataacaat gaccaaagaa accacttaca gtaactgcct caaaaagtaa acttttcaaa  163080
gtatcgggca gacttgctaa aactgtcctg gagatgttct acacatgatt cacctgaaga  163140
agaaagtgaa gacttcaatg gggacaaaca atagttacaa cagaagataa gtctccttca  163200
ccccactttc atcttttctt gaaaagcttt gtcaacttta aggcaataat tcaagaaatg  163260
tttcagaggc tactatgtgc aaagctgtgc taggccatga aggaaaacaa atgttgaata  163320
aaagagtctt tacaccctaa taggttaaaa tggggaaaaa cacaaaataa ccatttatta  163380
acaagaaagg taagcacata agacaggcac agatagttct atatgcatgt tcaaaagaac  163440
ctgagggaca ttagtgggag agacccaacc ctaggagaca aggaactata aggttcactc  163500
ttgctatacc tatttacata cctgctatgc accagcaggc cagggggttc tgtcagggct  163560
gggactggaa agaggtcaga aaggggttca ggaggcactc actctcagag ttgaagctga  163620 attaagaag agggtattgc taatagttac cagtggtgag agggaaaagg agagggcaa  163680 gataagagta cagtattaag agatatagga gtttctgttg tgttcagtgg aaataaatct  163740
aactagtaac catgaggatg cagattcaat ccctggcctt gctcagtgga ttaaggatct  163800
ggcgttgctg tgagctgtgg tgtaggttac aggtacaggt tgggtctggc attgctgtgg  163860
ctgtggtgta ggctggcagc tgcagctctg attcaacgct tagagtggga acctccacat  163920
gccatcgatg tggccctaaa aaagaccaaa ccaaaaaaaa aaaaaaaag agagagagag  163980 agatacaaac cgctatgtat aaaacagata agcaacaaac ataagttgta cagcacagag  164040
aaatacagcc attattttgt aataaacttta agtggaatat aatctataaa aatcactgca  164100
ttacacacct gaaactaatg caatttgtaa atcaactata cttcaattaa aaaaaaaact  164160
cagggcatta caaatactga attcacagca attaatcaag cttcactttt tgttattaag  164220
taggatatta tgagtatgaa gaaataaaac acattgaaag ctcaccattt cttttgtttt  164280
caaatcccag gaattaagtt cagacgtcaa tcttttccct gattttctat gacttttgt  164340 attttttcta ggagaagggc ttttatcaca aatagcagta ttcacatctt ttgacaacgt  164400
gtacttcttc ctatagatca cagattcttc aactgtctta tttaggagta ctgatttaaa  164460
agtagtttca gattcaatac gccaatcatt ctgcttggta ttttcagtat ttttctcctc  164520
tgaatgttta gaatgatcta gttgttgttg tttgtttctt ttgcaagctt ctgcttctgc  164580
tttatctatt ttgttatgct gcattagttc tttcccatac tgcaccttac tcgtttcctc  164640
agaattatca tcagacattg aagaggatga ttttttttta gtaaggtttt tgttgataat  164700
aatatctagt gggaaaatga gaattaatc cttattaaat ttataaactg atcatatta  164760 aaatttgtta aaaccaaat atttgttcag acatttcaga aacgagtatt tccctgaacc  164820
cttgttttat atacagagaa aactatgttt caccttgatt aaatgtgtct tctgatgaag  164880
aacttgctct taggttatta cacagcttaa tatttgttac aggtgtccaa catgcccatt  164940
tggagtgcat tttatttcca cagatattgt ctaaaatacc aggtaacctg gaaaataaat  165000
tcatttgctt atttcaaaac atcactagcc tatgactcta agaccttgat tttattagtc  165060
```

```
aatgtttatt gacagaaatt tgttaagtat gaagatattt tcttaagtca tgatgaaagc   165120
tgaaatttcc tatataattg ttcagattga agaatattac aaaaaagttc cattattgct   165180
acaattttgt atctacttaa ggcatgtgga agttccaggc tagggdtcaa attggagctg   165240
cagctgccag cctatgccac agccatagca atgccagatc caaggtgtgc ctgcaactta   165300
caccacagtt caccacaaca caggatcatt aacccactga gcaaggccag gaaccaaacc   165360
cacatcctca tggatactag ctggattctt aacctgctgg gccacaacgg gaactccagt   165420
atctacctaa ttatacctca catatcttac atgtgtattt tttatggcca tacccatggc   165480
atgtggaagt tcccaggcca ggggtagaat ccaaactgta gctgcagcaa taccagatcc   165540 tttaccccte tgagttgggc tgaggtttga atctacacta ctgcggccac ctcagcccct   165600
gcagttggat tcttaaccca ctgcactaca gcaggaacta cttacaagtg tatttaaact   165660
catattcata ttttattatt taaaaaatct tattcatttt aagtttctca atgtgaatac   165720
agttatgttg gttgatatgg aaaaaacata taggctactt taccattgtg ctatcataat   165780
aatacttgaa aattattaat tctaaaacca atactacatt ctaagtctat taagacctct   165840
tcctttaaat tttgatttga tgggtttct catacttaca caggtttatc tatttttccc   165900
actgcctgtg aatcaggaac tatctcctgg agttcatcta aataaaaaaa aaattacagt   165960
attttcattt tttcatgcag ttggcagggt gaaatggaag ccagtataga acttgatcaa   166020
tgttcacata ctggaatgga gagattgatc tcatcttccc catccctgac ccaaacttt   166080 tgggaacaaa ggctactatt atatttcctt gtaactacta agttttttgc ataaagctaa   166140
atatattcat tataaatctt ttttaaaat aaatgaaagc tagtgggatt aaaggcaagt   166200
ataaagacaa gtatatgaat atattttaca agaatgacta aaattaaacc aaaaagtact   166260
tactaaaatt ttggtttggg tattcaatgt ccttattttc tgccttttct ataactttag   166320
ttttgatatg ctataaatac aggagaaatt tcaatataag ttttaattaa ggaattcat   166380 aaaagcaact tttaaaagtc agagtattaa agtttaaaac ttttaaaatt tgccttatta   166440
aaagttagat agcatttcta tttatttcat aagtattatg cccattctag aatactgcat   166500
atcctaaaac acaagaaagt aacttttcatt gcagatgagg caaagatcc tacaaattgt   166560 ctgttctcag ccacagctag aggagtaatt cacttttcat ctcaagaatt tctagaacat   166620
ccatggcaca tctcctattg gtactgctct cacagcctgc atacattctg cctcttcact   166680
aacatacact ggaattggaa attatcaagt gtcaaatgat ttgataaaag ttttggccat   166740
tgcacaggtt aacttcttga ctacagcaag cttccctctt tccatatcca cagatacaca   166800
ctagcccaga tcaaacgaaa atttgccgtc actactggga aaacataccc tctagctaaa   166860
ataccttgct tcatcctgca tgtcttccct gcttactcca gccagtggtc ctttacactg   166920
ggaggggagc agtaggaaaa tgcacaggtg taattttgct tgtcacagtg accgaagggt   166980
tctcctgacg atgagtaagc acaggcctag gacactcatc ctttcatatt cagaaccata   167040
tgctacacaa ctgaagaaca gtgccccta ttaagaaaca ctctgaacca ctactttttt   167100
tccctagtat cttcaactct tgaccccttt aatgttctg ccacatatcc attaaatttt   167160
tttaaatcta ccatctattc ttctttacta taacaccaag gctgctcaac tttttggaag   167220
aaattacata tgtttcttaa ctaacgccat aataaaattc atggtcttaa ctctgaactg   167280
ggccctaaca ttgcctaatg cttgtactta ttctcagcct tttccattat ctcttatcag   167340
ttactccaaa tcttttgtgtg tcactgagcc tctacttcaa ggatccgtat ccaagagaag   167400
ttcgccatcc tcacagttca gagaaagcaa aagctattag gtgttcctca tctacaaact   167460
```

```
tctctgtatt ttggattacc gatttctcca tgatacatta tccattccct gccctgtgcc    167520
cgcttcaact acctagaatg aatgaatgcc cttcttgatg tccatctgac taagggccta    167580
tactgactct ttaaaaatca attcactctc catcttctaa aagagcatct ccttatcttc    167640
accctcccca ttctggggtt aggcacctgt ccctgtccta gatttctatt gcatcctata    167700
atctgagaac acttatacaa tattatatta acttattagt ttgtctaatt ctcatggtag    167760
actttgagat acttaaagac agattccatt agtataaaaa aaccctaatt tttataataa    167820
actaaagaat gatggcaaga ccatttctct taccaaacac ataaatcagt tacattaagt    167880
gaatatttct aaattttatt gttagcacag taaatgagtg ataagacctt actttcaagt    167940
gcaataaatg atatttaaat tttttaaaaa cacaatactt taaaaagtg agacactcac    168000 tgcttgcaaa agaagttagt tcaatatgta tttctacaat aacttgataa aattttattt    168060
aaaaatgctt tcaaagtaaa gttactttgt ctgtattatc ttctctattt ctttcttcac    168120
atggtctaga tttaagtgat acagcattat ccactccatt ttccgatgtt ttagaaaaac    168180 caggttttc catagaactt gtcatttgca gtggtggttt aattcttcct ctttgtggtg    168240
ttgctaaaaa agaggacaaa agactgctgt ttttgtagga ttttaaaaaa ctgtatgttg    168300
ttattactgt ggtactttt agctgatgaa gggtaaaaaa aggaggttct aggatgggtc    168360
tgaggtttct agctcaaatg agttaagtgg acatggatgt tatttaccaa ggtaagaaat    168420
ggagaaaaac tgccagggag agttgaaaga tgaatttatt ttggacctgc caggtttgag    168480
gagttcgtca acattagat aatttccctg taggcaacta gattttggga gcagaaggtc    168540
attattaaat tgtcataaag attaaataag atgtgtttat agcagctaat agtatcaaat    168600
tactttaaat tttttattta tcttactatg tacaggcacg gtctcaatat ttcacaatat    168660
ttgtattgaa tgaataactt ctatttaatt ctttaaacaa ttcgatgaag tagacacttt    168720
agttccattt catagaaagg ataaactggt tctaaactta gctagaggat aatctgtacc    168780
agggacacac ctggagtggg caaacaagcc taagaaggcc gactaattta acgttttgtc    168840
cactatgttg tgctgattcc cacttaaact ataataaatc actaatgctt gatattaata    168900
ttttgaataa tgtttatgtg tcaatatcca ttaaacctct cttagaagac atttgtggtt    168960 catatttat caattttag atcctcaatt tatcctctag gtaaattatg tccagaatat    169020
ttctgagttt taaaaatgcc tgcttaaat aacaatacta gttagaagtc ttttaagact    169080
ataaagctta catgtgttga ttaaaagtat tggactcctc acagtgtatc tctctgcacc    169140
aggaacaatc attgatgctt cagacatttt tcttttgcta ggagtaatta tcttaaacca    169200
tgaggaaaag ccacagtaaa catatatttt cttttgaaat taaacatcct actactttat    169260
tcctaacatt ttacattaac tacacataaa agatatataa atagcatgat atccagaaat    169320
ctgtgtttta ggctgactag aagataaatc tgtgttttat cctaatgttt ggttctgaat    169380
agatagccaa aacagttaag gagtgttgtt tcaaagaata tttacagaat agccagatta    169440
gaaatacagt acctttaaag attagctgaa aatatttat tgattatcta gttaatagta    169500
aatggctcac aatttactat tctatttcat aaggatgatg tctgcaacac ctatttacat    169560
aaacatttga gaaagctctt ataatgttaa acattcttca aaactttcac acattaaaaa    169620
gctgtattaa tattttgtga agactaaatc gcctttggag taaaaagccg ttataagaat    169680
tcagagactc aacggcacac aaactagtgt tcccaaaacg attcgcattt tctaacttta    169740
gcctagaatg actgataaga gcaacagaaa tagataagca gagccagaga ctgttggggc    169800
cagaagttcc agagggtgac acagaaagga gtacatgatg acgaactgta aagaggcaga    169860
```

```
agtgagctgt tttaaaaaa gcaactgccc ttgagaaaga gaaacaatac tgatggagtt    169920
ttgcacaggt atgtttatga ggcatggagg aagaggtggg aaaggataga agaaaagtga    169980
attctaagat taaccagaaa ataagctact gaaccagcag agtcttctta caggagttac    170040
agttcctagt ggtacataat gaatgtgatc caaaagttac ctattcatat aaatgcttca    170100
gttaatcctc atgaaaacac agtgggtatt taacaatagt gcttaacatc ttttccagat    170160
tttgtgttac gattcaaaag gtttaaggtg ggtggtgtct aagaattaaa taaggactca    170220
agttatgatt ctgatataaa gacacaaaac catggctttt ataatctaat catctgaggg    170280
aattataaaa cgacactttt aactttagga aggacacaga ccaaagggaa aaatagtaac    170340
acaatgaatg gaagagctta tgacagttat agttgtctac aggtgagaga tgagtaaaag    170400
ctaaaataat taggaagagc tccattaaga aaatgaaaat gaggagtttt ttgggggcac    170460
agtgcattag ggattcggct ttgtcactgc aatggctagg gtcgctgctg tggcacaggt    170520
ttgatccctg gcctgggaaa tttccatacg ctgcagatgt ggcagaaaaa aaaagaata    170580 tgaaaatgaa tgaagattta caaatggaag tacactttag ataagttaaa agaaaaggca    170640
caaatacaaa taccgtgaat gaaggcacag agacaagaat gagcatgaca taaaagagag    170700
acagtaaagc agctgaccat acttaagtgc agggtatttt gacagagtaa aattaaatca    170760
cgggagattt ccaaactaag tcaaaattta gattcaatgg gataaaccca gaaatcacaa    170820
ggctgagtgg aggacactgg tgttaagaaa aatcagtggt acaccacacc gggcagctta    170880
cagaatgaag caatagtatc aaaaacacta ttaggaggtt accatgcaac acaggtgtgc    170940
cagaatgagt agtggcagag ggagtaagga ggaaagggtg taagaggtac caggaacaat    171000
cactagcacc ttggttctag ttgtgagggg agaagaggct gggattgaga acataatcag    171060
aaaaattaac agtaacattc tcgaagtatg gaggcagatg caaatttgag gcaaaagggg    171120
ctttaggaaa gggcatgaag agacatacaa aaggaaatat tgaaagagta agtagagatg    171180
tagctataga agtttgaagt gaggtctggt atattttaag agcttaaatt atccacagga    171240
ggaaagctcc ctaaggagga agcacagaga tgtccagagg attgggtatc aagcttttag    171300
agcaaatcta catttagaag gtggcgagag aaagcatctc tgatgtagca acaggtaaga    171360
agagaattaa aatgctgata tagaagacaa aggataggac attaaaagag aactgtcagc    171420
aatgtcaagt gtcacagtaa gatgcggaga agactgctaa gaaatggctc tatcaagagt    171480
tcccgtcgtg gctcggtggt taatgaatct gactaggaac catgaggctg agggttcgat    171540
ccctggcctt gctcagtggg ttaaggatcc ggcgttgccg tgagctgtgg tgtaggttgc    171600
agatgcggct tggatccagc gttgctgtgg ctctggtgta ggccggcggc tacagcgccg    171660
attgaccccc tagcctggga atctctatgt gcctcgggag tggcccaaga aatggcaaaa    171720
agccaaaaaa aaaaaaaaaa aaaaaaaaaa aaagaaatg cttctatcag atgtggcctg    171780
gaggaggagt tcccgtggtg gctcagcagt tatcgaaccc aactagtatc catgaagatg    171840
tgcgttcgac ccctggcccc actcagtggg ttgaggatcc agtattgctg tgacctgtgg    171900
tgtaggtcgc agatgcggct cagatctggt gtggctgtgg ctgtggcgaa ggccggtagc    171960
tacaactctg attggacccc tagcctggga acctccatat gctgcaggtg cagccctaaa    172020 aaaccaaaa aaaaaaaaa gaaaaatgt ggcctggagg agatactcca tggaacaggc    172080
agaggaggaa aagaaccta atactttgct ttcgttcctc atgcagatca acgcaacatt    172140
acgttatcaa tttgtattct acaaaaagtg gtggttactg tcctttccta tacatctcta    172200
atttgaaatt tacacgtgtg cagtacacct tgccttaaac ccttaaccct tatacataaa    172260
```

```
cacaatttgc tgaaacactc tattttgtta gcgtttgtaa aaggcagagg gaatatcatg    172320
aaatgttatg gacaaattct agattttgt aattatatat atcaatgatt tgacctatgt    172380
tgttttataa atgactattc tgacaccata tatacctcgg gctgaccatg ttttctgtcc    172440
cctttattac tgtttttgat atgttttgga ggtttaacaa attcctcttg agggttagct    172500
ttttctttca aagtagaaag ttcttcaact ggtgaaattt gactttctgg gactagaatc    172560
tgttggaaaa gaaggaaaaa gtgcttaaaa ctgcaaacca tagaaagttt ccaaaaatca    172620
ctgaatgtct taaaaagca ctcattcatc tcacactcat aaaggtttat aattctttta    172680
tctatgcact gttacaaaag tgacccaaca aaaagcactc acttttttcaa atataattag    172740 acataaaata ggcctcggca ttagtgggag aacacatatt tctaattttt taagctaaca    172800
aaactggtat taattaataa tgatctacct tctgcactga aatgaattat tattaacaac    172860
ctgtttaaaa agtcacacac atcttattga ggcaccattt caagacaatt tagattttag    172920
acattcacct tcccagatgg actttattac tatgctatcg ttatttaggg ttaaacttag    172980
cccagcgata aacatcaagt aagtcagaca catacctggg atccacttgc atcgaaaagt    173040
atatgcacag atgttttggc aactgaaata ccttgttttc gggaaaattc ctaaaattaa    173100
attaaaggga tgtcattctc ctcccagttc ttcccatttt aatgcaatta tttcctgtat    173160
ctgcttcctt ccaaaactgc ccaatgttac caaagcatta ttatttatgt ctataaagac    173220
ttctctcaga acacatcaat gactccccag taaccacagt cttagcctgc cgttctgcat    173280
tttcctaagt gttcctcaca agcatattac ctgctattct tcaccacaaa ttttttaact    173340
gctacagacg aacatgtcct caacctatcc atgagttgaa acctagttcc caagaatggc    173400
attaggaagg gaggcctttg ggggttgctt agatcgtaag ggcagagtcc ttgggattgg    173460
tgcctttata aaagagaccc cagaaaactc gctcacccat tgaaccattt aaggacacag    173520
tgaaaaaatg gccatcaagg aagtaggaaa tgggccctca ccagacattg aatctgctgg    173580
catcctgatc tgattcccaa cctccagaac tctgagaaat aaatatttgt tgtttaaggc    173640
acccagtcta tagtattttt gtttagtagc ctgaacaaac taagacatgc accattcaag    173700
cttgtcaaca gaacgtctcc ccaaacataa catgaactgc actttaattc ccagttaata    173760
tctgattcat aatgtctttc acaatcctga aaagcatctt atctaaattt cattcataac    173820
tttaaggcca tttcaaggcc catttccaca gcctttcttt catatctgac tcttaatgag    173880
cattctcttt cttcaacttc tatacttcat attccatatg ccacttaatt acttttctg    173940 aggcatattc cttaatttgc acaatgttta atatcttgaa acaaggctt tgtctcatct    174000 cacttttaa acacatggta gaaattcatt aaatgttttg agtgtctgcc cctaattttg    174060
ccatctgaga ttcttctaa taggcatctc aaagggcatg gctaacaatg tgatggccat    174120
tccacaatac aaatttaaag gactaaaaat ctacatgtta ctttaagaac tgtagggaga    174180 aaaaaaaaa tcagtgaaac ttacagctcc aagtaactga aaggttcctg aattatgaaa    174240
aaaaaaatgt ttattaagaa gagtttaact taccctgtat ttatttgcac caaatatttt    174300
ttgtgtcaca ttagtgatct ctaatgatgc atcaaaatac aaaagcaatt ctttcccttt    174360
tcgtttacta attttttactg tatctttcag aattatagtc aggagcttct tcgagtctct    174420
cactgcatac aaagaaacca cactgattag tttatattca tttctatgac atcactctat    174480
aggtatacta taaataagta agtatgcag cataccaatt aaagtgacct gaaataaaat    174540
taacttgtag aatttaacag tatttaaatc aatcaatttc ggtactactt aagtaaacaa    174600
gtcagtttat ttttcaaagt ctcagtttcc tgatctctaa attataaggt agtacaataa    174660
```

```
ctaatgatct aaagccctga atacattcta gacgataata ggttttaat aaatattctt   174720
tgaacgcatc tcagaaaact attaatttaa aagaggcaaa gagaaaacaa ctttaattct   174780
gtaagtaact atttctagac acaagcacct attcaaacat ttctattaaa tccacagtgg   174840
ttacagaagt attgagagta acaaccttt gataaaaact tgagtgccag gaaattgtga   174900
gctaggaagg atacagtgct aatcctcaat aaaatcacca gcccagtgaa aactgtggaa   174960
ttctcattgt ggctcagtgg taccaaacct gactagaata catgaggact tgggttcgat   175020
ccctggttct gctcagtggg ttaaaggatc cagcgttgcc atgagctgtg gtgtaggtca   175080
cagacatggc ctggatctgg catttctgtg gctctgattc ggccctagt ctaggaaatt   175140
ccatatgctg tgggtatggc cctaaaataa ataaatgcaa tatttgcttc actgcttaaa   175200
tgaccctcat attagagttc agaattatca ccttgctgaa tgttttgtat ctatttgtac   175260
aaactattct ccacatgtat aatgactatc tatgtaagaa tttattgata cttgttatat   175320
tttattgctg aatttgttga aatttttgat atttgctttg actgcctaga ctatatcatg   175380
gtttgctttt tagttggaat attactgaga tgccagatct attttgctgc ttgctataaa   175440
attcaagtat ttataggagt tcctgtcatg gctcagcggg gcaagaacct gactagtatc   175500
cataaggatg caggtttgat ccatggcctc actcagtgag ttaagaatct gacattgcca   175560
tgagctgatg tgtgggttgc agatacagct cagatcccat gctgctgtgg ctgtggtgta   175620
ggccagaggc ttagctccaa atccacccct cgcctgggaa cttctatata ctacaggtgg   175680
ggtccttaag aaaaaagag aaaaaaattc aagtatttag atgtcaacat atatggattt   175740
tatatgttac ctagacattt ctgtaggatt ccagtatact atatttatat gaatataata   175800
acatgctttc ttctgcaaag ccattcaaaa agaacttaaa aattgtgtgt gtggagttcc   175860
cgttgtggct cagtggttaa cgaatctgac taggaaccat gaggttgtgg gttcaatccc   175920
tggccttgct cagtggggttg aggatccagt gttgccgtga gctgtggtgt aggttgcaga   175980
cgtggctcgg atcctgcact gctgtggctc tggtataggc cagcagctac agctccaatt   176040
cgaccctag cctgggacc tccatacgcc gcgagagcag cccaagaaaa tggcaaaaag   176100
acaaaaaaaa aaaaaattg tgtgtgcagc ctttattta tacattacta taacgaaca   176160
taaaaaagtc tcaccaggga gttcccgtcg tggcacagcg gaaacaaatc tgactaggaa   176220
ccatgaggct gcgggttcaa tccctggcct cgctcagtgg gttaaggatc cagtgttgcc   176280
ataagctgtg gtataggtcg cagatgtggc tcagatctgg tgttgctgtg gctgtggtgt   176340
aggctggtgg ctgtagctta gattagaccc ctagcctggg aacctccata tgcgacaggt   176400
gtggccctaa aatgcaaaaa cagaaaacaa acaaaaaagt ctaaccacac tctagcatgc   176460
tgctgcctcc catttccata atctgcaact gtagacattc tttttcacta gaaatactgc   176520
ttgatctcca gactctacac ttttttttt ttttaacttc catgagtttt ggtcacataa   176580
aaattcagat ctcacatgct ccacacagac tagaacactc ctttattaca aagggtacaa   176640
atgaatggtc agatggagag aggagagtgc aaagtctgga agggtcctga acacaggaga   176700
ccctgtccct atggagtctg gagtgcacta ccaaggggta gtataagaac tcaagtgttt   176760
ggagttccca ttgtggctca gtggttaacg aatccaacta ggaaccatgg gattgcaggt   176820
tcgatccctg gccttgctca gtgggttggg gatctggcgt tgccgtgagc tgtggtgtgg   176880
gttgcagatg tggctcagat cctgcattgc tgtggctctg gcataggcca gtggctacag   176940
ctctgacttg atccctagct ggggacttcc atatgctgca ggagcagccc aagaaatggc   177000
aaaagacaa aacaaacaa acaaacaaac aaatcccaac aactgaggtg tgtgtactga   177060
```

```
tgttaataca aaagagtcaa ctattatctt gacatctgaa atttcagtgg aaattttgga  177120
ggagtgcaag gtaaaacaga atgtagaaca ggaatgaata acagaagtaa agagttaata  177180
aaaactatta tctcaaaaat gactatgaat ggaaaaagaa ataaaccaca ggagaggacc  177240
ctatgttaaa tgaaatcata ctgtatgatt ccacttgaaa tagtcaattt catagaagaa  177300
aagctagaat ggtagttacc agaggctgag tagaagggg caaggggcac tgcttaatga   177360
gcatagagtt tcaaattctc aagatgacaa aagttctatt tcacaataat gcgaatatat  177420
atttaacact attgaactat atacttaaaa atggttaaga tggtaaattt tatatgattt  177480
ttaccgcaat aaaaataaga gaaactgagt aaggatgtat atggaaactt catgtactat  177540
tttatcaagt tttataatc aaaaactatt ctaaaattaa taatttagct ttaaaaaaag   177600
acccaaatca aattcccaga gatgaaaaat ataatgcctg agataatcat tgcataggat  177660
aggattggaa gcagattagg ccctacagaa gaaaatatta attagcagta aaacacagca  177720
atataaaact attcaaatga aaagagagtg gaaataaaag tatagggtgt agggtggaga  177780
acccagagaa tcagtgagtt gtgggagaac ttcacatgtg taatcagagc ctccagaggg  177840
gaggagaaaa aaagagcaga aaaaaatctc aagaacaatg gataaaaact ttcgaagtgg  177900
agtacctgcc atggtgtagt gggttaagag tctacagagg gtacagagct gcaggtttga  177960
tccctggccc aatacagtag gttaaagaat ccagcactgc ctagctgcgg ctcagattca  178020
atccctggcc ccaggaactt tcatatactg ctggtgcagt cataaaaaaa ataaacaaac  178080
aaacaaaaaa acctgtagaa gcaagcagtt caacgaaccc caagaacaaa caacatgaag  178140
aaaattatac taaaagcacc ataatcatac taatgagcag aaaaatttta aaagcagccg  178200
gggaaaaaag acttttaata aaaggagca aatgtgaaaa cgacagactt ctcatcagaa   178260
ataacgcaaa caaagagaca atagagtaaa atctttaaac tgaaagaaaa agaataggca  178320
atctagaatt ctatatgtat caaaaacact tttcaaaaat aaagacaagc taacaatttt  178380
atgacatgaa aaaggtgcaa gtgcaagaac tcattaccag aatatttgca ttaaaagaaa  178440
tattggagaa gtaactcagg cagaagaaaa atagtaccag atgaaaatct gggtctatat  178500 aaaatgaagcc acaacactgg aaatggtaaa tataaaatac ttaaaaaatc tctttaaaag  178560
ctaactggct gcataaagaa aaatattatt acagcatatt atgaagtctt tgacacatgc  178620
agagacaaaa gtaattttta gtactattga cagcaatgcc acaaaggtca ggaaaccaaa  178680
gtggaatata ttattattac tattaggttc ttacactatt cataaagagg tataatatta  178740
tttgtacaca ctattgaatt aaatatgtat aaaataaacc ctaaatcaac cactaaaaaa  178800
gtgagaataa agccaacaaa agaaatgcaa tgaaaccact gaaaatgaac taatacaaaa  178860
gaagaaaaag atgggaattc ccattgtggc tcagtgagtt aaggacctga cattgtcttt  178920
gtgaggatgt gggtttgaac cctggcctca ttcagtaggt taaggatctg gtgttgcctc  178980
aagctgtggt ataggtggca gatgtcactg cgatctggtg ttgtaggcct cagctgcagt  179040
tccagttcta cccctagctt gggaacttgc atatgctaca ggtgtagctg ttaaaaaaaa  179100
aaaaaaaaga gggagttccc atcatggcgc agtggttaac gaacccaact aggaaccatg  179160
aggttgcggg ttcggtccct gcccttgctc agtgggttaa cgatccagcg ttgccgtgag  179220
ctgtggtgta ggttgcagac acggctcgga tcccgcgttg ctgtggctct ggcgtaggcc  179280
ggtggctaca gctctgattc gaccccctagc ctgggaacct ccatatgccg caggagcggc  179340
ccaagaaata gcaacaacaa caacaaaaaa aagacaaaag acaaaaaaaa aaaagagaga  179400 aaagaaaaa aaatggcaga tggaacagca ggtagaaaaa aacaaaaacc agatgataaa   179460
```

```
tttaatgtag attaatagtc acaataaaaa ccacaattac aaggccaaga ctgtcaaatt  179520
atatttaaaa aacaacaccc agtatctgat gactataaga aatctgcttt aaatatacag  179580
acacaaatga cttaaaaaca atgaaaagtt ttgtcatgct ataattaatc aacagaaatc  179640
ctgaaagagt atgtaaatac tacataaagt atattacaga gcaaagaata ttaccatagg  179700
aaaaacagag tcatttcata aagataaagg ggtcaattta tgaagaaaat accactaaag  179760
gtttatacga ctaataatag aaattcaaaa cgtctgaagt aaaaaatgat aaaactgaaa  179820
agaataggaa aaaatcacaa ttacagtggt gacttaatac ccctctctca ataactgata  179880
gaacaagtag gtaaacaatc tgggaagata tatgactcta acaacactcc tgacccaacc  179940
ctcaacccaa cagcagaata cacattcctt tcaagtgcac acaaaaccaa ttacctagac  180000
aaactatatt ctgggtcata agataagcat catatatgta aaaggattct caaatcatac  180060
aacatactct ctgataacaa taaaattaag ttagaaatta gtaacaggaa gatatccctg  180120
aaatcccaag catgtagaaa ttaaataaaa tacttttaaa taaatctgtg tgtcaaggaa  180180
gaaatcaaaa gagaaattta agaatcaagt taatgaaaat ggaaacacaa cacactgtaa  180240
tttgtaggat gctgctaagg gagagtactt agggggagaa tttaaagcac taaaaggcta  180300
cattagacaa ggaaaaaaaa ggagttccca tcgtggctca gcagaaatga atacaaccac  180360
catccatgag gatgcagttt caatccctgg cttgtgcagt gggttaagga tctgggttg  180420 ccatgagctg tggtgtaggt agcagatgcg gctcggatct ggagtttctg tggctgtagg  180480
ccggcagcca caactccaat tcgaccccta gcctaggaac ttccatatgc catgagtgtg  180540
gccttaaaaa gacggggtgg gggggtctca gatcaatgac ttcagcttcc aacctgaaat  180600
gctagaaatg ggaaagcaaa ttaaaactaa agtaagctga agaaaagaaa taacattaag  180660
aatacagatc aattaaattg aaaataagaa aacaaaaata gagaacaatc agtgaaacca  180720
aaggctggtt ctttgaaaat atcaataaat ttggtatacc tctcatcaaa ctgactagga  180780
aaagtagcta agacaggagg ccaacactac agaatctaca gacagtaaaa agataataag  180840
gggccattat aaaccacttt attccaataa atttgacaac atggatgaaa tggatagatt  180900
tcttgaaaga caaagattac caaagtttac tcaggaaaa aaaataggta acctgaaaaa  180960
caatttatct attaataaac tgaatttgta gttaagagcc ttcagcaaag aaaagtaaaa  181020
gtctgagccc acattgcttc atttggtaaa tactaccaag cacttacaga agatacaata  181080
ccaactttac acacactctt agagaaaaat taaagactat ggattacttg ccaattaatt  181140
ctataaggct aagaattcct tgactctgaa acttgaagaa aaaaaaaaaa gacatacatt  181200
ataagaaaac aaaagagctt ctagaacatg aaataccaag ttgcctaact atatttcaca  181260
aatcatttcc aatgatatat tgttgcgaga catgtttcta cagtattttc ttagcctctt  181320
tgcttctatt ttctatgctg aaaattccat cttgttctgc tttactttat cccatattcc  181380
tgcttgaaaa acagtggcag tgctggtata tgacttaagc ttaaaatcaa agaagatgta  181440
aagaaatgga aagatattcc atgttcctgg attgggaaaa tcagtattgt aaaaatggcc  181500
atactaccca aagcaatcta cagattcaat gcaatcccta tcaaattacc catgacttt  181560 ttcacagaac tagaacaaac aatccaaaca tttatatgga acaataaaag acccagaatc  181620
gccaaagcaa tcctgagaaa caaaaaccaa gcaggaggca taactctccc agacttcagg  181680
aaatactaca agccacagt catcaagaca gtgtgggact ggtatcaaaa cagacagaca  181740
gaccaatgga acagaataga gaatccagaa ataaaccctg acacctatgg tcaattaatc  181800
tttgacaagg gaggcaagaa cataaagtgg gaaaagaaa gtctattcag caagcattgc  181860
```

```
tgggaaacct ggatagctgc atgcaaagca atgaaactag aacacaccct cacaccatgc    181920
acaaaaataa actccaaatg gctgaaagac ttaaatatac cacaggacac catcaaactc    181980
ctagaagaaa acataggcaa aacactctct gacatcaaca tcatgaatat tttctcaggt    182040
cagtctccca aagcaataga aattcgagca aaaataaacc catgggacct catcaaactg    182100
aaaagctttt gcacagcaaa ggaaacccaa agaaaacaa aagacaact ttcagaatgg      182160 gagaaaaatag tttcaaatga tgcaaccaac aagggcttaa tctctagaat atataaacaa   182220
cttatacaac ccaacagcaa aaaagccaat cagtcaatgg aaaaatgggc aaaagacctc    182280
aatagacatt tctccaaaga agatatacag atggccagca aacacatgaa aaaatgctca   182340
ccattgctga ttataagaga aatgcaaatc aaaactacca tgagatacca cctcacacca    182400
gtcagaatgg ccatcattaa taatccaca aataacaagt gctggagggg gtgtggagaa     182460
aagggaaccc tcctgcactg tcggtgggaa tgtaaactgg tacagccact atgggaaca    182520 gtttggagat accttagaaa tctatacata gaacttccat atgaccccgc aatcccactc    182580
ttgggcatat atccggacaa aactctactt aaaagagaca cgtacacccg catgttcatt    182640
gcagcactat tcacaatagc caggacatgg aaacaaccca atgtccatt gacagatgat    182700 tggattcgga agatgtggta tatatacaca atggaatact actcagccat aaaaaagaat    182760
gacataatgc catttgcagc aacatggatg gaactagaa aatctcatac tgagtgaaat    182820
gagccagaaa gacaaagaca ataccatat gatatcactt ataactggaa tctaatatcc     182880
agcacaaatg aacatctcct cagaaaagaa aatcatggac ttggagaaga gacttgtggc    182940
tgcctgatgg gaggggagg gagtgggagg gatcaggagc ttgggcttat cagacacaac    183000
ttagaataga tttacaagga gatcctgctg aatagcattg agaactttgt ctagatactc    183060
atgttgcaac agaagaaagg ctgggggaaa aatgtaattg taatgtatac atgtaaggat    183120
aacctgaccc ccttgctgta cagtaggaaa attaaaaaaa aaaaaaaaga acaaagacct    183180
gaaggcataa gttatccatg tggtcaggct gaatgaggac ttaatgcgtt ggtctagaca    183240
tgctggacct gtgcagacag gcaagccatt tgcacagcat ggtatgtcct ctaaagaatg    183300
agaggaagat gagcctcgtg gccccaaggg gtttatgagg ggtctttagg aggatatgca    183360
ttagcaagga gaacccaggt gcaaacctaa gcatgctgtc tgcagaagca cagtggtgat    183420
tctctaggtg ctatgcatag atagctgaca cccagcttcc tcaatgctca tgattgttaa    183480
atgcctaaag ggcagaataa aagcttaacc agctaccaga tatgtgactt ttaaaatgat    183540
agaagaacta tattctgtac ctacaaccccc cgcctcactt gacataatcc tagagagcag    183600
tatggtctct tgaggcgggg ctcttggtcc ctgaaacctt gagtcccccc atttccacaa    183660
ttaagataaa tgtctctgtg tcttgtttta tgttaacttt ttccttaagt ttcacagcac    183720
ctgttcttca gccctcacct gctgagctgg tctcgcaatg tataaaagat taatctatca    183780
caaccaagtg gtgtttatcc caggaaagca aagttgatta acatctgaaa atcaatgtat    183840
ttctattaag aaactaaata aggaaaaata tatatcatta ttaatagatg cagaaaaagc    183900
cttttcccaa acccagcact gttaatgatc aaggaaggct ctcatccgca aattacaaat    183960
aaaagagaat ttcctcaatc tgatagaggg catatatgaa aaactgttat cataaatatt    184020
tcatgttgga aaaacaact gctttcctcc ctaacatcgg ataccaggca aagatgtcgg    184080
ctctcatgac ttcttattcaa cactgtactg aaggttcagg gcagtacaag caggtaagtt   184140
gggcaagaat gaccacaaga cttgttggca aggacgtgga acaaccagaa ctcttataca    184200
ctggtggtaa aaatgtaaaa tggtaaaacc atttttggaca acagtttgga agtttctgaa    184260
```

```
ataggtaaca tatagctaag ctatggcaca gtcactatac tccttagtat ttatctaaga   184320
gaaacaaaaa cagatatcca catagataat aacataaata ttcgcagcaa cattttttaa   184380
tacctaaaaa ctgagaacat tccatatacc catcaactgg tgaataagta aattcaagta   184440
tattcataca gtggaacacc acccagcaat gaaaaggaat aaaccattga tatatataat   184500
actgctgagt cttaaaaaaa aaaacaaaac tacctattag ttttctagct agataaatac   184560
agtactgaaa gaaaatagtc aataattcct actgtatttt ttcaattata taaattctaa   184620
aaaatataaa ctaattcata gtagagaaaa tattagtgat tgcctgggga tggggtagga   184680
gatggataga ttaaaaggaa cctcaacatt tggaggcgat gtattttat tacttgattg     184740 caatgaagac tgcatgtgtg tttacacacg tgaagaccca cccactccct caatctgatg   184800
aaatatatct tcgaaagacc tttatccaac atcatgctta acagtcaagt atcactgttc   184860
ttccctaagc aaagatcatg agaactagga aacaatgacc actttgacca tttctaatca   184920
gtactaaact ggaggttcta gccatcgtac taaggcaaac ggaggaagga aggaataaag   184980
ggagaaaaga ctagcaggag ggagggaggg aggaaagaaa caaagacgaa gaaggaagtt   185040
agttaaggaa gggcataagg atcagaaagt agcaagtaaa accaagctct actcgcagat   185100
accatgacga tccctagacc accctcagga atctacactg caagtactag aaccaaacag   185160
agattttggc aaggtcatag gaaacaagcg aagtacttca aattcaactg tatttttata   185220
taccagtaaa aaatatttgg aaaatgaaat caagtcaatt ctatttacaa acatttaagg   185280
caagattgaa gacttaggaa gaagttcatc aaaggatgta tacgacttct acactggaaa   185340
ctacaaaaca ttgttgacag aaattaaaga cttaaataaa tggaaaaata tataccatgt   185400
tcatgaactc aaatactatt gttatgttat ttctccctgt atcaaaccac aaaccctgtc   185460
acaattctag ctggtaatgt gtagcaattg ataaaccaat tctaaaattt aagtggaaat   185520
tcaaaaggtc tagaatttcc aaaactgtct tgaaaaacac ccacaatgtc agaagactta   185580
cactagctga ctttgagact cactatgaat ctatggtaat aaactagcat agggaatggc   185640
aaatggatca atggaatgga gtataggaac aagacctgaa cctgaatcag tcattcgatt   185700
ttcaacaaag gaaccagaaa tccagtggga aaaggaaaac cttttttgtca aatagtcctg   185760 gaataactgt atattcatat gaaaaaatga acctaaactt ctgtgccata ccataaccaa   185820
gtattaattt gagatagata aaaatcctaa aaaaaaaaac caggagaaca tctttgtgac   185880
ttggtagtta ggcaaaaata tgttaggaca cacgaagcaa taaccacgaa agaaaataga   185940
tcatataaac ttcaagttta aaaacttctg ctcattaaag acactactgg cagagttcct   186000
gttttggcac agaggtaatg aatctgacta gtatccatga agatatgggt ttgatccctg   186060
gccttgatca ctgggtctag gatctggcga tgctgtgagc tgtggtgtag gtcgtagatt   186120
tggctcagat cccacgttgc tgtgggtgtg gggtaggccg gcagctgtag ctccgattta   186180
acctctagct tggtaacttc cataatgcca tgggtgtggc cctaaaaagc aaaaaaaaaa   186240 aaaaaaaaa aaaaaagac acccttggga aaatgaatat gtaagacaga tacagattgg    186300
gagaaaatac tcaaagaaca catatatgct aaaggattag tacccagcgt atgtaagaag   186360
tcaaaagtca ataaaaagat agtccaatta aaaaacggcc aaaatatttg aggaaatacc   186420
tcacagggaa gatacatgaa tagccattaa gtacatgaaa aagttctcaa catcactggt   186480
tattaggaaa atgcaaataa aacctattat gataccatta tatgcccact gaaataatta   186540
aaatatgtct tcatatctga atttgtgttg gtaccagttc tccaagttat atgacttctt   186600
ccaactagtg ttacacaact ccagttatag gagtggagaa agaataaatg tttggaccta   186660
```

```
atcaaacaaa tacgatacaa gggcaagagc cttgaacgca ctgacacatt gatcatggtt   186720
ttagattaga tagagaagga aataaataca aagtattgcg gggtaaggga atttgatgat   186780
attggactat caaatttatg aatgcaaaca tgcgaaaatg tgattttgct tttattagac   186840
tatgtggttt tccacacagt atgcaactta tactccatat aataagaatc aagaagacaa   186900
ttataggaaa aaagtttaat accttctatg ctgtatattt gcacttttc ctcaggcaca    186960
gtgactgctt cccactgatg atccttaaat ttaaaaatag attttggtaa aaataatttt   187020
ttttcctgct ttaaatctcc tttaaacatc atatacaaac agtaaaggta gttttttttt   187080
tttttttttt tttactaagt ataactaagt aacacatttc ttgctacatc aattgattac   187140
atattatact tgtcacattt aatatttgtt aattcttaaa ggtaaatgac agtactgatt   187200
acttttttga attataactc tttttttttc ttttttggg ccacacctgt ggcatatcaa    187260
agttcccagg ctaggggtca aatcggagct actgctgctg gcctaagcca caggcacagc   187320
aacaccagat ccgagtcacg tctgcaacct acaccatagg tcatagcaac accagatcct   187380
taacccactg agcaaggcca gggatcaaac ccgagtcctc atggatccca gtcgggttct   187440
ttaaccattg agccaggaag gaaattctaa attcctattc ttgatcaaaa aaagaatgat   187500
tatccattaa tatttactag agtatactcc tttaaaaaaa ttaccaaatc ctagagttcc   187560
ctttgtggca cagcagaaac aaaccctact agtatcaatg aggacttggg tttgatccct   187620
ggcctcactc aggggtcagg gatccagcaa tgccatgagc tgtggtgaag gtcacagagg   187680
aagcttggat cccatgttgc tgtggctggt agctatagct ccaattcaac ccctagcctg   187740
ggaacttcca tatgccatgg gtgtggccct aaaaagaaaa aaaaattacc aaatcttgtc   187800
atttgtcctc tgcaatgttt tgtgaaacca cagtcatcct ccaatttcca tgcattaatc   187860
accaccgggg cctgtgagtg ggctctgtgt tatgttctta gatacaaaca ttgaatgcat   187920
atcaataata acctaaaatg ttttttccctc ccgagtattt tccttgaaca tctgtataaa   187980
tgaataaaat aatatgaatt cacctaaaaa actcatagta acaattagaa ccattcttaa   188040
aagatgggat cctaaaacct tccaggaatc ttatgaggaa aatagattca aatctttagc   188100
tatttaagga acacccatcc tacagaaatt ccgctaaatc ctccacctct tcctgtact    188160
ctgagggcag cctccagcta aggtgctaac tctcccagac ctcaaagcct cagggtcagg   188220
aggaaagggt tggtatcctc ttctccccc agtgctttga gcagtttctt atttctctgc    188280
tgtaaaacct tgctcctttta tggcacacat gagctggcat acataccacg aacttcgaag   188340
agactcttct tcacatatgg agacacctgg tttaaagcct tcctttttta aaaaaaagtc   188400
tacattacat aaattttcaa acatgctttt aaaaatagaa atcatagtat ggcgaattca   188460
aactatgccc ttactcctat taccaacagg gtaatagttc caacagttac caacaggagt   188520
tcttgctgtg gcgcaatggg actggtggca tcttgggagc tcccttggga gctctgggat   188580
gcaggttcta ttcccagccc aggcacagtg ggggaaggat cctgcattac cttagctgcg   188640
gcttaggtca caagtgcagc tcagatctga tccctggcct gggaactcca tgtgccacag   188700
ggcacagaaa aaaccaaacc aaaccaaacc aaaccaacaa cccccaaaac cagttaccaa   188760
tatattgtgc ccacttgttt cgtcttcacc ccctactctc cctccattac actctcttcc   188820
tcttgacctc aatttttttct tcaatctctc accccagcca tcaatttaaa aacccctccc   188880
ttgaatccat acctcgcttt agctccttct atgttcttcc ccttaatttg tctttacttt   188940
ctctacaaat agttcaactt ttcaagactg cctaattcca atacttagtg aaactgctct   189000
ttcacagatc accagtttta acatttgttt tgacagtaat gatcatttcc tcccctaaaa   189060
```

```
cacagtttta tgattatcca gtaacattta ttactggata aatataactc ttcctttgcc   189120
ttttataagt tgatagcttt ttaatatgtt cttttttagc cggttcgtca agtgcccttc   189180
aggctagagt cccttctacc tatcctgtat aaatttgtgt tcttctcagt tctcttatct   189240
agacactcct taagtcccat gcttttattt atcatctaaa tatggagggc ttctaaatct   189300
ccacctatgg ctcaggtgtc tactctgaac ttcacaccaa tatatccaac tgcctacgag   189360
aggtcttcag ctgaatatcc tacaagcacc tccaaatcaa acactcaag gctgaactca    189420 tctttctcat acagaaatta tcatcctgtg acagcatctc catccaacca gttaccaact   189480
tttattaatc cttcttcttt ttattataaa taaataccat gtctacttaa ttcttcctct   189540 caagttttc tggaatccat ccatttccat cctttctcaa tgtcactttc taagactatg    189600
ccaccacaat ttctctcacc tggattacta caaaagtctc ctaactgcct ctggtcttgt   189660
cccttttaaa ccttttctct ccaccagggg aatctttcac acagatgtga tcctcagtgc   189720
ctagcgaatt atctggcaca cagtaagctc ttactaaata tttgttgaac tgatgttatg   189780
tcctatctat aaccctcctt tggctccaca ctgccttatt tcttgccaat ctcccttgaa   189840
ttctatgcac taaccatatt acgtatcctt cagttctttg agtattctat ctactcatta   189900
ttaaaatata tgagcccttg agtgagaaaa agacaagtcc ccaattaat aaatcttatg    189960 tcctatgagg ggaaaatggg caaaaaaaat cctagataaa ctaaaggatt ttaaatagca   190020
ataactacta gaaaggaaat aaaacaggac aatgtgatat gatatggctg gaaggctact   190080
ttatactgag ttaccacaga atacctctat aaggaggtaa tatttatgct gaaatctaaa   190140
tgggaaggaa ctaagatgca aagatctgga ggtccatagg cagaagaacc agcaaacaga   190200
aagacctgaa ataagcatga tctagaatgt ggctagaaca tagtaaacat agagaacact   190260
ctgagcgtat gagagaaaca accagggcca ggtcataaaa gccatcacac accgtgttaa   190320
agagacaacg gaaggatctt aggcagtcac aatattggag catagcatct agggggagcaa  190380 gagagtacag ggagaatgta ctgctgctcc agaaatccag gggagagagg agtctaacta   190440
taactgtggg aagaagagtc tctcagcacc tctagaccag tgtctggaac acagaaggca   190500
cttaatactt aaaaatgcat tttattctat cgctgtcacg tataatacta taattatttt   190560
ctggtctgaa tattccatta gaccaagcaa gtgaagtcag aaaccacatc aatcctattc   190620
tatcctcttc tcccaaaata aaatccagtt cctaaagaaa atccagttaa caatactcct   190680
acaaaccctg cagagattaa cacactaatg aaaaccatca gtaaccctga gtagtggtgc   190740
tagtttttgg aatccaattt tcagtaagca ttctaagaag gcacgttaaa ataaaaagaa   190800
aggaatgtgg aaatcctaaa aggcatttgg ctcatgtttg tctacagagt ttacctggaa   190860 caaaagcag gattttagaa gagacagaca aaaaaaaaa aaaaaacaaa aaaaacaaaa     190920 aaaaagcgt aaaaagcctc tttatattat cagcagccac aattaggtta gtaaatgcag    190980
atcaattcct gctcagatct tgtcaaagtg actacaagta tgccaatgta gcaaatatta   191040
agtgccagct atttggaaac aatgattcaa gaattttcct cagattaaaa agaggtcagt   191100
agaagacata ccacttggtt ggaaggttta aacacagcaa agacatagca cagaaagaaa   191160
agatctaaaa ttcacttcta gaggcagatc agatggcaga ggagtaagac atcttgctca   191220
cctctcaaaa cacatcaaga aaacacatct acatgtaaaa cgactcgcac agaacatcta   191280
ctgaatgctg gcagaagaac ttaaaccttc aagaagggca agaaactctt gacataactg   191340
ggtagaacaa aaggaaaaaa gagagagcga aaaaaggaat cagacaggac tagcactcct   191400
gaaagggagc tgtgaaagag aaaaggaacc cacatcctgg gaagccacct aaccgaccag   191460
```

```
gaggatcagc ttagacagag ggacctcaaa gtcaccgaga aaagcagagc agctggacta   191520
aggaggtcaa agtagagtga gagccacaga gatcatctga accaccagcc cggacaccac   191580
agcctgagac actcgggtgg gggctgggca ctgagactca ggctccgggg tcagtccggg   191640
gaagaggact aggctggctg tgtgggdaca gcctgagggg ctaaggagtg gtgcactaca   191700
ggcagaggag cagtgtgcta caggcttggg agtggaacgc cacagggag ggaacccagg   191760 agaagggctg ggcctgcagg agaagcaagg ctccattgtt gaggagggtg agaggaggag   191820
gggcggagcg tcagaggagt ctccttgggc ctgagcatgt gcccgcatgc tctcagaggg   191880
cagggccgcc gtggtgcagg ctacgggggg caagaagcca cttgctcagg ctacaggaga   191940
ctgggcgcat cttgtccagg ctgtgggtgg ccaggcacct cttgtgtggg ctgagggtag   192000
cgctgggcta agtgcaatgt ggtgcctctt gtgtgatcta caggaggcat ggacaaatgg   192060
cggtggtctt ctcagaggcc agggaggt gtggcctgcc accactgggg gccagcaagt   192120
tggctccgct tgcagtccag tcatcacagg ggttggcaaa aaagaaaaaa aaaaagagg   192180 gcactgcaac cacgcaccac acattgttgc tctcaggccc atgggaacac accagccctg   192240
cagctgccca tgccaaacac tctggtggt gtgcagatgc ttgatcactg ttccttccca   192300
agaccctaca actaggagca gttggtgcag cacctcctgc atggcctacg tgggacgagg   192360
tgcttcttgc atggtctaca ggtggcgggg gcaagccacc acagttatca ctgattctag   192420
aggttggcat gctacagcag gggtccgtga acaggcacca cttgaggctc caatcacctc   192480
agaggaaggc tttgcaaatg aacactacct gttgtggctc tcattctcct gggaattcac   192540
acatcctgct gctgccactg ccaaatgctc tgggcaccct gtcaatctgc ataaggctca   192600
ttaccacttc ccagggccct gcaactagga gtagccagtg gcaccttcct gcaggtcctt   192660
gctgctgtta agagcccagc aaccaggcac tgactataag ccctacccat ggccgctttc   192720
tccctggaaa cacactcagc accctgggaa taacagcctg ctcacaccaa agaaaaagac   192780
agcaaatatc caaactccca caccaaaaat aaatagtaac cccccacaaa atacaaaggg   192840
gtgctctcgc acagaagtag ccccccaacac tatagtttcg cttccctaaa cccacagaaa   192900
aagaaaaact taagcaagat gtagaagctc agaaaccatt cccagttaaa ggaacaggac   192960
aattcacctg aagtagcaaa aaatgaaacg gacttctgca gtctgaaaga cattgagtcc   193020
aaaagggaga cagtgaaaat actgaaggaa ttaaggctga atatcaacga actaaaagca   193080
gagataaaca gtaatgcaga ttcctttaga aaagaactag aaaataaaag gaggaacata   193140
aaaaattaga aaattcattt gcggagacac aaactgagct aaaggcacta aagagcagaa   193200
tgaataatgc agaggaacaa attagtgact tggaagatag aataatggaa atcatccaat   193260
caggacagca gacaacaaac caaatgaaaa aacacaaaag caatataagg gatttatggg   193320
aaaatataaa gtgggccaat ctacacataa tagaaattcc agaaggagaa gaaaaagaaa   193380 agggattga aaatatattt gaagaaatta tggctgaaaa ctttccaaat ctaaaggaaa   193440
ctgatatcaa gacacaggaa gcacagaggg ccccaaacaa gttgaaccca aacaagccca   193500
caccaagaca cattataata aaaacggcaa agttaaaga ctaaagagg attctaaagg   193560 cagcaaaaga aaaactaagc gttaactata agggaacccc cacagtgcta tcagctgatt   193620
tctctgattt ctctatagaa acactacatg tcagaaggga gtgacaagat atatttaaag   193680
ttctgaaagg aaaaattttg cagcctagaa tactctatcc agcaagaata tcatttaaaa   193740
tagaaataaa caatttctcc aacaaacaaa agctaaaaga gtacagcaat actaaatgca   193800
ttctaaaaga aatactgaaa gagcttctct aaataaaaaa aagaattaag aagaaatagg   193860
```

```
atggaggaaa ccacaattgg aaagcaatca cttaaataag ccatcataca aatctaaaca   193920
tgaagatgtt taaaaaaga aaaagacttc aaaatcatag aatgtgggga aggaaagtaa   193980 gaaaaaaga cttcaaaatc atagaatatg gggaaggaaa gtaagaaaat acattctttt   194040
tttttttttt taataatgtg tttaatccta catgactatc aagctaaagc aagcagatac   194100
aggaaaagat taacatactt aaaaaacagg gcaaccacaa atcaaaacca acactacat   194160 tcaaaaaaac taaaagaaa agtactcaag cataaaataa atggaaacca tacaaccaaa   194220 aaagaatgg aagaaaagag aaatatagac tcaactggaa aacaaggttt aaaatggcaa   194280
caaatacata tcaataatta ccttatatgt caatgactga atgctccaat caaaggacat   194340
agtgtggcag attggataaa aaagcaaaaa cctataatct gctgtctaca agagactctt   194400
cttagggcaa acgacacata tagactgaaa gtgaggggt gggaaaagat atttcacgcc   194460
aatggacaag acaggaaagc aggagttgca atacccatat cagacaaaac agactttcaa   194520
atgagggcca taagaaaga caaggagga cactatttaa tggtaaaagg atccattcaa   194580
gaagagaata ttacaatcat caatacatat gcccttaata tagttgcacc cagacactta   194640
caacaaatac taacagacat aaaaggagaa attgatggga atacaatcat agtaggagac   194700
tttaacaccc cactcacatc aatggacaga tcctctcgac agaaaatcaa taaggcaaaa   194760
gagatcctaa atgacacaat agaaaaatta gacttattcg acatttttcag gacattacat   194820 ccaaaaaaac cagaatatac attcttctca agtgcacatg gaacattcta aaggatggat   194880
cacatattgg ggcacaaagc taaccttaac aaatttaaga gtatagaaat tatttcaagt   194940
atcttctctg accacaatgg catgaaagta gaaatcaacc acaagcaaag aaatgagaca   195000
aaattaacta catggagact aaacaacatg ctactaaaaa accaatgggt caatgaggaa   195060
atcaagaagg aaattaaaaa ataccttgag tcaaatagta atgaagacac aaccattcaa   195120
aatctatggg atgccacaaa agcagtgctc agagggaaat tcatagcaat gaagggcttc   195180
ctcaaaaaga agaaaaatct caacaactta acctatcacc taaatgaatt acaaaaagag   195240
gaacaaatga aacctaaagt cagcagaagg aaggaaatca taaaaatcag aaaggaaatc   195300
aataaaatag agattcaaaa aacaatagaa aaaaaatta atgaaccaa gagctgattc   195360 tttgaaaagg taaacaaat tgacaaacca ctggccagaa taaccaagaa gaggagagaa   195420 aaaatccat ataaataaga aatgaaaaag gataaatcac aacagataca gcatacacac   195480 aaaaaaggt aagagaatac tctcaacaac tgtatgccaa ccaatttgac aacctggaag   195540
aaatggacaa ctttgtagag gcatacagcc cgccaaaact gaatcaagaa gaaatcaatt   195600
gaatagactg atccttagaa atgaaacagg gggagttccc gtcgtggcgc agtggttaac   195660
gaatccgact aggaaccatg aggttgcggg ttcggtccct gcccttgctc agtgggttaa   195720
caattcggcg ttgccgtgag ctgtggtgta gattgcagat gcggctcgga tcccgcgttg   195780
ctgtggctct ggcgtaggcc ggtggctaca gctctgattc aacccctagc ctgggaacct   195840
ccatatgccg cgggagcggc ccaagaaata gcaacaacaa caacaaaaga caaagatta   195900 aaaaaaaaaa aaaagaaag agaaataaaa cagaatatgt aataaaaaca ttccctataa   195960
acaaaagtca ggaccagatg gcttcacagg cgaattctgc caaacataca aagaacttat   196020
aacccatctt tcttgaattt ttctgaaagg ttgaaggagg aggagcactc ccaaggactc   196080
tctgaagcca ccatcaccct aataccaaaa ccagacaaag atactcccca aaaagaagat   196140
gatatgccaa tatctctgat gaatatagac tcaaaaattc tcaacaaaat tttagccaac   196200
tgaatccaac aacatagaag aaagatcaca caccacgacc aagtgggatt cagcccaggt   196260
```

```
tcacaaggac ggttcaacgt acgcaaatca atcaatgtca tacaccacat taacaaaaga  196320
aaagtcaaaa accacatgat catctcagta gatgcagaaa aagcatccga ccaagcccaa  196380
catccattca tgatcaaaac ttttaccaaa gtgggtatag agggcacata ccttaatata  196440
acagaagctg tttatgacaa acccagagca aatatactac tcaatggaga aaagctgaaa  196500
gcctacccac gaaaatctgg aactagacaa ggatgcccac ctcaccactt ttattcaaca  196560
tgtattgaaa gtcctagcca cagcaatcaa caaacaaaag aaacaaaagg tatccaaatt  196620
ggaagagaag aggtaaaagt gtcactgtgt gcagatgaca tgatactata cataggaaac  196680
cctaaggacg ccacacaaaa actactcaaa ctgatcaaca aattcagcca agtagcagga  196740
tataagatta acattcagaa atcagtcaca tttctgtata ctaacaatga aataccagag  196800
aaggaaaaca aaaatataat gccttttaaa attacacccc ccaaaattaa atacctagga  196860
ataaacctga caggaaggtg aaagacttac atgctgagaa ctataaaaga ggatgcaaag  196920
aaatggaaag atattccatg ctcctgagtt ggaaaaatta atattgtaaa aatggccata  196980
ctacccaagg caatctacag attcagtgca atccctatca aattacccat gacattttc   197040 acagaactag aacaaacagt ccgaaaattt atatggaacc acaaaagatc cagaattgcc  197100
acagcaatct caagaacaaa aaccaagcag gaggcatcac tctcccagac ttcaggcaat  197160
attacaaagc cacagtcatc aagacagtgt ggtactggta ccaaaacaga catacagacc  197220
aatggaacag aacagagaac ccagaaataa acccagacac ctatggtcaa ttaatcttcg  197280 acaaggagg caagaatata aaatggctaa agacagtct tttcagcaaa tggtgctggg  197340
agaactggac agtcacatgt aagtcagtga aactggaaca cacctaaca ccatgcacac  197400 acaaaaaaa aactaaactc aaaatggctt aaagacttaa atgtaagacg agacaccatc  197460
aaactcccag aagagaacat aagcaaaaca tcctctgata tcaaccttaa caaatgtttt  197520
ctcaggtcag tctcccaaag caacagaaat aaaagcgaaa acaaaaacca atggggccta  197580
atcaaactga caagcttttg cacagcaaag gaaaccataa aaaaacaaaa aaaaacaaga  197640
caacttacag aatgggagaa aatatagttt caaaggatgc aactgacaag ggcttaatct  197700
ctaaaatata caaacagttt atacaactca acagcaaaaa agccaacaat ccaattgaaa  197760
aatgggcaaa agacctgaac agacatttct ctgaagagga tatacagatg gccaacgggc  197820
acgtgaaaaa atgctcaaca tcactgatta tttgagaaat gcaaatcaaa actacatcga  197880
gataccacct cacactagtc agaatggccg tcattaacaa gtcaacaaat aacacatgct  197940
ggagagggcg tggagaaaag agaaccctcc tgcacgttgg tgggaatgta aattggtaca  198000
accactatgg agaacagtat ggaggtacct cggaaagcta aatatagaac taccacatga  198060
cccagcaatc ccactcttgg gcatatgtct ggacaaaact tcccttgaac aagatacata  198120
tacccctatg ttcattgcag cgctattcac aacagccaag acatggaaac aacctaaatg  198180
tccatcgaca gactaagaag atgtatatat acacaatgga tgactactca gccatagaaa  198240
gaacaaaata atgccatttg cagcaatatg gatggaacta gatactttca tactgagtga  198300
agtaagtcag aaaaagacaa acaccgtatg acttcatttg tatctggaat ctaatgtatg  198360
gcacaaatta acctttccac agaaaagaaa atcatggact tggagaacag actatggttg  198420
cccataggga gggggaggga ctaggaggga ctgggaattt gggcttaata gatgcaaact  198480
cttgcctttg gaatggatag gcaatgggat cctgctgcat agcaagggga actatgtctg  198540
gtcacttgtg atggagcatg ataatgtgag aaaaaaaaac atatacatgt atttgcgact  198600
gggtcaccct gctgtgcatt agaaaactga aagaacactg aatgtcagct ataaagggaa  198660
```

```
aaataaaaat catcatgtat gaaaaaataa aattcacttc tcaatactac cataataatc 198720
aatccttcac tattcttaaa tagaagattc tacaaatgag taagtccatt tgtcattatg 198780
tgtcaatgtt acatcttttt tttttttttt taggtttgca cctggggtgt atggaaatcc 198840
caggctaggg agctgcaggt gctggccttc atcacagcca ctgtaactcc atatccaagc 198900
cacatctgca acctacacca caggttgcag caacacttcc ttaacccact gagcaagacc 198960
agggattgaa cacccatgct catggatact ggtcgggctc ttaacccact gagccacaac 199020
tggaactcct gttgatgtta tttttaactg agtgcctctg tatttgaata actattaact 199080
tttccagatt caattcattt tgttcatgtg aatgttaaat tttatcatta acatgtaatt 199140
tacttctgaa aaacttatat taaaaaacta gcattaggaa ttcctgttat ggctcagcag 199200
taatgaaccc aactagtacc tgtaaggatg caggtttgat ccctggcctc actcagtggg 199260
ttaaggatcc ggcgttgcca tgagctgtgg tataggttgc agatgtggct tggaaatggc 199320
attcctatgg ctgcggtgta ggccagcagc tacagctcca attcgacccc tagcctggga 199380
acttccatat gctgcagatg aggccctaaa atgaaaaaaa caaacaaaaa acctagcatt 199440
aattttagca ttttttctgt tacaataaaa catcagaaat aattttcatt tctaattagc 199500
ttgataggtt accatgctaa tcaaaactac tggaggtaac agtgataact attaaaacag 199560
caagaaaata aatatacaaa gaaatccaca ttcttttttt tctttttttct ttttagggct 199620 gcacctgtga aacatggaag ttaccaggct agaggatgaa acagctgcag ctgccagcct 199680
ttgccacagc cacagcaaat ctgagctgca tctacaacct acgccatagc ttgcggcaat 199740
gctggatcct taacccagtg aaggaggcca gggaaagaat tgacatcctc atgaagacta 199800
gttgggttct taacctgctg agtcacaaca ggagttccca gaaatcccata ttcctaaatt 199860 gaatgacaat actgtgcata tgcgtgtgtg tgtgtgtgta gacacacaca tataaaatgg 199920
tacagaggaa ataaagctta catcattgtc tccagcgatg tagaaagaca gagtctggct 199980
cccaagatta aaatctatcc aaaagtcctc aagttttttca tctgacggta tttgcagcta 200040
ataaaataaa catataaaac tagtacacta cgctttcaaa agtgacaaaa gaaaattacg 200100
agcatgttat agttgaattt caggaaaaag aaaagaacat agctagaagg taaggggaga 200160
taaaaagcag acatgtacag catttaaatc aattcagaaa caagggaaag aaatgctgct 200220
taatacttca cacaggagaa agctagcttc aagaaatcac aactgttcca agtgcaaata 200280
aagtttaaag tattttcatg tttgaatatc ttcatcaaca ataaacaata atgggcttga 200340
ttaagaaaaa aataaaaaaa tttcaagtag agcttttata tttcatttat ccttggctac 200400
aaacatgcca tttcataaaa tgtcacttca gataaagaat aatgcattgg ctatatctgt 200460
gatgtaatta tgataacatt aataatgctc ttgtcaattt gtgacctgaa atcactcgat 200520
ccctgaatca aagttcatct attaaaattt attaaattga aaacttacct catatttatc 200580
aagaaacgct gataaacaag gaaatgtaaa gaccctgaaa taaagagcag cttgagttaa 200640
agaaaaaatt aacaagcctt cacagcataa tcttgatgag ccatacaaat cacacctagg 200700
atcaaaagga aattgggcag tagtgacaac ttaaaataaa ttgtatttcc ttcttcatca 200760 cttttttaaag attttaatgg aaatttcttt ctgagagaaa acatattact ttgaggatac 200820
tactcgacct accactttga ctaaagttaa actgtaccaa attacttttc atgctattga 200880
ctatgtgcag agattcctaa tttagtttat actagtaata taatggaagt tcccaaagga 200940
ttagatggga gaaggagaat agaagtgcta ataaaaatgg ctgaattcac ggaatacttt 201000
cttggtcaga tgctgttata agtacatagc atgtaaccat ctcattgaat ctttacaaca 201060
```

```
aacatataaa ggtagatatt attagtattc ttatcctata gctaaggaaa ctgaggcaag  201120
gaagcttaaa taacttgtcc aacattaaaa tagtaagagg ggaacctatt atccaaatct  201180
aaccagaatg actcttgcac ttaacctatc ttttgtttcc ttagtaggga aaacaaatgt  201240
gaactcattc atccaatgtg tcctgagcat ctataaggtg ccaggcactg cactaaaaat  201300
actcagttct tctgtcattg aaagaagtaa taaaaattta cattacctat ccttccatga  201360
ccattcctga ggttaaataa cctcagaaag aacatcctta gagtatgtta attataaaag  201420
ataatttata tctgctatat agttttactc cagtatgtga acaaaggagg tagctcaagt  201480
gatatttata cctagatttt taaaaattcc ttaaacatta aatttacaat ttagtacatg  201540
cagttctaaa atatagtaaa ccaatttag acaaagttat taactgatat tgactgaata  201600
aagttttcct ctaaaaagtg caagaaaaa aaaaaggagt tcccatcgtg gagcagcaga  201660
aactaatctg catccgacta ggaaccatga ggttgcaggt tcaatccctg gcctcgctca  201720
gtaggttaag gatctggtgt tgccatgagg tgtggtgtac gtcgcagaca tggctcagat  201780
ctggcgttgc tgtagctgtg gctgtggtgt aggctggcag ctgtagctcc aattcaaccc  201840
ccagcatggg aacctccata tgttgcgagt gcagcccaaa aaagcaaaaa taaaaaaatt  201900
aaaaaaaaaa aaaaaaacac taaaaagtac aaagtcaaat aagaccagtg gaggattatt  201960
tcagcctagc ggtgtgtgct ctctcttgag ctctgtttaa tcattaaatg gttgtatttt  202020
gcattgttta ccttctcttg tctccaagta tgccatttac aaggttgaga acatcctgc  202080 aatcctaatt ttaaaaaga gagagttttt aaaacacag caattataaa gaactattgt  202140
taacttgcta ttctgatact acttactgtt tcaaattcag agtctttaat tcctttaaat  202200
gcattagcaa caaatccat tgaaaaccac tgacatgcta gttcttgcct ctgttttct  202260 gtggtcattc tgcataaagc ttctacgata cccacttgta agtcataatc tttaaaaaaa  202320
attgttaatg tactattaaa attatgaaaa ttaagacttt acagaggtca ctatacttta  202380
taaagtgtta gaacaaccaa gagaaataag gaacatgtta taatttactc atcttttgcc  202440
attttcttca tattgactag aaatatctta tcattataga aatgaataca gaccaaataa  202500
caaaaacaaa tttactaaca gcagacagaa ctaaaaaaaa aattttttaag gaaatttaa  202560 aaaacgccca aatatgcaaa gattgtgtca ctttattatt aagagttgtg aacgcagaat  202620
aattcacaca aaagtctata aatcacaggt aatctttgtt ttccttacag ttattctaaa  202680
gcactttaaa ccagtggttt attctatacg taaatcacta catcaaattt tttgtctttt  202740
cagggttgca cccatggcat atggaagttc tcatgctagg gtcgaatcag agctgcagct  202800
accagcctat gccacagcca caacaatgtg ggatccgagc cttgtctgcg acctacacca  202860
tagctcacca catcactgga tccttaaccc actgagcaag accagggatt gaaccctcgt  202920
cctcagggat actagtcagg ttcattactg ctgatccacg atgggaactc ctacatcaaa  202980
attttctaat atgtaactct gaactggaga ttggctcatg ccatctgcct ctacatggat  203040
taaatcatga gctactgcag ctgctgacat gctgcacccc ctgagcggag ctcaaggtgg  203100
agaccagtta tgaggcactc tgtgctctgg gaaaagtgaa agaatggatc ttgaaacaga  203160 tattttata agatttatg agcccaatac ttgcatctcc tcatatccag aaaaactcca  203220
aaatccttca tgacaactga tgtctgtgtc tagtaataac cttaggacca gcgacaaaat  203280
tctataagat gtgtgcatgg tttatgcac ttccccttc accttcatca tatatatact  203340
gatattcccc ctttcgtctt tggggcagta tctcagagct gtctgaaata ctgctgccag  203400
ggctattctt tctaaaaaca gaaagatgtc acagtcatct gtgaatgtag ccactcgcaa  203460
```

```
gggtgagcta gtgagccctg agggaattca ggaaagaaac aaagaatact gaccccaatt 203520
gctgaagtgc catatcaaag ggtgattcca ctaagcccag acctttgctt cttcccctg  203580
aattccttaa cttgagataa tctggttctg taaatctttt gtttctacta ctcgcttgtt 203640
gctgaaaaag ctcctataaa tcctagctac cccctcacct cctcagagca gttttttcag 203700
ggctacctga gatgctgtct ccctgactta aatcctaatt ttgccccaag taaagcttaa 203760
ctctcagctt tcaggttgtg catttttta  aattgacata acttaggaaa gacaatttga 203820
gttctttaaa gaaaaacata gctttacaat tcaaatatat gagtcccaag aatatcaaac 203880
cttctaattt catataatac agttaagaca tttctgggca aagggaattc aaatctatta 203940
ggaaactgag ttatgattca tatatctacc attaggcaca aattatattt gacaactcct 204000
actataacac ttattatttt tagtccctca gatatttatc ctttaattac ttattagagc 204060
aattaaaact tgcttgattg tacatggaca gcttatacgt accctatttt cacattacaa 204120
tgttaacatt atttttgattg agatactata ttctaataat aaatttgaaa aatttcaaa  204180
tatgaacatt ttgaaaaaac atacctccag catctaaaat cctttctccc atactactcc 204240
tgtgaatcaa acaacagat  tatatactag gactactatc aattaaatat aaagctcata 204300
tgttgactag tatcaatacg actttggcag aaaacatatt cataaattat attagaaatc 204360
tacaatagtt tattattttt aattattaat ggatgtcatg gttgccttat ttgccttata 204420
aaacattatt atattcttga cctgaaccac taatttaccc ataaagcaca aattattaca 204480
tgagaatcaa catttcttgg ttaaagagta ttttcctggc atcttgaggc atcttgtcaa 204540
gcatagcatt cattttctt  agagtctaga aaagaaaaaa agttaatccg ttaactttat 204600
atattcaatg aaacattaag tacttagaga tatattctag gtacataaac ttagaagcct 204660
atttttttt  aatcacagtt aatcacagca tgttatacaa ggaataaagg gtggaggaaa 204720
gtatgtatgt ataaaatagt gaatacaaga aaatataaaa cacagaatat caaaaacaaa 204780
ataccatg   attcctgtac ctaaagcagt tatactctta gcagcatgac atgtgtttat 204840
tactactcta ttataggagt taaggaagca aatgatagta ccccattgat atctgttctt 204900
gtggtcacac acatgtacat acacatagac actaatacaa gttatttta  gcatttaaat 204960
acttaagaac tccaaatatg tagacagtat agtttatatt ttcatatgag ctataggtat 205020
acacaaactc acatgattat aaatttccaa cacacacata taatatactc atgtcaggca 205080
atgaattgtt aggacaatca aaacagacca tattaaaatt aatttaatgc caagataaca 205140
taattattca atttgataaa ttgctaccaa actttcttca ttttctcttt aggttttaaa 205200
agaaaatcta aaaaatgac  tttacctcct gctgaacaca aatattcact cttgagtcaa 205260
taaccagggc acaaattcgg ggtatgaaac tttccactac ttgcctttta cctgaataaa 205320
agtgttaagt tattggcaaa tgtgtacttt aaactctttt aaatgacaat cttttctcat 205380
atgagttaat ggaaaggaca tactagttca gttcagaaga aggcccactg actggcctgg 205440
caccaggaca catgaaattc agttctggtt ctgccactaa ctagctatgt aactgaaaaa 205500
tcaccattca acagatgtga ctaatcttaa ctctggcaaa ggaataaccc cagatccagc 205560
tgcttctttt aggcacataa agcagtatta cttttttgga taaacagata tagttcaaaa 205620
cttctatttt gaggttttca caaaaactgg cctcggtaat ttacagtcat actttcaaaa 205680
ctccataatg gccattaaca ccctttatct tataaagatc taaatatcct cacctatgtc 205740
taaatgtgac cctgtcctct caaaagacaa ggttttatta acattaacta tattcagaga 205800
aatctgccac atgctaattt catgatgcaa atttttaaaa taattttaaa taatggcaat 205860
```

```
actgcaacag aaaatgtaca gttttataag gtaactaact acattaaaag aaaaaaaatc    205920
actgaattac gtgaaaagat aaaatgattt acttaaaaaa agttgaatca cttcataatc    205980
atgggtgctt taggactgtt ttctcccta  aaaacttaag aattgagact agattgttag    206040
gtaattgcaa agaaacctat gaaaaggtag cattaactac tactgaaata aatagcaatt    206100
gatcttttaa aatgttttgg ctttgaaggc agcaaatagc tgtttcttta tttataagca    206160
attcaccagg ctcaattacc aatcatagat aattcttcct caaccaacac agagataaaa    206220
taacttgaac caactgtctg gcactaggca atgccaagca caagtgaaat tatgagttat    206280
aacatgttct gtattctcct tgtactactg agaattttgt ttcatgagac caaggacaaa    206340
ctatggccca cagaccaaat ctgacccact gccccttttc ctatggctgt attcatcagc    206400
aggtattctg tggaaatacc tatcatgatt tagtgagcca gtagtctcag gtgaagttca    206460
ttcattctga taaaatgagc caccatcaac caccactgaa aggctctggt aattagcttg    206520
ggctgcagag ttggtaaggt ttcttaatga attcaacctc aaactccaag gcaaaatagt    206580
atttacatga gaaacttata cttcagtaaa gttacttcaa tgaaactatg gtcatctgaa    206640
tcacaagtaa tgtgcagctg ctttatacat tttccaggct atcaaaagct aagacaggaa    206700
gtgacatctc cattcccaac acaaatttat aggggatata ttttttccaa gctccaacca    206760
cagacccagc agcatttta  gatgctgatg taagtgcaaa ggaaatttcc ttatttcaaa    206820
gttcatttaa ctgtgcaact gaagagcttc cacctaacct tcaactgaaa gtgattaaaa    206880
gtccttaaaa gtcattaaaa gtccttaaaa gtcatctcat ggcaatgaca ctctaaatgg    206940
caaatattaa gaacaaaagt ttgaaatatt tccataaatg acttccaagt gatgaatatg    207000
ctcaattaaa aatcatgttc atgaactgat accagtattc ggcattatct gcataaaaag    207060 acattttct  aatgcaataa atacaaaacc tcattacaga taagcatgaa caaataaaca    207120
tttgcaatta attttttaa  cagcaaacac taactctgaa ccttaactaa gaattaatga    207180
acccgactag catccatgag gatgcaggtt caatccctgg cctgctcagt gggttaagga    207240
tctggcatta ctgtaagctg tggtgtaggt cacagactca gctcggattc tgcgttgctg    207300
tggttctggc ataggctggc ggtacagctc tgattcgacc tctagcctgg gaacctccat    207360
gtgctgccag tgcagcccta aaagacaaaa taaataaata aataaaaatt aaaaagaga    207420 gactgagatt cttattaata gacctgtatc acaaaaacac tgtactagat tattgctata    207480
ttttgagttg cattaataaa acatttgtgg acatttgttt tctttccagt ttaataagta    207540
cttacataat accctcattt tctttcttgg cccacaaagt ctaaatatt  taccacctga    207600 cccttacag  aaaagatctg ttgatccatg aattaggtaa tgaactccta atacgacaat    207660
acaatgagaa ttgcaaaatt ataccaaaac tctaacagca aattattgtt ccaacagaaa    207720
tagaatgttc atgataccatt catcatcaat gtcatgtatg acctgaaaag aaagtgaata    207780
atatttaatt gaaacttac tctcttatac ttaaatcatt acaaatagta ttaaagtaac     207840
atgtaacttt tgaacttaac catgtgatta cttaattaat caggataaaa tcactagcca    207900
atctgttagt gatttttta  ggctcagggc atcgagaaca caaattgttt ttaaataaac    207960
acatgctttg taacattggt gaatcaacgt gactgttacc atcaaaagat caaaaagtc     208020 ttctatcata tttataacag cttcatcttt tgaacttcct tgactcagaa taatctcctt    208080 ggattttca  aaccaggcaa ccatgtaaaa aaaagaaatg tatacattag ttactttgaa    208140 ttcagttta  caatttaag  aatgtattca cacaaacagt aaacctaata gagaaatatc    208200 gaaataaat  tccagcattg catcaaagta aatttatgct cttaaacatc ttcacggttt    208260
```

```
ttgcttttg  ataattcact  atatgtcccc  cccccctt  tttttttgg  tcttttgcc   208320 tcttctaggg  ccgcttccca  tggcatatgg  aggttcccag  gctaggggtc  taatcggagc  208380
tgtagccgct  ggcctacacc  acagccacag  caacccggga  tccgagccgc  gtctgcaacc  208440
tacaccacag  ctcacggcaa  tgctggatcg  ttaacccact  gagcaagggc  agggatcgaa  208500
cccgcaacct  catggttcct  agtcggattc  gtttaccact  gagccacgac  gggaactcct  208560
atatgtttcc  attttaaaga  tgcaaatgga  tgaagttaat  tcatttccaa  agtagatgat  208620
c                                                                    208621
```

<210> SEQ ID NO 16
<211> LENGTH: 2889
<212> TYPE: DNA
<213> ORGANISM: Xenopus tropicalis

<400> SEQUENCE: 16

```
gtgaagccgt  gacaagctga  caggctctgg  aagcggatat  caccatcatg  catcccaaac    60
aggagtctaa  gctggaagca  atattgacc   acgggttgag  gaccaaagga  cacgaccttc   120 gcccctgaa   atcatttctt  ctgactgaat  cctgtgccgg  cacatccatt  aaatgcagca   180
aattccttct  tggaaaactt  gacaaactga  tatgcatgga  gcttgatcag  agagaagtaa   240
agaacgcatt  gctggttctt  aatgtaatac  ttaaatttgc  cagctgtatg  acactgaata   300
atgaggaatg  gctgactgct  tccataaaac  agggacttgt  acagaagatg  attatttggc   360
ttgaaaaatc  aacatatttt  ttggcttata  gtgaaaaaca  gaaaaatgaa  actgttctca   420
actttgcaga  agatttttt   gatattgtta  tgctcgttca  tgaccacagc  agtgagggaa   480
aaatgcagat  actggagcat  tcctcgtca   gagcatgttc  cttagtatcc  aacgctgcaa   540
caaatatctt  cgttaaacaa  gaggtagtgc  gtaggctgaa  tttaatgctg  aacactatgc   600
ctctggttgc  cagaaagaaa  atcctttcta  cagaagagat  gacttctgcc  atggcatcta   660
tggctaaaag  aatattagat  gctggcgatt  ttgatttgca  agtggcgatc  acagaagctt   720
tgtgccggat  gacatcagaa  gcgcaaagag  aactcaccag  tcagtggttt  cccatggaat   780
ttatcgctga  agcattcaaa  agaataaagg  attctgagtt  tgaaactgac  tgcaggaaat   840
tccttaacct  gatcaatgga  attttgggcg  gcaaaaaaag  cgttgttacc  ttgccttgtc   900
tgtctgcata  tcttgacaac  cacaagttcc  agatgccatg  tgatgaaaag  ctggaagaat   960
tctggattga  ttttaatacc  ggtacccaaa  gcatttcctt  ctacatttct  gcaggtgccg  1020
cagaggagca  tcagtgggac  acagtatgcg  tgaaagacag  tgatgtgatt  gtgtacagca  1080
ttgcagaagt  agacaataac  aagttactga  cagtggatct  gaaagcaccg  attgccgccg  1140
gtcagtatga  agggaagcag  atacggatat  attttagttg  tcctttggat  atcttgtctg  1200
ctgctcagag  ggtgtttgct  gcacaaaaga  taaggacttt  tattaaaaaa  caaccgcgt   1260 cagatgcaga  acaacagtc   cgtgttatat  ttgaagaatg  tcgatctcag  atccttctgt  1320
ctgaaagcca  agggtccaat  tcttctgtga  agcctgtggc  tgaaccagat  gtcaaagatt  1380
ttgctgggaa  aaaccaacct  ccctctgcag  cttcaagcct  caagcaaact  acttgtaacc  1440
acgagcataa  cactaacagc  ttaatgccta  caactcctgt  taaagttaaa  atgtcagaat  1500
cttcaatggt  tgggtctgga  ctgaagataa  ctaacatagc  cacaaacaac  cctgcatcta  1560
ggagaattag  gacaaaacct  cctttagaaa  tggtaaggcc  tgctgaaagg  aacactgtgc  1620
caccaaataa  atcccgaggt  gggtccccctt  gcagcgacag  aactcctcaa  ctgccaaagc  1680
ataaatccag  tactgatgct  gcatgtacat  tccaatatgt  aaacaaagct  cctaaagatg  1740
```

-continued

| | |
|---|---|
| aattaaatga gattgtgcca gacacacaat attgtgccac aaaggattca tctttattgc | 1800 |
| ctggtctcac taagagatct gtaaatcaac atgaaaggaa caggaagcag aaaacagtg | 1860 |
| gcggttttgg aaataaaata agtgtatcgt ctgtatgtat tgctaatcag ggaaagatca | 1920 |
| gcagccacct tgtcaagcag cattctaatg aaatatccac aactcccaca aaagaaatgt | 1980 |
| ctgctagatc atcagaatca agcattcaga acactgcga gaaacacttg aagagaaac | 2040 |
| ctaaagaact gatccaggct acagatttgt tagttgagaa tatcagaaga aagtacgcca | 2100 |
| ggctgacaga ggaggataaa agagaagaga atacgtttga gaggaaaaat gtggataaac | 2160 |
| atcccctgca tacaaacaag gataaaaata gaacaagagg cttcaatcag cacagcccta | 2220 |
| aagattttc aacgacgaca aaaaagccat ggaaggatgt ttatgatttc cagtttagcg | 2280 |
| caacagataa tccaacgatc aatcttgagg tatcagcacc tactgtgtcg gagaggatga | 2340 |
| gcagcaaagc gctggccatt ggcaagaaat caaccaaaaa caaacagaag ggaaagacag | 2400 |
| gcacagagat aaagactaaa gctcaccaaa ggcatctgtt cagtgatact gaaagtgaga | 2460 |
| gaggggggtga tgatactaaa tccaattaa gctggttgca agaacaacac agcaaaacga | 2520 |
| aacctcccat tgcaacctat agaaggcaaa aagcacagaa gcaacaagaa caaaccatgc | 2580 |
| catacaagat gaggcacata acaacaaata attcaccaga gcccaaaaca ggcaagaaat | 2640 |
| catataatag gagtggcggc aataagcata ataagctcaa gcgtccttgc agaacagctg | 2700 |
| ccaaaagcac caactataaa gatctctcca actcagagtc agatgctgag gtgcctttt | 2760 |
| caccccccgaa aagagaggag cctgtaagac gcagatgttt gaaataaaaa aaaaaaaaaa | 2820 |
| aaaaaaaaaa aaaaaaaaaa aaaaaaaaaa aaaaagaaa aaaaaaaaaa aaaaaaaaaa | 2880 |
| aaaaaaaaa | 2889 |

<210> SEQ ID NO 17
<211> LENGTH: 5559
<212> TYPE: DNA
<213> ORGANISM: Pan troglodytes

<400> SEQUENCE: 17

| | |
|---|---|
| gaggcgcaga gttgcgacgc tcggcagcat aggggggcggc tccaccgaca ctacgcggac | 60 |
| gcctccttcc gcagatacac agtcatcatc ttactagttc tctgtgttgc tcgctaacca | 120 |
| gtcccccagt tcagtagact ggggcccaaa gcctgcttac ttgacaggtg tttatttgt | 180 |
| cttgcttttt ttttttttaa atgaagtcaa aatgccaata agaccagatc tccagcagtt | 240 |
| ggaaaaatgc attgatgatg ctttaagaaa aaatgatttc aaacctttga aaacactttt | 300 |
| gcaaattgat atttgtgaag atgtgaagat taaatgcagc aaacagtttt tccacaaggt | 360 |
| ggacaacctt atatgcaggg aacttaataa agaggatatc cacaatgttt cagccatttt | 420 |
| ggtttctgtt ggaagatgtg gcaaaaatat cagtgtattg gggcaagctg gacttctaac | 480 |
| gatgataaaa caaggactaa tacaaaagat ggttgcctgg tttgaaaaat ccaaggacat | 540 |
| tattcagagt caaggaaatt caaaagatga agctgttcta aatatgatag aagacttagt | 600 |
| tgatcttctg ctggtcatac atgatgtcag tgatgaaggt aaaaaacaag tagtggaaag | 660 |
| tttcgtacct cgcatttgtt ccctggttat tgactcaaga gtgaatattt gtattcagca | 720 |
| agagataata aaaagaatga atgctatgct tgacaaaatg cctcaagatg cccggaaaat | 780 |
| actctctaac caagaaatgt taattctcat gagtagtatg ggagaaagga tttagatgc | 840 |
| tggagattat gacttacagg taggcattgt agaagctttg tgtagaatga ccacagaaaa | 900 |
| acaaagacaa gaactggcac atcagtggtt ttcaatggat tttattgcta aggcatttaa | 960 |

-continued

```
aagaattaag gactctgaat ttgaaacaga ttgcaggata tttctcaacc ttgtaaatgg    1020
catgcttgga gacaaaagaa gggtctttac atttccttgt ttatcagcat tcttgataa    1080 atatgagctg caaataccat cagatgaaaa acttgaggaa ttttggattg attttaatct   1140
tgggagtcag actctctcat tctacattgc tggagataat gatgatcatc aatgggaagc   1200
agttactgtg ccagaggaaa aagtacaaat atacagcatt gaagtgagag aatcaaagaa   1260
gctactgaca ataattctga aaaatacagt aaaaattagc aaaagagaag ggaaagaatt   1320
gcttttgtat tttgatgcat cactagaaat cactaatgta actcaaaaaa ttttggtgc    1380 aaataaacat agggaatcta tcagaaaaca aggtatttca gttgccaaaa cgtcgctgca   1440 tatactttt gatgcaagtg gatcacagat tctagtgcca gaaagtcaaa tctcaccagt    1500
cggagaagag ctcgttagtt taaggaaaa atcaaagtcc ccaaaggaat ttgctaaacc    1560
ttcaaaatat atcaaaaaca gtgacaaagg gaatagaaat aatagtcagc ttgagaaaat   1620
tactcctagc aaaagaaaaa tgtctgaagc atcaatgatt gtttctggtg cagatagata   1680
cactatgaga agtccagtac ttttcagcaa cacatcaata ccaccacgaa gaagaagaat   1740
taaaccacca ctgcaaatga tgagttctgc agagaaacct agtgtttctc aaacatcaga   1800
aaatagagtg gataatgctg catcactgaa atctagatca tcagaagaaa gacatagaag   1860
agataataca gacaaacata tcaaaactgc taagtgtgta gaaaacacag aaaataagaa   1920
tgttgaattc ccaaaccaaa attttagtga actccaggat gttataccag attcacagcc   1980
agtggaaaaa agagatcatg ctatattacc tggtgtttta gacaacatct gtggaaataa   2040
aatacacagc aaatgggcat gttggacacc tgtaacaaac attgaactat gtaataacca   2100
aagagcaagt acttcatcag gagacacatt gaatcaagat attgttataa ataaaaaact   2160
tactaaacaa aaatcatcct cttcaatatc tgatcataat tctgaaggaa caggaaaagt   2220
gaaatataag aaagaacaaa ccgaccatat caaaatagat aaagcagaag tagaagtttg   2280
caagaaacac aatcagcaac aaaatcatcc taaatattca gggcagaaaa atactgaaaa   2340
tgccaagcag agtgattggc ctgttgaatc tgaaactact tttaaatcgg ttctcctaaa   2400
taagacaatt gaagaatcgc tgatatataa gaagaaatac atattgtcaa agatgtgaa    2460 tactgctact tgcgataaaa atccatctgc tagcaaaaat gtgcaaagtc atagaaaagc   2520
agagaaagaa ttgacttctg agcttgattc ctgggatttg aaacaaaaaa aaatgagaga   2580
aaagtcaaaa gggaaagaat ttaccgatgt agcagaatcc ttgataagcc aaatcaataa   2640
aagatacaaa acaaaagatg acatcaagtc tacaagaaaa ttaaaggagt ctttgattaa   2700
cagtgatttt tcaaacaaac tgttgtacct actcagtaag gaaaaagttc agaaaaaaag   2760
ctacagaaaa ctgaagacta cctttgttaa tgttacttct gaatgcccag tgaatgatgt   2820
ttacaatttt aatttgaatg gagctgatga ccctatcata aaacttggaa tccaagagtt   2880
tcaagctaca gctaaagaag cttgtgcgga taggtcaatt agattggtag gtccaaggaa   2940
tcatgatgaa cttaaatctt ctgtcaaaac aaaagataaa aaattataa caaatcatca    3000 aaagaaaaat ctgtttagtg atactgaaac agagtacaga tgtgatgaca gcaagactga   3060
tattagctgg ctaagagaac caaaatcaaa accacagcta atagactata gcagaaataa   3120
aaatgtgagg aatcataaaa gtggaaaatc aagatcatcc ttggaaaagg acagccaag    3180 ctctaaaatg acacccagta aaaatatcat gaaaaagacg gacaagacaa ttccggaagg   3240
aagaatcaga cttccacgaa aagcaaccaa aacaaaaaaa aattataaag atctctcaaa   3300
ttcagaatca gagtgtgaac aagaattttc acattcattt aaagagaaca taccagtaaa   3360
```

```
ggaggagaat atccattcca gaatgaaaac ggtaaagcta ccaaagaaac aacagaaagt    3420
cttctgtgct gaaacagaaa aggaactatc aaaacaatgc aaaaactcat ctctactaaa    3480
agatgctata cgagataatt gccttgactt atctcccaga tctttatctg gcagtccatc    3540
atctatagaa gtaacgagat gtatagagaa ataacagaa aaggatttta ctcaggatta    3600
tgactgcata acaaaatcta tatccactta tccaaaaact tcatcacttg aatccttaaa    3660
tagtaacagt ggagttggag gtacaataaa gtcacccaaa acaatgaga aaaacttcct    3720 gtgtgcaagt gaaagttgtt caccaattcc acgaccactg tttttgccca gacatactcc    3780
aactaagagt aatactattg taaatagaaa aaaaaaaagt tctctggtac ttacacaaga    3840
aacacaaaac tgtaacagct attcagatgt aagcagttat agttcagaag aacggtttat    3900
ggaaattgaa tctccacata tcaatgaaaa ttatatacaa agcaaaagag aggaaagtca    3960
tttagcatct tcattatcca agtctagtga aggaagagag aaaacgtggt ttgatatgcc    4020
ctgtgatgct actcatgtat caggccccac ccaacatctt agtcgcaaaa gaatatatat    4080
agaagataat ctaagtaatt ccaatgaagt agaaatggaa gagaaaggag aaaggagagc    4140
aaacttgctt cccaaaaaac tgtgtaaaat tgaagatgca gatcatcata tcccacaaaat    4200 gtctgaaagt gtatcttcat tatcaacaaa tgactttctt attccttggg agacctggcg    4260
aaatgaattt gcaggtatag atgactta tgagacttac gagaggctca attcagaatt    4320
taagagaagg aataatatcc gacataaaat gttgagttat tttactacgc agtcttggaa    4380
aacagctcag caacatctga gaacaataaa tcatcaaagt caggactcta ggattaaaaa    4440
acttgataaa ttccaattca ttatcataga ggagctggag aattttgaaa aagattcaca    4500
gtctttaaaa gatttggaaa aggaattttgt ggactttgg gaaagatat ttcagatgtt    4560 cagtgcatat caaaaaattt tacttcttag gcttcatctt ttgaaaactt cattggctaa    4620
aagtgtcttc tgtaatactg ataatgaaga aactgttttt acatccgaga tgtgtttgat    4680
gaaagaagat atgaaagtgc tgcaagacag gcttcttaag gacatgctag aagaggagct    4740
tcttaatgta cgcagagaac tgatgtcagt attcatgtct catgaaagaa atgctaatgt    4800
gtgaaatcta gttttatca ccatacttta tctaattatt attctctgtg tataactgag    4860
gaaataagaa tagtcctaca aagagaaaaa tatacatgtc accgaagcaa gtgtacccct    4920
tataggaacc ctcaaattaa aaaaaaatgt ctttttaatgg atgagaggga accactataa    4980
catgagtcca agcccagaag acttctgtct atacaatatt tttttttact tttggagata    5040
gaagctttaa gaaactttt tgagttaatt atactcataa aatgagtttc tttaataaat    5100
taaattttat tgtgtaaaat gtattattac ataaaatgtg tttttgaatc aatgcagttt    5160
ggggatgaat ataattaaaa tatgtttaat aacttagaat tcaactaata aaaatttagc    5220
cacacttaca aggggagga agtccctagt ttaaaatgta taactgagtg gtagatcagt    5280
actttcagca cactgttgga aacatttatt cagatatggc tctaatgtat taggaagcac    5340
taaatggcct aaaaaagcta ctacattgcc taaatatgtt aattcaatat agaagtccta    5400
tttcataagc aggctgtttg acaaatactt ttaatctagt agtcattgta atatcttgct    5460
agattaattt ataaaaatga gtatacattt gatttgcttt taatgaagtt gaaataaatg    5520
cttatgtcac ttgaataaat ataaatcatt atattccta                           5559
```

<210> SEQ ID NO 18
<211> LENGTH: 1225
<212> TYPE: PRT
<213> ORGANISM: Homo sapiens

<400> SEQUENCE: 18

```
Met Ser Ser Pro Leu Gln Arg Ala Val Gly Asp Thr Lys Arg Ala Leu
1               5                   10                  15

Ser Ala Ser Ser Ser Ser Ala Ser Leu Pro Phe Asp Asp Arg Asp
            20                  25                  30

Ser Asn His Thr Ser Glu Gly Asn Gly Asp Ser Leu Leu Ala Asp Glu
            35                  40                  45

Asp Thr Asp Phe Glu Asp Ser Leu Asn Arg Asn Val Lys Lys Arg Ala
        50                  55                  60

Ala Lys Arg Pro Pro Lys Thr Thr Pro Val Ala Lys His Pro Lys Lys
65                  70                  75                  80

Gly Ser Arg Val Val His Arg His Ser Arg Lys Gln Ser Glu Pro Pro
                85                  90                  95

Ala Asn Asp Leu Phe Asn Ala Val Lys Ala Ala Lys Ser Asp Met Gln
            100                 105                 110

Ser Leu Val Asp Glu Trp Leu Asp Ser Tyr Lys Gln Ser Gln Asp Ala
            115                 120                 125

Gly Phe Leu Glu Leu Val Asn Phe Phe Ile Gln Ser Cys Gly Cys Lys
130                 135                 140

Gly Ile Val Thr Pro Glu Met Phe Lys Lys Met Ser Asn Ser Glu Ile
145                 150                 155                 160

Ile Gln His Leu Thr Glu Gln Phe Asn Glu Asp Ser Gly Asp Tyr Pro
                165                 170                 175

Leu Ile Ala Pro Gly Pro Ser Trp Lys Lys Phe Gln Gly Ser Phe Cys
            180                 185                 190

Glu Phe Val Arg Thr Leu Val Cys Gln Cys Gln Tyr Ser Leu Leu Tyr
            195                 200                 205

Asp Gly Phe Pro Met Asp Asp Leu Ile Ser Leu Leu Thr Gly Leu Ser
210                 215                 220

Asp Ser Gln Val Arg Ala Phe Arg His Thr Ser Thr Leu Ala Ala Met
225                 230                 235                 240

Lys Leu Met Thr Ser Leu Val Lys Val Ala Leu Gln Leu Ser Val His
                245                 250                 255

Gln Asp Asn Asn Gln Arg Gln Tyr Glu Ala Glu Arg Asn Lys Gly Pro
            260                 265                 270

Gly Gln Arg Ala Pro Glu Arg Leu Glu Ser Leu Leu Glu Lys Arg Lys
        275                 280                 285

Glu Leu Gln Glu His Glu Glu Ile Glu Gly Met Met Asn Ala Leu
    290                 295                 300

Phe Arg Gly Val Phe Val His Arg Tyr Arg Asp Val Leu Pro Glu Ile
305                 310                 315                 320

Arg Ala Ile Cys Ile Glu Ile Gly Cys Trp Met Gln Ser Tyr Ser
                325                 330                 335

Thr Ser Phe Leu Thr Asp Ser Tyr Leu Lys Tyr Ile Gly Trp Thr Leu
            340                 345                 350

His Asp Lys His Arg Glu Val Arg Val Lys Cys Val Lys Ala Leu Lys
        355                 360                 365

Gly Leu Tyr Gly Asn Arg Asp Leu Thr Ala Arg Leu Glu Leu Phe Thr
    370                 375                 380

Ser Arg Phe Lys Asp Arg Met Val Ser Met Ile Met Asp Arg Glu Tyr
385                 390                 395                 400

Ser Val Ala Val Glu Ala Val Arg Leu Leu Ile Leu Ile Leu Lys Asn
                405                 410                 415
```

```
Met Glu Gly Leu Leu Thr Asp Ala Asp Cys Glu Ser Val Tyr Pro Val
            420                 425                 430

Val Tyr Pro Ser Asn Arg Gly Leu Ala Ser Ala Ala Gly Glu Phe Leu
            435                 440                 445

Tyr Trp Lys Leu Phe Tyr Pro Glu Cys Glu Ile Arg Thr Met Gly Gly
            450                 455                 460

Arg Glu Gln Arg Gln Ser Pro Gly Ala Gln Arg Thr Phe Phe Gln Leu
465                 470                 475                 480

Leu Leu Ser Phe Phe Val Glu Ser Glu Leu His Asp His Ala Ala Tyr
                    485                 490                 495

Leu Val Asp Ser Leu Trp Asp Cys Ala Gly Ala Arg Leu Lys Asp Trp
            500                 505                 510

Glu Gly Leu Thr Ser Leu Leu Leu Glu Lys Asp Gln Asn Leu Gly Asp
            515                 520                 525

Val Gln Glu Ser Thr Leu Ile Glu Ile Leu Val Ser Ser Ala Arg Gln
            530                 535                 540

Ala Ser Glu Gly His Pro Pro Val Gly Arg Val Thr Gly Arg Lys Gly
545                 550                 555                 560

Leu Thr Ser Lys Glu Arg Lys Thr Gln Ala Asp Asp Arg Val Lys Leu
                    565                 570                 575

Thr Glu His Leu Ile Pro Leu Leu Pro Gln Leu Leu Ala Lys Phe Ser
            580                 585                 590

Ala Asp Ala Glu Lys Val Thr Pro Leu Leu Gln Leu Leu Ser Cys Phe
            595                 600                 605

Asp Leu His Ile Tyr Cys Thr Gly Arg Leu Glu Lys His Leu Glu Leu
            610                 615                 620

Phe Leu Gln Gln Leu Gln Glu Val Val Lys His Ala Glu Pro Ala
625                 630                 635                 640

Val Leu Glu Ala Gly Ala His Ala Leu Tyr Leu Leu Cys Asn Pro Glu
                    645                 650                 655

Phe Thr Phe Phe Ser Arg Ala Asp Phe Ala Arg Ser Gln Leu Val Asp
            660                 665                 670

Leu Leu Thr Asp Arg Phe Gln Gln Glu Leu Glu Glu Leu Leu Gln Ser
            675                 680                 685

Ser Phe Leu Asp Glu Asp Glu Val Tyr Asn Leu Ala Ala Thr Leu Lys
            690                 695                 700

Arg Leu Ser Ala Phe Tyr Asn Thr His Asp Leu Thr Arg Trp Glu Leu
705                 710                 715                 720

Tyr Glu Pro Cys Cys Gln Leu Leu Gln Lys Ala Val Asp Thr Gly Glu
                    725                 730                 735

Val Pro His Gln Val Ile Leu Pro Ala Leu Thr Leu Val Tyr Phe Ser
            740                 745                 750

Ile Leu Trp Thr Leu Thr His Ile Ser Lys Ser Asp Ala Ser Gln Lys
            755                 760                 765

Gln Leu Ser Ser Leu Arg Asp Arg Met Val Ala Phe Cys Glu Leu Cys
            770                 775                 780

Gln Ser Cys Leu Ser Asp Val Asp Thr Glu Ile Gln Glu Gln Ala Phe
785                 790                 795                 800

Val Leu Leu Ser Asp Leu Leu Ile Phe Ser Pro Gln Met Ile Val
                    805                 810                 815

Gly Gly Arg Asp Phe Leu Arg Pro Leu Val Phe Phe Pro Glu Ala Thr
            820                 825                 830

Leu Gln Ser Glu Leu Ala Ser Phe Leu Met Asp His Val Phe Ile Gln
            835                 840                 845
```

```
Pro Gly Asp Leu Gly Ser Gly Asp Ser Gln Glu Asp His Leu Gln Ile
    850                 855                 860
Glu Arg Leu His Gln Arg Arg Leu Leu Ala Gly Phe Cys Lys Leu
865                 870                 875                 880
Leu Leu Tyr Gly Val Leu Glu Met Asp Ala Ala Ser Asp Val Phe Lys
                885                 890                 895
His Tyr Asn Lys Phe Tyr Asn Asp Tyr Gly Asp Ile Ile Lys Glu Thr
            900                 905                 910
Leu Thr Arg Ala Arg Gln Ile Asp Arg Ser His Cys Ser Arg Ile Leu
        915                 920                 925
Leu Leu Ser Leu Lys Gln Leu Tyr Thr Glu Leu Leu Gln Glu His Gly
    930                 935                 940
Pro Gln Gly Leu Asn Glu Leu Pro Ala Phe Ile Glu Met Arg Asp Leu
945                 950                 955                 960
Ala Arg Arg Phe Ala Leu Ser Phe Gly Pro Gln Gln Leu Gln Asn Arg
                965                 970                 975
Asp Leu Val Val Met Leu His Lys Glu Gly Ile Gln Phe Ser Leu Ser
            980                 985                 990
Glu Leu Pro Pro Ala Gly Ser Ser  Asn Gln Pro Pro Asn  Leu Ala Phe
        995                 1000                 1005
Leu Glu  Leu Leu Ser Glu Phe  Ser Pro Arg Leu Phe  His Gln Asp
    1010                 1015                 1020
Lys Gln  Leu Leu Leu Ser Tyr  Leu Glu Lys Cys Leu  Gln His Val
    1025                 1030                 1035
Ser Gln  Ala Pro Gly His Pro  Trp Gly Pro Val Thr  Thr Tyr Cys
    1040                 1045                 1050
His Ser  Leu Ser Pro Val Glu  Asn Thr Ala Glu Thr  Ser Pro Gln
    1055                 1060                 1065
Val Leu  Pro Ser Ser Lys Arg  Lys Arg Val Glu Gly  Pro Ala Lys
    1070                 1075                 1080
Pro Asn  Arg Glu Asp Val Ser  Ser Ser Gln Glu  Ser Leu Gln
    1085                 1090                 1095
Leu Asn  Ser Ile Pro Pro Thr  Pro Thr Leu Thr Ser  Thr Ala Val
    1100                 1105                 1110
Lys Ser  Arg Gln Pro Leu Trp  Gly Leu Lys Glu Met  Glu Glu Glu
    1115                 1120                 1125
Asp Gly  Ser Glu Leu Asp Phe  Ala Gln Gly Gln Pro  Val Ala Gly
    1130                 1135                 1140
Thr Glu  Arg Ser Arg Phe Leu  Gly Pro Gln Tyr Phe  Gln Thr Pro
    1145                 1150                 1155
His Asn  Pro Ser Gly Pro Gly  Leu Gly Asn Gln Leu  Met Arg Leu
    1160                 1165                 1170
Ser Leu  Met Glu Glu Asp Glu  Glu Glu Leu Glu  Ile Gln Asp
    1175                 1180                 1185
Glu Ser  Asn Glu Glu Arg Gln  Asp Thr Asp Met Gln  Ala Ser Ser
    1190                 1195                 1200
Tyr Ser  Ser Thr Ser Glu Arg  Gly Leu Asp Leu Leu  Asp Ser Thr
    1205                 1210                 1215
Glu Leu  Asp Ile Glu Asp Phe
    1220                 1225

<210> SEQ ID NO 19
<211> LENGTH: 1240
<212> TYPE: PRT
```

<213> ORGANISM: Mus musculus

<400> SEQUENCE: 19

```
Met Pro Thr Leu Trp Ser Pro Ser Thr Gln His His Gly Ser Ser Ser
1               5                   10                  15
Gly Ser Glu Ser Ser Pro Leu Gln Lys Ser Val Arg Arg Ala Gln Met
            20                  25                  30
Ala Leu Ser Pro Cys Ser Ser Ser Ile Leu Pro Cys Asp Asp Arg Asp
        35                  40                  45
Ser Gln Gly Thr Ala Glu Trp Asp Ser Pro Ser Thr Asn Glu Asp Ser
    50                  55                  60
Asp Phe Glu Asp Ser Leu Arg Arg Asn Val Lys Lys Arg Ala Ala Lys
65                  70                  75                  80
Gln Pro Pro Lys Ala Val Pro Ala Ala Lys His Arg Lys Lys Gln Ser
                85                  90                  95
Arg Ile Val Ser Ser Gly Asn Gly Lys Asn Glu Ser Val Pro Ser Thr
            100                 105                 110
Asn Tyr Leu Phe Asp Ala Val Lys Ala Ala Arg Ser Cys Met Gln Ser
        115                 120                 125
Leu Val Asp Glu Trp Leu Asp Asn Tyr Lys Gln Asp Glu Asn Ala Gly
    130                 135                 140
Phe Leu Glu Leu Ile Asn Phe Phe Ile Arg Ala Cys Gly Cys Lys Ser
145                 150                 155                 160
Thr Val Thr Pro Glu Met Phe Lys Thr Met Ser Asn Ser Glu Ile Ile
                165                 170                 175
Gln His Leu Thr Glu Glu Phe Asn Glu Asp Ser Gly Asp Tyr Pro Leu
            180                 185                 190
Thr Ala Pro Gly Pro Ser Trp Lys Lys Phe Gln Gly Ser Phe Cys Glu
        195                 200                 205
Phe Val Lys Thr Leu Val Tyr Gln Cys Gln Tyr Ser Leu Leu Tyr Asp
    210                 215                 220
Gly Phe Pro Met Asp Asp Leu Ile Ser Leu Leu Ile Gly Leu Ser Asp
225                 230                 235                 240
Ser Gln Val Arg Ala Phe Arg His Thr Ser Thr Leu Ala Ala Met Lys
                245                 250                 255
Leu Met Thr Ser Leu Val Lys Val Ala Leu Gln Leu Ser Leu His Lys
            260                 265                 270
Asp Asn Asn Gln Arg Gln Tyr Glu Ala Glu Arg Asn Lys Gly Pro Glu
        275                 280                 285
Gln Arg Ala Pro Glu Arg Leu Glu Ser Leu Leu Glu Lys Arg Lys Glu
    290                 295                 300
Phe Gln Glu Asn Gln Glu Asp Ile Glu Gly Met Met Asn Ala Ile Phe
305                 310                 315                 320
Arg Gly Val Phe Val His Arg Tyr Arg Asp Ile Leu Pro Glu Ile Arg
                325                 330                 335
Ala Ile Cys Ile Glu Glu Ile Gly Tyr Trp Met Gln Ser Tyr Ser Thr
            340                 345                 350
Ser Phe Leu Asn Asp Ser Tyr Leu Lys Tyr Ile Gly Trp Thr Leu His
        355                 360                 365
Asp Lys His Lys Glu Val Arg Leu Lys Cys Val Lys Ala Leu Ala Gly
    370                 375                 380
Leu Tyr Ser Asn Gln Glu Leu Ser Leu Arg Met Glu Leu Phe Thr Asn
385                 390                 395                 400
Arg Phe Lys Asp Arg Met Val Ser Met Val Met Asp Arg Glu Cys Glu
```

-continued

```
                405                 410                 415
Val Ala Val Glu Ala Ile Arg Leu Leu Thr Leu Ile Leu Lys Asn Met
                420                 425                 430

Glu Gly Val Leu Thr Ser Ala Asp Cys Glu Lys Ile Tyr Ser Ile Val
                435                 440                 445

Tyr Ile Ser Asn Arg Ala Met Ala Ser Ser Ala Gly Glu Phe Val Tyr
    450                 455                 460

Trp Lys Ile Phe His Pro Glu Cys Gly Ala Lys Ala Val Ser Asp Arg
465                 470                  475                 480

Glu Arg Arg Ser Pro Gln Ala Gln Lys Thr Phe Ile Tyr Leu Leu
                485                 490                 495

Leu Ala Phe Phe Met Glu Ser Glu His His Asn His Ala Ala Tyr Leu
                500                 505                 510

Val Asp Ser Leu Trp Asp Cys Ala Gly Ser Tyr Leu Lys Asp Trp Glu
                515                 520                 525

Ser Leu Thr Asn Leu Leu Gln Lys Asp Gln Asn Leu Gly Asp Met
                530                 535                 540

Gln Glu Arg Met Leu Ile Glu Ile Leu Val Ser Ser Ala Arg Gln Ala
545                 550                 555                 560

Ala Glu Gly His Pro Pro Val Gly Arg Ile Thr Gly Lys Lys Ser Leu
                565                 570                 575

Thr Ala Lys Glu Arg Lys Leu Gln Ala Tyr Asp Lys Met Lys Leu Ala
                580                 585                 590

Glu His Leu Ile Pro Leu Leu Pro Gln Leu Leu Ala Lys Phe Ser Ala
                595                 600                 605

Asp Ala Glu Asn Val Ala Pro Leu Leu Gln Leu Leu Ser Tyr Phe Asp
    610                 615                 620

Leu Ser Ile Tyr Cys Thr Gln Arg Leu Glu Lys His Leu Glu Leu Leu
625                 630                 635                 640

Leu Gln Gln Leu Gln Glu Val Val Lys His Val Glu Pro Glu Val
                645                 650                 655

Leu Glu Ala Ala Ala His Ala Leu Tyr Leu Leu Cys Lys Pro Glu Phe
                660                 665                 670

Thr Phe Phe Ser Arg Val Asp Phe Ala Arg Ser Gln Leu Val Asp Phe
                675                 680                 685

Leu Thr Asp Arg Phe Gln Gln Glu Leu Asp Asp Leu Met Gln Ser Ser
                690                 695                 700

Phe Leu Asp Glu Asp Glu Val Tyr Ser Leu Thr Ala Thr Leu Lys Arg
705                 710                 715                 720

Leu Ser Ala Phe Tyr Asn Ala His Asp Leu Thr Arg Trp Glu Ile Ser
                725                 730                 735

Glu Pro Cys Ser Arg Leu Leu Arg Lys Ala Val Asp Thr Gly Glu Val
                740                 745                 750

Pro His Gln Val Ile Leu Pro Ala Leu Thr Leu Val Tyr Phe Ser Ile
                755                 760                 765

Leu Trp Thr Val Thr His Ile Ser Glu Ser Thr Ser His Lys Gln Leu
                770                 775                 780

Met Ser Leu Lys Lys Arg Met Val Ala Phe Cys Glu Leu Cys Gln Ser
785                 790                 795                 800

Cys Leu Ser Asp Val Asp Pro Glu Ile Gln Glu Ala Phe Val Leu
                805                 810                 815

Leu Ser Asp Leu Leu Ile Phe Ser Pro Gln Met Ile Val Gly Gly
                820                 825                 830
```

-continued

Arg Asp Phe Leu Arg Pro Leu Val Phe Phe Pro Glu Ala Thr Leu Gln
        835                 840                 845

Ser Glu Leu Ala Ser Phe Leu Met Asp His Val Phe Leu Gln Pro Gly
    850                 855                 860

Glu Leu Gly Asn Gly Gln Ser Gln Glu Asp His Val Gln Ile Glu Leu
865                 870                 875                 880

Leu His Gln Arg Arg Leu Leu Ala Gly Phe Cys Lys Leu Leu Leu
                885                 890                 895

Tyr Gly Val Leu Glu Leu Asp Ala Ala Ser Asp Val Phe Lys His Tyr
            900                 905                 910

Asn Lys Phe Tyr Glu Asp Tyr Gly Asp Ile Ile Lys Glu Thr Leu Thr
        915                 920                 925

Arg Ala Arg Gln Ile Asp Arg Cys Gln Cys Ser Arg Ile Leu Leu Leu
    930                 935                 940

Ser Leu Lys Gln Leu Tyr Thr Glu Leu Ile Gln Glu Gln Gly Pro Gln
945                 950                 955                 960

Gly Leu Thr Glu Leu Pro Ala Phe Ile Glu Met Arg Asp Leu Ala Arg
                965                 970                 975

Arg Phe Ala Leu Ser Phe Gly Pro Gln Gln Leu His Asn Arg Asp Leu
            980                 985                 990

Val Val Met Leu His Lys Glu Gly Ile Lys Phe Ser Leu Ser Glu Leu
        995                 1000                1005

Pro Pro Ala Gly Ser Ser His Glu Pro Pro Asn Leu Ala Phe Leu
    1010                1015                1020

Glu Leu Leu Ser Glu Phe Ser Pro Arg Leu Phe His Gln Asp Lys
    1025                1030                1035

Arg Leu Leu Leu Ser Tyr Leu Glu Lys Cys Leu Gln Arg Val Ser
    1040                1045                1050

Lys Ala Pro Asn His Pro Trp Gly Pro Val Thr Thr Tyr Cys His
    1055                1060                1065

Ser Leu His Pro Leu Glu Ile Thr Ala Glu Ala Ser Pro Arg Gly
    1070                1075                1080

Pro Pro His Ser Lys Lys Arg Cys Val Glu Gly Pro Cys Arg Pro
    1085                1090                1095

Gln Glu Glu Glu Ser Ser Gln Glu Glu Ser Leu Gln Leu Asn
    1100                1105                1110

Ser Gly Pro Thr Thr Pro Thr Leu Thr Ser Thr Ala Val Lys Arg
    1115                1120                1125

Lys Gln Ser Leu Arg Thr Val Gly Lys Lys Gln Lys Gly Arg Pro
    1130                1135                1140

Gly Pro Gly Pro Gly Pro Pro Glu Leu Ile Cys Ser Gln Gln
    1145                1150                1155

Leu Leu Gly Thr Gln Arg Leu Lys Met Ser Ser Ala Pro Cys Phe
    1160                1165                1170

Gln Ile Arg Cys Asp Pro Ser Gly Ser Gly Leu Gly Lys Gln Leu
    1175                1180                1185

Thr Arg Leu Ser Leu Met Glu Glu Asp Glu Glu Glu Leu Arg
    1190                1195                1200

Leu Leu Asp Glu Glu Trp Gln Arg Gly Asp Lys Met Leu His Ser
    1205                1210                1215

Pro Ser Ser Pro Ser Glu His Gly Leu Asp Leu Leu Asp Thr Thr
    1220                1225                1230

Glu Leu Asn Met Glu Asp Phe
    1235                1240

```
<210> SEQ ID NO 20
<211> LENGTH: 1256
<212> TYPE: PRT
<213> ORGANISM: Rattus norvegicus

<400> SEQUENCE: 20

Met Pro Thr Leu Trp Ser Pro Ser Thr Gln His His Gly Ser Ser Ser
1               5                   10                  15

Gly Ser Met Ser Ser Pro Leu Arg Lys Ser Val Arg Cys Ala Gln Met
            20                  25                  30

Ala Leu Ser Pro Cys Ser Ser Asn Ile Gln Pro Cys Asp Asp Arg Asp
        35                  40                  45

Ser Gln Gly Thr Ala Glu Trp Asp Ser Ser Thr Ser Glu Asp Ser
    50                  55                  60

Asp Phe Glu Asp Ser Leu Arg Arg Asn Val Arg Lys Arg Ala Ala Lys
65                  70                  75                  80

Arg Pro Pro Lys Ala Ile Pro Val Ala Lys His Pro Lys Lys Gln Ser
                85                  90                  95

His Ile Val Pro Gly Gly Asn Asp Lys Asn Lys Ser Val Pro Pro Thr
            100                 105                 110

Ser Asp Leu Phe Asp Ala Val Lys Ala Ala Arg Ser Cys Ala Gln Ser
        115                 120                 125

Leu Val Asp Glu Trp Leu Glu Asn Tyr Lys Gln Asp Glu Asn Ala Gly
    130                 135                 140

Phe Leu Glu Leu Val Asn Phe Phe Ile Arg Ala Cys Gly Cys Lys Ser
145                 150                 155                 160

Thr Val Thr Pro Glu Met Phe Lys Thr Met Ser Asn Ser Glu Ile Ile
                165                 170                 175

Gln His Leu Thr Glu Glu Phe Asn Glu Asp Ser Gly Asp Tyr Pro Leu
            180                 185                 190

Thr Ala Pro Gly Pro Ser Trp Lys Lys Phe Gln Gly Ser Phe Cys Glu
        195                 200                 205

Phe Val Lys Thr Leu Val Cys Gln Cys Gln Tyr Ser Leu Leu Phe Asp
    210                 215                 220

Gly Phe Pro Met Asp Asp Leu Ile Ser Leu Leu Ile Gly Leu Ser Asp
225                 230                 235                 240

Ser Gln Val Arg Ala Phe Arg His Thr Ser Thr Leu Ala Ala Met Lys
                245                 250                 255

Leu Met Thr Ser Leu Val Lys Val Ala Leu Gln Leu Ser Leu His Lys
            260                 265                 270

Asp Asn Asn Gln Arg Gln Tyr Glu Ala Glu Arg Asn Lys Gly Pro Glu
        275                 280                 285

Gln Arg Ala Pro Glu Arg Leu Glu Ser Leu Leu Glu Lys Arg Lys Glu
    290                 295                 300

Phe Gln Glu Asn Gln Glu Glu Ile Glu Gly Met Met Asn Ala Ile Phe
305                 310                 315                 320

Arg Gly Val Phe Val His Arg Tyr Arg Asp Ile Leu Pro Glu Ile Arg
                325                 330                 335

Ala Val Cys Ile Glu Glu Ile Gly Cys Trp Met Gln Ser Tyr Ser Thr
            340                 345                 350

Ser Phe Leu Asn Asp Ser Tyr Leu Lys Tyr Ile Gly Trp Thr Leu His
        355                 360                 365

Asp Lys His Lys Glu Val Arg Leu Lys Cys Val Lys Ala Leu Ala Gly
    370                 375                 380
```

```
Leu Tyr Ser Asn Gln Glu Leu Ser Ser Arg Met Glu Leu Phe Thr Asn
385                 390                 395                 400

Arg Phe Lys Asp Arg Met Val Ser Met Val Met Asp Arg Glu Ser Glu
            405                 410                 415

Val Ala Val Glu Ala Ile Arg Leu Leu Thr Leu Ile Leu Lys Asn Met
        420                 425                 430

Glu Gly Val Leu Thr Ser Ala Asp Cys Glu Lys Ile Tyr Ser Ile Val
            435                 440                 445

Tyr Ile Ser Asn Arg Ala Met Ala Ser Ala Gly Glu Phe Val Tyr
450                 455                 460

Trp Lys Ile Phe His Pro Glu Cys Gly Ala Lys Ala Val Ser Gly Arg
465                 470                 475                 480

Glu Arg Arg Ser Pro Gln Ala Gln Arg Thr Phe Ile Tyr Leu Leu
            485                 490                 495

Leu Ala Phe Phe Met Glu Ser Glu His His Asp His Ala Ala Tyr Leu
                500                 505                 510

Val Asp Ser Leu Trp Asp Cys Ala Gly Ser Tyr Leu Lys Asp Trp Glu
            515                 520                 525

Ser Leu Thr Ser Leu Leu Gln Lys Asp Gln Asn Leu Gly Asp Met
530                 535                 540

Gln Glu Arg Met Leu Ile Glu Ile Leu Val Ser Ser Ala Arg Gln Ala
545                 550                 555                 560

Ala Glu Gly His Pro Pro Val Gly Arg Ile Thr Gly Lys Lys Ser Leu
                565                 570                 575

Thr Ala Lys Glu Arg Lys Leu Gln Ala Tyr Asp Lys Val Lys Leu Ala
            580                 585                 590

Glu His Leu Ile Pro Leu Leu Pro Gln Leu Leu Ala Lys Phe Ser Ala
            595                 600                 605

Asp Ala Glu Asn Val Ala Pro Leu Leu Arg Leu Leu Ser Tyr Phe Asp
            610                 615                 620

Leu Asn Ile Tyr Cys Thr Gln Arg Leu Glu Lys His Leu Glu Leu Leu
625                 630                 635                 640

Leu Gln Gln Leu Gln Glu Val Val Lys His Val Glu Pro Glu Val
                645                 650                 655

Leu Glu Ala Ala Ala His Ala Leu Tyr Leu Leu Cys Lys Pro Glu Phe
            660                 665                 670

Thr Phe Phe Ser Arg Val Asp Phe Ala Arg Ser Gln Leu Val Asp Leu
            675                 680                 685

Leu Thr Asp Arg Phe Gln Gln Glu Leu Asp Asp Leu Met Gln Ser Ser
690                 695                 700

Phe Leu Asp Glu Asp Glu Val Tyr Ser Leu Thr Ala Thr Leu Lys Arg
705                 710                 715                 720

Leu Ser Ala Phe Tyr Asn Ala His Asp Leu Thr Arg Trp Glu Ile Ser
            725                 730                 735

Glu Pro Cys Ser Arg Leu Leu Arg Lys Ala Val Asp Thr Gly Glu Val
            740                 745                 750

Pro His Gln Val Ile Leu Pro Ala Leu Thr Leu Val Tyr Phe Ser Ile
            755                 760                 765

Leu Trp Thr Val Thr His Ile Ser Glu Ser Thr Ser Gln Lys Gln Leu
            770                 775                 780

Met Ser Leu Lys Lys Arg Met Val Ala Phe Cys Glu Leu Cys Gln Ser
785                 790                 795                 800

Cys Leu Ser Asp Val Asp Pro Glu Ile Gln Glu Gln Ala Phe Val Leu
```

```
                    805                 810                 815
Leu Ser Asp Leu Leu Leu Ile Phe Ser Pro Gln Met Val Gly Gly
            820                 825                 830
Arg Asp Phe Leu Arg Pro Leu Val Phe Phe Pro Glu Ala Thr Leu Gln
            835                 840                 845
Ser Glu Leu Ala Ser Phe Leu Met Asp His Val Phe Leu Gln Pro Gly
850                 855                 860
Glu Leu Gly Asn Gly Gln Ser Gln Glu Asp His Val Gln Ile Glu Leu
865                 870                 875                 880
Leu His Gln Arg Arg Arg Leu Leu Ala Gly Phe Cys Lys Leu Leu Leu
            885                 890                 895
Tyr Gly Val Leu Glu Leu Asp Ala Ala Ser Asp Val Phe Lys His Tyr
            900                 905                 910
Asn Lys Phe Tyr Glu Asp Tyr Gly Asp Ile Ile Lys Glu Thr Leu Thr
            915                 920                 925
Arg Ala Arg Gln Ile Asp Arg Cys Gln Cys Ser Arg Ile Leu Leu Leu
            930                 935                 940
Ser Leu Lys Gln Leu Tyr Thr Glu Leu Ile Gln Glu Gln Gly Pro Gln
945                 950                 955                 960
Asp Leu Thr Glu Leu Pro Ala Phe Ile Glu Met Arg Asp Leu Ala Arg
            965                 970                 975
Arg Phe Ala Leu Ser Phe Gly Pro Gln Gln Leu His Asn Arg Asp Leu
            980                 985                 990
Val Val Met Leu His Lys Glu Gly Ile Lys Phe Ser Leu Ser Glu Leu
            995                 1000                1005
Pro Pro Ala Gly Ser Ser Arg Glu Pro Pro Asn Ile Ala Phe Leu
            1010                1015                1020
Glu Leu Leu Ser Glu Phe Ser Pro Arg Leu Phe His Gln Asp Lys
            1025                1030                1035
Gln Leu Leu Leu Ser Tyr Leu Glu Lys Cys Leu Gln Arg Val Ser
            1040                1045                1050
Met Ala Pro Ser His Pro Trp Gly Pro Val Thr Thr Tyr Cys His
            1055                1060                1065
Ser Leu His Leu Val Glu Asn Thr Ala Glu Ala Ser Ser Gln Gly
            1070                1075                1080
Pro Pro His Ser Lys Lys Arg Cys Ile Glu Val Pro Arg Arg Leu
            1085                1090                1095
Gln Glu Glu Glu Ser Ser Ser Gln Gly Glu Ser Leu Gln Leu Asn
            1100                1105                1110
Ser Gly Pro Thr Thr Pro Thr Leu Thr Ser Thr Ala Val Lys Arg
            1115                1120                1125
Arg Gln Ser Pro Arg Thr Val Gly Lys Arg Gln Lys Gly Gly Pro
            1130                1135                1140
Gly Pro Gly Pro Gly Pro Gly Pro Gly Pro Gly Pro Gly Pro Gly
            1145                1150                1155
Pro Gly Pro Gly Pro Gly Pro Gly Pro Glu Leu Ile Cys Ser Gln
            1160                1165                1170
Gln Leu Ser Gly Thr Gln Arg Leu Lys Met Ser Ser Ala Pro Cys
            1175                1180                1185
Phe Gln Ile Arg Cys Asp Pro Ser Gly Ser Gly Leu Gly Lys Gln
            1190                1195                1200
Met Thr Arg Leu Ser Leu Met Glu Glu Asp Glu Glu Glu Glu Leu
            1205                1210                1215
```

```
Arg Leu Leu Asp Glu Glu Trp Gln Cys Gly Asp Lys Leu Leu His
    1220                1225                1230

Ser Pro Ser Ser Pro Ser Glu His Gly Leu Asp Leu Leu Asp Thr
    1235                1240                1245

Thr Glu Leu Asn Met Glu Asp Phe
    1250                1255

<210> SEQ ID NO 21
<211> LENGTH: 1226
<212> TYPE: PRT
<213> ORGANISM: Pan troglodytes

<400> SEQUENCE: 21

Met Ser Ser Pro Leu Gln Arg Ala Met Gly Asp Thr Lys Arg Ala Leu
1               5                   10                  15

Ser Ala Ser Ser Ser Ser Ala Ser Leu Pro Phe Asp Asp Arg Asp
            20                  25                  30

Ser Asn His Thr Ser Glu Gly Asn Gly Asp Ser Leu Leu Ala Asp Glu
            35                  40                  45

Asp Thr Asp Phe Glu Asp Ser Leu Asn Arg Asn Val Lys Lys Arg Ala
50                  55                  60

Ala Lys Arg Pro Pro Lys Thr Thr Pro Val Ala Lys His Pro Lys Lys
65          70                  75                  80

Gly Ser Arg Val Val His Arg Tyr Ser Arg Lys Gln Ser Glu Pro Pro
                85                  90                  95

Ala Asn Asp Leu Phe Asn Ala Val Lys Ala Ala Lys Ser Asp Met Gln
            100                 105                 110

Ser Leu Val Asp Glu Trp Leu Asp Ser Tyr Lys Gln Asp Gln Asp Ala
            115                 120                 125

Gly Phe Leu Glu Leu Val Asn Phe Phe Ile Gln Ser Cys Gly Cys Lys
            130                 135                 140

Gly Ile Val Thr Pro Glu Met Phe Lys Lys Met Ser Asn Ser Glu Ile
145                 150                 155                 160

Ile Gln His Leu Thr Glu Gln Phe Asn Glu Asp Ser Gly Asp Tyr Pro
                165                 170                 175

Leu Ile Ala Pro Gly Pro Ser Trp Lys Lys Phe Gln Gly Ser Phe Cys
            180                 185                 190

Glu Phe Val Arg Thr Leu Val Cys Gln Cys Gln Tyr Ser Leu Leu Tyr
            195                 200                 205

Asp Gly Phe Pro Met Asp Asn Leu Ile Ser Leu Leu Thr Gly Leu Ser
            210                 215                 220

Asp Ser Gln Val Arg Ala Phe Arg His Thr Ser Thr Leu Ala Ala Met
225                 230                 235                 240

Lys Leu Met Thr Ser Leu Val Lys Val Ala Leu Gln Leu Ser Val His
                245                 250                 255

Gln Asp Asn Asn Gln Arg Gln Tyr Glu Ala Glu Arg Asn Lys Gly Pro
            260                 265                 270

Gly Gln Arg Ala Pro Glu Arg Leu Glu Ser Leu Leu Glu Lys Arg Lys
            275                 280                 285

Glu Leu Gln Glu His Gln Glu Glu Ile Glu Gly Met Met Asn Ala Leu
            290                 295                 300

Phe Arg Gly Val Phe Val His Arg Tyr Arg Asp Val Leu Pro Glu Ile
305                 310                 315                 320

Arg Ala Ile Cys Ile Glu Glu Ile Gly Cys Trp Met Gln Ser Tyr Ser
                325                 330                 335
```

-continued

```
Thr Ser Phe Leu Thr Asp Ser Tyr Leu Lys Tyr Ile Gly Trp Thr Leu
            340                 345                 350

His Asp Lys His Arg Glu Val Arg Leu Lys Cys Val Lys Ala Leu Lys
        355                 360                 365

Gly Leu Tyr Gly Asn Arg Asp Leu Thr Thr Arg Leu Glu Leu Phe Thr
    370                 375                 380

Ser Arg Phe Lys Asp Arg Met Val Ser Met Val Met Asp Arg Glu Tyr
385                 390                 395                 400

Asp Val Ala Val Glu Ala Val Arg Leu Leu Ile Leu Ile Leu Lys Asn
                405                 410                 415

Met Glu Gly Val Leu Thr Asp Ala Asp Cys Gly Ser Val Tyr Pro Val
            420                 425                 430

Val Tyr Ala Ser His Arg Gly Leu Ala Ser Ala Ala Gly Glu Phe Leu
        435                 440                 445

Tyr Trp Lys Leu Phe Tyr Pro Glu Cys Glu Ile Arg Met Met Gly Gly
    450                 455                 460

Arg Glu Gln Arg Gln Ser Pro Gly Ala Gln Arg Thr Phe Phe Gln Leu
465                 470                 475                 480

Leu Leu Ser Phe Phe Val Glu Ser Glu Leu His Asp His Ala Ala Tyr
                485                 490                 495

Leu Val Asp Ser Leu Trp Asp Cys Ala Gly Ala Arg Leu Lys Asp Trp
            500                 505                 510

Glu Gly Leu Thr Ser Leu Leu Glu Lys Asp Gln Asn Leu Gly Asp
        515                 520                 525

Val Gln Glu Ser Thr Leu Ile Glu Ile Leu Val Ser Ser Ala Arg Gln
    530                 535                 540

Ala Ser Glu Gly His Pro Pro Val Gly Arg Val Thr Gly Arg Lys Gly
545                 550                 555                 560

Leu Thr Ser Lys Glu Arg Lys Thr Gln Ala Asp Asp Arg Val Lys Leu
                565                 570                 575

Thr Glu His Leu Ile Pro Leu Leu Pro Gln Leu Leu Ala Lys Phe Ser
            580                 585                 590

Ala Asp Ala Glu Lys Val Thr Pro Leu Leu Gln Leu Leu Ser Cys Phe
        595                 600                 605

Asp Leu His Ile Tyr Cys Thr Gly Arg Leu Glu Lys His Leu Glu Leu
    610                 615                 620

Phe Leu Gln Gln Leu Gln Glu Val Val Lys His Ala Glu Pro Ala
625                 630                 635                 640

Val Leu Glu Ala Gly Ala His Ala Leu Tyr Leu Leu Cys Asn Pro Glu
                645                 650                 655

Phe Thr Phe Phe Ser Arg Ala Asp Phe Ala Arg Ser Gln Leu Val Asp
            660                 665                 670

Leu Leu Thr Asp Arg Phe Gln Gln Glu Leu Glu Glu Leu Leu Gln Ser
        675                 680                 685

Ser Phe Leu Asp Glu Asp Glu Val Tyr Asn Leu Ala Ala Thr Leu Lys
    690                 695                 700

Arg Leu Ser Ala Phe Tyr Asn Ala His Asp Leu Thr Arg Trp Glu Leu
705                 710                 715                 720

Tyr Glu Pro Cys Cys Gln Leu Leu Gln Lys Ala Val Asp Thr Gly Glu
                725                 730                 735

Val Pro His Gln Val Ile Leu Pro Ala Leu Thr Leu Val Tyr Phe Ser
            740                 745                 750

Ile Leu Trp Thr Leu Thr His Ile Ser Lys Ser Asp Ala Ser Gln Lys
        755                 760                 765
```

```
Gln Leu Ser Ser Leu Arg Asp Arg Met Val Ala Phe Cys Glu Leu Cys
    770             775                 780

Gln Ser Cys Leu Ser Asp Val Asp Thr Glu Ile Gln Glu Gln Ala Phe
785             790                 795                 800

Val Leu Leu Ser Asp Leu Leu Leu Ile Phe Ser Pro Gln Met Ile Val
                805                 810                 815

Gly Gly Arg Asp Phe Leu Arg Pro Leu Val Phe Phe Pro Glu Ala Thr
            820                 825                 830

Leu Gln Ser Glu Leu Ala Ser Phe Leu Met Asp His Val Phe Ile Gln
        835                 840                 845

Pro Gly Asp Leu Gly Ser Gly Asp Ser Gln Glu Asp His Leu Gln Ile
    850                 855                 860

Glu Arg Leu His Gln Arg Arg Leu Leu Ala Gly Phe Cys Lys Leu
865             870                 875                 880

Leu Leu Tyr Gly Val Leu Glu Met Asp Ala Ala Ser Asp Val Phe Lys
            885                 890                 895

His Tyr Asn Lys Phe Tyr Asn Asp Tyr Gly Asp Ile Ile Lys Glu Thr
        900                 905                 910

Leu Thr Arg Ala Arg Gln Ile Asp Arg Ser His Cys Ser Arg Ile Leu
    915                 920                 925

Leu Leu Ser Leu Lys Gln Leu Tyr Thr Glu Leu Leu Gln Glu His Gly
930                 935                 940

Pro Gln Gly Leu Asn Glu Leu Pro Ala Phe Ile Glu Met Arg Asp Leu
945             950                 955                 960

Ala Arg Arg Phe Ala Leu Ser Phe Gly Pro Gln Gln Leu Gln Asn Arg
            965                 970                 975

Asp Leu Val Val Met Leu His Lys Glu Gly Ile Lys Phe Ser Leu Ser
        980                 985                 990

Glu Leu Pro Pro Ala Gly Ser Ser Asn Gln Pro Pro Asn Leu Ala Phe
    995                 1000                1005

Leu Glu Leu Leu Ser Glu Phe Ser Pro Arg Leu Phe His Gln Asp
    1010            1015            1020

Lys Gln Leu Leu Leu Ser Tyr Leu Glu Lys Cys Leu Gln His Val
    1025            1030            1035

Ser Gln Ala Pro Gly Arg Pro Trp Gly Pro Val Thr Thr Tyr Cys
    1040            1045            1050

His Ser Leu Ser Pro Val Glu Asn Thr Ala Glu Thr Ser Pro Gln
    1055            1060            1065

Val Leu Pro Ser Ser Lys Arg Arg Arg Val Glu Gly Pro Ala Lys
    1070            1075            1080

Pro Asn Arg Glu Asp Val Ser Ser Gln Glu Glu Ser Leu Gln
    1085            1090            1095

Leu Asn Ser Ile Pro Pro Thr Pro Thr Leu Thr Ser Thr Ala Val
    1100            1105            1110

Lys Ser Arg Gln Pro Leu Trp Gly Leu Lys Glu Met Glu Glu Glu
    1115            1120            1125

Asp Gly Ser Glu Leu Asp Phe Ala Gln Gly Ser Gln Pro Val Ala
    1130            1135            1140

Gly Thr Glu Arg Ser Arg Phe Leu Gly Pro Gln Tyr Phe Gln Thr
    1145            1150            1155

Pro His Asn Pro Ser Gly Pro Gly Leu Gly Asn Gln Leu Met Arg
    1160            1165            1170

Leu Ser Leu Met Glu Glu Asp Glu Glu Glu Glu Leu Glu Ile Gln
```

```
                    1175                1180                1185

Asp Glu  Ser Asn Glu Glu  Arg Gln Asp Thr Asp  Met Gln Ala Ser
         1190               1195                1200

Ser Tyr  Cys Ser Thr Ser  Glu Arg Gly Leu Asp  Leu Leu Asp Ser
         1205               1210                1215

Thr Glu  Leu Asp Ile Glu  Asp Phe
         1220               1225

<210> SEQ ID NO 22
<211> LENGTH: 432
<212> TYPE: PRT
<213> ORGANISM: Ornithorhynchus anatinus

<400> SEQUENCE: 22

Met Ala Arg Arg Trp Gly Val Ala Cys Val Ser Lys Arg Val Gly Asp
1               5                   10                  15

Glu Asn Glu Ala Gln Arg Ala Gly Glu Val Asp Lys Asn Glu Gly Ile
            20                  25                  30

Glu Leu Gly Gly Ser Gly Arg Arg Leu Glu Arg Leu Asp Phe Trp Val
        35                  40                  45

Val Phe Cys Leu Ser Thr Pro Gly Pro Ala Leu Gly Ser Glu Leu
    50                  55                  60

Val His Ser Pro Leu Ala Val Arg Glu Pro Val Arg Ser Pro Ser Ser
65                  70                  75                  80

Pro Pro Thr Arg Leu Ala Leu Leu Ala Gly Gly Ser Arg Asn Gly Pro
                85                  90                  95

Val Leu Pro Ile Phe Phe Thr Ile Leu Pro Pro Ser Gly Thr Val
            100                 105                 110

Thr Leu Glu Met Phe Lys Thr Leu Gln Asn Ser Glu Ile Ile Gln Gln
        115                 120                 125

Met Thr Glu Lys Phe Asn Glu Asp Ser Val Glu Tyr Pro Leu Ser Ala
130                 135                 140

Ser Gly Pro Thr Trp Lys Lys Phe Arg Gly Ser Phe Cys Glu Phe Val
145                 150                 155                 160

Ser Ser Leu Val His Gln Cys Arg Tyr Ser Phe Leu Tyr Asp Glu Phe
                165                 170                 175

Leu Met Asp Thr Leu Ile Ser Leu Leu Thr Gly Leu Ser Asp Ser Gln
            180                 185                 190

Val Arg Ala Phe Arg His Thr Ser Thr Leu Arg Arg Pro Ala Ser Phe
        195                 200                 205

Leu Gln Pro Arg Arg Asp Gly Gly Pro Ala Lys Thr Pro Pro Cys Cys
    210                 215                 220

Asp Ile Pro Pro Pro Phe Pro Asn Leu Leu Gln His Arg Pro Pro Leu
225                 230                 235                 240

Leu Ala Phe Pro Gln Ala Lys Pro Ala Gly Pro Ala Gly Pro Ala Arg
                245                 250                 255

Val Pro Gly Asp Gly Ala Ser Arg Leu Pro Val Ile Cys His Ala Lys
            260                 265                 270

Asp Thr Ser Gly Pro Phe Pro Phe Val Gln Val Ser Gly Arg Asp Pro
        275                 280                 285

Val Ala His Pro Pro Ala Lys Ala Glu Arg Glu Lys Gly Leu Pro
    290                 295                 300

Pro Ser Ala Ile Pro Val Arg Ser Gln Gly Ala Glu Gly Leu Leu Ala
305                 310                 315                 320

Arg Ile His Ala Gly Gly Asp Arg Gly Gly Gly Gly Arg Thr Gly Leu
```

```
                    325                 330                 335
Pro Val Pro Cys Gln Thr Phe Pro Ala Cys His Arg Asn Gly Asp Leu
                340                 345                 350

Thr Gly Gly Tyr Arg Leu Gly Arg Ser Ala Ser Thr Ser Gly Val Arg
            355                 360                 365

Gln Ala Ala Leu His Thr Pro Arg Pro Cys Ser Gln Ala Arg Glu Ser
        370                 375                 380

Pro Ser Gln Val Arg Lys Ala Asp Gly Ser Leu Thr Gly Leu Leu Gly
385                 390                 395                 400

Leu Gly Leu Arg Glu Gly Gly Pro Glu Glu Pro Val Leu Glu Thr Arg
                405                 410                 415

Ala Gly Gly Gly Ala Ser Glu Gly Arg Glu Gly Trp Arg Pro Gly Arg
            420                 425                 430

<210> SEQ ID NO 23
<211> LENGTH: 1140
<212> TYPE: DNA
<213> ORGANISM: Homo sapiens

<400> SEQUENCE: 23
gcacaccgga ctgcgttttt tttccgaacg cccgcagcag ggtcagaagg gaggtggtcg      60
ccctccgtcg tggtctggcg tgtattccga gcgttggtgt ctggcggttt ccgagcgttg     120
gtgtctggcg gtttccgacc gttggtgtct ggcggtttcc gaccgttggt gtctggcacg     180
cgccaccctc tcttgctttg gttgcgccat gccgatgtac cagacaagaa gacaagaaaa     240
tgatttgagg acagcttcaa tcgcggtgtg aagaagaaag cagcaaaacg accactgaaa     300
acaacgccgg tggcaaaata tccaaagaaa gggtcccaag cggtacatcg tcatagccgg     360
aaacagtcag agccaccagc caatgatatt ttcaatgctg cgaaagctgc caaaagtgac     420
atgcagggat gtccttcctg agatccgtgc tatctgcatt gaggaaattg ggtgttggat     480
gcaaagctac agcacgtctt tcctcaccga cagctattta aaatatattg gttggactct     540
gcatgataag caccgagaag tccgcgtgaa gtgcgtgaag ctctgaaagg gctgtacgg      600 taaccgggac ctgaccgcac gcctggagct cttcactggc cgcttcaagg actggatggt     660
ttccatgatc gtggacagag agtacagtgt ggcagtggag gccgtcagat tactgatact     720
tatccttaag aacatggaag gggtgctgat ggacgtggac tgtgagagcg tctaccccat     780
tgtgtaggcc tctaattgag gcctggcctc tgctgtgggt gaatttctgt actggaaact     840
tttctaccct gagtgcgaga taagaacgat gggtggaaga gagcaacgcc agagcccagg     900
cgcccagagg acttttcttcc agcttctgct gtccttcttt gtggagagca aggtgacata     960
cacagagaga actctggctg ttgtgcatag gacctacaag tgggctgggg ttggtggctc    1020
acgcctgtaa gcccagcact tgggaggct gaggtgggag gatcctttga gcccaggagt    1080
ttgagaccag cttgggcaac atagtgagac cctgtctcta ccaaaaaaaa aaaaaaaaaa    1140

<210> SEQ ID NO 24
<211> LENGTH: 4246
<212> TYPE: DNA
<213> ORGANISM: Mus musculus

<400> SEQUENCE: 24
ccgcgttttt ttctaaggct taaccgcccg ccaccagagg aagaagagca gctgcggcgg      60
gcgtctcgcg accgaggtgg gatgtccact gagacctgaa aggacctctg aggtggtgac     120
ctttcttcag ccgtgttcat ctaaagctgg attaacatgc ctactctgtg gtcaccttct     180
```

```
acccagcacc atggctcttc ctcaggcagt gagtcttccc cacttcaaaa gtctgtgaga      240
cgtgcacaga tggccttgtc tccttgttcc tcctccatcc taccctgtga tgacagagac      300
tcacagggaa ctgcagagtg ggatagtccc tcaactaacg aagacagcga ctttgaagac      360
agcttaagac gaaatgtgaa gaagagagca gcaaagcaac cacccaaagc tgttccagca      420
gcaaaacatc ggaagaagca gtcccgaata gtatctagtg gaatggcaa gaatgaatca       480 gtgccatcaa ccaattacct ttttgatgct gtgaaagctg ctagaagttg catgcagtct      540
ttggtggatg agtggctaga taactacaag caagatgaaa atgcaggatt cttggagctc      600
attaattttt tcatccgagc ctgtggatgt aaaagcactg tgactcctga gatgttcaag      660
acaatgtcca attcagagat catccaacac taacggaag agtttaatga ggactcgggg       720
gactatcccc tgcagctcc aggtccctcc tggaagaagt tccagggaag cttctgtgag       780
tttgtgaaga cattggtcta tcagtgccag tacagtctcc tctatgatgg cttttcctatg    840 gatgacctta tctccctgct cattggcctc tcagattccc aggtccgagc ctttcgtcat      900
actagtaccc tggctgccat gaagctaatg acttctctgg taaaagttgc actccagttg      960
agtctgcaca aagacaacaa tcaacgtcag tatgaggctg aacgaaacaa ggggccagag     1020
cagagagcac cggaacgact ggagagtctg ctggagaaac gaaaagagtt ccaagagaat     1080
caagaggaca tagaggggat gatgaatgcc atcttcagag gtgtctttgt ccatcggtac     1140
agggacatcc ttcctgagat ccgcgctatc tgcattgagg agattgggta ttggatgcaa     1200
agctacagca cctccttcct taatgacagc tacctaaaat acatcggctg gaccctgcat     1260
gataagcaca aggaagttcg cctgaagtgt gtgaaggctc tggcagggct gtacagcaac     1320
caggagctga gcttacggat ggagctcttt acaaatcgct tcaaggaccg gatggtttcc     1380
atggtcatgg acagagagtg tgaagtagca gtggaggcca tcagattgct gacccttatt     1440
ctgaagaaca tggagggagt gctgactagt gcagactgtg agaaaattta ctccattgta     1500
tacatttcta atcgtgctat ggcctcttct gcagggaat ttgtgtattg gaagatcttc      1560
catcctgaat gtggggcaaa agcagtgagt gatagagagc gacgccggag tccacaagcc     1620
cagaagactt tcatttatct tttactggcc ttctttatgg agagtgagca tcacaaccat     1680
gctgcttact tagtagacag cttgtgggac tgtgcggggt cttacctgaa ggactgggag     1740
agtctgacaa acctgttgct gcagaaagac cagaatctgg gtgatatgca agagagaatg     1800
ctgatagaaa tccttgtgtc tagtgcccgg caagctgcag agggtcaccc tccagtgggg     1860
cgcatcactg gaaagaagag tctgacggcc aaagaacgca agcttcaagc ctatgataag     1920
atgaagctgg ctgagcacct catcccctc ttgccccagc tccttgccaa gttctcagca     1980
gatgcagaga atgttgctcc cttgctccag ctgctcagtt actttgacct cagcatatat     2040
tgcactcagc gcttggaaaa gcacttggag ctgcttctgc aacaactcca ggaggtggtg     2100
gtgaagcatg tagagcctga ggtgcttgag gcagcagccc atgccctcta tctgctctgc     2160
aaaccagagt tcaccttctt cagcagagtg gactttgcca gaagccaatt agtagatttt     2220
ctgactgata gattccagca ggagcttgat gacctaatgc agtcatcctt cctagatgag     2280
gatgaggtat acagcctgac agccaccctg aagcgtctct ctgcctttta caatgctcat     2340
gacctgaccc gatgggagat ctctgaacca tgttctcgac tcctccggaa ggctgtagac     2400
acaggagaag ttcctcacca ggtgattttg ccagccttga ctctggtata tttttccatt     2460
ctctggacag taacccacat ttcagagtct acttctcata gcagctgat gagtctgaag      2520 aaaagaatgg tagccttctg tgagctttgc caaagctgcc tctcagacgt ggacccagag     2580
```

-continued

| | | |
|---|---|---|
| atccaggagc aggcttttgt cttattaagt gacctgcttc tcatcttcag ccctcagatg | 2640 |
| attgtagggg gacgggattt ccttaggcct cttgtctttt ttccggaagc tactctccag | 2700 |
| tcggaactag ccagcttcct catggaccat gtctttctcc agcctggaga actgggcaac | 2760 |
| ggtcagtcac aggaggatca cgtccagata gaacttctgc accagaggcg ccgcctgctt | 2820 |
| gcaggatttt gtaagctgct gctttatggg gtattggagc tggatgcagc ctcagacgtt | 2880 |
| ttcaaacact acaacaagtt ctatgaagac tatggtgaca ttatcaagga acattaact | 2940 |
| cgagcaagac aaattgacag atgtcagtgc tctcggatcc tgctcctgag cctaaagcag | 3000 |
| ctctacacag aactgataca ggagcagggc ccccagggcc tgacagaact gccagccttc | 3060 |
| attgagatga gagacttggc tcggaggttt gccttgagct ttggaccca gcagctccat | 3120 |
| aaccgagatc ttgtggtcat gctgcacaag gaaggcatca gttctcatt gtctgagctt | 3180 |
| cctcctgctg gttcttctca tgagccccca aatcttgcat tcctggagct tctttcagag | 3240 |
| ttctcccctc gcctcttcca tcaggacaag cggctactac tatcctacct ggaaaagtgt | 3300 |
| ctgcagcgtg tctccaaggc acctaaccat ccctggggtc cagtcaccac ctactgccac | 3360 |
| tccccttcacc ctctagagat cacagcagag gccagccctc gtggaccccc ccactccaag | 3420 |
| aagaggtgtg ttgaaggccc ctgcaggcct caggaagaag agtcctcatc ccaggaagaa | 3480 |
| agccttcagc tgaacagtgg ccccacaacc cctaccctca cctccaccgc agtgaagagg | 3540 |
| aagcagtctc tgaggacagt gggcaagaag caaaaaggta gaccaggacc aggaccagga | 3600 |
| ccaggaccag agctgatctg cagtcagcaa ctcttaggca cccagaggtt gaagatgtcg | 3660 |
| agtgcaccat gtttccagat tcgatgtgat ccttcaggct ctggcttggg caagcagctg | 3720 |
| acccgactca gccttatgga agaagatgag gaagaagagc taagacttct ggatgaagaa | 3780 |
| tggcaacgtg gagacaagat gcttcatagc ccttcttctc ccagtgagca tgggttggac | 3840 |
| ctattagata caacagagct gaacatggag gatttctgat gggactttag gcctctcccc | 3900 |
| ttctccactt accactgcaa gtccttgagt gagcagaagg aaggagtaaa atgaagcatt | 3960 |
| ctttgggtcc tagccaagta ctttaaagga aaagagaaat ggccttattt ttcaaatctc | 4020 |
| tatttctttc tgaagtgggt gctatatata gatgctatga gccttgtcat ccttaatgcg | 4080 |
| ccatcgcttt atgcttttgc ctgtttgcag tgataggagt tgggtaggga gggctttacg | 4140 |
| tcagcactga agtttagtaa aacttctatt tgatattttg tccccaaaca ctgccaaact | 4200 |
| ttcaataaac atgttcagct atctcataaa aaaaaaaaa aaaaaa | 4246 |

<210> SEQ ID NO 25
<211> LENGTH: 4181
<212> TYPE: DNA
<213> ORGANISM: Rattus norvegicus

<400> SEQUENCE: 25

| | | |
|---|---|---|
| aactgtgttc atctagaggt cattcttcca agctcaaaca ctggattaac atgcctactc | 60 |
| tgtggtcacc ctccacccag caccatggct cttcctcagg cagtatgtcc tcccctcttc | 120 |
| gaaagtctgt gagatgtgca cagatggcct tgtctccttg ttcttccaac atccaaccct | 180 |
| gtgatgacag agactcccag ggaactgcag aatgggatag ttcctcaact agtgaagaca | 240 |
| gtgactttga agatagctta agaagaaatg tgaggaagag agcagcaaaa cgaccaccca | 300 |
| aagctatccc agtggcaaaa catccgaaga agcagtccca catagtacct ggtgggaatg | 360 |
| acaagaacaa gtcagtgccg ccaaccagtg acctttttga tgctgtgaaa gctgctagaa | 420 |
| gttgtgcgca gtctttggta gatgagtggc tagaaaacta caagcaagat gaaaatgcag | 480 |

```
gattcttgga acttgttaat tttttcatcc gagcctgtgg atgtaaaagc actgtcacac    540
ccgagatgtt caagacaatg tccaactcag agatcatcca gcacctaaca gaagagttta    600
atgaggactc aggtgactat cccctgacag ctccaggtcc atcctggaag aagttccagg    660
gaagcttctg tgagtttgtg aagacactag tctgtcagtg ccagtacagc ctcctctttg    720
acggctttcc aatggatgac cttatctccc tgctcattgg cctctcagat tcccaggtcc    780
gagcctttcg tcatactagt actttggctg ccatgaagct aatgacttct ctggtaaaag    840
ttgcactcca gttgagtctg cacaaagaca acaatcaacg tcagtatgag gcagaacgaa    900
acaaggggcc agagcagagg gcaccagagc ggctcgagag tctgctggag aaacgaaaag    960
agttccaaga gaatcaagag gagatagagg ggatgatgaa tgccatcttc aggggtgtct   1020
ttgttcatcg gtacagggac atccttcctg agatccgtgc tgtctgcatc gaggagatcg   1080
ggtgttggat gcaaagctac agcacctcct ttcttaatga cagctaccta aaatatattg   1140
gctggaccct gcatgacaag cacaaggaag tccgcctaaa gtgtgtgaag ctctggcag    1200 ggctgtacag caaccaggag ctgagttcac ggatggagct ctttactaat cgcttcaagg   1260
accggatggt ttccatggtc atggacagag agagtgaagt agcagtggag gccatcagat   1320
tgctgaccct tattctgaag aacatggagg gagtactgac tagtgcagat tgtgagaaaa   1380
tttactccat tgtatacatt tctaatcgtg ccatggcctc ttctgcaggg gaatttgtgt   1440 actgaagat tttccatcct gaatgtgggg caaaagcagt gagtggcagg gagcgacgcc    1500
ggagtccaca gcccagagg actttcattt accttttatt ggccttcttt atggagagtg   1560
agcatcacga ccatgctgct tacctagttg acagcttgtg ggactgtgca gggtcttacc   1620
tgaaggactg ggagagtctg acaagtctgt tgctgcagaa agaccagaat ctgggtgata   1680
tgcaagagag aatgttgata gaaatcctgg tgtccagtgc ccggcaagct gcagagggtc   1740
acccaccagt ggggcgcatc actggaaaga agagtctgac cgccaaagaa cgcaagcttc   1800
aagcttatga taaggtgaag ctggctgagc acctcatccc cctcttgccc cagctccttg   1860
ccaagttctc agcagatgca gagaacgttg ctcccttgct ccggctgctc agttactttg   1920
acctcaacat ttattgcact cagcgcttgg agaagcactt ggagctgctt ctgcaacaac   1980
tccaggaggt ggtggtgaag cacgtagagc ctgaggtgct tgaggctgca gcacatgccc   2040
tctatttgct ctgcaagcca gagttcacct tcttcagcag agtggacttc gccagaagcc   2100
aattagtaga tctgctgact gatagattcc agcaggagct tgacgaccta atgcagtcat   2160
ccttcctaga tgaggatgag gtatacagtc tgacagccac tctgaagcgt ctctctgcct   2220
tttacaatgc tcatgacctg actcgctggg agatctctga accatgttct cgactcctcc   2280
ggaaggctgt agacacagga gaagttcctc accaggtgat tttgccagcc ttgactctgg   2340
tatatttttc cattctctgg acagtgaccc acatttcaga gtctacttcc caaaagcagc   2400
tgatgagtct gaagaaaaga atggtagcct tctgtgaact ttgccaaagc tgcctctcag   2460
acgtggaccc agagatccag gagcaggctt ttgttttatt aagtgacctg cttctcatct   2520 tcagcccca gatggttgta gggggccggg atttccttag gcctcttgtc ttttttccgg   2580
aagctactct ccagtcggaa ctagccagct tcctcatgga ccatgtcttt ctccagcctg   2640
gagaattggg caacggtcaa tcacaggagg atcacgtcca aatagagctt ctgcaccaga   2700
ggcgccgcct gcttgcagga ttttgtaagc tgttgcttta tggggtattg gaactggatg   2760
cggcctcaga tgttttcaaa cactacaaca gttctatga agattatggt gacattatca   2820
aggaaacatt aactcgggcg agacaaattg accgatgtca gtgctctcgg atcctgctcc   2880
```

```
tgagcctaaa gcagctctac acagaactga tacaggagca ggggcccag gacctgacag    2940 aactgccagc cttcattgag atgagagacc tggcccggag gtttgccttg agctttggac    3000
cccagcagct ccataacaga gatcttgtgg tcatgctgca caaggaaggc atcaagttct    3060
cattgtctga gcttcctcct gctggctctt ctcgagagcc cccaaatatt gcattcctgg    3120
agcttctttc agagttctcc ccccgcctct tccatcagga caaacagcta ctactatcat    3180
acctggaaaa gtgtctgcag cgtgtctcca tggcacctag ccatccctgg ggtccagtca    3240
ccacctactg ccactccctc catctagtag agaacacagc agaggccagc tctcaggggc    3300 cccccactc caagaagagg tgtattgaag ttccccgcag gcttcaggaa gaagagtctt    3360
catcccaggg agaaagcctt cagctgaaca gtggcccac aacacctaca ctcacctcca    3420
cagcagtgaa gagaaggcag tctccgagga cagtaggcaa gaggcaaaaa ggtggaccag    3480
gaccaggacc aggaccagga ccaggaccag gaccaggacc aggaccagga ccaggaccag    3540
gaccaggacc agagctgatc tgcagtcagc agctctcagg cacccagagg ttgaaaatgt    3600
cgagtgcacc gtgtttccag attcgatgtg atccttctgg ctctggcttg ggcaagcaga    3660
tgacccgact cagccttatg gaagaagatg aggaagaaga gctgagactt ctggatgaag    3720
aatggcaatg tggagacaag ctacttcata gcccttcttc tcccagtgag catgggctgg    3780
acctattaga tacaacagag ctgaacatgg aggattctg atgggactta ggcttctccc    3840
cttctccact taccacactg caaggccatg agtgagcaaa cgaaggagta aaatgaagca    3900
ttctttgggt cccagccaag tactttaagg gaatagagaa atggccttat tcaaacctcc    3960
atttctttct gaagtgggtg ctgtatatag atgctatgag ccctgtgatc cttaattcac    4020
cctagcttta tgcttttgcc tgtttgaagt ggtgggagtt gggtagggag ctttacctca    4080
gtattgaagt ttaataaacc ttctgtttga tatctcttcc ccaaacactg ccaagctctc    4140
aataaacatg ttcacatcag ctaaaaaaaa aaaaaaaaa a                         4181

<210> SEQ ID NO 26
<211> LENGTH: 4220
<212> TYPE: DNA
<213> ORGANISM: Pan troglodytes

<400> SEQUENCE: 26
tcttgtacgt tcccgcgctt ttttggaatc tttcgccccc ggaagggcag cggcgggcgc      60
ctgtgtggaa ggtggggtgg ccagagagac ccgagggacc tgagctggat cgccatacct     120
accctgtggt cctcatcttc ctgtcctcat agctcctcct ctccaagcat gtcttccccg     180
ttgcaaagag ctatgggaga taccaagagg gccttgtctg catcttctag ttcctctgcc     240
agtctaccct ttgatgacag ggactcaaac catacctcag aggggaatgg cgactctttg     300
ttagctgatg aagacactga ctttgaagac agcttgaatc gcaatgtgaa gagagagca     360 gcaaaacgac caccgaaaac aacaccggtg gcaaaacatc caaagaaagg gtcccgagtg     420
gtacatcgtt atagccggaa acagtcagag ccaccagcca atgatctttt caatgctgtg     480
aaagccgcca aaagtgacat gcagtctttg gtagatgagt ggctggatag ctacaagcaa     540
gaccaggatg caggatttct ggagcttgtt aacttttca tccaatcttg cggatgtaaa      600
ggcattgtga cccccgagat gttcaagaag atgtccaact cagagatcat ccagcaccta     660
acagagcagt ttaatgagga ctcggggac taccctctca tagctccagg tccatcctgg     720
aagaagttcc agggcagctt ctgtgaattt gtgaggacat tggtctgtca gtgccagtac     780
agcctcctct atgatggctt ccctatggac aacctcatct ccctgctcac tggcctctca     840
```

```
gactcacaag tccgcgcctt ccgtcacact agcaccctgg ctgctatgaa actgatgacc      900
tccctggtaa aagttgccct ccaactgagt gtgcaccaag ataacaatca gcgtcagtat      960
gaggctgaaa gaaacaaggg gccagggcag agggcacctg agcggctgga gagcctgttg     1020
gagaaacgca aagagctcca agagcatcaa gaggagattg aggggatgat gaatgccctc     1080
ttcaggggtg tctttgttca tcggtacagg gatgtccttc ctgagatccg tgctatctgc     1140
attgaggaaa ttgggtgttg gatgcaaagc tacagcacgt ctttcctcac cgacagctat     1200
ttaaaatata ttggttggac tctgcatgat aagcaccgag aagtccgcct gaagtgtgtg     1260
aaggccctga aagggctgta cggtaaccgg gacctgacca cacgcctgga gctcttcacc     1320
agccgcttca aggaccggat ggtttccatg gtcatggaca gagagtatga tgtggcagtg     1380
gaggctgtca gattactgat acttatcctt aagaacatgg aaggggtgct gacgacgcg      1440 gactgtgaga gcgtctaccc cgttgtgtat gcctctcatc gaggcctggc ctctgccgca     1500
ggcgaatttc tgtactggaa actcttctac cctgagtgcg agataagaat gatgggtgga     1560
agagagcaac gccagagccc aggcgcccag aggactttct tccagcttct gctgtccttc     1620
tttgtggaga gcgagctcca tgaccacgct gcttacttag tagacagtct gtgggactgt     1680 gcagggctc ggctgaagga ctgggagggt ctgacaagcc tgctgctgga aaggaccag       1740 aacctgggtg atgtgcagga gagcacactg atagaaatcc ttgtgtccag tgcccggcaa     1800
gcttcagagg ggcacccgcc tgtgggccgg gtcactggga ggaagggctt aacctctaag     1860
gagcgcaaga cccaagccga tgacagggtg aagttgactg agcacctcat ccccctgctg     1920
ccccagctcc tggccaagtt ctcagctgat gcagagaagg tcactcccct gctccagctt     1980
ctcagctgct ttgacctcca catctactgc actgggcgct tggagaagca cctggagctg     2040
ttcctgcagc aactccagga ggtggtggtg aagcatgcag agccagcggt gcttgaggct     2100
ggggcgcatg ccctctacct gctctgtaat cccgaattca ctttcttcag ccgggcggac     2160
tttgcccgca gccagctagt agatttgctg actgaccgct tccagcagga gcttgaagag     2220
ctgttacagt cgtccttcct agatgaggat gaggtatata atctggcagc cactctgaaa     2280
cgcctctctg ccttctacaa cgctcatgac ctgactcgct gggagctcta tgagccatgt     2340
tgccaactcc tgcagaaggc tgtggacaca ggagaggttc ctcaccaggt tatcctgcca     2400
gccttgactc ttgtctattt ttccattctc tggacactaa cccacatttc taaatcagat     2460
gcttcccaga agcagctgtc gagtttgagg gacagaatgg tggccttctg tgaactctgc     2520
cagagttgcc tctcagatgt ggatactgag atccaggagc aggcttttgt cttattaagt     2580
gatctacttc tcatctttag ccctcagatg attgttgggg gccgtgattt ccttaggcca     2640
cttgtctttt ttcctgaagc tactctccag tctgagctag ccagcttcct catgaccac      2700 gtcttcatcc agccgggaga cctgggcagt ggtgattccc aggaggatca tttacagata     2760
gagcggctac accagcggcg ccgcctccta gccgggttct gcaagctgtt gctttatggg     2820
gtgctggaga tggatgcagc ctcagatgtt ttcaaacact acaacaagtt ctacaatgac     2880
tatggtgaca ttatcaagga aacattaact agagcaaggc agattaccg aagtcattgt      2940 tcccgaatcc tgctgctgag cctcaagcag ctgtacacag aactgctgca ggagcatggg     3000
ccccagggcc tgaatgagct tcctgccttc atcgagatga gggaccggc ccggaggttt      3060 gccttgagtt ttggacccca gcagctgcag aaccgtgacc tcgtggtcat gctacacaag     3120
gaaggcatca agttctccct tgtctgagctt cctccagctg ctcctccaa tcagcctcca     3180 aatctggcat tcctggagct cctttcagag ttttcccccc gactcttcca tcaggacaag     3240
```

```
cagcttttac tgtcctatct agaaaagtgc ctgcagcatg tctcccaggc acctggccgt    3300
ccctggggcc cagtcaccac ctactgccac tccctcagcc ctgtggagaa cacagcagag    3360
accagccctc aggtcctccc cagctccaag aggaggcgcg ttgaagggcc tgccaagcct    3420
aacagagagg acgtctcctc gtcccaggaa gaaagtctgc agctgaacag catcccgccc    3480
acgcccaccc tcacctccac agctgtgaag agcaggcagc cctgtggggg gttgaaagag    3540
atggaggaag aagatggctc agagttggat tttgcccagg gcagtcagcc cgttgcaggc    3600
accgagaggt caaggttctt gggtccacaa tatttccaga ctccacacaa cccttcaggt    3660
cctggcctgg caaccagct gatgcgactc agccttatgg aagaggacga ggaagaagag    3720
ttagaaatcc aggatgagtc aaatgaagaa cggcaggata cagacatgca agcaagtagc    3780
tactgttcca ccagtgagcg cgggctgac ctcttagatt ctacagagct ggatattgag    3840
gatttctgac aggactctgg gcccctcccc agctccactc cctacctcaa gaatgtgacc    3900
atttggaaaa ggcagagaaa aggagcaaaa tgaagcattc ccccaggctt cagccctggg    3960
ctctgagggg aaagagttgg gcattgtttt tctaacctaa cctttccctc tggggtagag    4020
aagccgagag accctgtcct ccctaatgca ctgtggccca gtccccttgc ctttttcctg    4080
ttctgtttgg agtggagaag ggcagcacct ctgtgtttaa tggaaatagc ccatggtttt    4140
ctggattttt ggaacatctt tctcagccta ttttgtgtcc taatgattcg ctcaataaac    4200
atgtttgaat ccacacgttc                                                4220
```

<210> SEQ ID NO 27
<211> LENGTH: 1299
<212> TYPE: DNA
<213> ORGANISM: Ornithorhynchus anatinus

<400> SEQUENCE: 27

```
atggcgcggc ggtgggggt ggcgtgtgtg agcaagaggg tgggagatga gaacgaagca      60
cagcgagccg gtgaggtcga caagaatgaa ggtatcgagc tcgggggtag tgggagaaga    120
ctggaaagac tagattttg ggtcgtcttc tgcctctcaa ccccaccggg ccccgctctg    180
ggttccgaac tcgtgcactc tccgctcgct gtcagggagc cggtccgttc ccatccctcc    240
cccccaaccc gactcgccct cttggccggc ggaagccgta acggcccgt cctcccaatt    300 tttttacca tccttcctcc cccatcaggc acggtgaccc tggagatgtt caagaccctg    360
cagaactcag agatcatcca acagatgacg gagaagttta cgaggactc ggtggaatac    420 cccttgtcag cctccggccc gacctggaag aaattccggg ggagtttctg tgagttcgtc    480
agctcgctgg tgcatcagtg ccgctacagc ttcctctacg acgaattcct catggatacc    540
ctcatctccc tgctcacggg cctctccgac tcccaggtcc gcgccttccg ccacaccagc    600
accctgcgtc gccccgcctc tttcctccag ccccgcaggg acggggggtcc cgccaagacc    660 ccgccgtgct cgacatccc gccgcccttc cccaacctcc tccagcaccg gccgccgctc    720
ctcgccttcc cgcaggccaa gccggccggt cccgccggcc ccgccagggt ccccggggac    780 gggcgtccc gcctgcccgt catctgccac gccaaggata cttccggccc ttcccccttc    840
gtccaagtgt ctgggcggga tccggttgcc cacccgccgg ccaaagcgga gcgggaggag    900
aaggggctcc cgccctcggc catccccgtg aggagccagg gggccgaggg cctgctggcc    960
cgaatccacg ccggaggaga ccgaggcggc gggggccgga cggggctccc cgtgccctgc   1020
cagaccttcc ccgcctgcca ccgcaacgga gacttgacgg ggggctaccg ccttgggcgc   1080
tcagcctcca cctccggggt ccgccaggca gccctccaca ccccgcgccc ctgcagccag   1140
```

-continued

```
gcccgggagt cgcccagcca ggtgaggaag gcggacggat ccctgacggg cctcctcggg    1200
ctcggcctca gggagggcgg cccggaggag ccggtcttgg agacgagggc aggaggagga    1260
gcttctgagg gccgggaggg atggcggccc ggacggtga                           1299
```